US012690968B2

(12) United States Patent
Cohen et al.

(10) Patent No.: US 12,690,968 B2
(45) Date of Patent: Jul. 28, 2026

(54) DELIVERY APPARATUS AND METHODS FOR IMPLANTING PROSTHETIC HEART VALVES

(71) Applicant: Edwards Lifesciences Corporation, Irvine, CA (US)

(72) Inventors: Oren Cohen, Kadima (IL); Elazar Levi Schwarcz, Netanya (IL); Denis Zhmakin, Haifa (IL); Ofir Witzman, Harish (IL); Noam Miller, Givatayim (IL); Eitan Atias, Netanya (IL)

(73) Assignee: Edwards Lifesciences Corporation, Irvine, CA (US)

( * ) Notice: Subject to any disclaimer, the term of this patent is extended or adjusted under 35 U.S.C. 154(b) by 919 days.

(21) Appl. No.: 17/939,102

(22) Filed: Sep. 7, 2022

(65) Prior Publication Data

US 2023/0024690 A1 Jan. 26, 2023

Related U.S. Application Data

(63) Continuation of application No. PCT/US2021/022467, filed on Mar. 16, 2021.

(60) Provisional application No. 62/990,299, filed on Mar. 16, 2020.

(51) Int. Cl.
*A61F 2/24* (2006.01)
(52) U.S. Cl.
CPC ............ *A61F 2/2466* (2013.01); *A61F 2/243* (2013.01); *A61F 2250/001* (2013.01)

(58) Field of Classification Search
CPC ..... A61F 2/2439; A61F 2/2466; A61F 2/9517
See application file for complete search history.

(56) References Cited

U.S. PATENT DOCUMENTS

| | | | |
|---|---|---|---|
| 519,297 | A | 5/1894 | Wanek et al. |
| 4,035,849 | A | 7/1977 | Angell et al. |
| 4,592,340 | A | 6/1986 | Boyles |
| 4,955,895 | A | 9/1990 | Sugiyama et al. |
| 4,994,077 | A | 2/1991 | Dobben |
| 5,059,177 | A | 10/1991 | Towne et al. |
| 5,176,698 | A | 1/1993 | Burns et al. |
| 5,192,297 | A | 3/1993 | Hull |
| 5,266,073 | A | 11/1993 | Wall |
| 5,325,845 | A | 7/1994 | Adair |
| 5,358,496 | A | 10/1994 | Ortiz et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Alvin J Stewart
(74) *Attorney, Agent, or Firm* — Klarquist Sparkman, LLP

(57) ABSTRACT

A delivery apparatus for implanting a prosthetic heart valve includes one or more shafts and a handle coupled to the one or more shafts. The handle comprises one or more knobs, one or more adjustment mechanisms, and/or one or more control mechanisms. The knobs are configured for actuating the one or more adjustment mechanisms and/or the one or more control mechanisms. The one or more adjustment mechanisms are configured for moving the shafts relative to each other and/or relative to the handle. The one or more control mechanisms are configured for limiting the direction of movement and/or force applied to the one or more shafts.

18 Claims, 66 Drawing Sheets

(56)                    References Cited

U.S. PATENT DOCUMENTS

| | | | |
|---|---|---|---|
| 5,411,552 | A | 5/1995 | Andersen et al. |
| 5,554,185 | A | 9/1996 | Block et al. |
| 5,591,195 | A | 1/1997 | Taheri et al. |
| 5,599,305 | A | 2/1997 | Hermann et al. |
| 5,632,760 | A | 5/1997 | Sheiban et al. |
| 5,639,274 | A | 6/1997 | Fischell et al. |
| 5,728,068 | A | 3/1998 | Leone et al. |
| 5,749,890 | A | 5/1998 | Shaknovich |
| 5,782,809 | A | 7/1998 | Umeno et al. |
| 5,824,044 | A | 10/1998 | Quiachon et al. |
| 5,840,081 | A | 11/1998 | Andersen et al. |
| 5,908,405 | A | 6/1999 | Imran et al. |
| 5,916,147 | A | 6/1999 | Boury |
| 5,944,690 | A | 8/1999 | Falwell et al. |
| 5,961,536 | A | 10/1999 | Mickley et al. |
| 5,968,068 | A | 10/1999 | Dehdashtian et al. |
| 6,019,777 | A | 2/2000 | Mackenzie |
| 6,027,510 | A | 2/2000 | Alt |
| 6,033,381 | A | 3/2000 | Kontos |
| 6,143,016 | A | 11/2000 | Bleam et al. |
| 6,162,208 | A | 12/2000 | Hipps |
| 6,168,614 | B1 | 1/2001 | Andersen et al. |
| 6,174,327 | B1 | 1/2001 | Mertens et al. |
| 6,217,585 | B1 | 4/2001 | Houser et al. |
| 6,235,050 | B1 | 5/2001 | Quiachon et al. |
| 6,251,092 | B1 | 6/2001 | Qin et al. |
| 6,379,372 | B1 | 4/2002 | Dehdashtian et al. |
| 6,383,171 | B1 | 5/2002 | Gifford et al. |
| 6,454,799 | B1 | 9/2002 | Schreck |
| 6,458,153 | B1 | 10/2002 | Bailey et al. |
| 6,461,382 | B1 | 10/2002 | Cao |
| 6,471,672 | B1 | 10/2002 | Brown et al. |
| 6,500,147 | B2 | 12/2002 | Omaleki et al. |
| 6,514,228 | B1 | 2/2003 | Hamilton et al. |
| 6,527,979 | B2 | 3/2003 | Constantz et al. |
| 6,579,305 | B1 | 6/2003 | Lashinski |
| 6,582,462 | B1 | 6/2003 | Andersen et al. |
| 6,652,578 | B2 | 11/2003 | Bailey et al. |
| 6,730,118 | B2 | 5/2004 | Spenser et al. |
| 6,733,525 | B2 | 5/2004 | Yang et al. |
| 6,764,504 | B2 | 7/2004 | Wang et al. |
| 6,767,362 | B2 | 7/2004 | Schreck |
| 6,830,584 | B1 | 12/2004 | Seguin |
| 6,893,460 | B2 | 5/2005 | Spenser et al. |
| 6,908,481 | B2 | 6/2005 | Cribier |
| 7,011,094 | B2 | 3/2006 | Rapacki et al. |
| 7,018,406 | B2 | 3/2006 | Seguin et al. |
| 7,018,408 | B2 | 3/2006 | Bailey et al. |
| 7,137,993 | B2 | 11/2006 | Acosta et al. |
| 7,276,084 | B2 | 10/2007 | Yang et al. |
| 7,318,278 | B2 | 1/2008 | Zhang et al. |
| 7,320,702 | B2 | 1/2008 | Hammersmark et al. |
| 7,320,704 | B2 | 1/2008 | Lashinski et al. |
| 7,374,571 | B2 | 5/2008 | Pease et al. |
| 7,393,360 | B2 | 7/2008 | Spenser et al. |
| 7,435,257 | B2 | 10/2008 | Lashinski et al. |
| 7,510,575 | B2 | 3/2009 | Spenser et al. |
| 7,585,321 | B2 | 9/2009 | Cribier |
| 7,594,926 | B2 | 9/2009 | Linder et al. |
| 7,597,709 | B2 | 10/2009 | Goodin |
| 7,618,446 | B2 | 11/2009 | Andersen et al. |
| 7,780,723 | B2 | 8/2010 | Taylor |
| 7,785,366 | B2 | 8/2010 | Maurer et al. |
| 7,959,661 | B2 | 6/2011 | Hijlkema et al. |
| 8,029,556 | B2 | 10/2011 | Rowe |
| 8,167,932 | B2 | 5/2012 | Bourang et al. |
| RE43,882 | E | 12/2012 | Hopkins et al. |
| 8,449,606 | B2 | 5/2013 | Eliasen et al. |
| 8,475,523 | B2 | 7/2013 | Duffy |
| 8,568,472 | B2 | 10/2013 | Marchand et al. |
| 9,061,119 | B2 | 6/2015 | Le et al. |
| 9,119,716 | B2 | 9/2015 | Lee et al. |
| 9,795,477 | B2 | 10/2017 | Tran et al. |
| 11,273,038 | B2 | 3/2022 | Tang et al. |
| 2001/0002445 | A1 | 5/2001 | Vesely |

| | | | |
|---|---|---|---|
| 2001/0007082 | A1 | 7/2001 | Dusbabek et al. |
| 2002/0032481 | A1 | 3/2002 | Gabbay |
| 2002/0058995 | A1 | 5/2002 | Stevens |
| 2002/0165461 | A1 | 11/2002 | Hayzelden et al. |
| 2003/0040792 | A1 | 2/2003 | Gabbay |
| 2003/0050694 | A1 | 3/2003 | Yang et al. |
| 2003/0120341 | A1 | 6/2003 | Shennib et al. |
| 2004/0093061 | A1 | 5/2004 | Acosta et al. |
| 2004/0133263 | A1 | 7/2004 | Dusbabek et al. |
| 2004/0143197 | A1 | 7/2004 | Soukup et al. |
| 2004/0186563 | A1 | 9/2004 | Lobbi |
| 2004/0186565 | A1 | 9/2004 | Schreck |
| 2004/0260389 | A1 | 12/2004 | Case et al. |
| 2005/0080474 | A1 | 4/2005 | Andreas et al. |
| 2005/0096736 | A1 | 5/2005 | Osse et al. |
| 2005/0137689 | A1 | 6/2005 | Salahieh et al. |
| 2005/0149160 | A1 | 7/2005 | McFerran |
| 2005/0203614 | A1 | 9/2005 | Forster et al. |
| 2005/0203617 | A1 | 9/2005 | Forster et al. |
| 2005/0245894 | A1 | 11/2005 | Zadno Azizi |
| 2006/0025857 | A1 | 2/2006 | Bergheim et al. |
| 2006/0282150 | A1 | 12/2006 | Olson et al. |
| 2007/0005131 | A1 | 1/2007 | Taylor |
| 2007/0073389 | A1 | 3/2007 | Bolduc et al. |
| 2007/0088431 | A1 | 4/2007 | Bourang et al. |
| 2007/0100356 | A1 | 5/2007 | Lucatero et al. |
| 2007/0112355 | A1 | 5/2007 | Salahieh et al. |
| 2007/0112422 | A1 | 5/2007 | Dehdashtian |
| 2007/0203575 | A1 | 8/2007 | Forster et al. |
| 2007/0219612 | A1 | 9/2007 | Andreas et al. |
| 2007/0239254 | A1 | 10/2007 | Chia et al. |
| 2007/0244546 | A1 | 10/2007 | Francis |
| 2007/0265700 | A1 | 11/2007 | Eliasen et al. |
| 2008/0065011 | A1 | 3/2008 | Marchand et al. |
| 2008/0103520 | A1 | 5/2008 | Selkee |
| 2008/0125853 | A1 | 5/2008 | Bailey et al. |
| 2008/0294230 | A1 | 11/2008 | Parker |
| 2009/0024428 | A1 | 1/2009 | Hudock |
| 2009/0069889 | A1 | 3/2009 | Suri et al. |
| 2009/0138079 | A1 | 5/2009 | Tuval et al. |
| 2009/0157175 | A1 | 6/2009 | Benichou |
| 2009/0192585 | A1 | 7/2009 | Bloom et al. |
| 2009/0228093 | A1 | 9/2009 | Taylor et al. |
| 2009/0276040 | A1 | 11/2009 | Rowe et al. |
| 2009/0281619 | A1 | 11/2009 | Le et al. |
| 2009/0299456 | A1 | 12/2009 | Melsheimer |
| 2009/0319037 | A1 | 12/2009 | Rowe et al. |
| 2010/0030318 | A1 | 2/2010 | Berra |
| 2010/0036472 | A1 | 2/2010 | Papp |
| 2010/0036473 | A1 | 2/2010 | Roth |
| 2010/0049313 | A1 | 2/2010 | Alon et al. |
| 2010/0076402 | A1 | 3/2010 | Mazzone et al. |
| 2010/0076541 | A1 | 3/2010 | Kumoyama |
| 2010/0082089 | A1 | 4/2010 | Quadri et al. |
| 2010/0094394 | A1 | 4/2010 | Beach et al. |
| 2010/0121425 | A1 | 5/2010 | Shimada |
| 2010/0145431 | A1 | 6/2010 | Wu et al. |
| 2010/0161036 | A1 | 6/2010 | Pintor et al. |
| 2010/0174363 | A1 | 7/2010 | Castro |
| 2010/0198347 | A1 | 8/2010 | Zakay et al. |
| 2010/0274344 | A1 | 10/2010 | Dusbabek et al. |
| 2011/0015729 | A1 | 1/2011 | Jimenez et al. |
| 2011/0054596 | A1 | 3/2011 | Taylor |
| 2011/0137331 | A1 | 6/2011 | Walsh et al. |
| 2011/0160846 | A1 | 6/2011 | Bishop et al. |
| 2012/0123529 | A1 | 5/2012 | Levi et al. |
| 2012/0239142 | A1 | 9/2012 | Liu et al. |
| 2013/0030519 | A1 | 1/2013 | Tran et al. |
| 2013/0046373 | A1 | 2/2013 | Cartledge et al. |
| 2013/0317598 | A1 | 11/2013 | Rowe et al. |
| 2014/0296962 | A1 | 10/2014 | Cartledge et al. |
| 2017/0065415 | A1 | 3/2017 | Rupp et al. |
| 2018/0153689 | A1 | 6/2018 | Maimon et al. |
| 2018/0344456 | A1 | 12/2018 | Barash et al. |
| 2022/0287838 | A1* | 9/2022 | Cohen ..................... A61F 2/243 |
| 2023/0338140 | A1* | 10/2023 | Cartledge ................. A61F 2/95 |

(56)  References Cited

U.S. PATENT DOCUMENTS

FOREIGN PATENT DOCUMENTS

| | | | |
|---|---|---|---|
| EP | 0592410 | B1 | 10/1995 |
| EP | 0850607 | A1 | 7/1998 |
| FR | 2815844 | A1 | 5/2002 |
| WO | 1991017720 | A1 | 11/1991 |
| WO | 1998029057 | A1 | 7/1998 |
| WO | 1999012483 | A1 | 3/1999 |
| WO | 2001049213 | A2 | 7/2001 |
| WO | 2001054625 | A1 | 8/2001 |
| WO | 2001076510 | A2 | 10/2001 |
| WO | 2002022054 | A1 | 3/2002 |
| WO | 2002036048 | A1 | 5/2002 |
| WO | 2002047575 | A2 | 6/2002 |
| WO | 2002060352 | A1 | 8/2002 |
| WO | 2003030776 | A2 | 4/2003 |
| WO | 2003047468 | A1 | 6/2003 |
| WO | 2004019825 | A1 | 3/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2010121076 | A2 | 10/2010 |
| WO | WO-2013126529 | A2 * | 8/2013 .......... A61F 2/9517 |
| WO | WO-2021113507 | A1 | 6/2021 |
| WO | WO-2021178543 | A1 | 9/2021 |

* cited by examiner

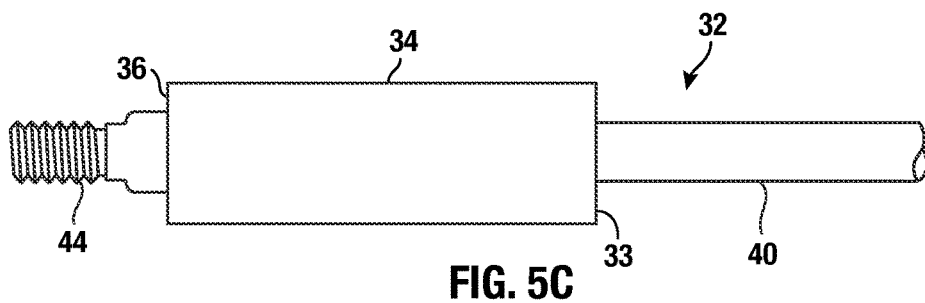
FIG. 5C
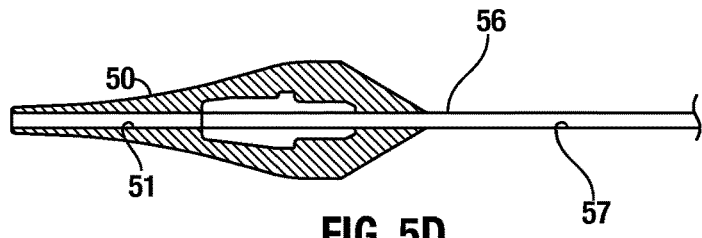
FIG. 5D
FIG. 6A
FIG. 6B

242a, 242b 242a, 242b 46c, 82

232

220, 220a, 220b 248a, 248b, 248c 240, 240a, 240b 236, 236a, 236b 238, 238a, 238b 46c, 82

232

248a, 248b, 248c 220, 220a, 220b

224

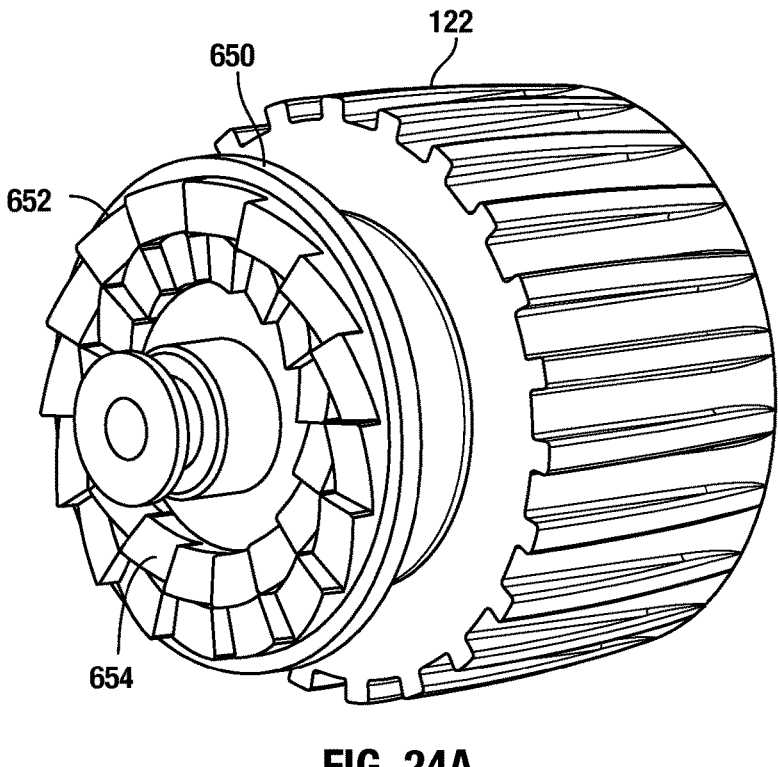
FIG. 24A
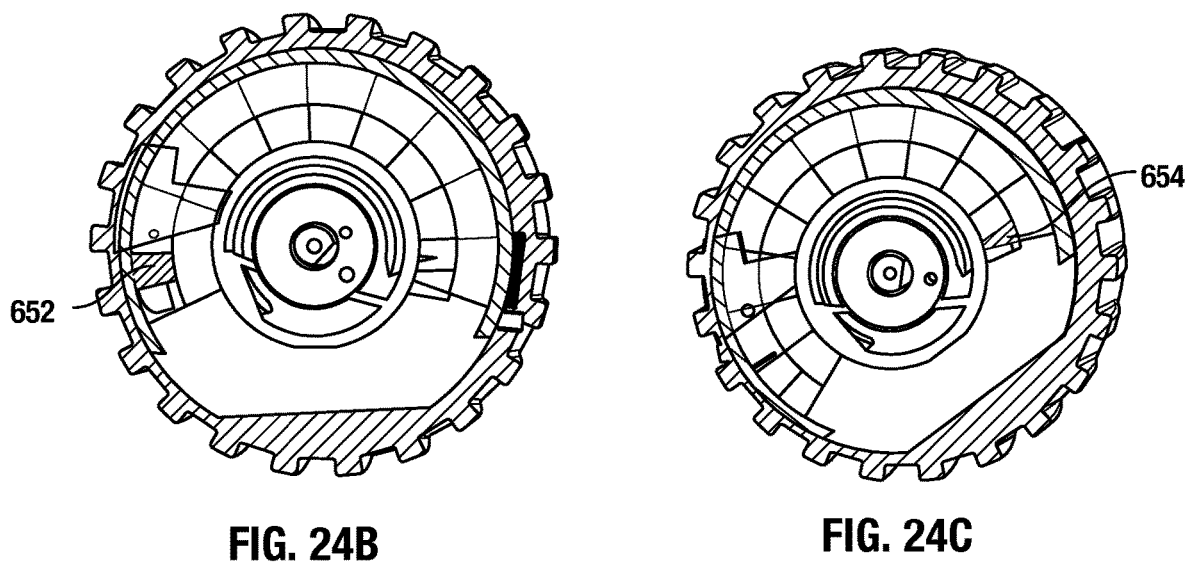
FIG. 24B          FIG. 24C

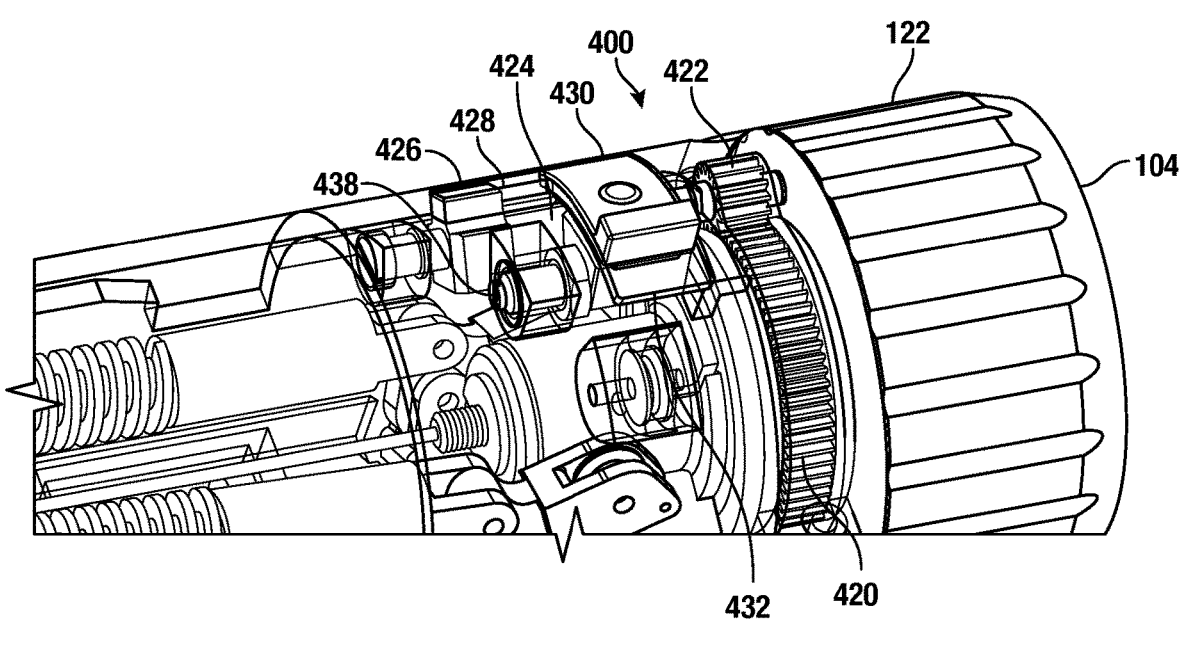
FIG. 25A
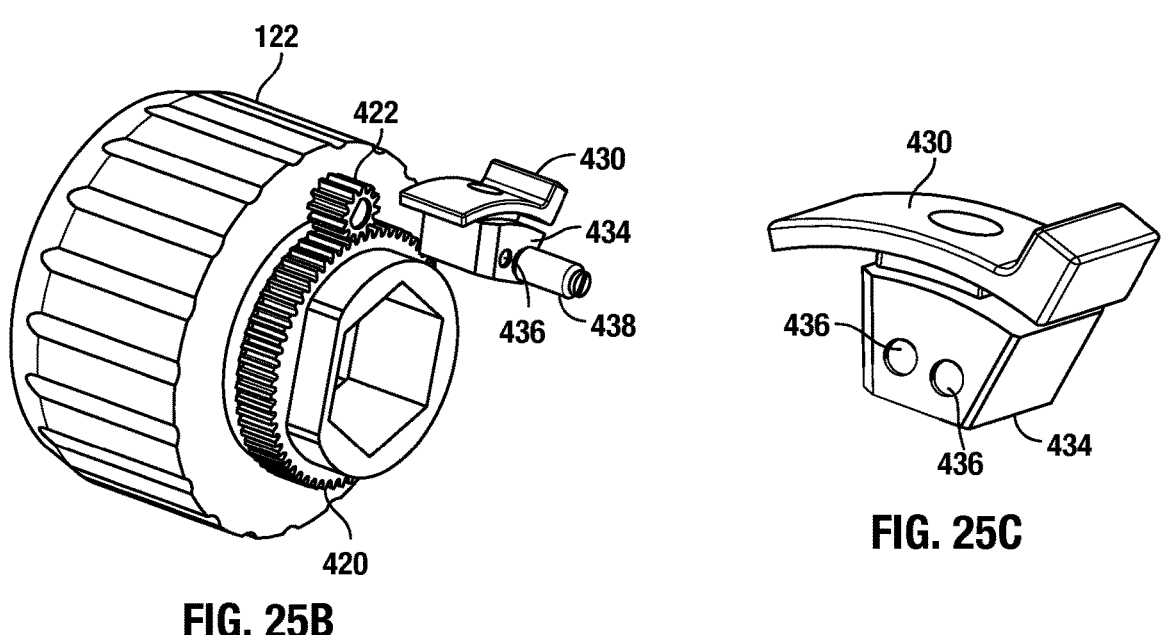
FIG. 25B
FIG. 25C

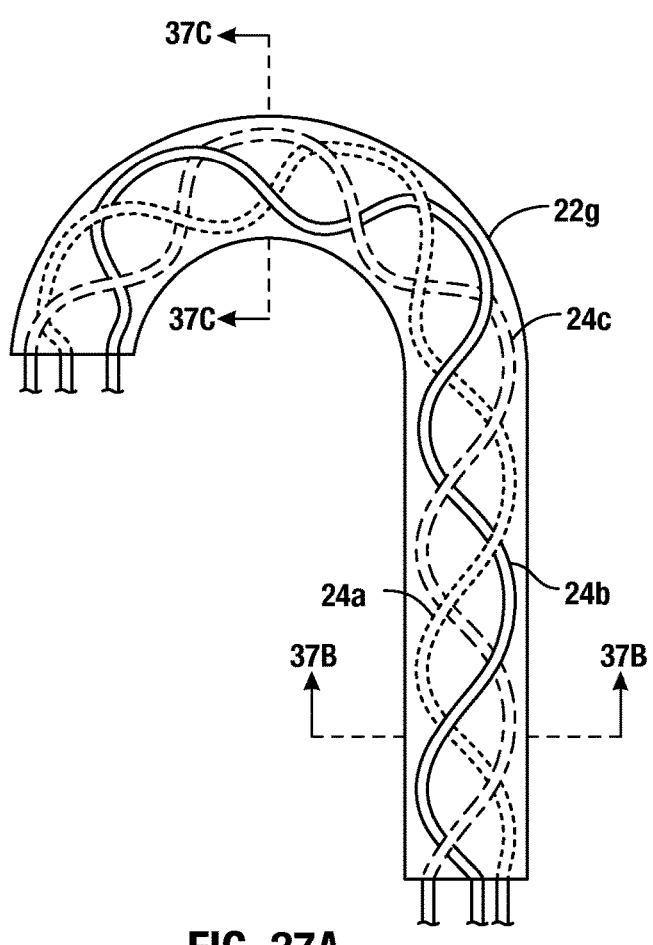
FIG. 37A
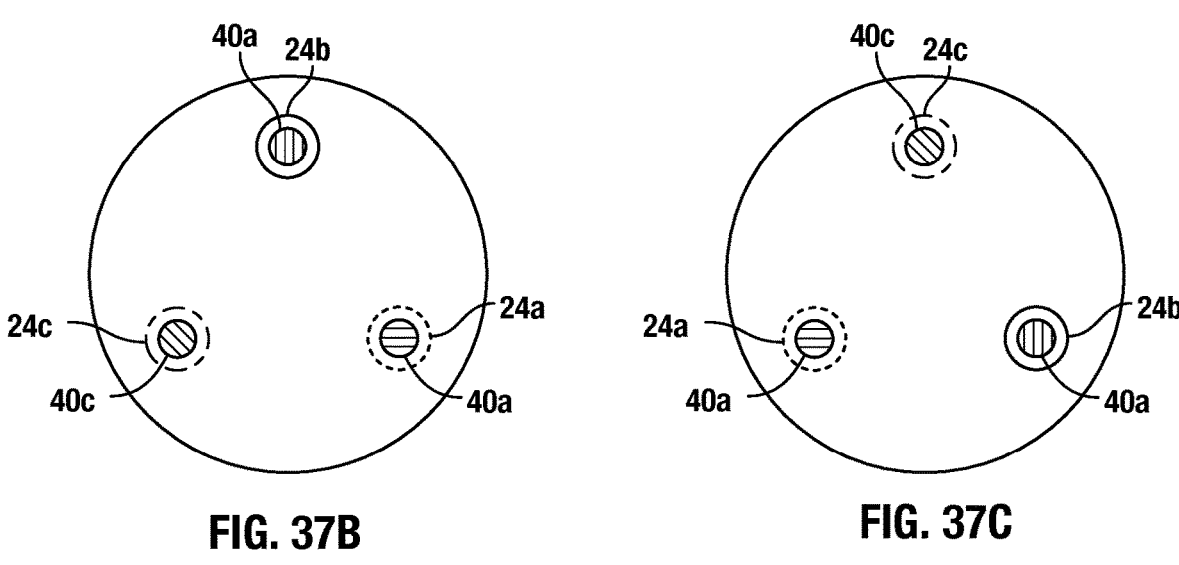
FIG. 37B                                        FIG. 37C

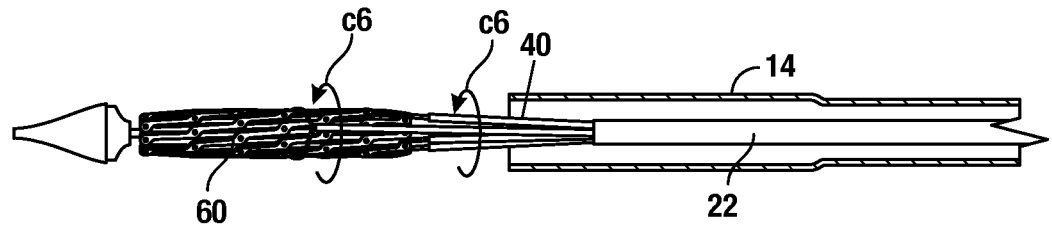
FIG. 38C
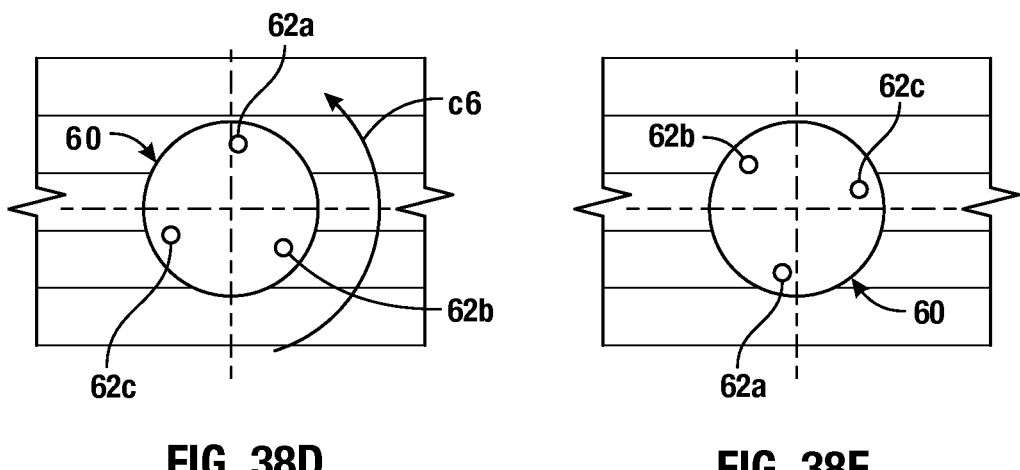
FIG. 38D
FIG. 38E
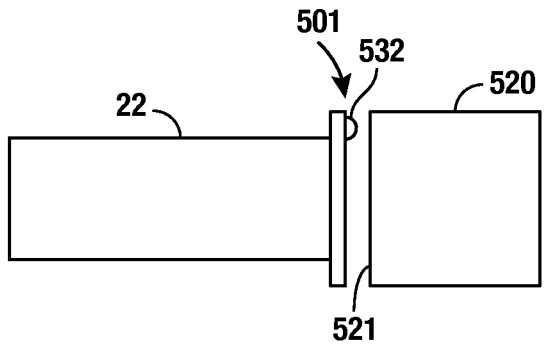
FIG. 38F
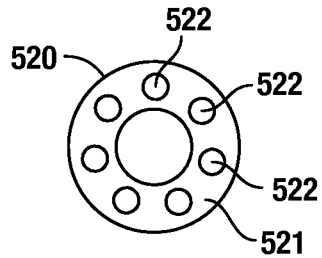
FIG. 38G

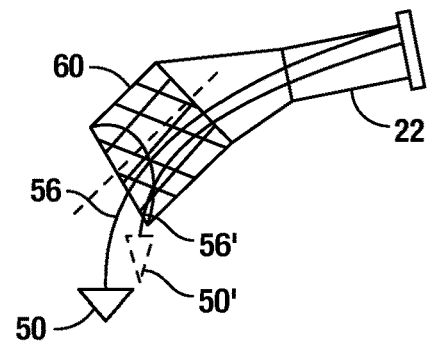
FIG. 45A
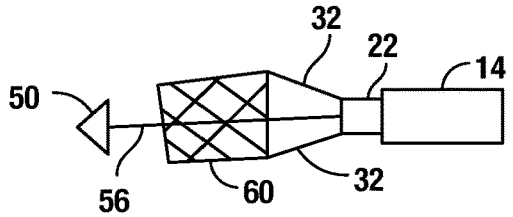
FIG. 45B
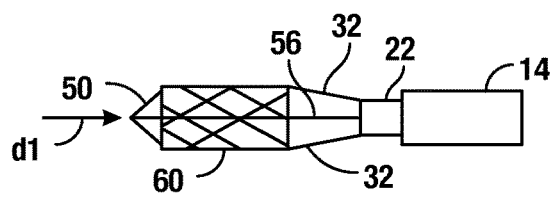
FIG. 45C
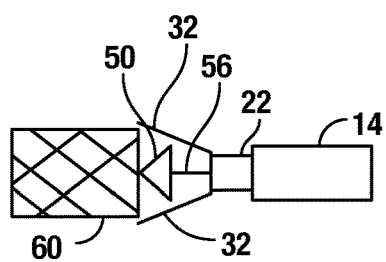
FIG. 46A
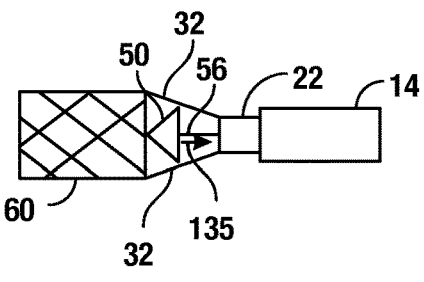
FIG. 46B
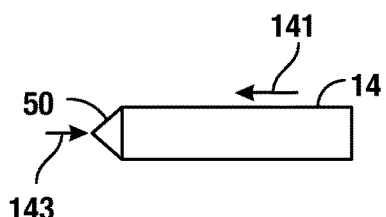
FIG. 46C
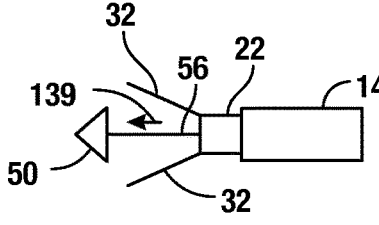
FIG. 46D
FIG. 46E

DELIVERY APPARATUS AND METHODS FOR IMPLANTING PROSTHETIC HEART VALVES

CROSS-REFERENCE TO RELATED APPLICATION

This application is a continuation of PCT Application No. PCT/US2021/022467, entitled "DELIVERY APPARATUS AND METHODS FOR IMPLANTING PROSTHETIC HEART VALVES," filed Mar. 16, 2021, which claims priority to U.S. Provisional Application No. 62/990,299, entitled "DELIVERY APPARATUS AND METHODS FOR IMPLANTING PROSTHETIC HEART VALVES," filed Mar. 16, 2020, wherein each of above-referenced applications is incorporated by reference herein in its entirety.

FIELD

The present disclosure relates to implantable prosthetic devices, such as prosthetic heart valves, and to delivery apparatus and methods for implanting prosthetic heart valves.

BACKGROUND

The human heart can suffer from various valvular diseases. These valvular diseases can result in significant malfunctioning of the heart and ultimately require repair of the native valve or replacement of the native valve with an artificial valve. There are several known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable.

In one specific example, a prosthetic heart valve can be mounted in a crimped state on the distal end of a delivery apparatus and advanced through the patient's vasculature (e.g., through a femoral artery and the aorta) until the prosthetic heart valve reaches the implantation site in the heart. The prosthetic heart valve is then expanded to its functional size, for example, by inflating a balloon on which the prosthetic heart valve is mounted, actuating a mechanical actuator that applies an expansion force to the prosthetic heart valve, or by deploying the prosthetic heart valve from a sheath of the delivery apparatus so that the prosthetic heart valve can self-expand to its functional size.

Prosthetic heart valves that rely on a mechanical actuator for expansion can be referred to as "mechanically-expandable" prosthetic heart valves. Mechanically-expandable prosthetic heart valves can provide one or more advantages over self-expandable and balloon-expandable prosthetic heart valves. For example, mechanically-expandable prosthetic heart valves can be expanded to various diameters. Mechanically-expandable prosthetic heart valves can also be compressed after an initial expansion (e.g., for repositioning and/or retrieval).

Despite these advantages, mechanically-expandable prosthetic heart valves can present several challenges. For example, it can be difficult to control the forces applied to the prosthetic heart valve and/or the delivery apparatus during the implantation procedure. These difficulties can be compounded when the delivery apparatus is disposed in a tortuous pathway, such as a patient's vasculature. It can also be difficult to release a mechanically-expandable prosthetic heart valve from the delivery apparatus. Additionally, given the number of moving components to control, typical delivery apparatus can be difficult and/or time-consuming for a user to operate. Accordingly, there is a need for improved delivery apparatus and methods for implanting mechanically-expandable prosthetic heart valves.

SUMMARY

Described herein are prosthetic heart valves, delivery apparatus, and methods for implanting prosthetic heart valves. The disclosed delivery apparatus and methods can, for example, reduce the difficulty and/or the time needed to implant a prosthetic heart valve. The disclosed delivery apparatus are relatively simple and easy to use and include various safeguards, which can help to ensure a prosthetic heart valve is safely and securely implanted.

In one representative example, a delivery apparatus for implanting a prosthetic heart valve comprises one or more shafts and a handle coupled to the one or more shafts. The handle comprises one or more knobs, one or more adjustment mechanisms, and/or one or more control mechanisms. The one or more adjustment mechanisms are configured for moving the shafts relative to each other and/or relative to the handle. The one or more control mechanisms are configured for limiting the direction of movement and/or force applied to the one or more shafts.

In another representative example, a delivery assembly comprises the preceding delivery apparatus and a prosthetic heart valve, which can be coupled to the delivery apparatus.

In another representative example, a method of implanting a prosthetic heart valve comprises rotating a first knob of a handle of a delivery apparatus to retract a first shaft of the delivery apparatus relative to a prosthetic heart valve, rotating a second knob of the handle to adjust the radial expansion of the prosthetic heart valve, and rotating a third knob of the handle to release the prosthetic heart valve from the delivery apparatus.

In another representative example, an assembly for implanting a prosthetic heart valve comprises a prosthetic heart valve configured to be moved between a compressed state and an expanded state and a delivery apparatus comprising one or more shafts and a handle. The prosthetic heart valve is releasably coupled to at least one of the shafts of the delivery apparatus. The handle is configured for positioning the prosthetic heart valve and for adjusting the prosthetic heart valve between the compressed state and the expanded state.

In another representative example, a delivery apparatus for implanting a prosthetic heart valve comprises a first shaft, a second shaft extending through the first shaft, a third shaft extending through the second shaft, and a handle. The first shaft comprises a distal end portion and a proximal end portion. The distal end portion of the first shaft comprises a capsule configured to receive the prosthetic heart valve in a radially compressed state. The second shaft comprises a distal end portion and a proximal end portion. The distal end portion of the second shaft is configured for contacting the prosthetic heart valve. The third shaft comprises a distal end portion and a proximal end portion. The distal end portion of the third shaft is configured to be releasably coupled to the prosthetic heart valve. The handle comprises a main portion and a first knob rotatably coupled to the main portion. The proximal end portions of the first shaft, the second shaft, and the third shaft are coupled to the main portion of the handle. The handle is configured such that rotating the first knob in a first direction from a first rotational position to a second rotational position relative to the main portion results in axial movement of the first shaft relative to the second shaft and the third shaft. The handle is further configured such that rotating the first knob in the first direction from the second rotational position to a third rotational position relative to the main portion results in axial movement of the first shaft and the second shaft relative to the third shaft.

In another representative example, a delivery apparatus for implanting a prosthetic heart valve comprises a first shaft having a first end portion and a second end portion, a second shaft extending through the first shaft and having a first end portion and a second end portion, a nosecone coupled to the first end portion of the second shaft, and a handle comprising a main portion and an adjustment mechanism. The second end portion of the first shaft is coupled to the main portion of the handle. The second end portion of the second shaft is coupled to the adjustment mechanism. The adjustment mechanism is configured such that moving the adjustment mechanism axially relative to the main portion results in the second shaft moving axially relative to the first shaft.

In another representative example, a delivery apparatus for implanting a prosthetic heart valve comprises a first shaft and a handle. The first shaft has a first end portion and a second end portion. The first end portion of the first shaft is configured to be releasably coupled to a prosthetic heart valve. The handle comprises a main portion, a rotatable knob, and a locking mechanism. The rotatable knob is rotatably coupled to the main portion and to the second end portion of the first shaft. The locking mechanism is configured to restrict relative rotational movement of the rotatable knob and the main portion.

In another representative example, a delivery apparatus for a prosthetic heart valve comprises a handle having a cavity, a plurality of actuation assemblies comprising a plurality of movable portions, a plate member disposed within the cavity, and a drive assembly operatively coupled to the plate member. Each of the movable portions has a proximal end portion disposed within the cavity and a distal end portion disposed outside of the cavity. The plate member is axially movable relative to the handle. The plate member has a first state in which the plate member moves freely relative to the movable portions and a second state in which the plate member engages the movable portions such that further axial movement of the plate member results in axial displacement of the movable portions. The drive assembly is operable to move the plate member axially relative to the handle.

In another representative example, a delivery assembly comprises the preceding delivery apparatus and a mechanically-expandable prosthetic heart valve comprising a plurality of actuators. The movable portions of the actuation assemblies are releasably coupled to the plurality of actuators.

In another representative example, a method comprises inserting a distal end of the preceding delivery assembly into a vasculature of a patient; advancing the distal end of the delivery assembly through the vasculature of the patient to position the prosthetic heart valve at a select implantation location; disengaging the movable portions of the actuation assemblies from the actuators of the prosthetic heart valve; axially moving the plate member relative to the handle to engage the movable portions of the actuation assemblies; and pulling the plate member and the movable portions of the actuation assemblies to retract the movable portions of the actuation assemblies from the prosthetic heart valve.

In another representative example, a delivery apparatus for a prosthetic heart valve comprises a handle, an actuation assembly, a drive assembly, a first sensor member, and a second sensor member. The handle has a proximal end, a distal end, and a cavity extending from the proximal end to the distal end. The actuation assembly comprises an actuation member and a sleeve member. The actuation member has a proximal end portion disposed within the cavity and a distal end portion disposed outside of the cavity. The sleeve member is disposed around the distal end portion of the actuation member. The first sensor member is coupled to the actuation member and rotatable with the actuation member. The second sensor member is positioned to detect changes in a rotational position of the first sensor member.

In another representative example, a delivery apparatus for a prosthetic heart valve comprises a handle, an actuation assembly, a drive assembly, an electrical circuit, and a current sensor. The handle has a proximal end, a distal end, and a cavity extending from the proximal end to the distal end. The actuation assembly comprises an electrically conductive actuation member and a sleeve member. The electrically conductive actuation member has a proximal end portion disposed within the cavity and a distal end portion disposed outside of the cavity. The sleeve member is disposed around the distal end portion of the electrically conductive actuation member. The drive assembly is coupled to the actuation members and the handle and operable to rotate the actuation members from within the cavity. The electrical circuit has an electrical path comprising the handle and the electrically conductive actuation member, wherein the electrical circuit has an open state corresponding to the electrically conductive actuation member being engaged with the prosthetic heart valve and a closed state corresponding to the electrically conductive actuation member being disengaged from the prosthetic heart valve. The current sensor is coupled to the electrical circuit to detect an electrical state of the electrical circuit.

In another representative example, a delivery apparatus for a prosthetic heart valve comprises a handle, a first shaft, a second shaft, and a knob. The handle comprises a proximal portion, a distal portion, and a longitudinal axis. The proximal portion and the distal portion are telescopically movable relative to each other along the longitudinal axis. The first shaft is coupled to the distal portion and has a first lumen. The second shaft extends through the first lumen and is coupled to the distal portion such that relative movement between the proximal portion and the distal portion results in axial movement of both the first shaft and the second shaft. The knob is coupled to the first shaft, and rotation of the knob moves the first shaft axially relative to the handle and independently of the second shaft.

In another representative example, a delivery apparatus for a prosthetic heart valve comprises a handle, a first movable component, a second movable component, a first shaft, a second shaft, and a knob. The handle comprises an inner track. The first movable component is positioned along the inner track and axially movable along the inner track. The first shaft has a proximal end and a distal end. The second movable component is positioned along the inner track and axially movable along the inner track. The second shaft has a proximal end and a distal end. The proximal end of the first shaft is coupled to the first movable component, and the proximal end of the second shaft is coupled to the second movable component. The knob is coupled to the first movable component and rotatable to move the first movable component along the inner track. The first movable component is axially movable along the inner track between a first position in which the first movable component is axially separated from the second movable component and movement of the first movable component along the inner track results only in movement of the first shaft and a second position in which the first component engages the second movable component and movement of the first movable component results in movement of both the first shaft and the second shaft.

In another representative example, a delivery apparatus for a prosthetic heart valve comprises a handle, a first shaft, a second shaft, a third shaft, and a sliding mechanism. The first shaft has first end portion, a second end portion, and a first lumen extending from the first end portion to the second end portion. The first end portion of the first shaft is coupled to the handle. The second shaft has a first end portion, a second end portion, and one or more second lumens. The second shaft extends through the first shaft. The third shaft extends through one of the one or more second lumens. The slider mechanism is coupled to the handle and the third shaft and operable to displace the third shaft axially relative to the handle.

In another representative example, a delivery apparatus for a prosthetic heart valve comprises a handle having a first portion and a second portion that is rotatable relative to the first portion. A receptacle is formed within the second portion and rotatable with the second portion of the handle. The delivery apparatus further includes a shaft having a first end portion, a second end portion, and one or more lumens. A plurality of actuation members extend through the one or more lumens of the shaft. The actuation members are rotatable by rotation of the receptacle.

In another representative example, a delivery apparatus for a prosthetic heart valve comprises a handle, a slidable knob, a multi-lumen shaft, and a first shaft. The handle has a proximal portion, a distal portion, and a cavity extending from the proximal portion to the distal portion. The proximal portion includes a slot. The slidable knob is slidably engaged with the slot. The multi-lumen shaft has a proximal end portion, a distal end portion, and a plurality of first lumens. The proximal end portion of the multi-lumen shaft is disposed within the cavity. The first shaft extends through one of the first lumens. The first shaft has a proximal end portion and a distal end portion. The proximal end portion of the first shaft is coupled to the slidable knob. Movement of the slidable knob along the slot results in axial displacement of the first shaft relative to the handle.

In another representative example, a delivery apparatus for a prosthetic heart valve comprises a handle, a multi-lumen shaft, a plurality of actuation members, a recompression member, and a pull force mechanism. The handle has a proximal portion, a distal portion, and a cavity extending from the proximal portion to the distal portion. The multi-lumen shaft has a proximal end portion, a distal end portion, and a plurality of first lumens. The proximal end portion of the multi-lumen shaft is disposed within the cavity. The plurality of actuation members extend through one or more of the first lumens. Each of the actuation members has a distal threaded head, a proximal actuation flexible portion, and an actuation torque-transferring portion extending between the distal threaded head and the proximal actuation flexible portion. The recompression member extends through one of the first lumens. The pull force mechanism is disposed at least partially within the cavity. The pull force mechanism is coupled to the proximal actuation flexible portions and the recompression member. The pull force mechanism is operable to apply a pull force to the proximal actuation flexible portions in a first mode and apply the pull force to the recompression member in a second mode.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosure will become more apparent from the following detailed description, claims, and accompanying figures.

BRIEF DESCRIPTION OF THE DRAWINGS

FIG. 5C is a side view of an example implementation of an actuation assembly of the delivery apparatus.

FIG. 5D is a cross-sectional view of a distal portion of the delivery apparatus shown in FIG. 5A and illustrates a nosecone attached to a nosecone shaft.

FIGS. 6A and 6B illustrate engagement and release, respectively, of an actuation assembly of the delivery apparatus from a locker/actuator of the prosthetic heart valve.

FIGS. 23A-24C illustrate another example implementation of a force limiting mechanism for the handle.

FIG. 25A is a detail of a handle illustrating an example implementation of a valve expansion limiting mechanism.

FIG. 25B is a perspective view of a knob coupled to the valve expansion limiting mechanism of FIG. 25A.

FIG. 25C is a perspective view of a component of a clicking sound mechanism coupled to the knob of FIG. 25B.

FIG. 37A is a side view of a twisted multi-lumen shaft.

FIG. 37B is a cross-sectional view of the twisted multi-lumen shaft, taken along line 37B-37B as shown in FIG. 37A.

FIG. 37C is a cross-sectional view of the twisted multi-lumen shaft, taken along line 37C-37C as shown in FIG. 37A.

FIG. 38C is a side view of a distal end portion of a delivery apparatus illustrating rotation of a valve by the valve rotation mechanism of FIG. 38B.

FIGS. 38D and 38E illustrate rotational positions of lockers/actuators of the valve of FIG. 38C before and after rotation.

FIGS. 38F and 38G illustrate a clicking sound mechanism.

FIGS. 45A-45C illustrate use of the nosecone shaft displacement to facilitate repositioning of a prosthetic heart valve in an implantation procedure.

FIGS. 46A-46E illustrate use of the nosecone shaft displacement to reduce the risk of valve migration in an implantation procedure.

DETAILED DESCRIPTION

General Considerations

Figure 1:
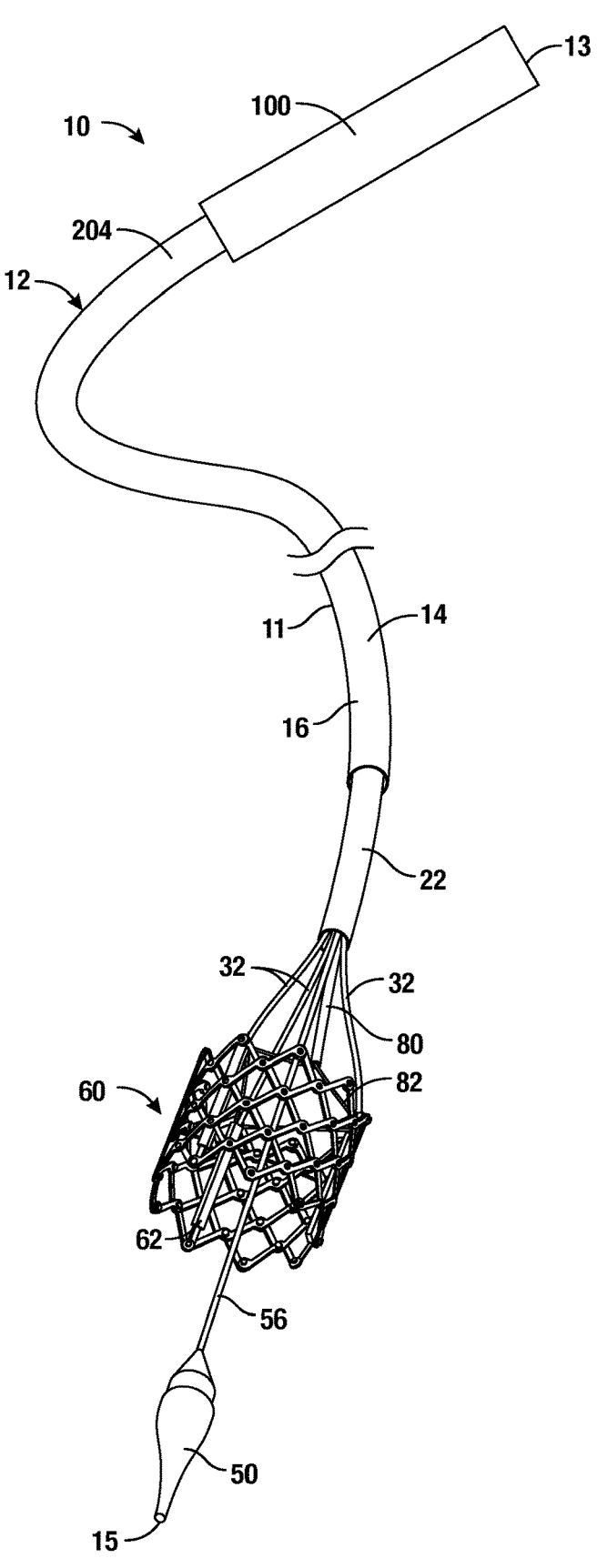
FIG. 1 is a perspective view of an exemplary delivery assembly including a delivery apparatus coupled to a prosthetic heart valve.

For purposes of this description, certain aspects, advantages, and novel features of the examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved.

Although the operations of some of the disclosed examples are described in a particular, sequential order for convenient presentation, this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

In the interest of conciseness, and for the sake of continuity in the description, same or similar reference characters may be used for same or similar elements in different figures, and description of an element in one figure will be deemed to carry over when the element appears in other figures with the same or similar reference character. In some cases, the term "corresponding to" may be used to describe correspondence between elements of different figures. In an example usage, when an element in a first figure is described as corresponding to another element in a second figure, the element in the first figure is deemed to have the characteristics of the other element in the second figure, and vice versa, unless stated otherwise.

The word "comprise" and derivatives thereof, such as "comprises" and "comprising", are to be construed in an open, inclusive sense, that is, as "including, but not limited to". The singular forms "a", "an", "at least one", and "the" include plural referents, unless the context dictates otherwise. The term "and/or", when used between the last two elements of a list of elements, means any one or more of the listed elements. The term "or" is generally employed in its broadest sense, that is, as meaning "and/or", unless the context clearly dictates otherwise.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Introduction to the Disclosed Technology

Described herein are prosthetic heart valves, delivery apparatus, and methods for implanting prosthetic heart valves. The disclosed delivery apparatus and methods can, for example, be used to implant a mechanically-expandable prosthetic heart valve.

In some examples, a delivery apparatus can include a handle. The handle can be configured for manipulating the delivery apparatus and/or a prosthetic heart valve that is releasably coupled to the delivery apparatus. In certain examples, the handle can include one or more knobs and/or actuators. For example, in particular examples, the handle can comprise three rotatable knobs. A first (e.g., a distal) knob can be configured for bi-directional axial translation of an outer shaft with a distal capsule. A second (e.g., a proximal) knob can be configured for both expansion and contraction of the valve. In some instances, the second knob can simultaneously operate two rails around which an actuation member and a recompression member may be simultaneously wrapped in opposite directions. A third (e.g., an intermediate) knob can be coupled to a gear rain that enables actuation members to be simultaneously rotated around their central axes. In some examples, a slidable knob can also be provided that enables bi-directional axial translation of a nosecone at a distal end of the delivery apparatus.

The handle may further include one or more additional components. For example, the handle can include tensioning assemblies configured to apply a minimal tension on an actuation member and a recompression member. This can prevent or reduce slack formation within the handle. As another example, the handle can include an equal force distribution mechanism configured to apply an equal pull force to each of the plurality of the actuation members. As another example, the handle can include a force limiting mechanism configured to limit the amount of force that can be applied to expand or compress the prosthetic heart valve.

As another example, the handle can include a ratcheting mechanism configured to reduce the likelihood of unintentional over-tightening the threaded heads of the actuation members within the respective rack members of a prosthetic heart valve.

In some instances, one or more of the knobs of the handle can be rotated manually. Additionally or alternatively, one or more actuators (e.g., buttons, switches, circuitry, and/or software) can be used to actuate one or more automated mechanisms (e.g., an electric motor) to move and/or assist in moving the components of the handle, the delivery apparatus, and/or a prosthetic heart valve coupled to the delivery apparatus.

FIG. 1 illustrates an exemplary delivery assembly 10 including a delivery apparatus 12 and a prosthetic valve 60. For clarity of illustration, FIG. 1 does not show all the details of the prosthetic valve 60, but the details of an exemplary prosthetic valve 60 can be found in FIG. 2. The delivery apparatus 12 includes a handle 100 and a shaft assembly 11 coupled to the handle 100. The prosthetic valve 60 can be coupled to one of the shafts of the shaft assembly 11 and carried to an implantation location within the patient's body by advancing the shaft assembly 11 through the patient's vasculature. The handle 100 include controls and mechanisms to deploy the prosthetic valve 60 at the implantation location.

The prosthetic valve 60 can be configured to replace a native heart valve (e.g., aortic, mitral, pulmonary, and/or tricuspid valves). The prosthetic valve 60 can be a mechanically-expandable prosthetic heart valve, which can allow the prosthetic heart valve to be compressed for delivery through the patient's vasculature and then expanded at the implantation location. Examples of mechanically-expandable prosthetic heart valves are disclosed in U.S. Publication Nos. 2018/0153689, 2018/0344456, and 2019/0060057, U.S. Provisional Application No. 62/869,948, U.S. Publication Nos. 2015/0135506 and 2014/0296962, and U.S. Provisional Application No. 62/945,039, the disclosures of which are incorporated herein by reference.

Figure 2:
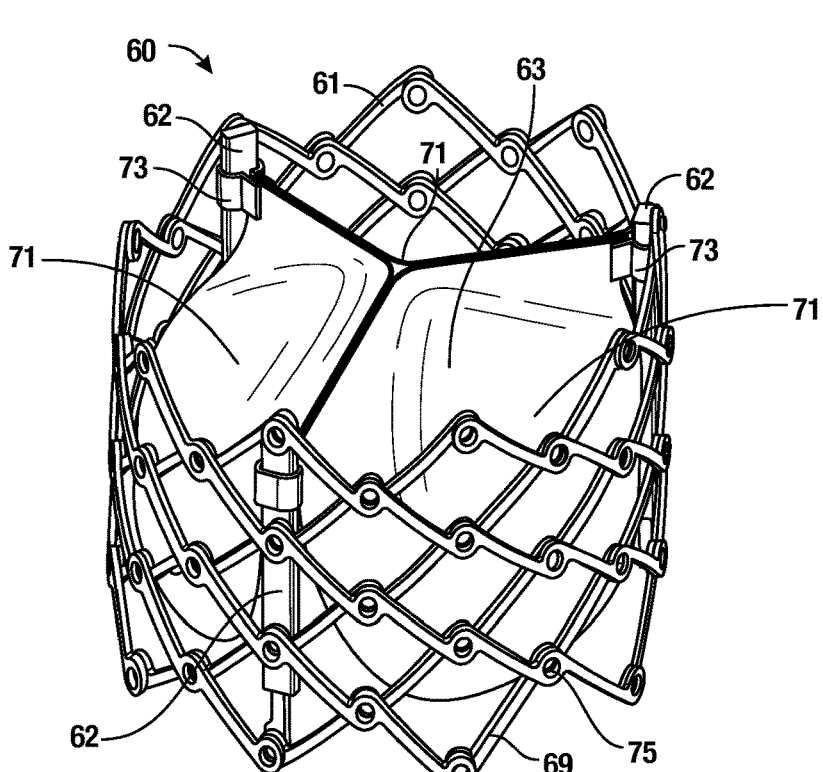
FIG. 2 is a perspective view of an exemplary prosthetic heart valve.

FIG. 2 illustrates an exemplary prosthetic valve 60 that is mechanically expandable and that can serve as a basis for describing operations of the delivery apparatus 12. However, the delivery apparatus 12 is not limited to the example of the prosthetic valve 60 shown in FIG. 2. As illustrated by FIG. 2, the prosthetic valve 60 includes a frame 61 (or stent), one or more lockers/actuators 62 coupled to the frame 61, and a valvular structure 63. The lockers/actuators 62 are configured to move the frame 61 between a radially expanded configuration and a radially compressed configuration (or crimped state). In addition, the lockers/actuators 62 can lock the frame 61 in a desired radially expanded configuration. Three lockers/actuators 62 are shown in FIG.

2 for illustrative purposes. However, the prosthetic valve 60 can have fewer or greater than three lockers/actuators 62 in other examples.

The valvular structure 63 is mounted within and coupled to the frame 61 and controls flow of blood through the frame 61 when the prosthetic valve 60 is implanted within the patient's anatomy. The valvular structure 63 includes leaflets 71 that cycle between closed and open states during use of the valve. The leaflets 71 can be made of a flexible material. For example, the leaflets 71 can be made in whole or in part from biological material, bio-compatible synthetic materials, or other such materials. Suitable biological material can include, for example, bovine pericardium (or pericardium from other sources). The leaflets 71 can be arranged to form commissures 73, which can, for example, be mounted to the lockers/actuators 62 or to the frame 61.

Figure 3A:
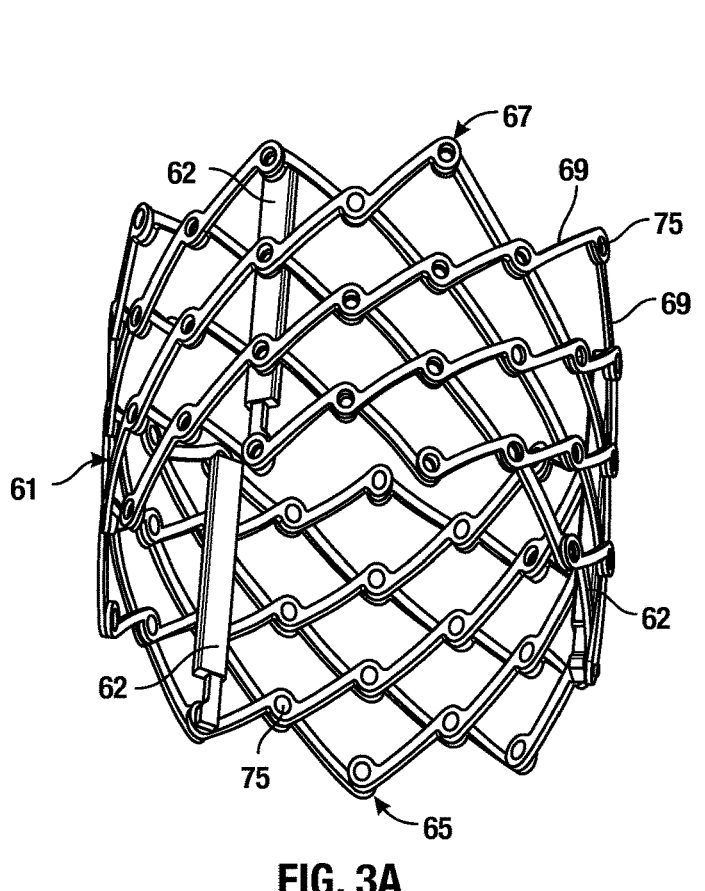
FIG. 3A is a perspective view of a frame of the prosthetic heart valve with the frame shown in a radially expanded configuration.
Figure 3B:
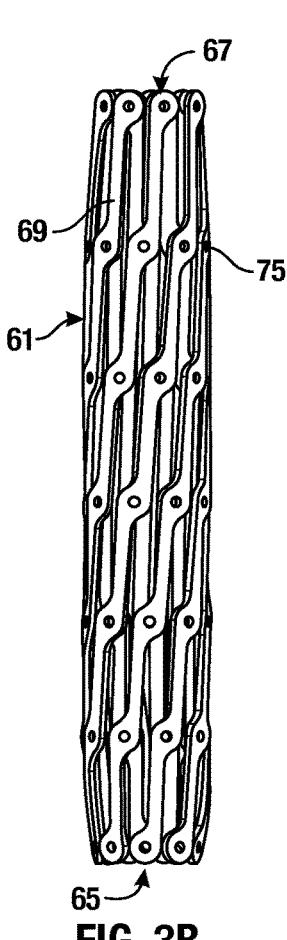
FIG. 3B is a perspective view of the frame of the prosthetic heart valve with the frame shown in a radially compressed configuration.

Referring to FIGS. 3A and 3B, the frame 61 includes an inflow end 65, an outflow end 67, and a plurality of interconnected struts 69 arranged to form an annular shape. The terms "inflow" and "outflow" are related to a normal flow direction through the valve. The struts 69 may form a lattice-type pattern as shown or a different pattern in other cases. In one example, the struts 69 are pivotably coupled to one another by hinges 75 (such as rivets and the like). The struts 69 can pivot about the hinges 75 to move the frame 61 between a radially expanded configuration (shown in FIG. 3A) and a radially compressed configuration (shown in FIG. 3B). In alternative implementations, the frame 61 may have struts that are coupled together by compliant joints. An exemplary mechanically-expandable frame with compliant joints is disclosed in U.S. Provisional Application No. 63/138,599, which is incorporated herein by reference.

In one implementation, the lockers/actuators 62 are mounted to and spaced circumferentially around an inner surface of the frame 61. The lockers/actuators 62 and can be operated to pivot the struts 69 about the respective hinges 75 and thereby cause radial expansion or compression of the frame 61. The locking portions of the lockers/actuators 62 can allow the frame 61 to be held in a desired radial expansion configuration. In an alternative example, the lockers/actuators 62 can be integrally formed with the frame 61.

Figure 4A:
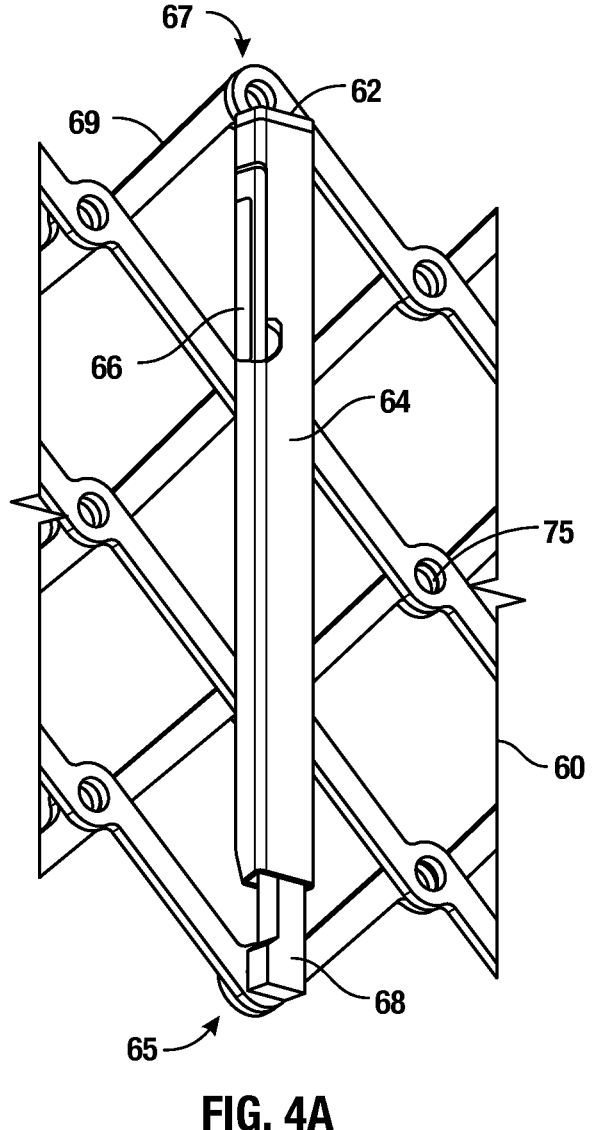
FIG. 4A is a detail of the prosthetic heart valve shown in FIG. 2 and illustrates an example of a locker/actuator of the prosthetic heart valve.
Figure 4B:
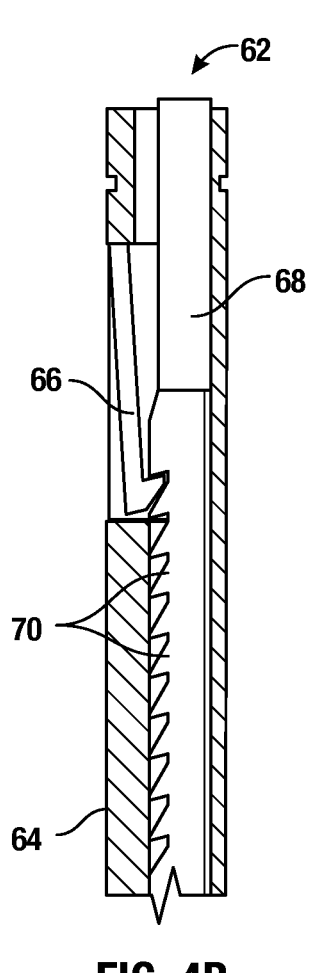
FIG. 4B is a cross-sectional view of the locker/actuator shown in FIG. 4A.

FIGS. 4A and 4B illustrate an exemplary locker/actuator 62. The actuation portion of the locker/actuator 62 includes a rack member 68 and a housing member 64. The rack member 68 extends into the housing member 64 and is axially movable relative to the housing member 64. The rack member 68 is coupled to the frame 61 at a first location, such as at a hinge 75 that is close to the inflow end 65. The housing member 64 is coupled to the frame 61 at a second location, such as at a hinge 75 that is close to the outflow end 67. The first and second locations are such that the rack member 68 and the housing member 64 extend in an axial direction of the frame. Relative movement between the rack member 68 and the housing member 64 in the axial direction causes the struts 69 to pivot about the respective hinges 75, resulting in radial expansion or radial compression of the frame 61. As an example, moving the rack member 68 in a direction towards the outflow end 67 (e.g., in the proximal direction) radially expands the frame 61, and moving the rack member 68 in a direction towards the inflow end 65 (e.g., in the distal direction) radially compresses the frame 61.

The locker portion of the locker/actuator 62 includes ratcheting teeth 70 on the rack member 68 and a spring-biased tooth or pawl 66 on the housing member 64. The pawl 66 engages the ratcheting teeth 70 to form a ratcheting-type mechanism that limits relative movement between the rack member 68 and the housing member 64 to a specific direction. In one example, the ratcheting-type mechanism formed by the pawl 66 and ratcheting teeth 70 may allow the rack member 68 to move relative to the housing member 64 in a direction towards the outflow end 67 while preventing the rack member 68 from moving relative to the housing member 64 in a direction towards the inflow end 65. The ratcheting-type mechanism can be used to lock the frame/ prosthetic heart valve in a desired expanded state.

Further details regarding lockers/actuators for prosthetic heart valves can be found in U.S. Provisional Application No. 62/928,291, which is incorporated by reference herein.

Figure 5A:
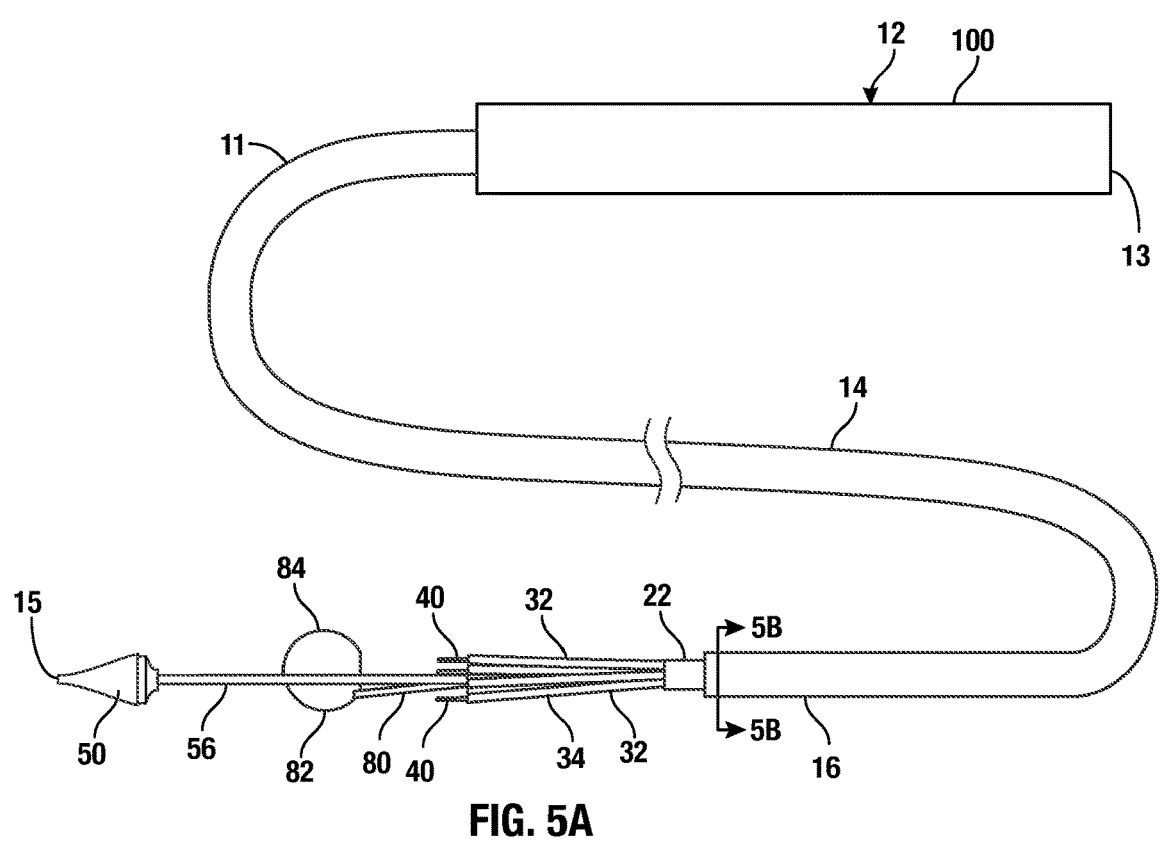
FIG. 5A is a side view of an example implementation of the delivery apparatus.
Figure 5B:
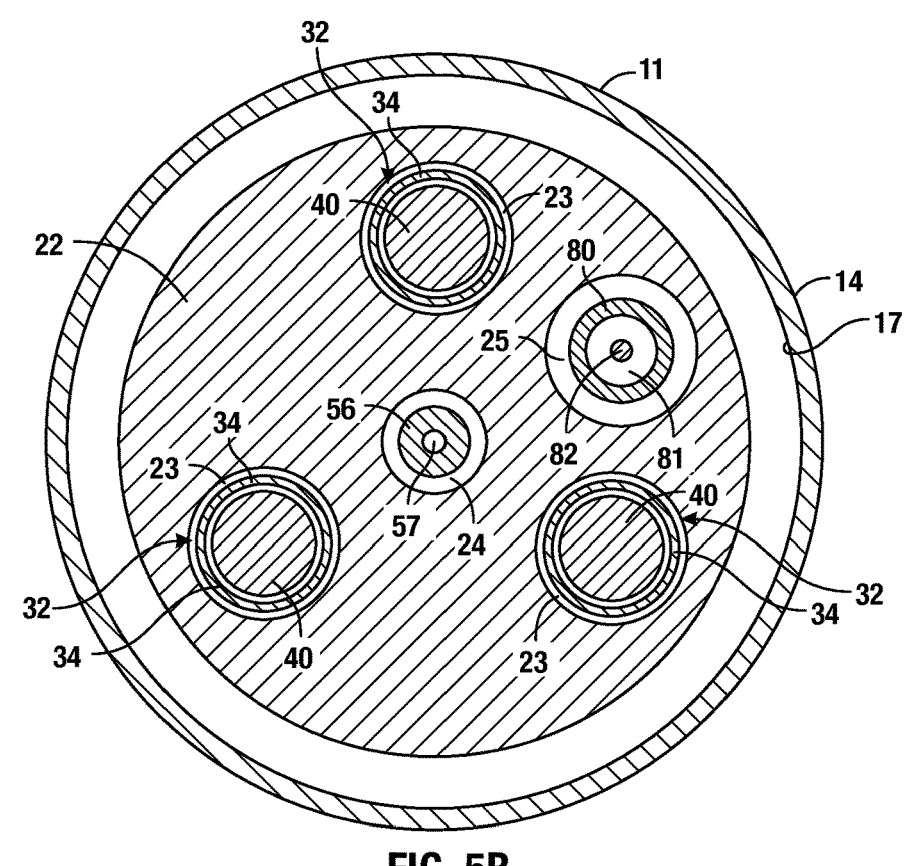
FIG. 5B is a cross-sectional view of the delivery apparatus of FIG. 5A, taken along line 5B-5B as shown in FIG. 5A.

Referring to FIGS. 5A and 5B, the handle 100 and the shaft assembly 11 extend between a proximal end 13 and a distal end 15 of the delivery apparatus 12. The shaft assembly 11 includes an outer shaft 14 having a lumen 17 and a multi-lumen shaft 22 extending through the lumen 17. The delivery apparatus 12 can include one or more actuation assemblies 32 that can engage the lockers/actuators 62 (shown in FIGS. 4A and 4B) of the prosthetic valve 60 (shown in FIG. 2). Three actuation assemblies 32 are shown for illustrative purposes. However, the delivery apparatus 12 can have any number of actuation assemblies 32 (e.g., between 1 and 18). The actuation assemblies 32 can be operated by one or more controls and mechanisms of the handle 100.

The actuation assemblies 32 extend through lumens 23 of the multi-lumen shaft 22 and distally from the multi-lumen shaft 22. The lumens 23 can be angularly spaced apart about a central axis of the multi-lumen shaft 22. Each actuation assembly 32 can include a sleeve member 34 and an actuation member 40 (see FIG. 5C). In some cases, a proximal end 33 of the sleeve member 34 can be coupled to the multi-lumen shaft 22 (e.g., by a sleeve coupler), while the actuation member 40 extends through the respective lumen 23 of the multi-lumen shaft 22 and through the respective sleeve member 34. A distal end portion of the actuation member 40 is formed as a threaded head 44 (see FIG. 5C).

As shown in FIG. 6A, each actuation assembly 32 can be connected to a respective locker/actuator 62 of the prosthetic valve 60 by engaging the distal threaded head 44 of the actuation member 40 with the threaded bore 72 of the rack member 68 of the locker/actuator 62 of the prosthetic valve 60. The distal threaded head 44 can be screwed into the threaded bore 72 such that the distal end 36 of the sleeve member 34 abuts a proximal end 65 of the housing member 64, which would allow distally-directed forces from the handle 100 of the delivery apparatus to be applied to the housing member 64 through the sleeve member 34.

While the actuation member 40 is threadedly engaged with the rack member 68, the handle 100 (shown in FIG. 5A) of the delivery apparatus can be operated to pull the actuation member 40 in a proximally oriented direction d1, causing the rack member 68 to move in the same direction. At the same time, distally-directed forces are applied to the housing member 64 through the sleeve member 34 such that proximal movement of the housing member 64 is prevented or restricted, resulting in relative axial movement between the rack member 68 and the housing member 64. The relative axial movement between the rack member 68 and the housing member 64 can be used to radially expand the prosthetic valve 60. After expanding the prosthetic valve 60, the actuation assembly 32 can be released from the locker/ actuator 62 by rotating the actuation member 40 (e.g., in direction cl as shown in FIG. 6B) to disengage the distal threaded head 44 of the actuation member 40 from the threaded bore 72 of the rack member 68.

Returning to FIGS. 5A and 5B, the shaft assembly 11 includes a nosecone shaft 56 that extends through a lumen 24 of the multi-lumen shaft 22 and distally from the multi-lumen shaft 22. The lumen 24 can be radially centrally disposed within the multi-lumen shaft 22. The nosecone shaft 56 defines a guidewire lumen 57 for receiving a guidewire. In addition, the nosecone shaft 56 defines a loading/unloading area for the prosthetic valve 60 (shown in FIG. 1).

A nosecone 50 is attached to a distal end of the nosecone shaft 56. As shown in FIG. 5D, the nosecone 50 has a central opening 51 for receiving a guidewire. The central opening 51 in the nosecone 50 is aligned with the guidewire lumen 57 in the nosecone shaft 56. During an implantation procedure, a guidewire may be initially inserted in a patient's vasculature. A proximal end of the guidewire can be inserted into the central opening 51 of the nosecone 50 such that the delivery apparatus 12 can be advanced through the patient's vasculature to an implantation location over the guidewire. As the delivery apparatus 12 is advanced through the patient's vasculature, the guidewire passes through the nosecone 50 into the nosecone shaft 56.

Referring to FIGS. 5A and 5B, the shaft assembly 11 can include a recompression shaft 80 that extends through a lumen 25 of the multi-lumen shaft 22 and distally from the multi-lumen shaft 22. In one example, the lumen 25 is disposed radially outward relative to the centrally disposed lumen 24. A recompression member 82 extends through a lumen 81 of the recompression shaft 80, forming a loop 84 extending distally from the recompression shaft 80. The recompression member 82 may be a wire, cable, suture, or other material that can be formed into a loop. The recompression member 82 can be used to recompress the prosthetic heart valve after an initial expansion of the prosthetic heart valve.

Figure 7A:
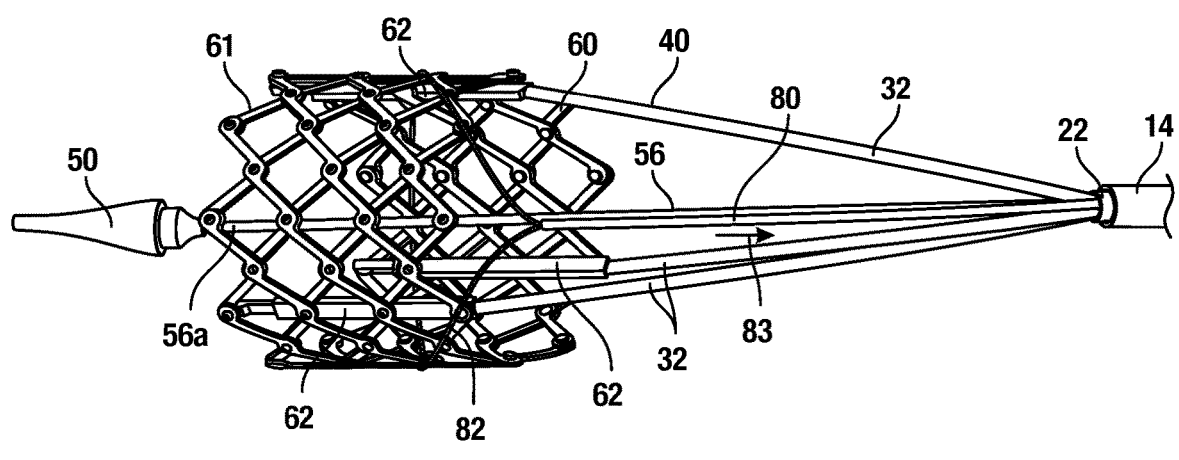
FIG. 7A is a side view of a distal portion of the delivery assembly and illustrates a recompression member looped around the prosthetic heart valve with the prosthetic heart valve in a radially expanded configuration.
Figure 7B:
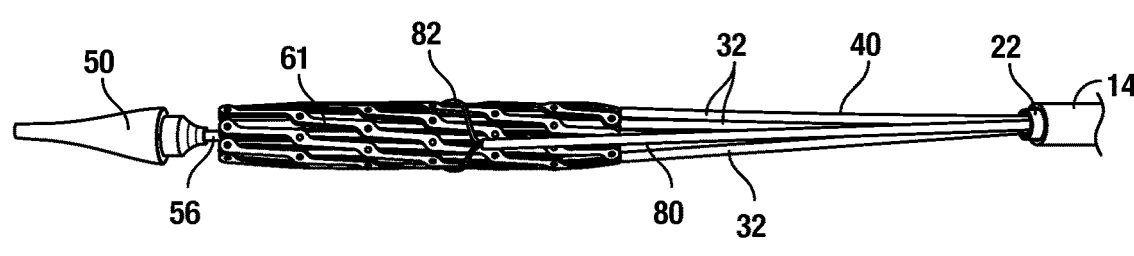
FIG. 7B is a side view of the distal portion of the delivery assembly shown in FIG. 7A after compressing the prosthetic heart valve with the recompression member.

FIG. 7A shows the prosthetic valve 60 disposed around the nosecone shaft 56 and in an expanded state. The loop 84 extends around the prosthetic valve 60 in a lasso-like manner. The prosthetic valve 60 can be recompressed by pulling the recompression member 82 through the lumen of the recompression shaft 80 in a proximal direction, as indicated by arrow 83, to apply tension to the loop 84, which would result in contraction of the prosthetic valve 60, as shown in FIG. 7B. In another example, a loop 84 can extend around or between the sleeves 40 of the actuation assemblies 32 and can be similarly tensioned to contract the prosthetic valve 60, as explained further in U.S. Provisional Application No. 62/928,320, which is incorporated herein by reference.

Returning to FIG. 5A, a distal capsule 16 is attached to the outer shaft 14. The distal capsule 16 can be integrally formed with the outer shaft 14 or can be a separate member that is attached to the outer shaft 14. The distal capsule 16 can be sized to accommodate the prosthetic heart valve when the prosthetic heart valve is in a compressed configuration and disposed around the nosecone shaft 56. The handle 100 can be operated to move the outer shaft 14 between an extended state to position the distal capsule 16 over the prosthetic heart valve and a retracted state to remove the distal capsule 16 from the prosthetic heart valve.

Figure 8A:
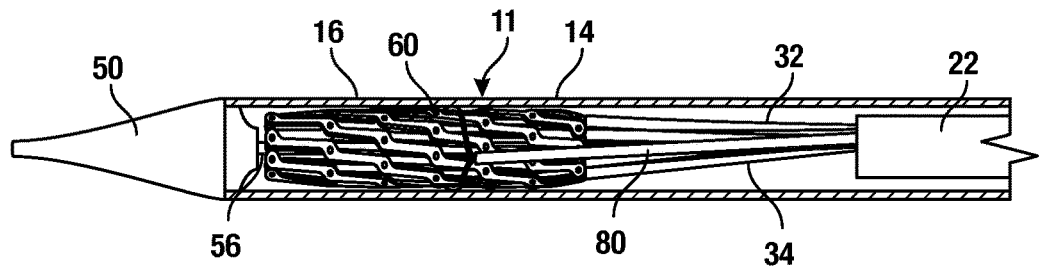
FIG. 8A is a side view of a distal portion of the delivery assembly with the prosthetic heart valve enclosed within an exemplary distal capsule of the delivery apparatus.

FIG. 8A shows the outer shaft 14 extended to position the distal capsule 16 over the prosthetic valve 60. The distal capsule 16 can abut the nosecone 50 as shown such that there are no gaps in the delivery apparatus when the prosthetic heart valve is encapsulated therein. The outer shaft 14 acts as a cover for the structures extending between the proximal end of the prosthetic valve 60 and the distal end of the multi-lumen shaft 22 (e.g., portions of the actuation assemblies 32 and the recompression shaft 80, if present). The sleeve members 34 of the actuation assemblies 32 can press against the prosthetic valve 60 and provide a retaining force to prevent proximal axial displacement of the prosthetic valve 60 when the outer shaft 14 is retracted to remove the distal capsule 16 from the prosthetic valve 60.

Figure 8B:
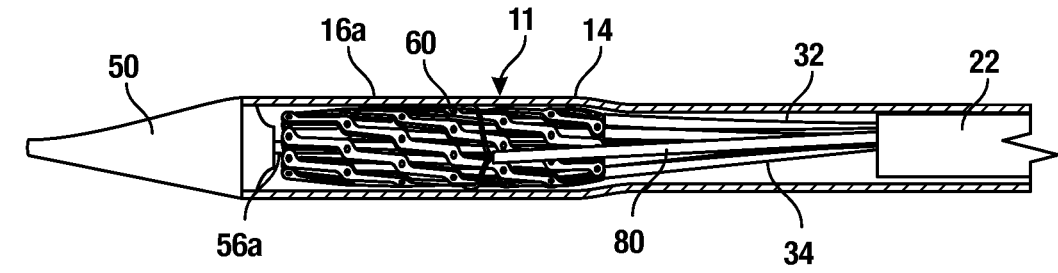
FIG. 8B is a side view of a distal portion of the delivery assembly with the prosthetic heart valve enclosed within another exemplary distal capsule of the delivery apparatus.

In the example illustrated by FIG. 8A, the distal capsule 16 and the outer shaft 14 have the same diameter, which is selected to accommodate the prosthetic valve 60. As a result, the outer shaft 14 can be larger than necessary around the structures extending between the multi-lumen shaft 22 and the prosthetic valve 60. FIG. 8B shows an example where the diameter of the distal capsule 16a is enlarged compared to the diameter of the outer shaft 14. In the example illustrated by FIG. 8B, the outer shaft 14 is sized to closely envelop the structures extending between the proximal end of the prosthetic valve 60 and the distal end of the multi-lumen shaft 22, while the distal capsule 16a is sized to closely envelop the prosthetic valve 60 in the compressed configuration. As in the previous example, the sleeve members 34 of the actuation assemblies 32 can press against the prosthetic valve 60.

Figure 8C:
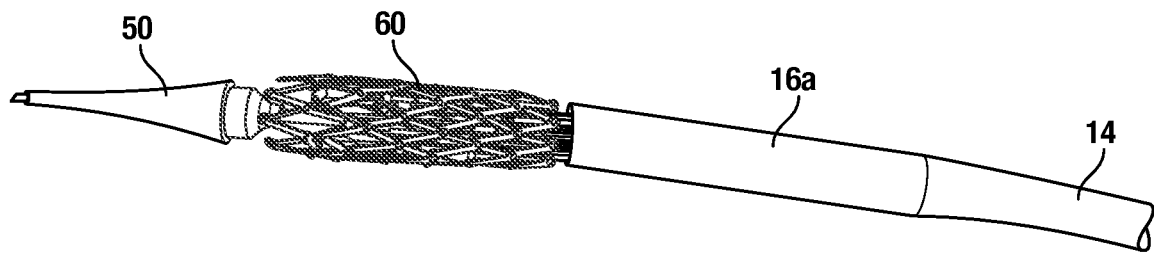
FIG. 8C illustrates an axial position of the prosthetic heart valve relative to a nosecone after retracting an outer shaft of the delivery apparatus to remove the distal capsule shown in FIG. 8B from the prosthetic heart valve.
Figure 8D:
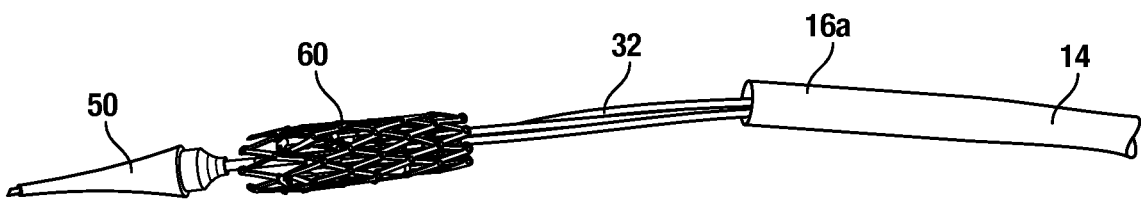
FIG. 8D illustrates the axial position of the prosthetic heart valve relative to the nosecone after further retracting the outer shaft to expose the actuation assemblies of the delivery apparatus.

The combination of the sizing of the outer shaft 14/distal capsule 16a as illustrated by FIG. 8B and the retaining force of the sleeve members 34 can prevent undesirable axial displacement of the prosthetic valve 60 during removal of the distal capsule 16a from the prosthetic valve 60. FIGS. 8C and 8D show a distal portion of a delivery assembly based on the principle illustrated in FIG. 8B. As shown, the prosthetic valve 60 retains its axial position (which can be observed relative to the nosecone 50) after retracting the outer shaft 14 to remove the distal capsule 16a from the prosthetic valve 60.

Figure 9A:
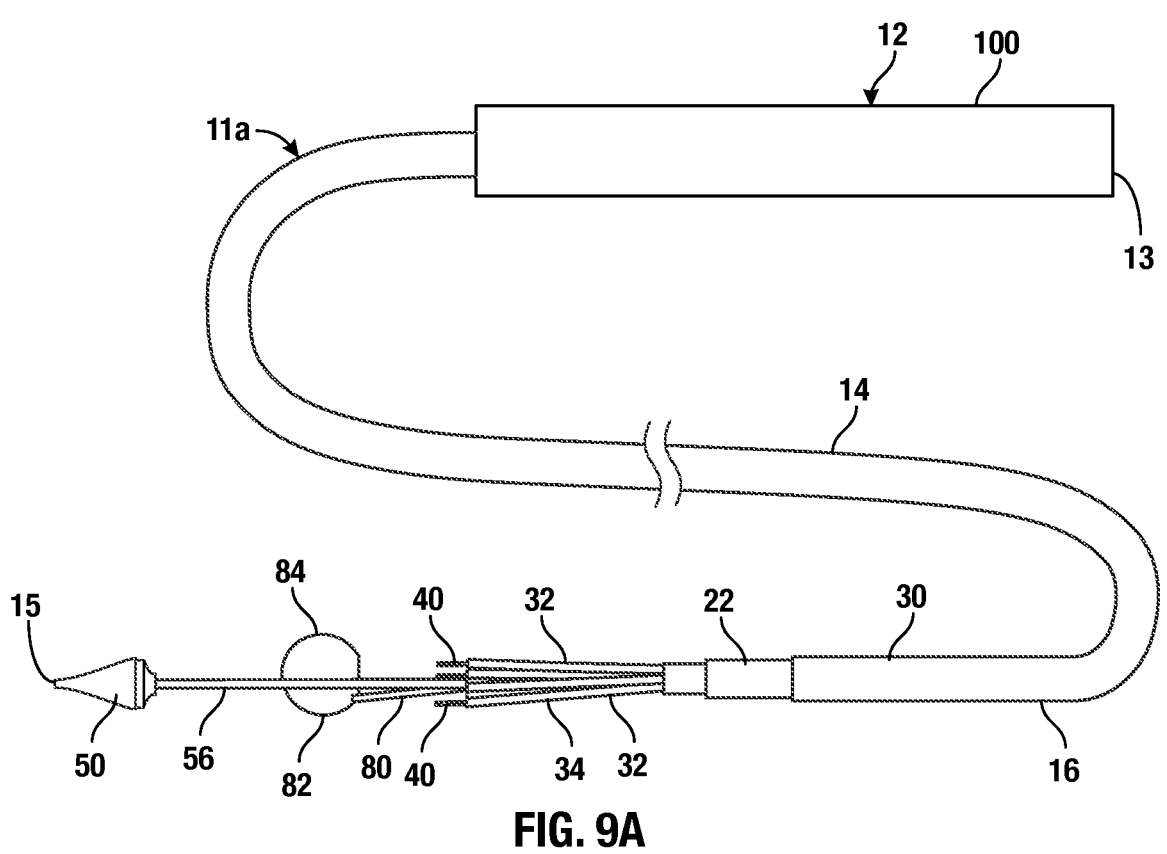
FIG. 9A is a side view of an example implementation of the delivery apparatus with an additional shaft between an outer shaft and a multi-lumen shaft.

FIG. 9A illustrates an alternative shaft assembly 11a. The main difference between the shaft assembly 11a and the shaft assembly 11 illustrated in FIGS. 5A and 5B is that the shaft assembly 11a includes an additional shaft 30 (or "commander shaft") between the outer shaft 14 and the multi-lumen shaft 22. A proximal portion of the commander shaft 30 can be disposed within the handle 100 in the same way that the proximal portions of the outer shaft 14 and multi-lumen shaft 22 are disposed within the handle 100. The commander shaft 30 has an extended state and a retracted state corresponding to the extended and retracted states, respectively, of the outer shaft 14.

Figure 9B:
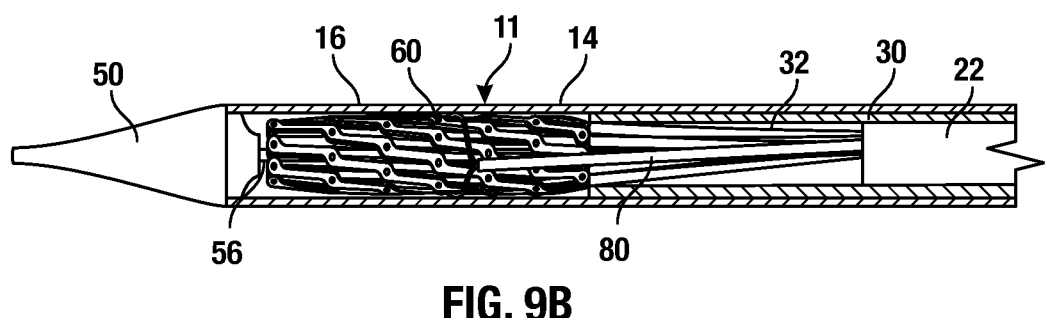
FIG. 9B is a side view of a distal portion of the delivery assembly including the delivery apparatus shown in FIG. 9A with the outer shaft and the additional shaft in their respective extended states.
Figure 9C:
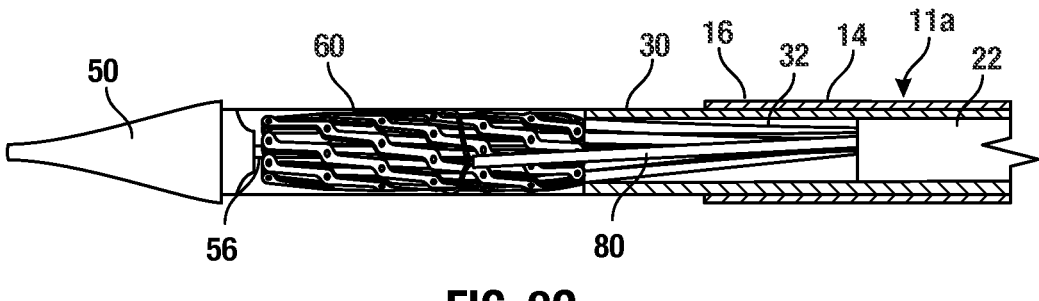
FIG. 9C illustrates the positions of the outer shaft and additional shaft of FIG. 9B after a first stage of shaft retraction.

FIG. 9B shows the commander shaft 30 and the outer shaft 14 in the extended states. In the extended state, the commander shaft 30 extends to the proximal end of the prosthetic valve 60, covering structures extending between the distal end of the multi-lumen shaft 22 and the proximal end of the prosthetic valve 60. The outer shaft 14 extends over the commander shaft 30 to position the distal capsule 16 over the prosthetic valve 60. The commander shaft 30 extending to the proximal end of the prosthetic valve 60 can restrain axial movement of the prosthetic valve 60. When the outer shaft 14 is retracted to remove the distal capsule 16 from the prosthetic valve 60, as shown in FIG. 9C, the commander shaft 30 can remain extended to the proximal end of the prosthetic valve 60 so as to prevent undesirable proximal displacement of the prosthetic valve 60 during removal of the distal capsule 16. Once the distal capsule 16 is removed from the prosthetic valve 60, the outer shaft 14 can be further retracted along with the commander shaft 30 to expose the structures between the distal end of the multi-lumen shaft 22 and the proximal end of the prosthetic valve 60.

Figure 10A:
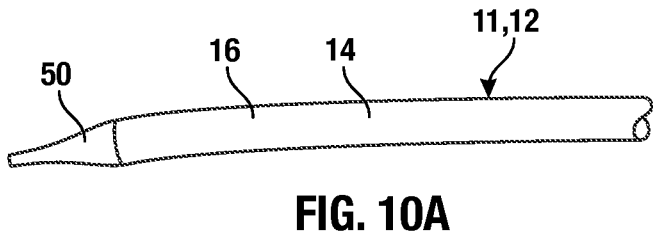
FIGS. 10A-10D illustrate stages in delivery of a prosthetic heart valve to an implantation location.
Figure 10B:
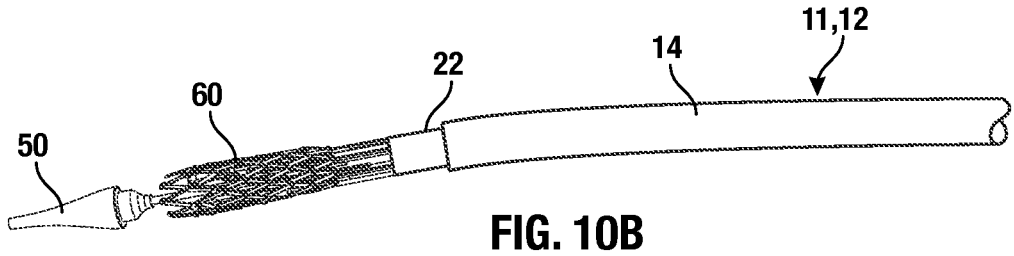
Figure 10C:
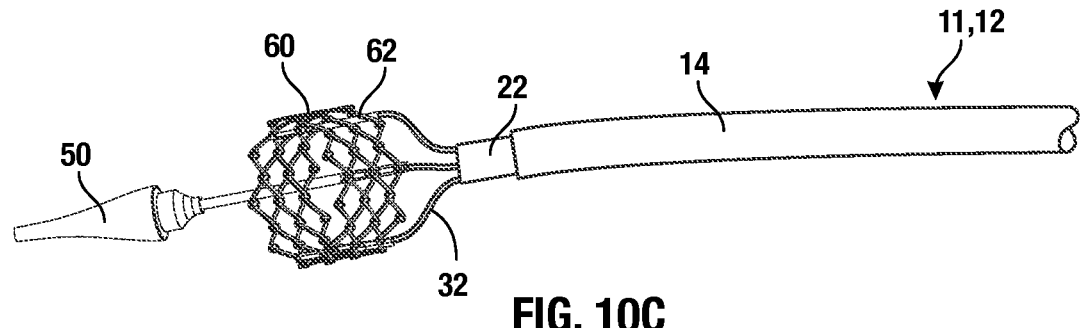

FIGS. 10A-10D illustrate stages of a valve implantation procedure using the delivery apparatus 12. As shown in FIG. 10A, the prosthetic valve 60 is encapsulated within the distal capsule 16 (which can alternatively be the distal capsule 16a shown in FIG. 8B) of the delivery apparatus 12 (see FIGS. 8A, 8B, and 9B). The distal end portion of the delivery apparatus 12 is then inserted into a patient's body and guided to an implantation location. At the implantation location, the outer shaft 14 is retracted to remove the distal capsule 16 from the prosthetic valve 60 and thereby expose the prosthetic valve 60, as shown in FIG. 10B. The prosthetic valve 60 is radially expanded to the desired working diameter, as shown in FIG. 10C.

Figure 10D:
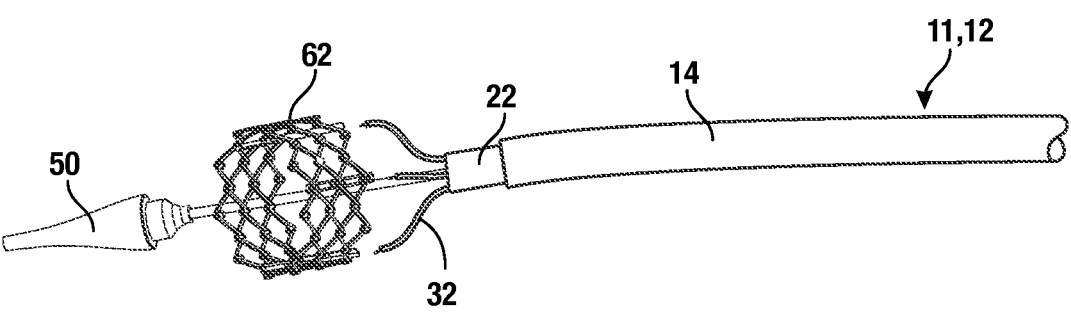

After the prosthetic valve 60 is secured to the native anatomy, the delivery apparatus 12 is released from the prosthetic valve 60 (e.g., by disengaging the actuation assemblies 32 from the lockers/actuators 62 of the prosthetic valve 60), as shown in FIG. 10D. After the delivery apparatus 12 is released from the prosthetic valve 60, the delivery apparatus 12 is prepared for withdrawal from the patient's body (e.g., by extending the outer shaft 14 to cover the actuation assemblies 32). Then, the delivery apparatus 12 is withdrawn from the patient's body.

The various functions of the delivery apparatus 12 are accessible through the handle 100. For example, the handle 100 can include one or more mechanisms for executing one or more of the following functions: retraction of the outer shaft 14 (or any other additional relevant shaft) to expose the prosthetic valve 60; expansion of the prosthetic valve 60 via the actuation assemblies 32 (e.g., by pulling the actuation members 40 while retaining the sleeve members 34 pressed against the valve); recompression of the prosthetic valve 60 via the recompression member 82 (e.g., by pulling the recompression member 82 to apply tensioning force to the distal loop 84); release of the actuation members 40 from the prosthetic valve 60 (e.g., by simultaneously rotating the plurality of actuation members 40 so as to unscrew the actuation members from the corresponding lockers/actuators of the valve); and/or additional handle mechanisms supplementary advantageous functionalities, which are further described below.

In the description below, the prosthetic valve 60 is assumed to have three lockers/actuators 62, and the delivery apparatus 12 is assumed to have three actuation assemblies 32 to releasably engage the three lockers/actuators 62. However, the mechanisms described in this disclosure can be adapted to support any number of actuation assemblies and lockers/actuators.

Figure 11:
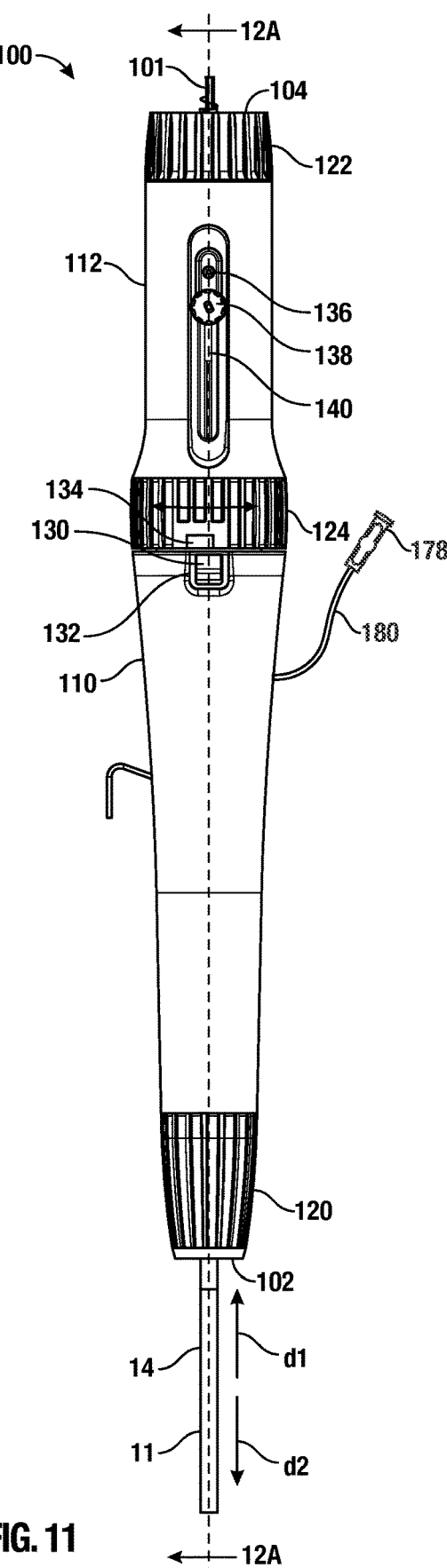
FIG. 11 is an elevation view of an example implementation of a handle of the delivery apparatus.

Referring to FIG. 11, an exemplary handle 100 includes a distal end 102, a proximal end 104, and a longitudinal axis 101 extending from the distal end 102 to the proximal end 104 and defining an axial direction of the handle. The handle 100 includes a proximal portion 112 and a distal portion 110, which are coupled together to define a cavity 107 (shown in FIG. 12A) extending from the distal end 102 to the proximal end 104. A proximal end portion of the shaft assembly 11 extends into the cavity 107.

In the implementation illustrated by FIG. 11, the handle 100 includes a rotatable knob 120, a rotatable knob 122, and a rotatable knob 124. The rotatable knob 120 can be located at the distal end 102 of the handle, the rotatable knob 122 can be located at the proximal end 104 of the handle, and the rotatable knob 124 can be located at an intermediate location between the rotatable knob 120 and the rotatable knob 122.

The handle 100 can have additional knobs, such as a slidable knob 136 and a safety knob 130. A clinician can engage the knobs to perform one or more operations of the delivery apparatus. Surface features or texture can be formed on the knobs to aid in manual grasping and adjustment of the knobs.

In one example, the rotatable knob 120 operates a first mechanism that can axially displace the outer shaft 14 relative to the handle. In one example, the rotatable knob 122 operates a second mechanism that can expand and recompress the prosthetic heart valve. In one example, the rotatable knob 124 operates a third mechanism that can release the actuation members 40 from the prosthetic heart valve. In one example, the safety knob 130, when engaged with the rotatable knob 124, can prevent unintentional release of the actuation members 40 from the prosthetic heart valve. In one example, the slidable knob 136 operates a fourth mechanism that can displace the nosecone shaft 56 (shown in FIG. 1) relative to the handle.

Figures 47A, 47B:
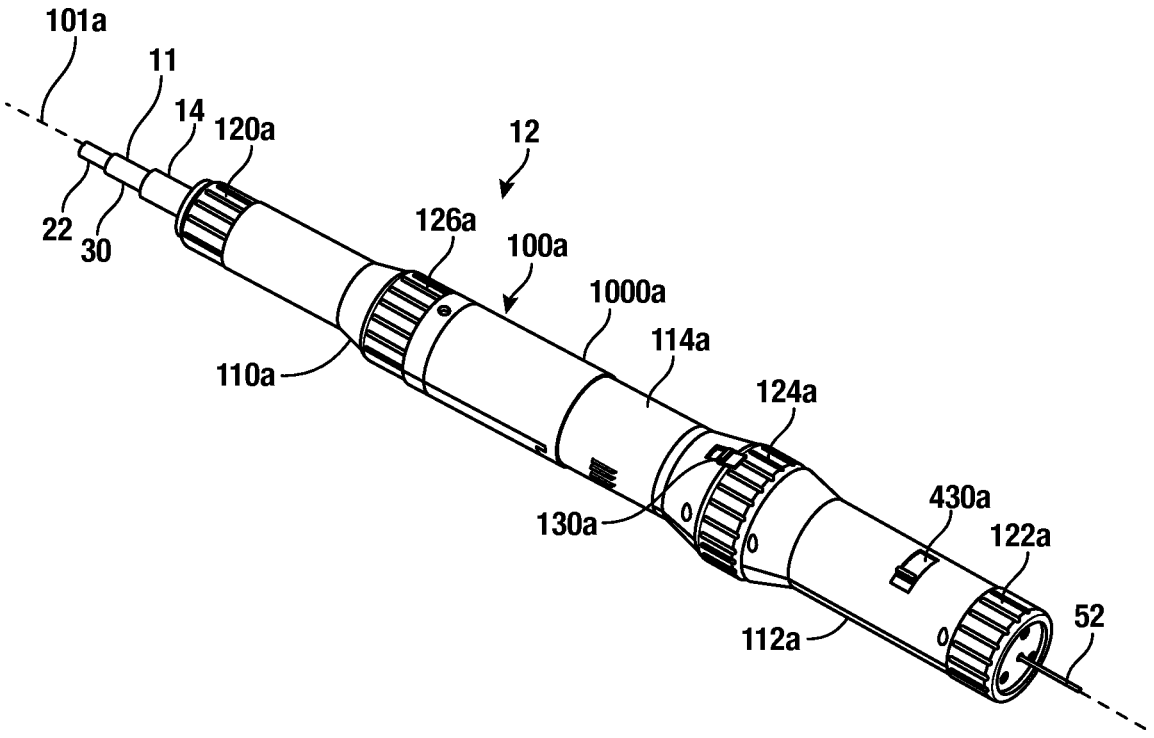
FIGS. 47A-47C are perspective views of a handle of the delivery apparatus, according to another implementation.
Figure 47C:
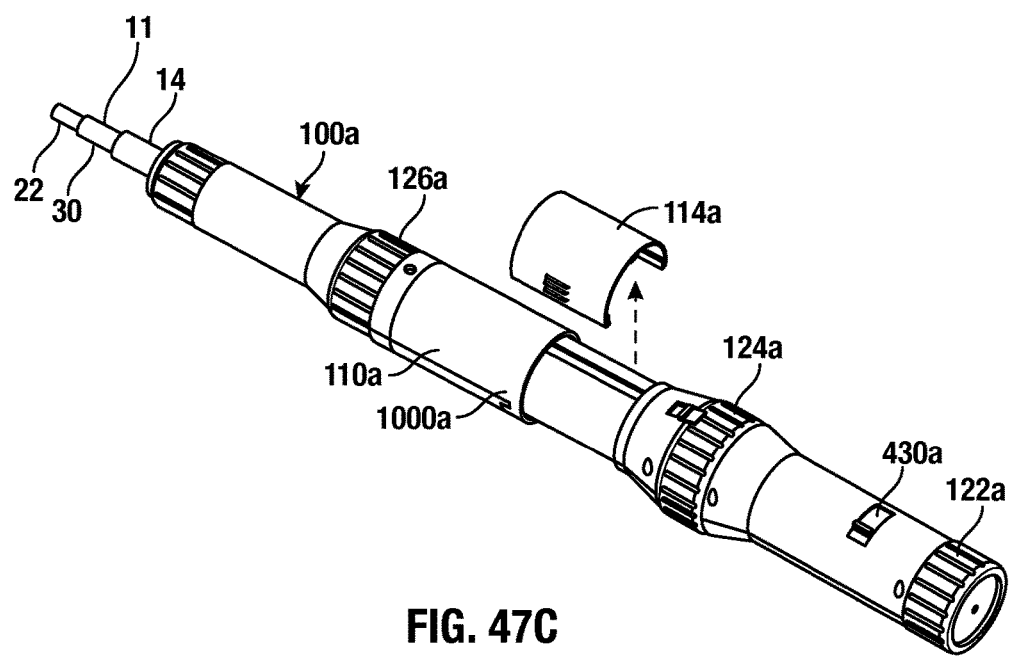
Figure 48:
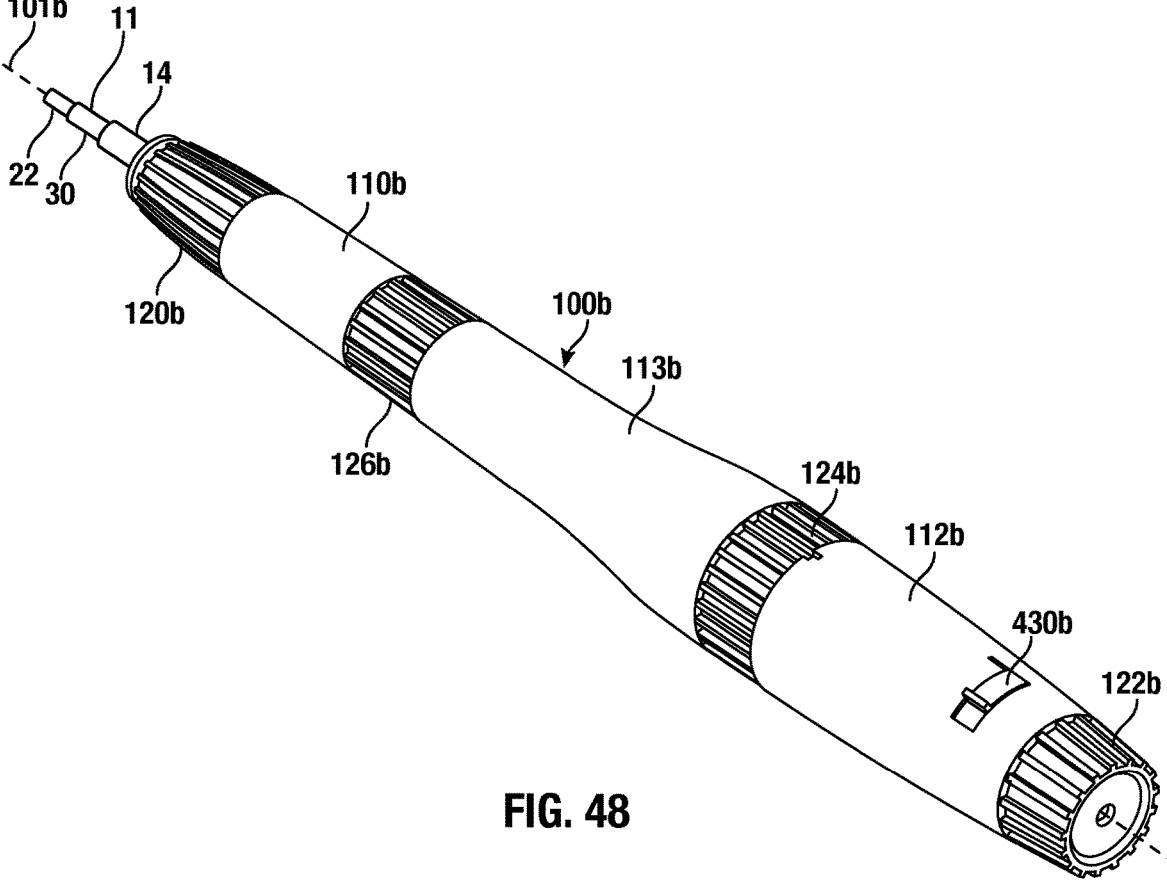
FIG. 48 is a perspective view of a handle of the delivery apparatus, according to another implementation.

In other implementations, the handle 100 can include a fourth rotatable knob (FIGS. 47A-48 show handle implementations with a fourth rotatable knob 126a, 126b) that operates a steering mechanism. For example, the steering mechanism can include at least one pull wire that is attached at its distal end to the outer shaft 14 (or other shaft of the shaft assembly) such that rotation of the fourth knob can vary the tension of the pull wire, which can be effective to vary the curvature of the outer shaft 14 (or of the shaft assembly). The steering mechanism can be omitted if the shaft assembly is sufficiently flexible to navigate the curvatures of the patient's vasculature.

Figure 12A:
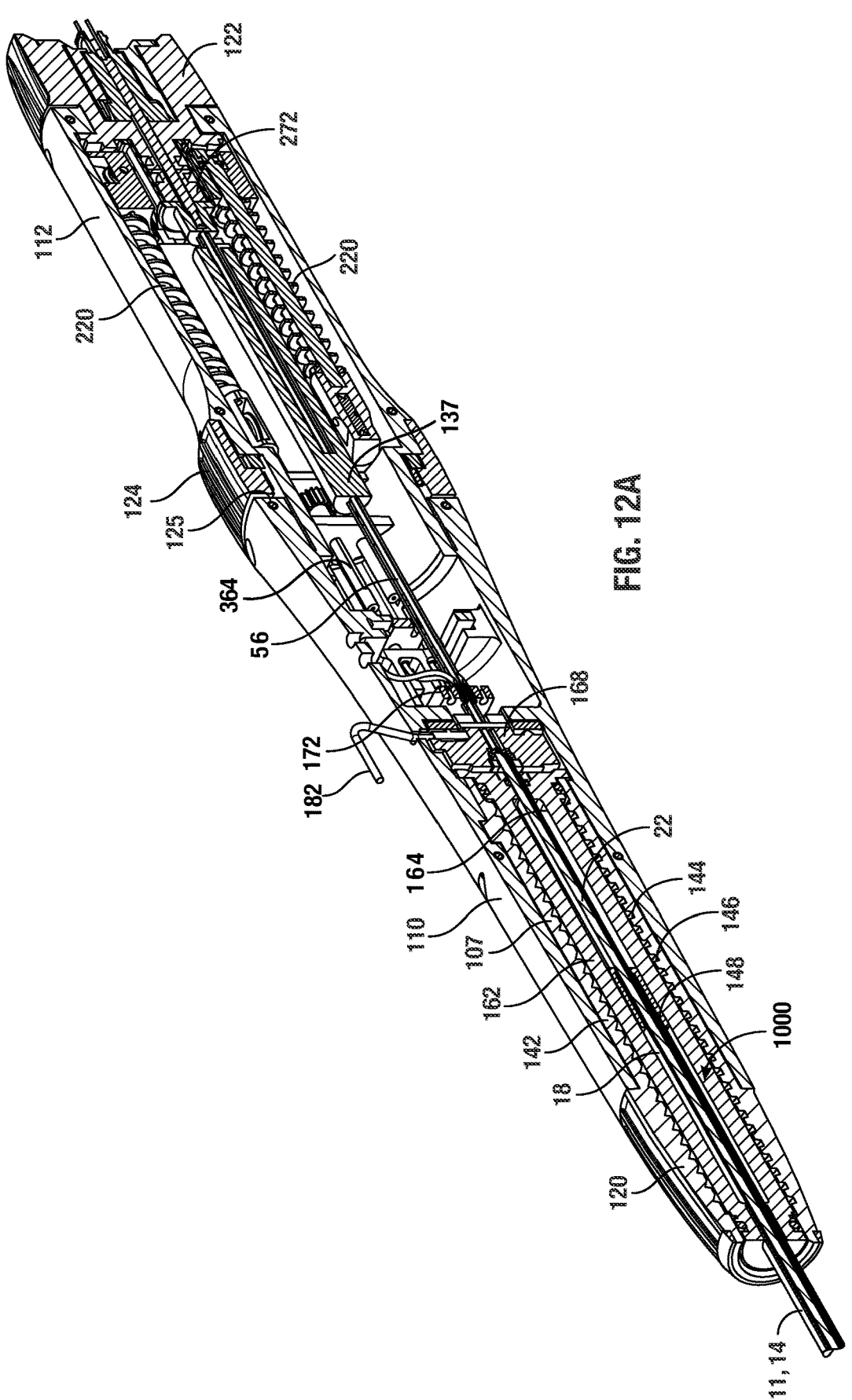
FIG. 12A is a cross-sectional view of the handle shown in FIG. 11, taken along line 12A-12A as depicted in FIG. 11.
Figure 12B:
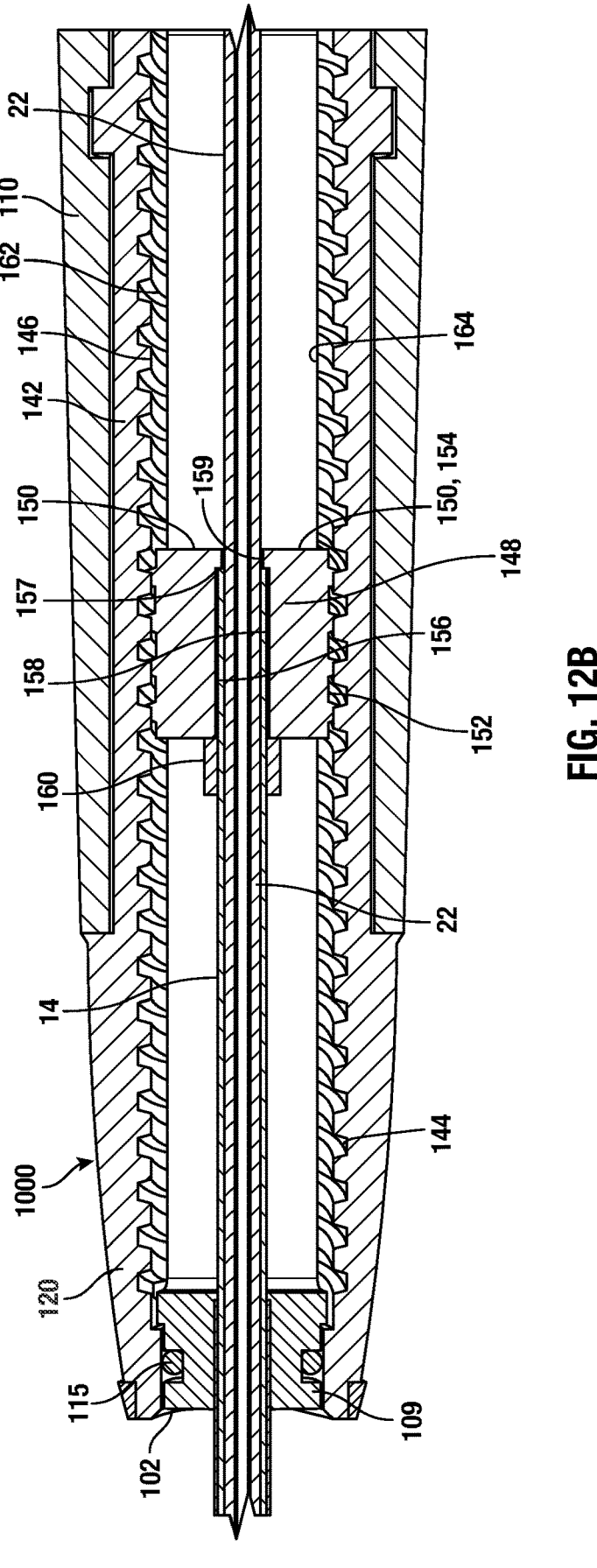
FIG. 12B is an enlarged view of a distal portion of the handle shown in FIG. 12A.
Figure 13:
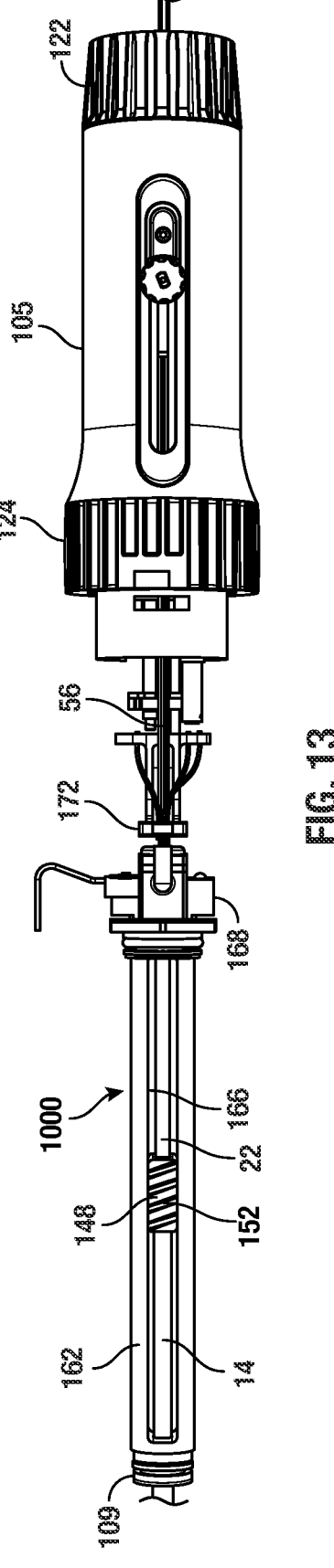
FIG. 13 is an elevation view of the handle of FIG. 11 with some components removed to expose a portion of a shaft displacement mechanism.

Referring to FIGS. 12A, 12B, and 13, a first mechanism 1000 (i.e., a shaft displacement mechanism) that can be controlled by the rotatable knob 120 to displace the outer shaft 14 relative to the handle 100 includes a lead member 142, an axial guide 162, and a nut 148 (or carriage). The lead member 142 is received in a portion of the cavity 107 within the distal portion 110. A distal end portion of the lead member 142 protrudes from a distal end of the distal portion 110. In one example, the rotatable knob 120 is attached to or integrally formed with the protruding distal end portion of the lead member 142 such that rotation of the rotatable knob 120 results in rotation of the lead member 142.

The lead member 142 includes a lead bore 144 with a lead internal thread 146. An axial guide 162 is disposed within the lead bore 144 and is coaxial with the lead bore 144. The axial guide 162 is axially and rotationally fixed relative to the distal portion 110, which means that the axial guide 162 does not rotate when the lead member 142 is rotated. The axial guide 162 includes a guide central bore 164, which can have a substantially tubular profile, and two guide slots 166 (see FIG. 13) extending radially outward from the guide central bore 164 toward lead internal thread 146 in opposite directions. The guide central bore 164 and guide slots 166 extend axially along the length of the axial guide 162.

As shown more clearly in FIG. 12B, the nut 148 is disposed within the axial guide 162. The nut 148 has a nut central portion 154 and two nut radial projections 150 extending radially outward from the nut central portion 154 in opposite directions and toward the lead internal thread 146. The nut central portion 154 can be formed and dimensioned to be situated within the guide central bore 164, while the axial guide slots 166 can be dimensioned to accommodate the respective nut radial projections 150.

The outer surfaces of each nut radial projection 150 comprises a nut outer thread 152 (see FIG. 13) that engages the lead internal thread 146 through the axial guide slots 166

(see FIG. 13). Thus, rotation of the lead member 142 by the rotatable knob 120 results in translation of the nut 148 along the axial guide 162. The axial guide 162 ensures that the translation of the nut 148 will occur only along the axial direction of the handle, preventing rotational movement of the nut 148.

The nut central portion 154 has a nut bore 156 extending therethrough. The nut bore 156 has a nut distal bore portion 158 having a first diameter and a nut proximal bore portion 159 having a second diameter that is smaller than the first diameter. A shoulder or step 157 is formed in the transition between the nut distal bore portion 158 and the nut proximal bore portion 159. A proximal end portion 18 of the outer shaft 14 extends into the nut distal bore portion 158 and abuts the shoulder 157.

The proximal end portion 18 of the outer shaft 14 can be rigidly coupled to the nut 148, for example, by attaching the proximal end portion 18 to the nut distal portion 158 and/or shoulder 157 using any suitable method, such as gluing, welding, clamping, threads, and the like. The rigid connection between the proximal end portion 18 and the nut 148 will allow the outer shaft 14 to move axially as the nut 148 moves axially in response to rotation of the rotatable knob 120 and the lead member 142.

The length of the lead bore 144, the length of the axial guide 162, and/or the length of the nut 148 can be selected to provide the desired axial translation range of the outer shaft 14. The number and spacing of the threads in the lead internal thread 146 and the mating threads in the nut outer threads 152 can be selected to provide the desired proportion between the amount of rotatable knob 120 rotations and the extent of axial translation of the outer shaft 14. In some cases, the nut 148 can have a nut distal extension 160 that allows the length of the nut distal bore portion 158 to be extended without adjusting the axial length of the nut radial projections 150. The longer nut bore 156 may improve engagement between the nut 148 and the proximal end portion 18 of the outer shaft 14.

The rotatable knob 120 is configured to operate the first mechanism 1000 to axially displace the outer shaft 14. For example, rotation of the rotatable knob 120 in a first direction can advance the outer shaft 14 distally, and rotation of the rotatable knob 120 in a second direction that is opposite to the first direction can retract the outer shaft 14 proximally.

Prior to inserting the distal end portion of the delivery apparatus 12 into the patient's body, the distally oriented movement of the outer shaft 14 can be used to position the distal capsule 16, 16a of the delivery apparatus 12 over the prosthetic valve 60 (see FIG. 10A). At the implantation location, the proximally oriented movement of the outer shaft 14 can be used to expose the prosthetic valve 60 (see FIG. 10B). After the actuation members 40 are released from the prosthetic valve 60 (see FIG. 10C), the distally oriented movement of the outer shaft 14 can be used to place the outer shaft 14 in close proximity to the nosecone 50, which would ensure that the delivery apparatus 12 can be easily retrieved without encountering resistance that may otherwise arise between the patient's anatomy and the exposed borders of the nosecone 50.

The first mechanism 1000 can include a guide head 168 disposed adjacent to a proximal end of the axial guide 162. In one example, the guide head 168 is rotationally and axially fixed relative to the distal portion 110. In some cases, the guide head 168 can be integrally formed with a proximal end of the axial guide 162, in which case the guide head 68 can be alternatively referred to as a guide proximal body portion 168. As shown more clearly in FIG. 14A, the guide head 168 has a central bore 169, which is aligned with the central bore 164 of the axial guide 162. A shoulder 170 can be formed between a distal portion 169*a* and a proximal portion 169*b* of the central bore 169.

Figure 14A:
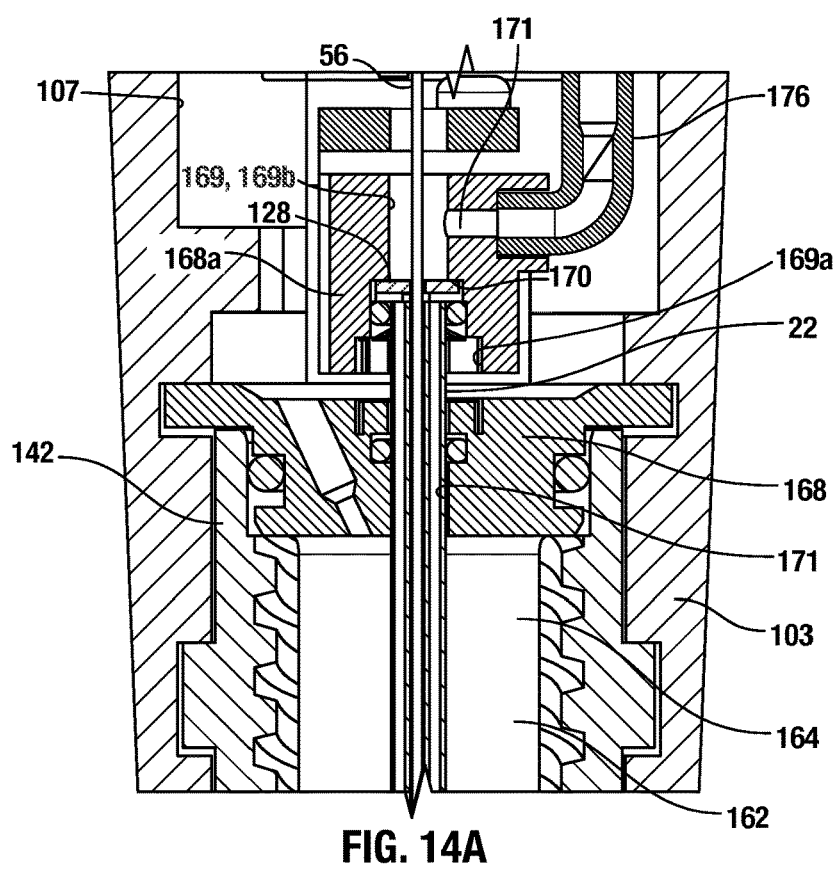
FIG. 14A is a cross-sectional view of a portion of the handle shown in FIG. 11 illustrating a guide head with a fitting for a flushing port.

As shown in FIGS. 12A and 12B, the multi-lumen shaft 22 extends through the outer shaft 14 into the guide central bore 164 of the axial guide 162. As shown in FIG. 14A, the multi-lumen shaft 22 further extends into the distal portion 169*a* of the central bore 169 of the guide head 168. In one example, the proximal end of the multi-lumen shaft 22 includes a flange 28 with openings that match the lumens 23, 24, 25 (see FIG. 5B) of the multi-lumen shaft 22. The actuation members 40, the nosecone shaft 56, and the recompression member 82 can extend through the respective openings in the flange 28 into the cavity 107 of the handle. In one example, the flange 128 can be attached to the proximal shoulder 170 of the guide head 68 such that the multi-lumen shaft 22 is rotationally and axially fixed relative to the guide head 168.

As shown in FIG. 14A, the guide head 168 can further include an opening 171 that is fluidly connected to the proximal portion 169*b* of the central bore 169. A fitting 176 is installed in the opening 171. A flushing port 180 can be connected to the fitting 176 (as shown in FIG. 14B). The flushing port 180 can be a flexible tube with an internal conduit. The flushing port 180 can extend along the cavity 107 and through an opening in the distal portion 110 to the outside of the handle 100 (as shown in FIG. 11). A connector 178, such as a Luer connector of a stopcock, can be provided on the end of the flushing port 180 that is disposed outside the handle 100 (as shown in FIG. 11). Fluid can be supplied into the proximal portion 169*b* of the central bore 169 through the flushing port 180. The fluid can enter the lumens of the multi-lumen shaft 22 through the openings in the flange 128, thereby allowing flushing of the lumens of the multi-lumen shaft 22.

Figure 14C:
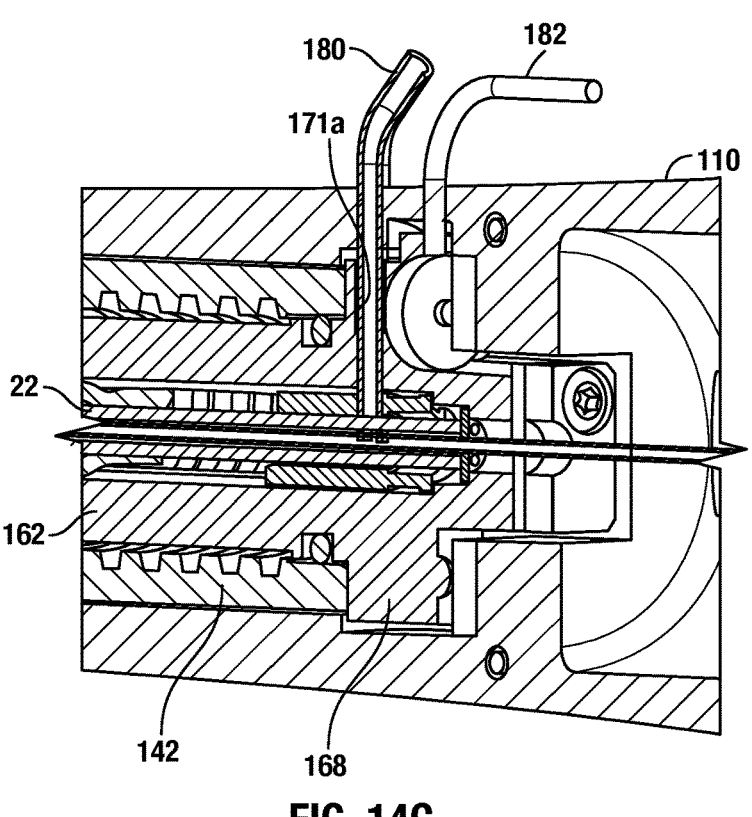
FIG. 14C illustrates an alternative implementation of a flushing path within the handle.
Figure 14B:
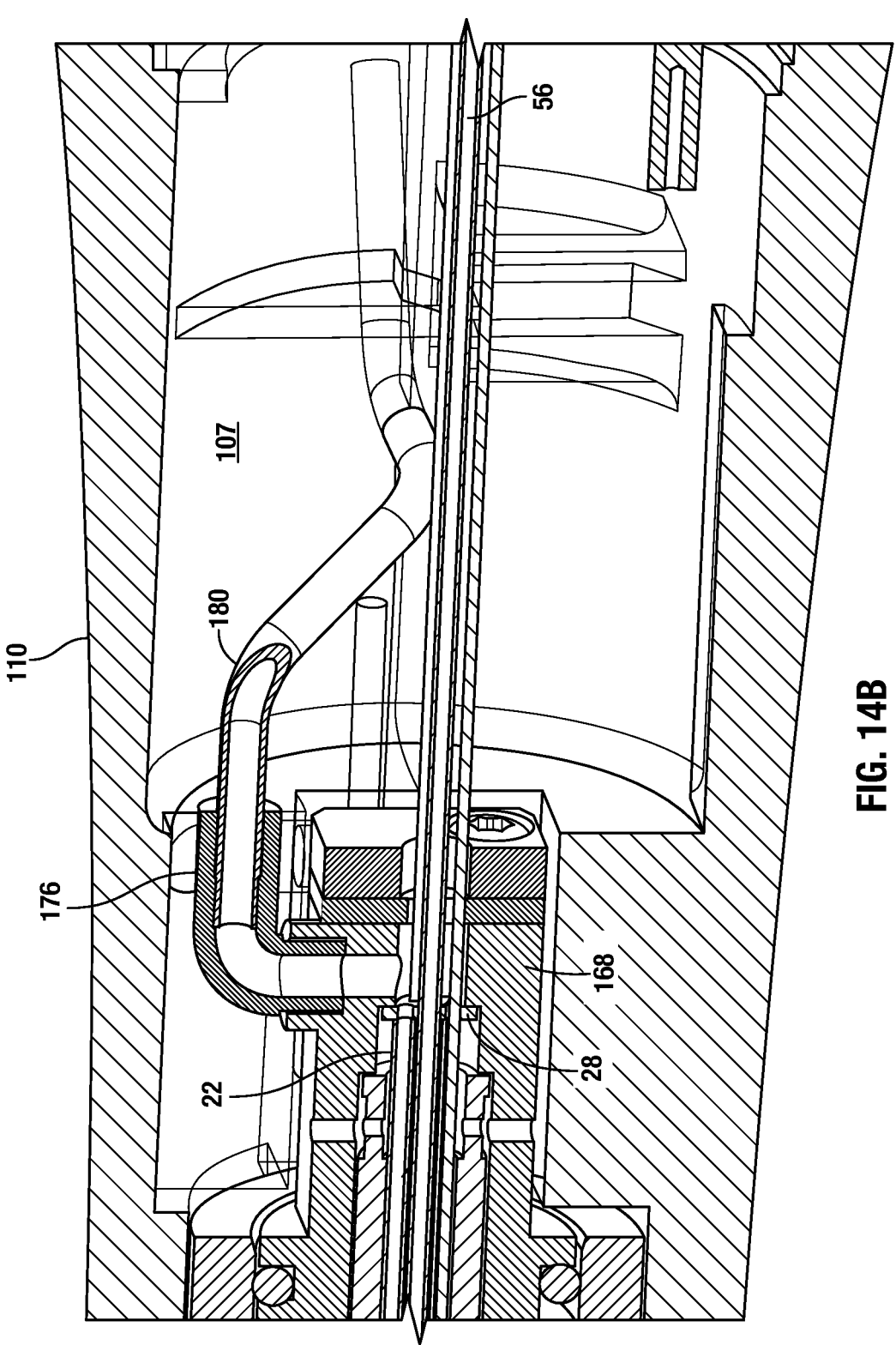
FIG. 14B is a cross-sectional view of a portion of the handle shown in FIG. 11 illustrating a flushing port extending through the handle.

FIG. 14C shows another example where the guide head 168, formed integrally with the proximal end of the axial guide 162, includes an opening 171*a* that is oriented radially relative to the longitudinal axis of the handle. The opening 171*a* is aligned with a similar opening in the distal portion 110. The flushing port 180 extends from the outside of the handle into the opening 171*a* and can be used to flush lumens of shafts in the handle.

Referring to FIGS. 15A-15D, guide plates 173, 175 can be attached to a proximal end of the guide head 168. The guide plates 173, 175 can have central openings for passage of the actuation members 40, recompression member 82, and nosecone shaft 56 into the cavity 107 of the handle. In one example, a spreader plate 172 can be positioned proximally to the guide plate 175. In some cases, the spreader plate 172 can be fixedly coupled to the guide plate 175 or otherwise fixed relative to the multi-lumen shaft 22. The spreader plate 172 includes apertures 174 to receive the actuation members 40 and the recompression member 82. The spacing between the apertures 174 is larger compared to the spacing between the lumens from which the actuation members 40 and recompression member 82 emerge such that the actuation members 40 and recompression member 82 are spread out in the proximal direction.

Figure 15A:
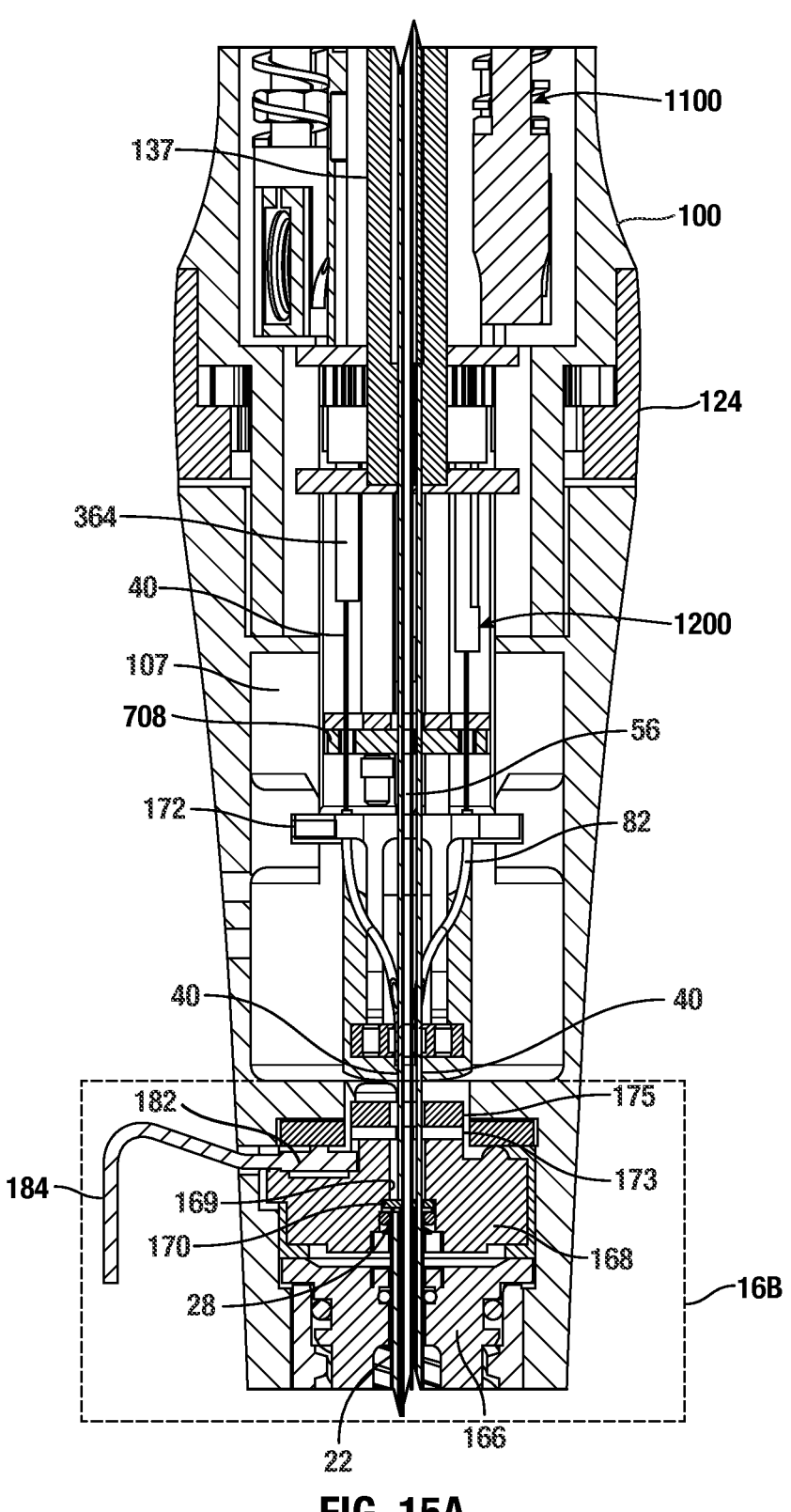
FIG. 15A is a cross-sectional view of a portion of the handle shown in FIG. 11.
Figure 15B:
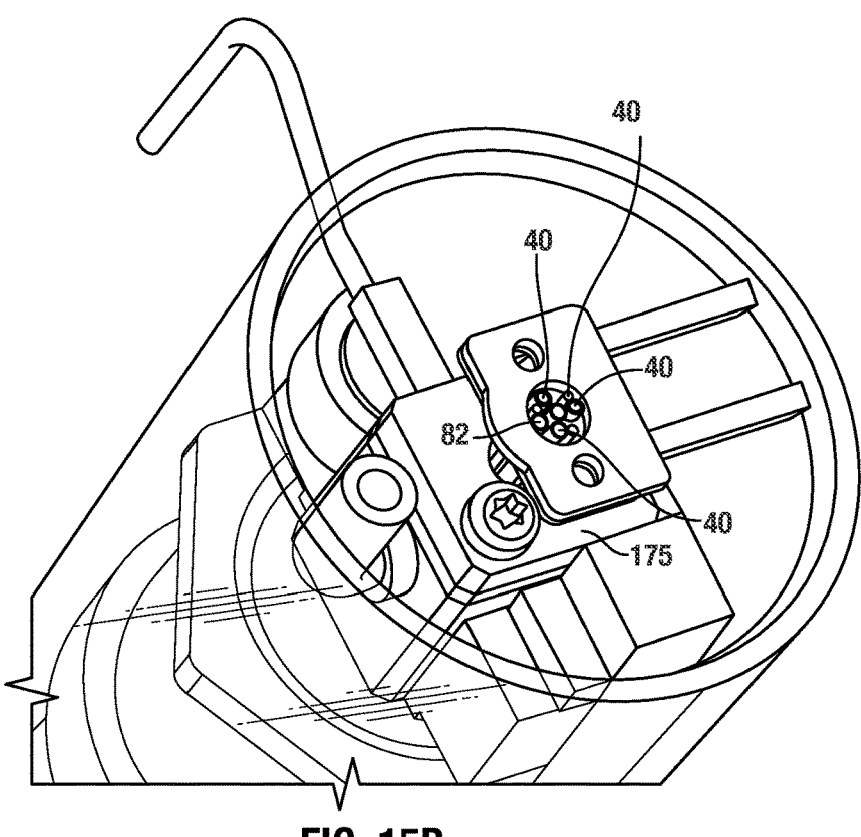
FIGS. 15B and 15C are details of a portion of the handle shown in FIG. 11 illustrating structures extending proximally from a multi-lumen shaft.
Figure 15C:
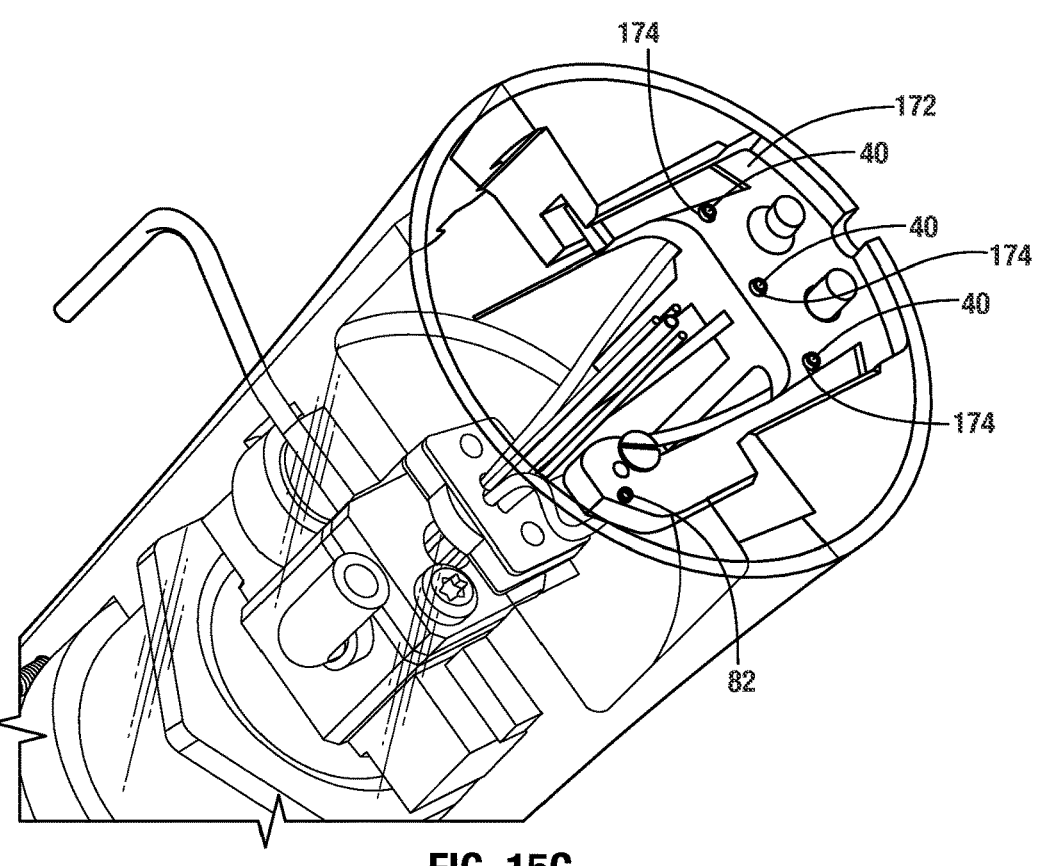
Figure 15D:
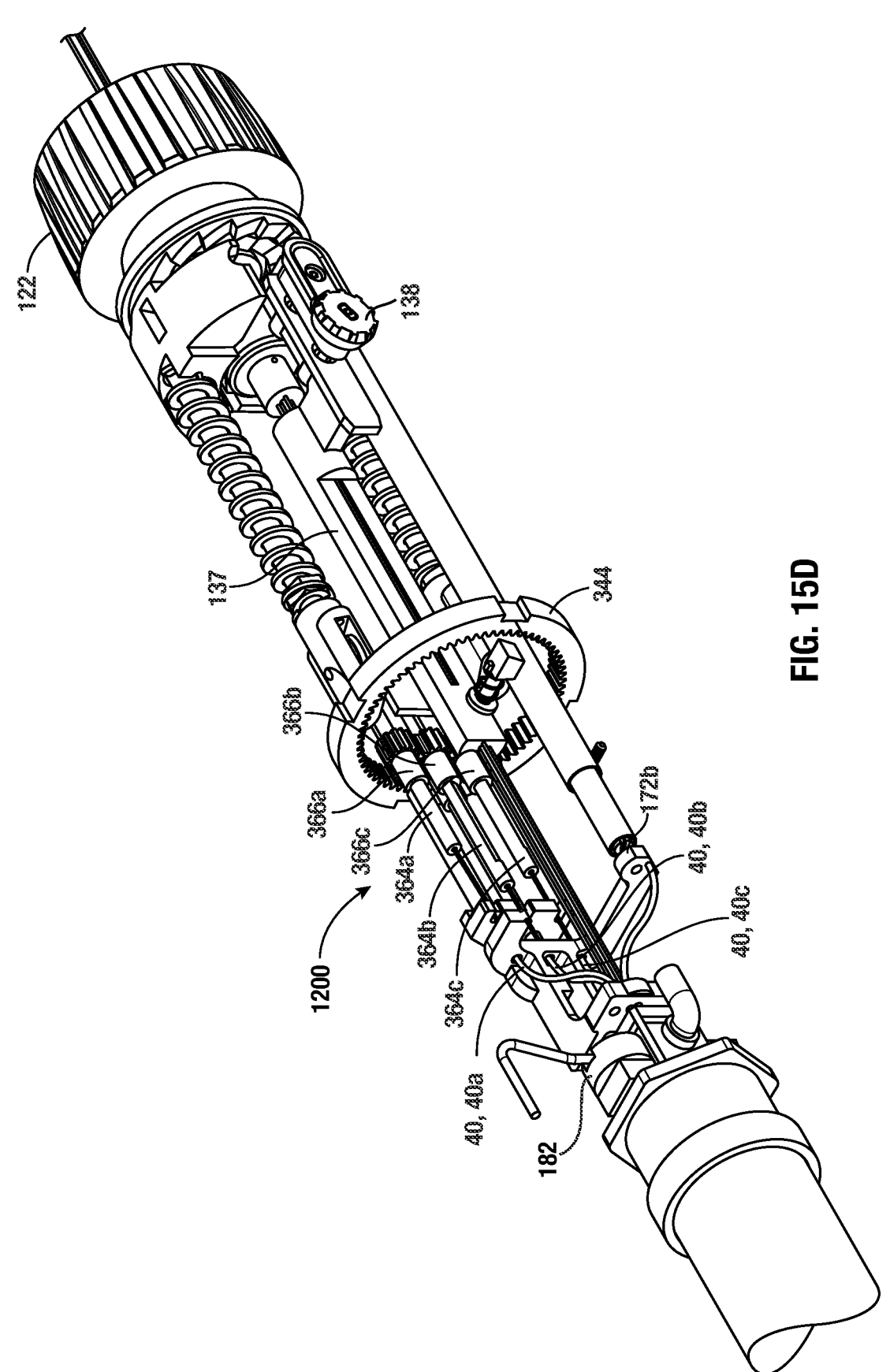
FIG. 15D is a perspective view of the handle shown in FIG. 11 with some components removed to illustrate actuation and recompression members extending proximally within the handle.
Figures 16A, 16B:
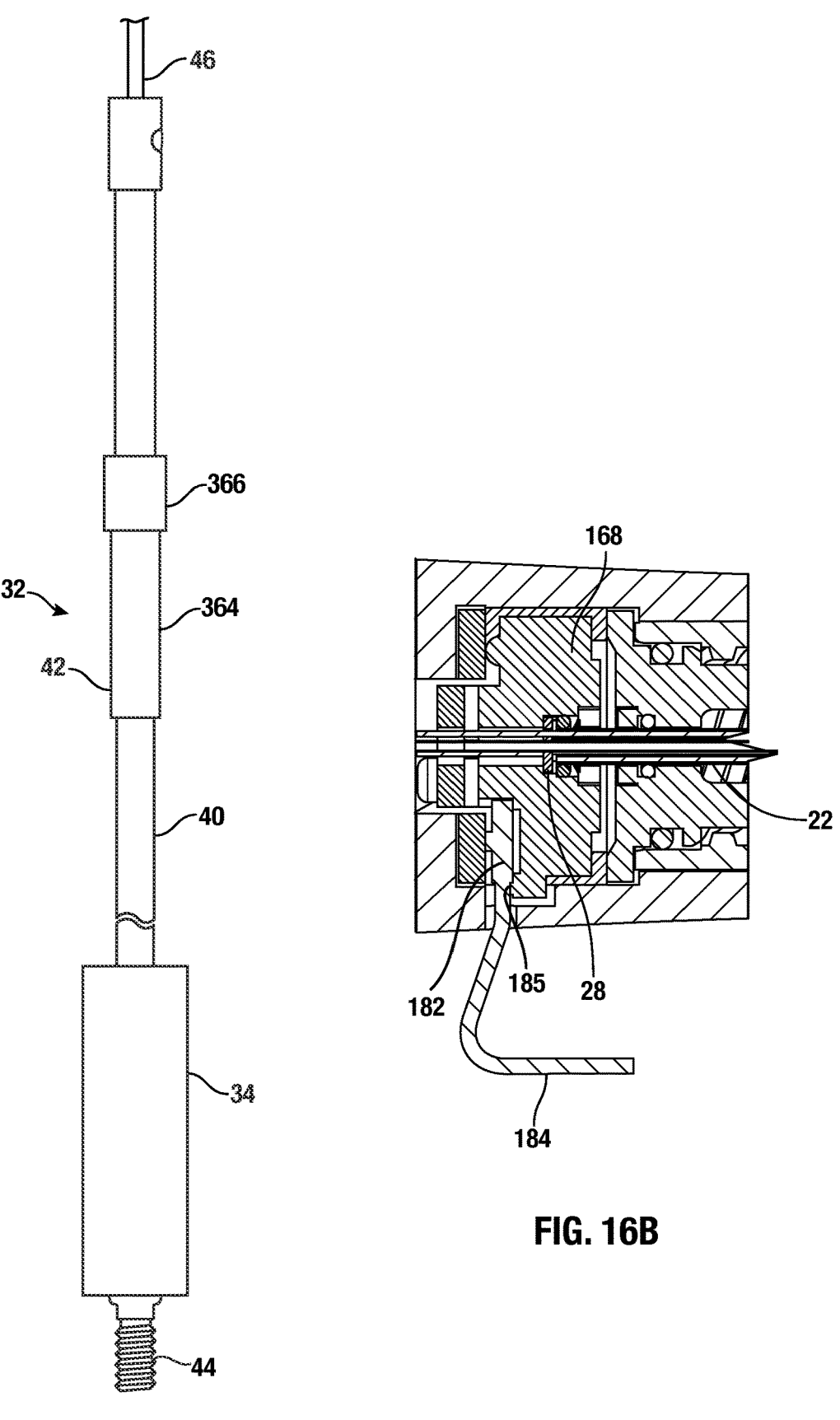
FIG. 16A is an elevation view of an example implementation of an actuation assembly of the delivery apparatus.
FIG. 16B is a detail view of the region 16B depicted in FIG. 15A.

Referring to FIG. 16A, each actuation assembly 32 can further include an actuation tube 364, which can be positioned within the cavity of the handle and proximal to the multi-lumen shaft 22 (as shown in FIG. 15D, for example). The actuation member 40 extends through a respective actuation tube 364. The actuation member 40 can include an actuation torque-transferring portion 42 and an actuation flexible portion 46. The actuation torque-transferring portion 42 extends from the distal threaded head 44 into the handle. The actuation flexible portion 46 is disposed proximally to the actuation torque-transferring portion 42 and is coupled to the actuation torque-transferring portion 42.

The actuation torque-transferring portion 42 can comprise a relatively rigid material, formed as a torque-transferring wire, cable, and the like. The actuation flexible portion 46 can be formed as a flexible string, wire, cable, and the like and configured to be flexible enough to wrap around various components, such as pulleys or reels. The actuation member 40 passes through the actuation tube 364 such that the actuation flexible portion 46 extends proximally from the actuation tube 364 for routing around pulleys and the like. In some cases, the actuation torque-transferring portion 42 can be rigidly attached to the actuation tube 364 such that both may move axially together within the handle. In some cases, the actuation tubes 364 can comprise a distal portion 366 that is provided with an enlarged diameter and which may include a coupler configured to couple the actuation torque-transferring portion 42 to the actuation flexible portion 42.

Referring to FIG. 16B, a load cell 182, which is an example of a force sensor, can be disposed between the guide head 168 and an internal radial extension of the handle. When the prosthetic valve 60 is expanded, the resistive force of the sleeve members 34 that is pressed against the housing members 64 of the lockers/actuators 62 is translated through the multi-lumen shaft 22 and the flange 28 to a proximally oriented force 185 of the guide head 168 and applied to the load cell. The axial force measured by the load cell 182 can be used to calculate the radial force applied by the valve 60 against the surrounding native anatomy (such as a native aortic annulus). The load cell 182 can be operatively coupled to an external device via one or more wires or cable 184. Alternatively, or additionally, the load cell may wirelessly transmit signals to an external device.

Figure 17:
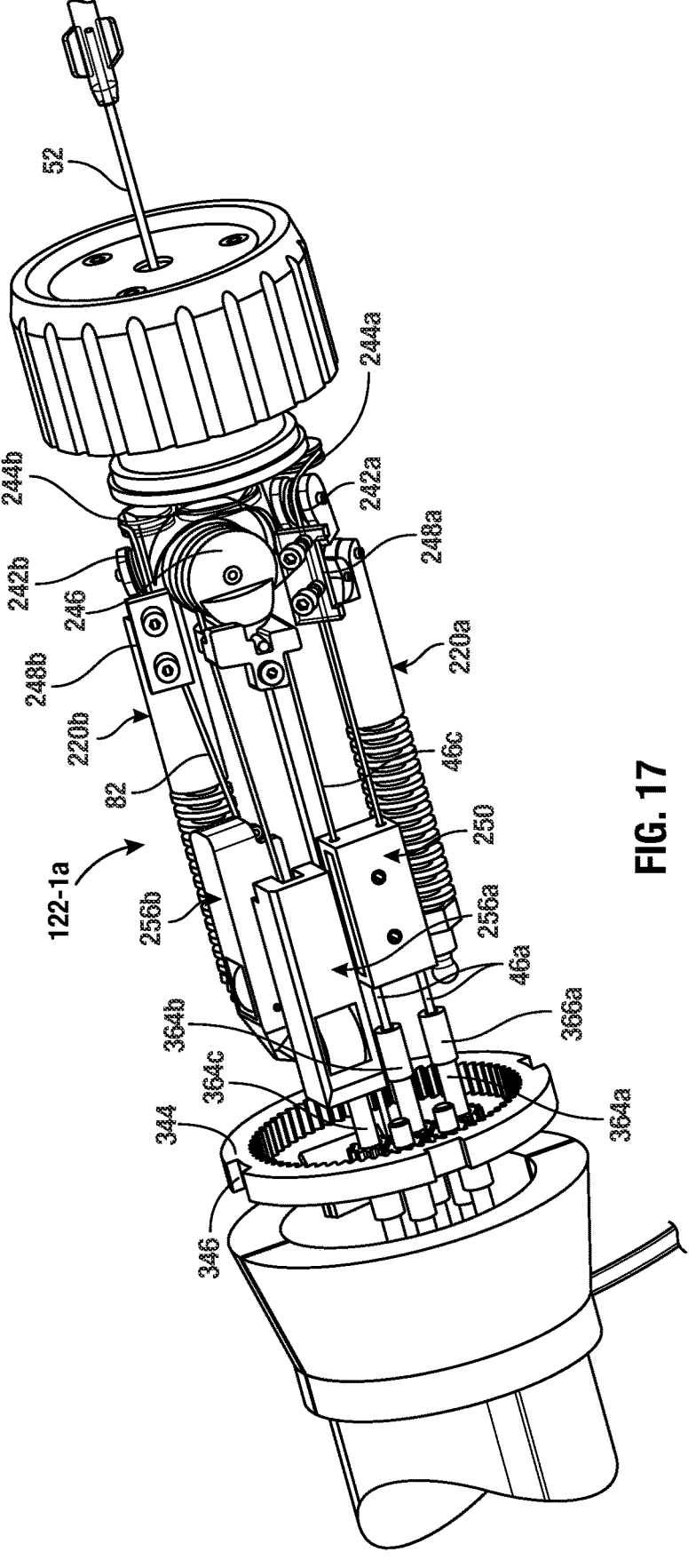
FIG. 17 is a perspective view of the handle of FIG. 11 with some components removed to illustrate a valve expansion and recompression mechanism.
Figure 18:
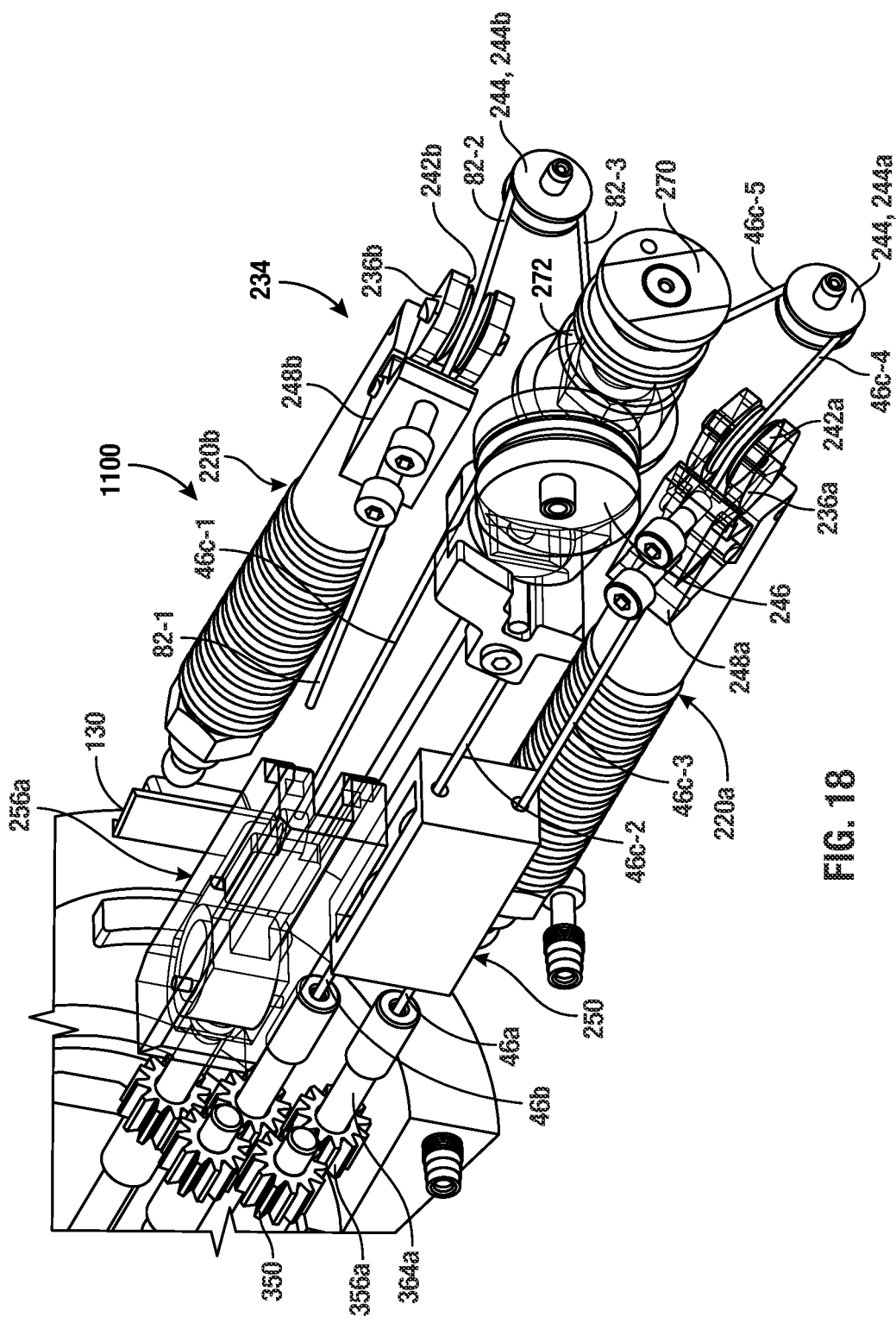
FIG. 18 is a perspective view of the handle of FIG. 11 with some components removed to further illustrate the valve expansion and recompression mechanism.
Figure 19:
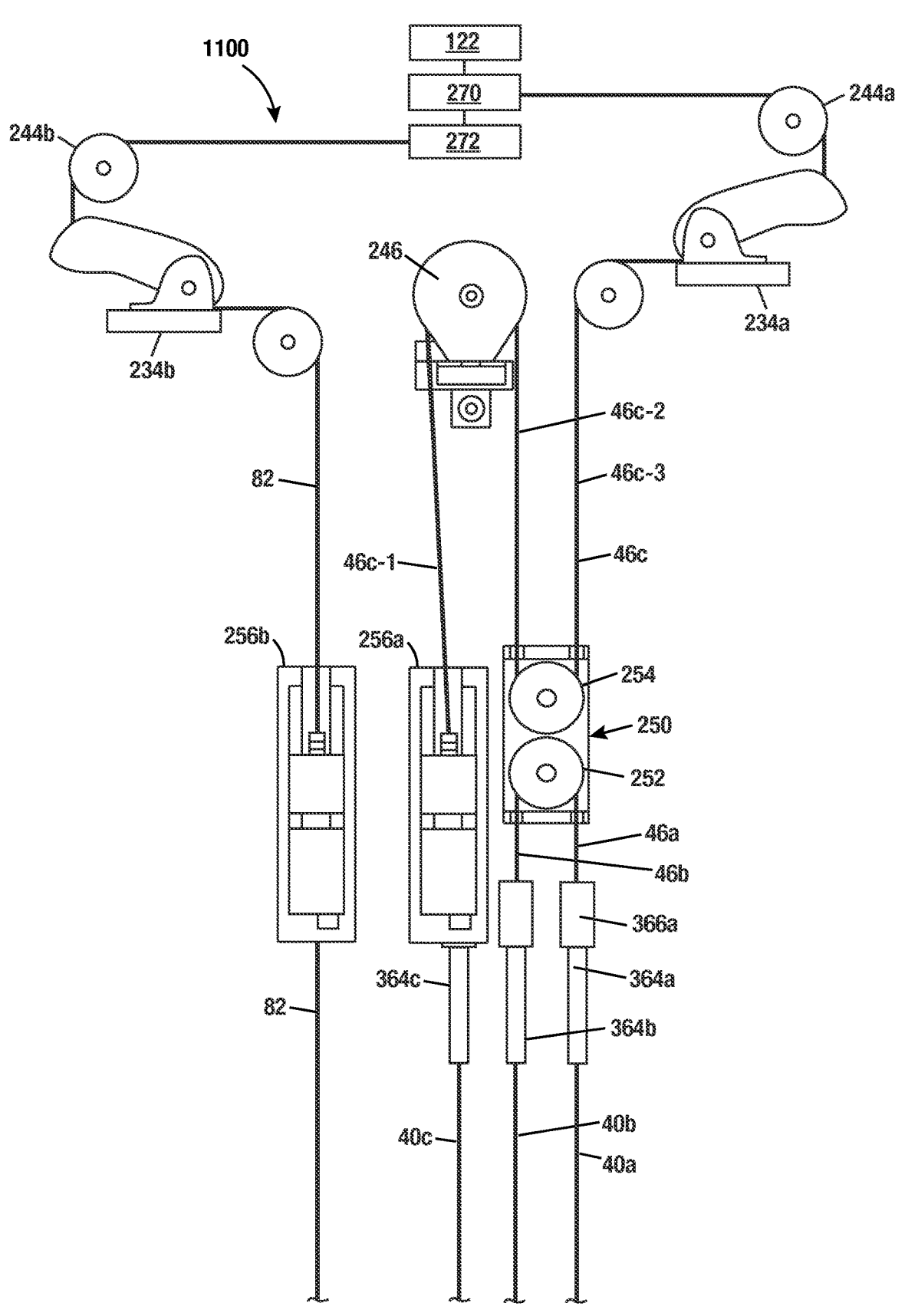
FIG. 19 is a simplified schematic of the valve expansion and recompression mechanism shown in FIGS. 17 and 18.

FIGS. 17-19 illustrate various portions of a second mechanism 1100 (i.e., a valve expansion and compression mechanism) that can be controlled by the rotatable knob 122 of the handle. The second mechanism 1100 can be controlled to simultaneously pull all the actuation members 40 of the actuation assemblies 32 and thereby expand the prosthetic heart valve attached to the actuation members 40. In some examples, the second mechanism 1100 can be controlled to pull the recompression member 82 and thereby recompress the valve. In some examples, the rotatable knob 122 can control both the expansion and the recompression parts of the mechanism 1100. For example, rotation of the rotatable knob 122 in a first direction (which can be clockwise or counterclockwise) can result in expansion of the prosthetic heart valve, and rotation of the rotatable knob 122 in a second direction that is opposite to the first direction can result in compression of the valve. Movement of the actuation members 40 and the recompression member 82 can be synchronized such that the expansion and recompression parts of the mechanism do not interfere with each other.

In one implementation, the second mechanism 1100 can include a force balancing assembly 250, tensioning assemblies 256 (identified separately as 256*a*, 256*b*), and a re-routing pulley 246. The force balancing assembly 250 can balance the pull force applied to the actuation members 40 (identified separately as 40*a*, 40*b*, 40*c*), thereby mitigating risk of overloading any one of the lockers/actuators of the prosthetic valve. The tensioning assemblies 256*a*, 256*b* can maintain a minimal tension in the actuation members 40 and recompression member 82, respectively.

In one example, the force balancing assembly 250 can include a first balancing pulley 252 and a second balancing pulley 254, each of which can freely rotate around its axis within the assembly. The first and second actuation flexible portions 46a, 46b of the first and actuation members 40a, 40b extend proximally (i.e., towards the proximal end of the handle) from the respective actuation tubes 364a, 364b and are connected together to form a single flexible portion that is routed around the first balancing pulley 252. The first balancing pulley 252 can freely rotate around its axis to transfer tension between the actuation flexible portions 46a, 46b. As a result, a difference in tension is not created between the actuation flexible portions 46a, 46b.

The third actuation flexible portion 46c of the third actuation member 40c extends proximally from the actuation tube 364c and through the first tensioning assembly 256a. A section 46c-1 of the third actuation flexible portion 46c extends from the first tensioning assembly 256a, in a proximal direction, to and around the re-routing pulley 246. The section 46c-2 of the third actuation flexible portion 46c extends from the re-routing pulley 246, in a distal direction, into the force balancing assembly 250 and around the second balancing pulley 254. The third section 46c-3 extends again proximally from the second balancing pulley 254.

The rotatable knob 122 can be rotated to apply a pull force to the section 46c-3 of the third actuation flexible portion 46c, which would create tension in the third actuation flexible portion 46c. This tension is translated to an axial movement of the force balancing assembly 250 as a whole, which in turn results in tension in both of the first and second actuation flexible portions 46a, 46b, thus keeping an equal tension among all the actuation flexible portions 46a, 46b, 46c at all times. In this manner, it suffices to apply a pull force to a single actuation flexible portion, specifically, the third actuation flexible portion 46c, to simultaneously pull all three actuation members 40a, 40b, 40c along an equal distance.

Further details of the force balancing assembly, including examples of application thereof in implementations having more than three actuation assemblies, can be found in U.S. Provisional Application No. 62/945,039, which is incorporated herein by reference.

The recompression member 82 can be released while the rotatable knob 122 is rotated in one direction to pull the third actuation flexible portion 46c, and the third actuation flexible portion 46c can be released while the second knob is counterrotated to pull the recompression member 82. Preferably, the third actuation flexible portion 46c and the recompression member 82 are kept in a minimally tensioned state at all times, including their released phases, to prevent formation of slacks within the handle since slacks formed within the handle might result in synchronization imbalance between the third actuation flexible portion 46c and the recompression member 82 during rotation of the rotatable knob 122 in either direction. The third actuation flexible portion 46c and the recompression member 82 can be kept in a minimally tensioned state by the respective tensioning assemblies 256a, 256b.

Figure 20A:
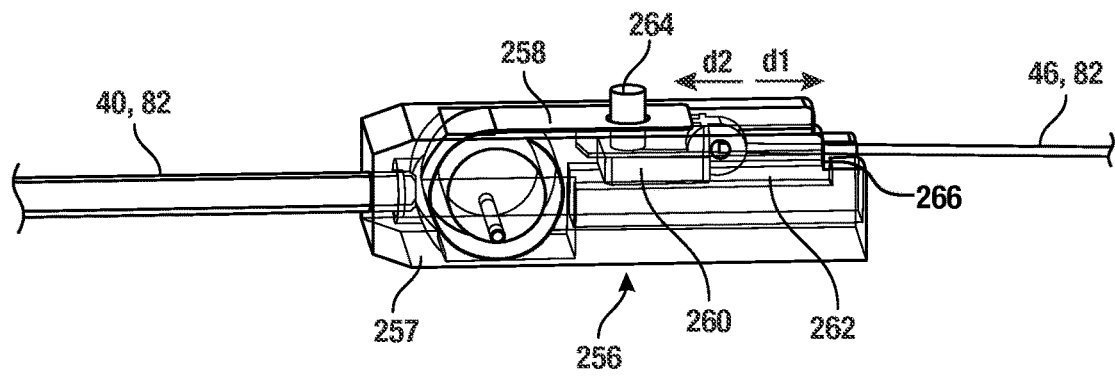
FIG. 20A is a perspective view of an example implementation of a tensioning assembly included in the valve expansion and recompression mechanism.

Referring to FIG. 20A, in one example, the tensioning assembly 256 (which can be used as any of the tensioning assemblies 256a, 256b) includes a housing 257 and a tension applying spring 258 attached to one end of the housing 257. The tensioning assembly 256 includes a spring slider 260 disposed within a spring slider slot 262 formed within the housing 257. The spring slider 260 is axially movable within the spring slider slot 262.

The spring slider 260 can be coupled at one end to the spring 258 and at another end to a flexible string that needs to be tensioned (e.g., the actuation flexible portion 46c or the recompression member 82). The actuation flexible portion 46c (or in a similar manner the recompression member 82) can be attached to, or extend through, an eyelet of the spring slider 260. The spring slider 260 can include a ping 264 extending through, and coupled to, the free end of the spring 258. In one example, the spring 258 can be a constant force spring.

In use, when a pull force is applied to the actuation flexible portion 46c (or the recompression member 82), the spring slider 260 can slide in a proximal direction within the spring slider slot 260 (i.e., in direction d1), for example, until the spring slider 260 reaches a proximal slot stop feature 266 (such as a bent or protruding extension configured to prevent further proximal movement of the slider 260). At this point, if further pull force is applied, the whole tensioning assembly 256 may translate proximally along with the actuation member 40c (or with the recompression member 82). When the actuation flexible portion 46c (or the recompression member 82) is released from the pull force, the spring 258, which can be a constant force spring, pulls the slider 260 in a distal direction within the slot 262 (i.e., in the direction d2), thereby tensioning the actuation member 40c (or the recompression member 82) enough to prevent slack formation.

Figure 20B:
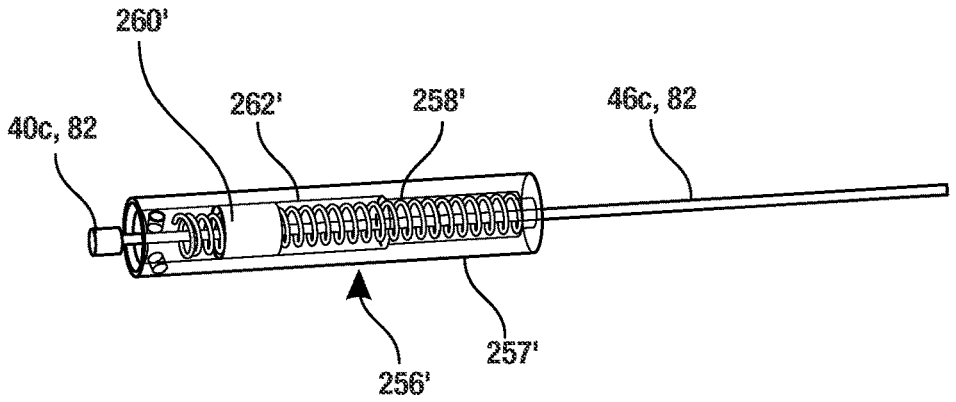
FIG. 20B is a perspective view of another example implementation of a tensioning assembly included in the valve expansion and recompression mechanism.

FIG. 20B shows an alternative tensioning assembly 256' that uses an extension spring 258' instead of a constant force spring. The alternative tensioning assembly 256' can include a housing 257' having a slot 260' in which the extension spring 258' and a slider 260' are arranged. The spring 258' is attached to the slider 260' such that the slider 260' can move axially within the slot 260' in response to changes in tension of the spring 258'. The actuation flexible portion 46c (or the recompression member 82) extends through the spring 258' and is coupled to the slider 260'.

When a pull force is applied to the actuation flexible portion 46c (or the recompression member 82), the slider 260' can slide in a proximal direction within the slot 260'. When the actuation flexible portion 46c (or the recompression member 82) is released from the pull force, the spring 258' pulls the slider 260' in a distal direction within the slot 260', thereby tensioning the actuation member 40c to prevent slack formation. It has been found that a small sized extension spring 258' can be used instead of a constant force spring 258, since the tension force the spring needs to apply in order to tension the actuation member 40c (or the recompression member 82) is relatively small. This configuration may advantageously provide a more compact, small-sized tensioning assembly.

In some cases, the handle 100 can include one or more mechanisms to limit the amount of force that can be applied to expand or compress the prosthetic valve. For example, the handle 100 can include force limiting mechanisms 234 (identified separately as 234a, 234b). The first force limiting mechanism 234a can be coupled to the third actuation flexible portion 46c to limit the amount of force that can be applied to expand the prosthetic valve 60 by rotation of the rotatable knob 122. The second force limiting mechanism 234b can be coupled to the recompression member 82 to limit the amount of force that can be applied to compress the prosthetic valve 60.

Figure 21A:
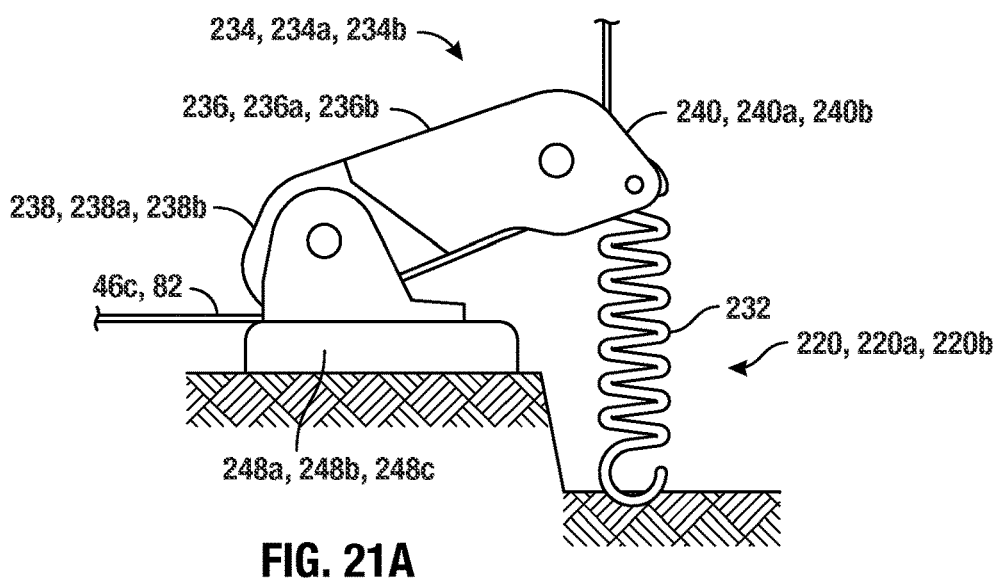
FIGS. 21A-21B illustrate an example implementation of a force limiting mechanism.
Figure 21B:
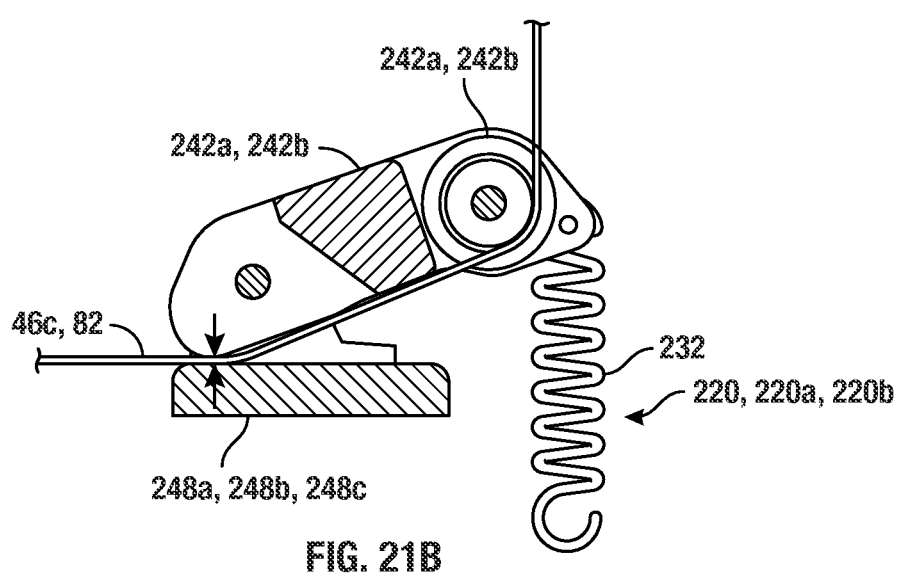

FIGS. 21A and 21B show an example force limiting mechanism 234 including a pivoting arm 236 having a first end portion 238 that is pivotally coupled to a base portion 248. The force limiting mechanism 234 can include an arm pulley 242 that is coupled to a second end portion 240 of the pivoting arm 236. The force limiting mechanism 234 can further include a guide pulley 244 (shown in FIG. 18) that is laterally and/or axially offset from the pivoting arm 236. The guide pulley 244 can extend along a plane that is substantially perpendicular to the plane of the arm pulley 242.

As shown in FIG. 18, the section 46c-3 of the actuation flexible portion 46c extending proximally from the force balancing assembly 250 can be routed around the first pivoting arm 236a of the first force limiting mechanism 234a and partially around the first arm pulley 242a. The following section 46c-4 of the actuation flexible portion 46c extends from the arm pulley 242a to the first guide pulley 244a. The actuation flexible portion 46c is partially routed around the first guide pulley 244a and thereby redirected such that the following section 46c-5 of the third actuation flexible portion 46c extends toward an expansion reel 270 and has its proximal end attached to the expansion reel 270. In this manner, rotation of the expansion reel 270 in a specific direction can wrap the third actuation flexible portion 46c around the expansion reel 270, tensioning the actuation flexible portion 46c to simultaneously pull all three actuation members 46a, 46b, 46c as previously described.

Similarly, a section 82-1 of the recompression member 82 extends proximally from the second tensioning assembly 256b. The section 82-1 is routed around the second pivoting arm 236b of the second force limiting mechanism 234b and partially around the second arm pulley 242b. The following section 82-2 of the recompression member 82 extends from the arm pulley 242b to the second guide pulley 244b. The recompression member 82 is partially routed around the second guide pulley 244b and thereby redirected such that the following section 82-3 extends towards a recompression reel 272 and has its proximal end attached to the recompression reel 272. In this manner, rotation of the recompression reel 272 in a direction opposite to the expansion-applying direction can wrap the recompression member 82 around the recompression reel 272, tensioning the recompression member 82 to recompress the valve 60.

Because of the routing of the actuation member 40c around the arm pulley 242a and the guide pulley 244a, when a pull force is applied to the actuation member 40c, a pivoting force is applied to the pivoting arm 236a, causing the arm to pivot. When the pivoting arm 236a pivots to a certain degree corresponding to a maximum predefined pull force, the actuation member 40c is pinched in the gap between the first end portion 238a and the base portion 248a (as shown in FIG. 21B), thereby preventing the actuation member 40c from being further pulled by the expansion reel 270.

Similarly, when a pull force is applied to the recompression member 82, a pivoting force is applied to the arm 236b, causing the arm to pivot. When the arm 236b pivots to a certain degree corresponding to a maximum predefined pull force, the recompression member 82 is pinched in the gap between the first end portion 238b and the base portion 248b (as shown in FIG. 21B), thereby preventing the recompression member 82 from being further pulled by the recompression reel 272.

Further details concerning the force limiting mechanism 234, and alternative examples thereof, are elaborated in U.S. Provisional Application No. 62/870,372, the disclosure of which is incorporated herein by reference.

Figure 21C:
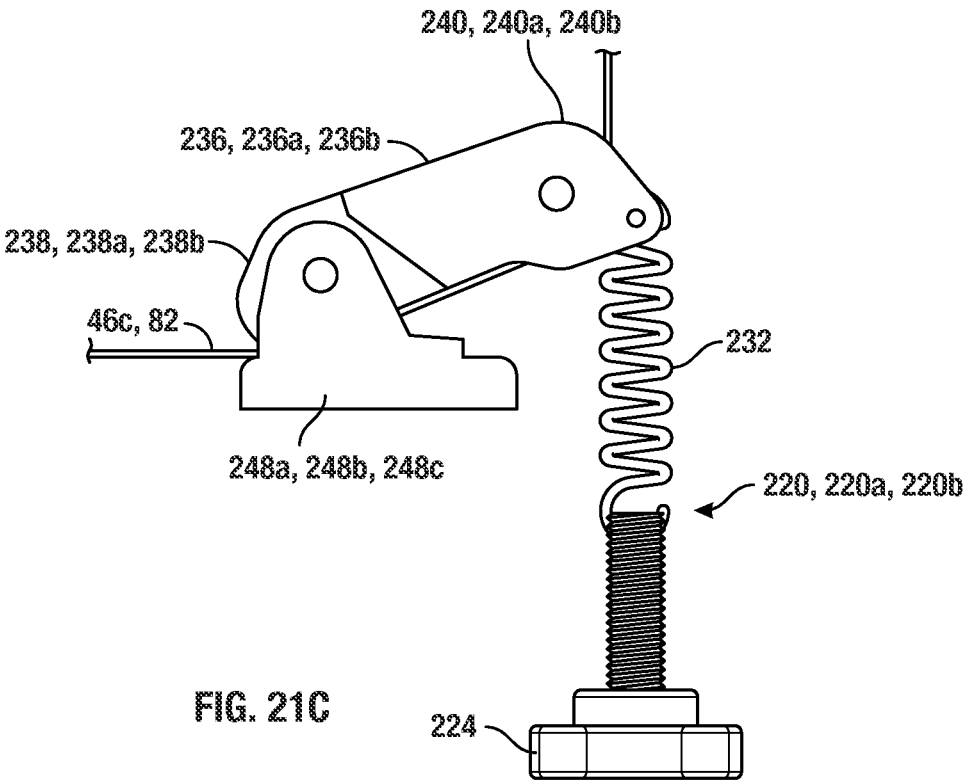
FIG. 21C illustrates the force limiting mechanism of FIGS. 21A-21B with an adjustable biasing assembly.

FIG. 21C illustrates an adjustable biasing assembly 220 that can be positioned to bias the pivoting arm 236 of the force limiting mechanism 234 to a release position. The adjustable biasing assembly 220 includes a biasing spring 232 (or any other biasing member) disposed between a stationary fixed end and the pivoting arm 236. The adjustable biasing assembly 220 can further include an adjustment nut 224 that can be rotated to adjust the degree of pre-expansion or pre-compression of the spring 232. Each of the pivoting arms 236a, 236b of the force limiting mechanisms 234a, 234a can be provided with an adjustable biasing assembly 220a, 220b.

Figure 22A:
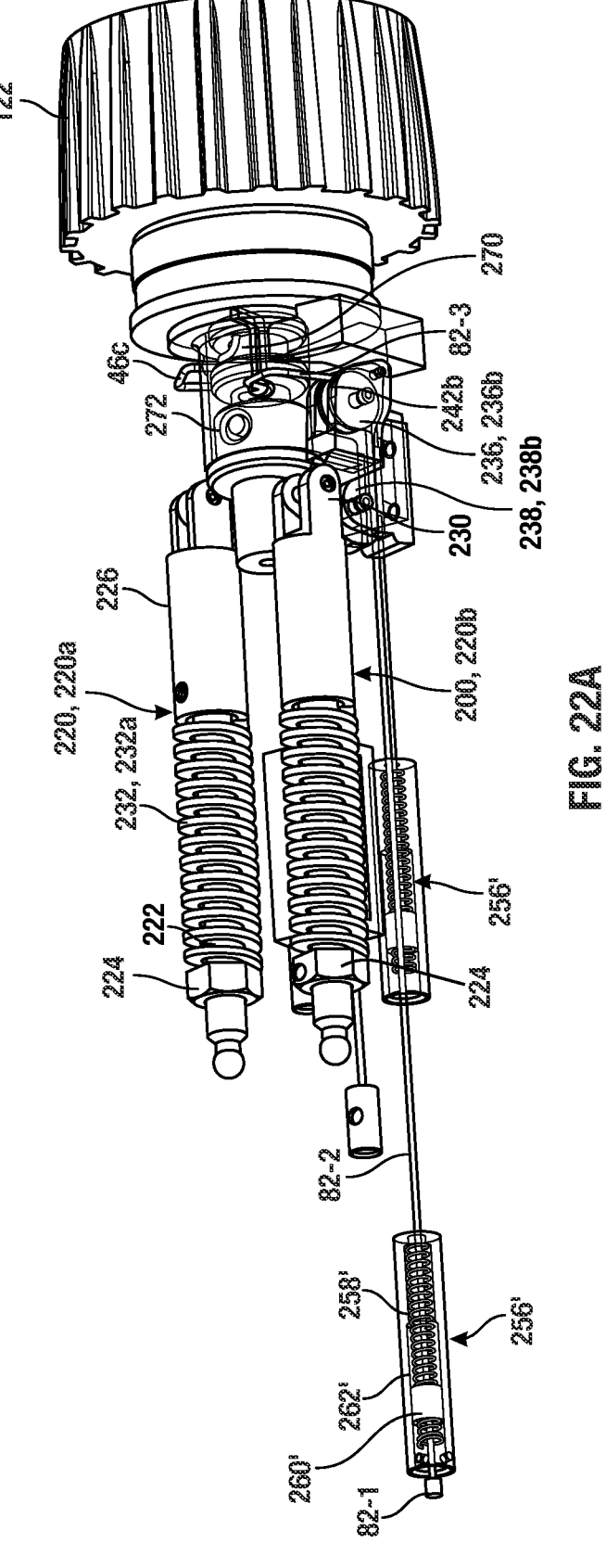
FIGS. 22A-22C is a detail of a portion of the handle including a force limiting mechanism according to FIGS. 21A-21C.
Figure 22B:
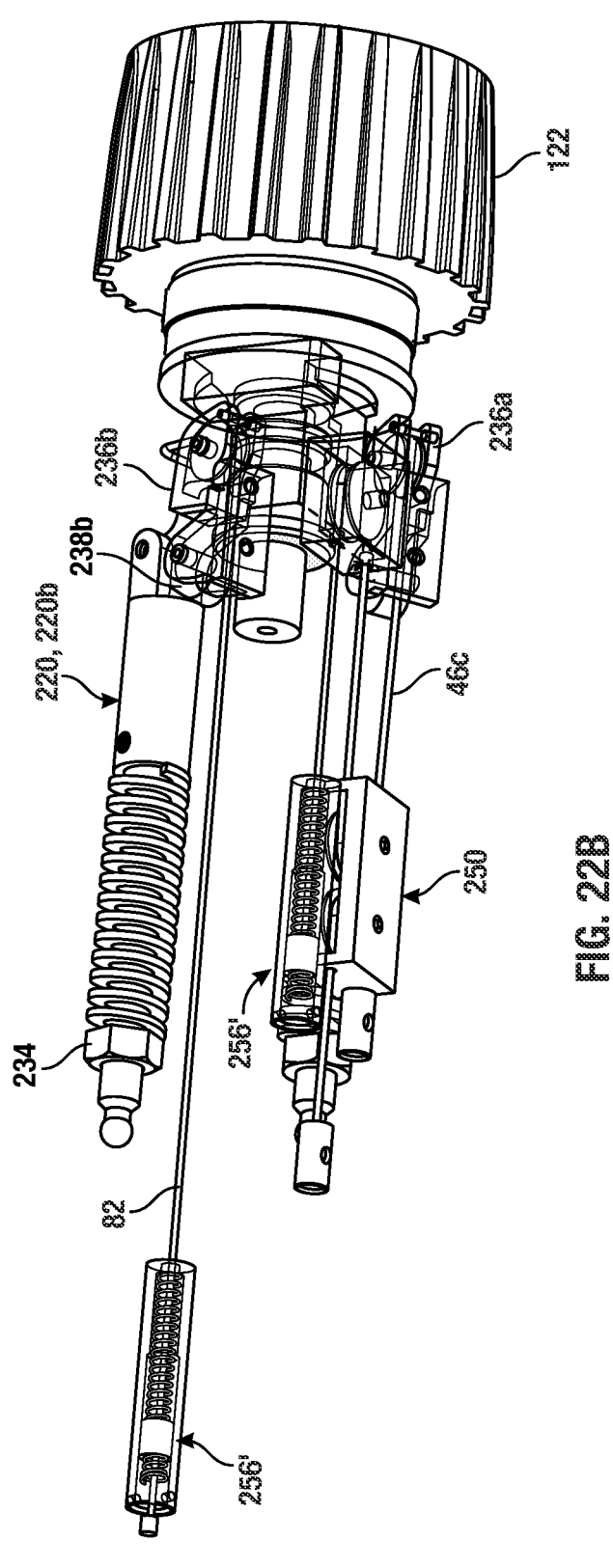
Figure 22C:
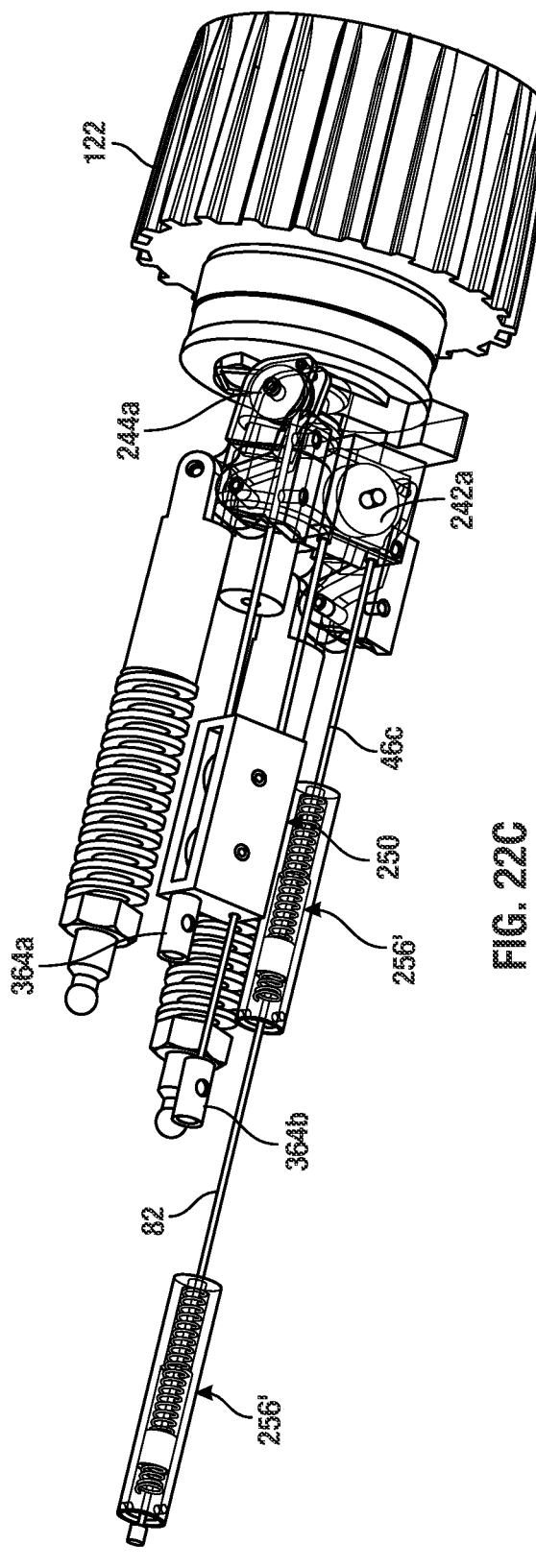

FIGS. 22A-22C illustrate an implementation of the adjustable biasing assembly 220 including a plunger 222 that is axially movable within a cylinder 226. A biasing spring 232 is disposed around the plunger 222, between the adjustment nut 224 and a distal edge of the cylinder 226. The cylinder 226 is attached at an opposite attachment end 230 to the pivoting arm 236, and more specifically to the first end portion 238 (see FIG. 21C) of the pivoting arm 236 of the force limiting mechanism. When a force is applied to pivot the arm 232 toward a pinching position, the arm first end portion 238 pushes the cylinder 226 in a distally oriented direction, toward the adjustment nut 224, to compress the biasing spring 232. The adjustment nut 224 can be preset to a desired position, to preset the resistive force of the spring 232. When force is no longer applied (by the third actuation member 40c or the recompression member 82) on the arm 236, the spring extends and urges the arm 236 back to its released position.

The rotatable knob 122 can be coupled to the expansion reel 270 and the recompression reel 272 such that rotation of the rotatable knob 122 in a specific direction (which can be clockwise or counterclockwise) is translated to rotation of both reels 270, 272 in the same direction, and rotation of the rotatable knob 122 in an opposite direction causes both reels 270, 272 to rotate therewith in the opposite direction. In one example, the third actuation flexible portion 46c and the recompression member 82 are attached to the expansion reel 270 and the recompression reel 272, respectively, from opposite directions (as shown in FIG. 18). When both reels are rotated in a specific direction, for example, in a direction configured to expand the prosthetic valve 60, the third actuation flexible portion 46c is wrapped around the expansion reel 270, while the recompression member 82 is unwrapped from the recompression reel 272. Similarly, when both reels are rotated in an opposite direction, for example in a direction configured to compress the prosthetic valve 60, the recompression member 82 is wrapped around the recompression reel 272, while the third actuation flexible portion 46c is unwrapped from the expansion reel 270.

FIGS. 23A-24C illustrate a force limiting mechanism 634 with an adjustable biasing assembly 620 that can serve as an alternative to the previously described force limiting mechanism 234 with the adjustable biasing assembly 220. The force limiting mechanism 634 includes a base guide member 630. The adjustable biasing assembly 620 includes a plunger 622 having its proximal portion axially movable within a respective bore of the base guide member 630. A distal portion 626 of the plunger 622 is attached to, or integrally formed with, a distal pulley housing 636 having a distal pulley 638 coupled to its interior passageway. The adjustable biasing assembly 620 includes a biasing spring 632 and an adjustment nut 624 disposed around the plunger 622. The biasing spring 632 extends between the base guide member 630 and the adjustment nut 624.

In some examples, the force limiting mechanism 634 further includes a proximal plate 650, which is coupled to, or integrally formed with, the rotatable knob 122, and is configured to rotate therewith. The plate 650 comprises at least one set of circumferential serrated teeth, and the plunger 622 comprises a plunger proximal tooth 628, configured to engage with the serrated teeth. FIGS. 24A-24C shows different views of the proximal plate 650.

In one example, the proximal plate 650 can have two sets of circumferential serrated teeth: outer serrated teeth 652 and inner serrated teeth 654 that is disposed radially inward relative to the outer serrated teeth 652. The force limiting mechanism 634 can have two adjustable biasing assemblies 620a, 620b, as shown in FIG. 23E. The adjustable biasing assembly 620a, which can be configured to cooperate with the third actuation flexible portion 46c, has its plunger proximal tooth 628a radially aligned for engagement with the outer serrated teeth 652. The adjustable biasing assembly 620b, which can be configured to cooperate with the recompression member 82, has its plunger proximal tooth 628b radially aligned for engagement with the inner serrated teeth 654.

Figure 23A:
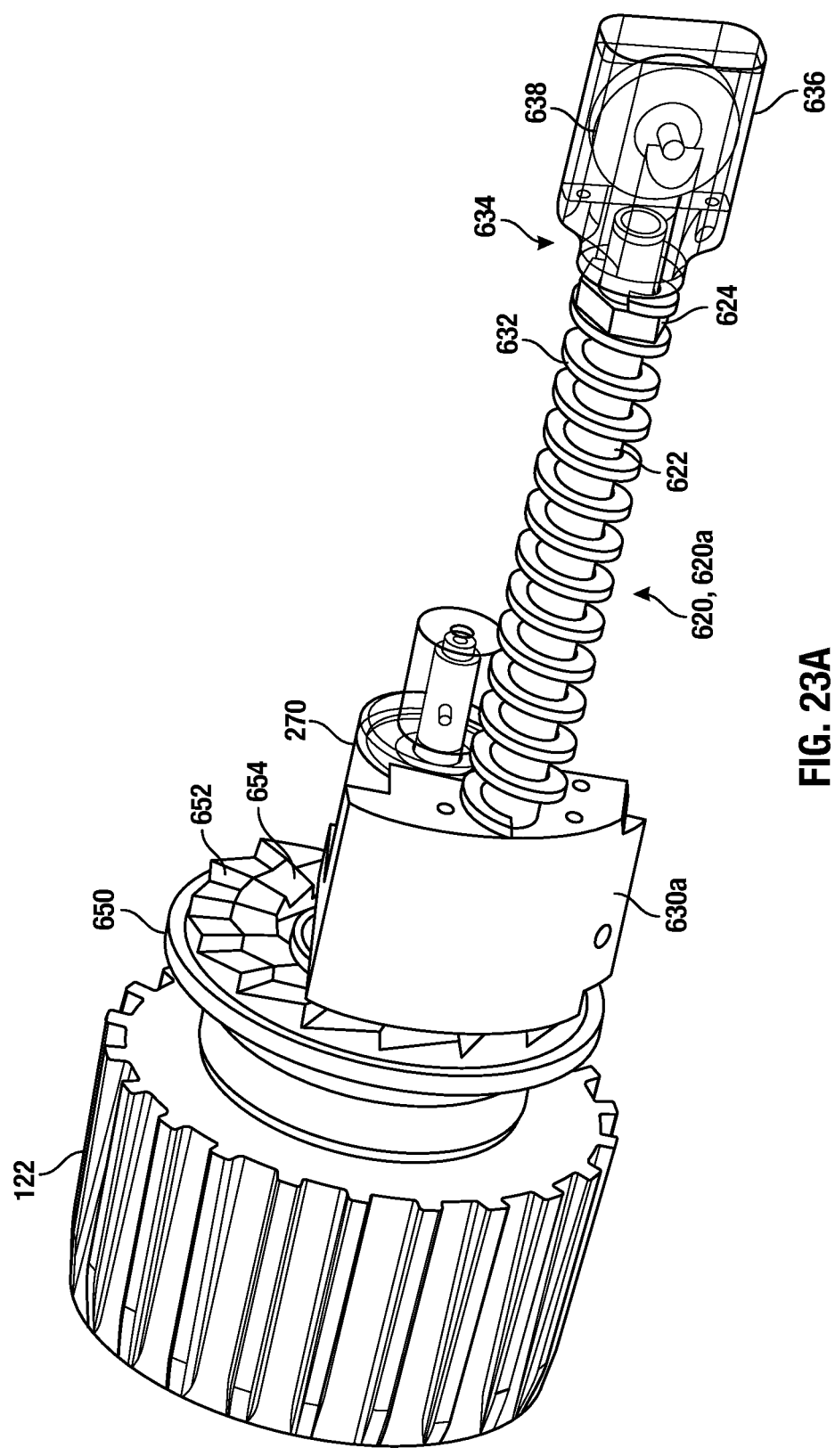
Figure 23B:
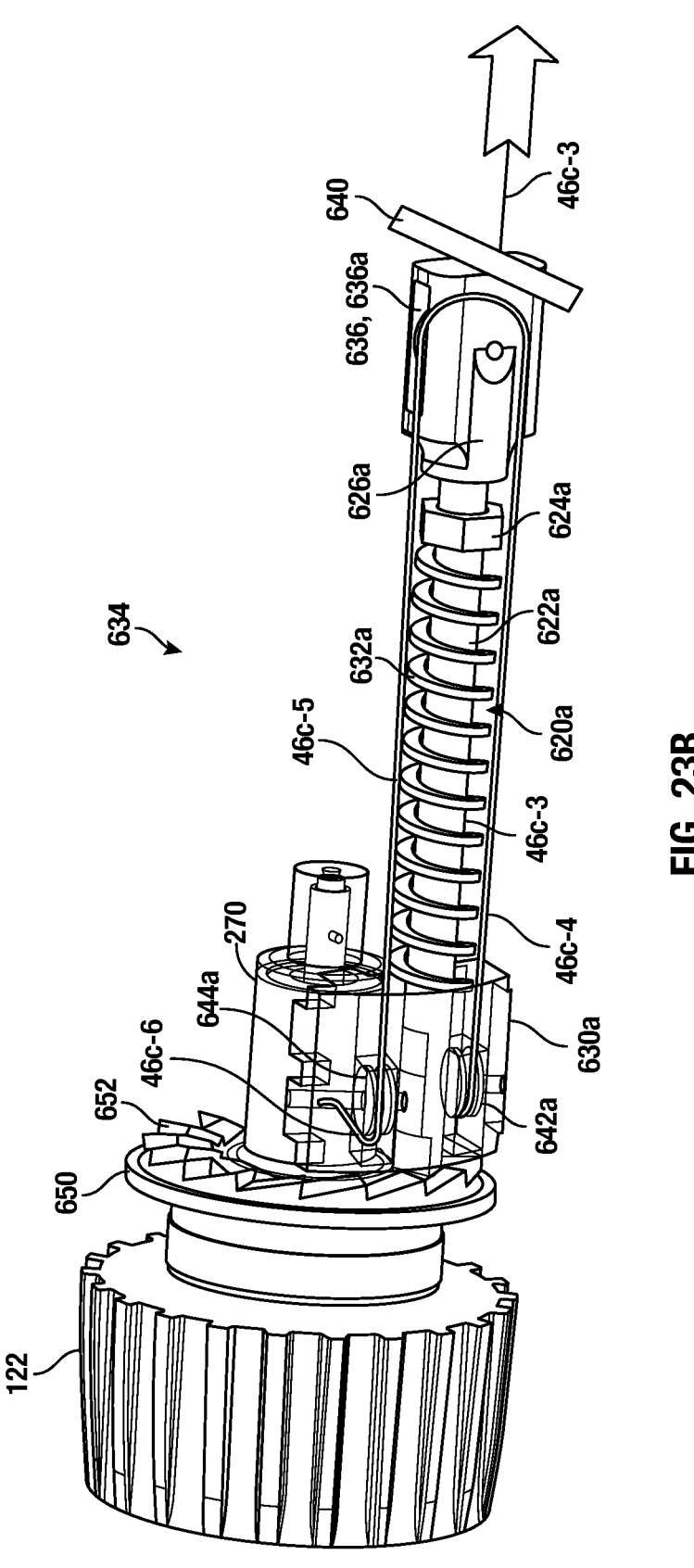
Figure 23C:
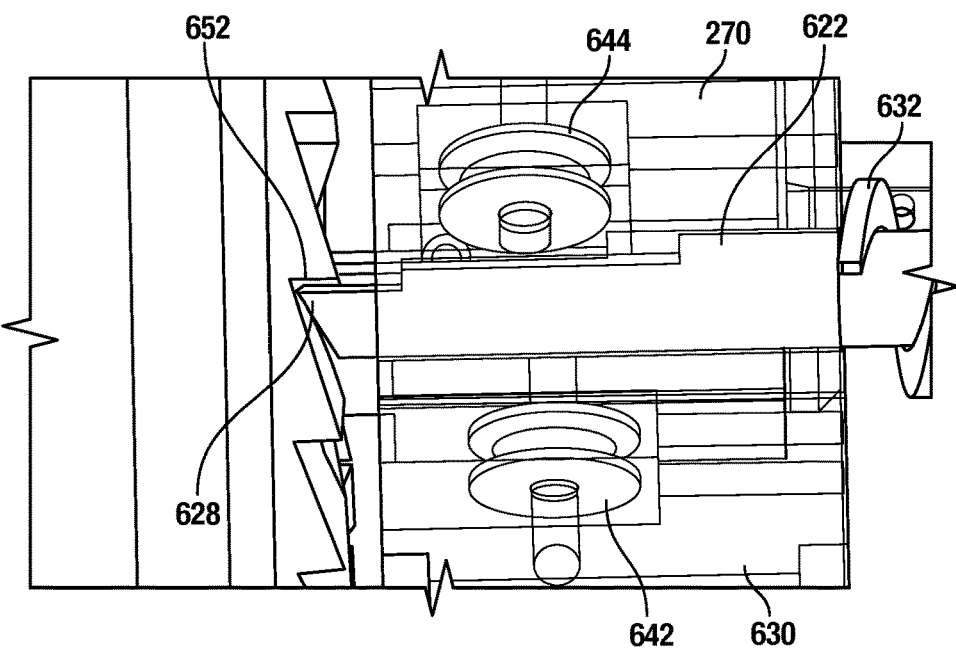
Figure 23D:
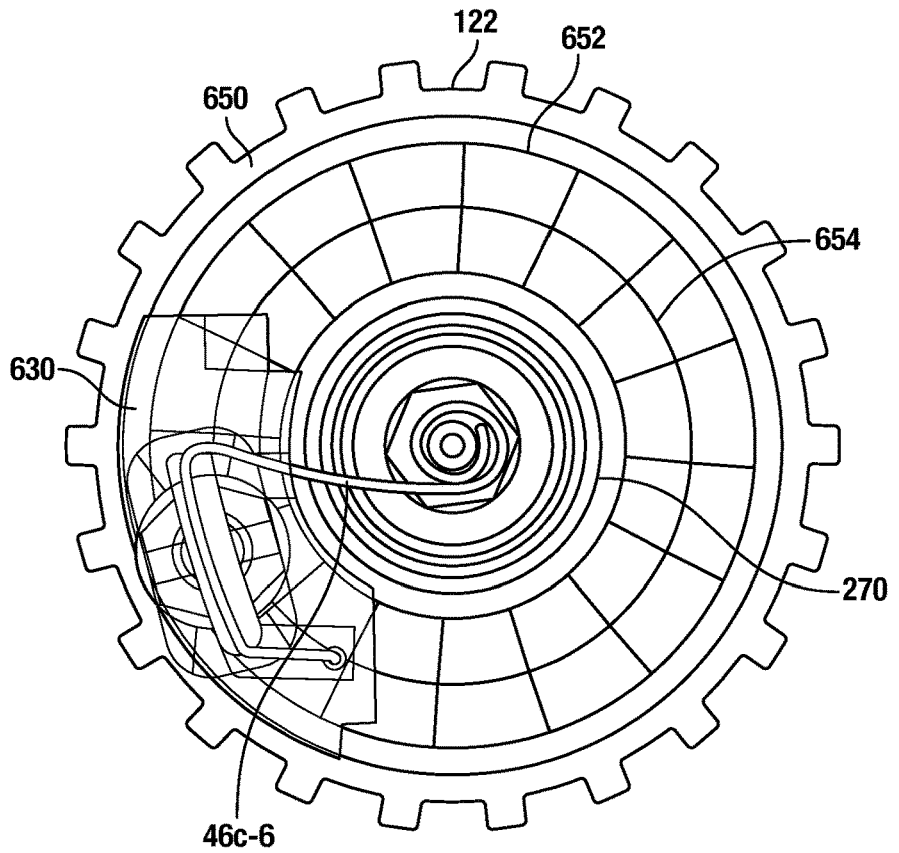
Figure 23E:
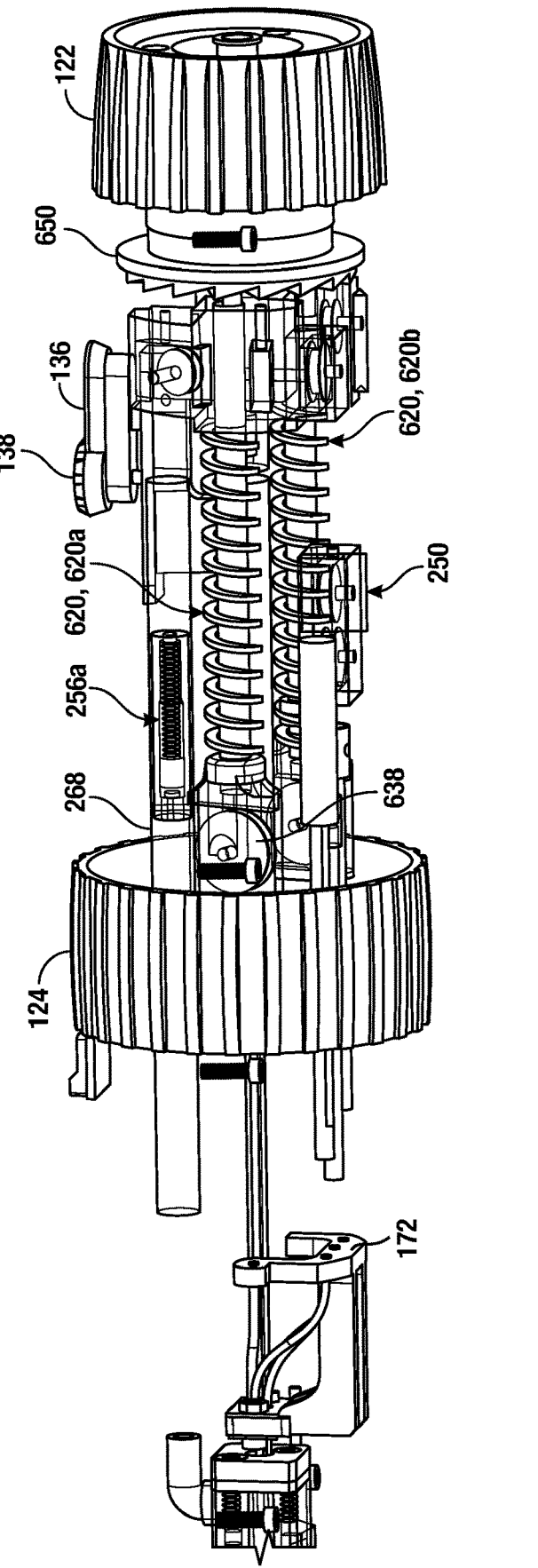
Figure 23F:
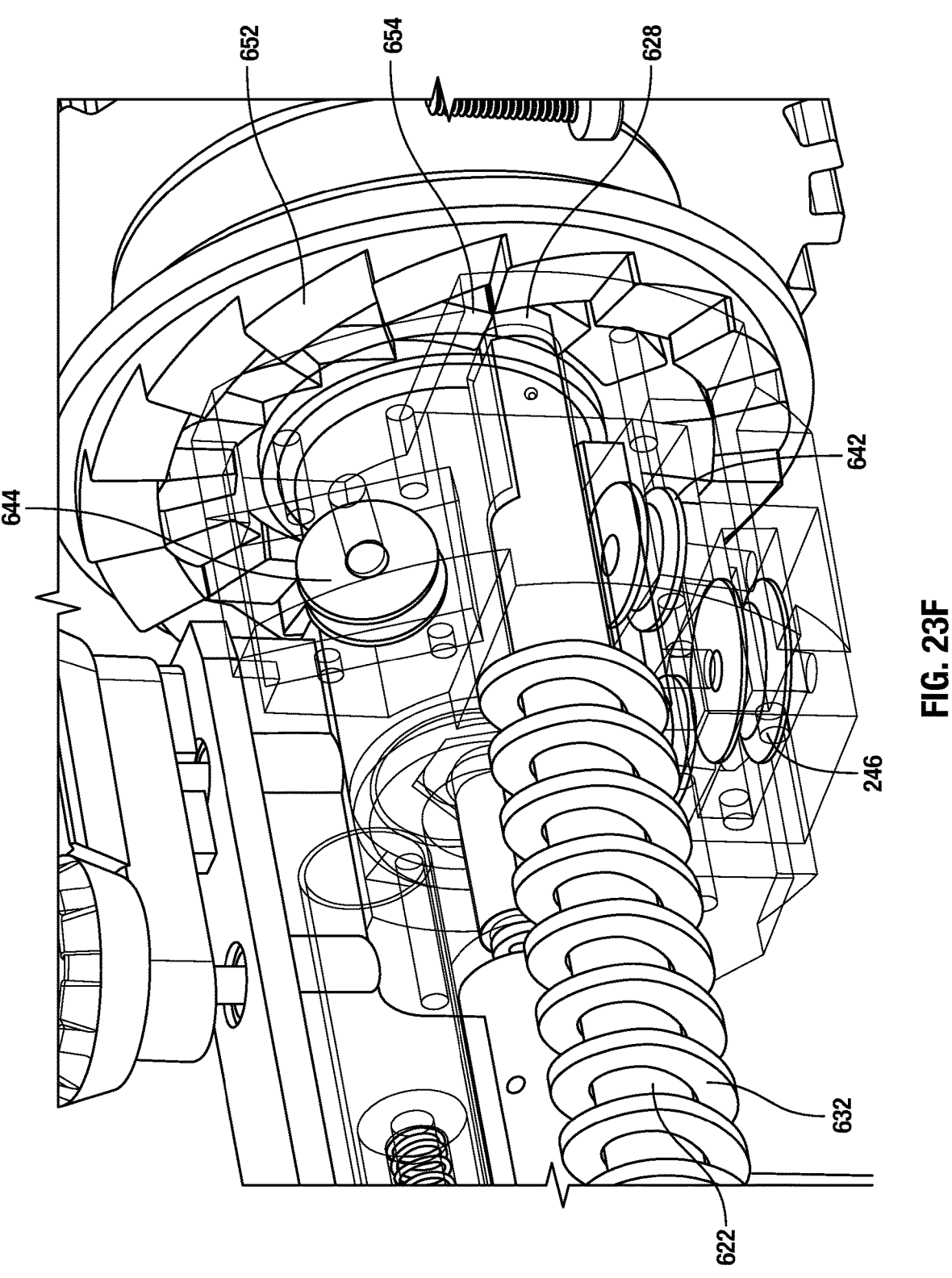

As illustrated in FIG. 23B for the adjustable biasing assembly 620a, the section 46c-3 of the third actuation flexible portion 46c extends proximally from the force balancing assembly 250 (similar to FIGS. 17 and 18), toward and around a reverting pulley 642a, reverting its following extension 46c-4 to the distal direction. The reverting pulley 642a can be coupled, for example, to the base guide member 630a. The following section 46c-4 extends from the reverting pulley 642a, toward and around the distal pulley 238a, reverting its following extension 46c-5 to the distal direction. The following section 46c-5 extends from the distal pulley 238a toward the guide pulley 644a and is partially routed therearound such that the following section 46c-6 extends from the guide pulley 644a to the expansion reel 270.

In use, when the rotatable knob 122 is rotated in a direction configured to promote expansion of the prosthetic valve 60, the section 46c-6 of the third actuation flexible portion 46c wraps around the expansion reel 270, while the following sections 46c-5 and 46c-4 of the third actuation flexible portion 46c extend around the adjustable biasing assembly 620a in a manner configured to pull the plunger 622a proximally toward the plate 650. The plunger proximal tooth 628a is axially offset and distal to the outer serrated teeth 652 when the prosthetic valve 60 is in a compressed state. As the plunger 622a axially translates in the proximal direction during valve expansion, the proximal tooth 628a moves closer to the outer serrated teeth 652 until the proximal tooth 628a is engaged with the outer serrated teeth 652 in a ratcheting manner that prevents further proximal movement of the plunger 622a. This engagement serves to prevent further rotation of the rotatable knob 122 in the same direction, thereby preventing further expansion of the prosthetic valve 60.

The outer serrated teeth 652 are angled to prevent further rotation of the second knob in the same direction (i.e., expansion) when engaged with the plunger proximal tooth 628, but the tooth 628 is allowed to slide along the teeth 652 when the second knob is rotated in an opposite direction (i.e., to recompress the prosthetic valve 60 while releasing the third actuation flexible portion 46c).

The adjustment nut 624 can be preset to a desired position to set the resistive force of the spring 632. When force is no longer applied to the plunger 622 by further rotation or holding in place the second knob 622 (and assuming that the prosthetic valve 60 is not locked in an expanded state by the locker/actuators 62), the spring 632 may extend and urge the plunger 652 back to its released position.

In some examples, the handle can include a distal stop feature 640 (shown in FIG. 23B) positioned distal to the distal pulley housing 636 and immovable relative to the handle. The distal stop feature 640 can be configured to limit the maximum translation of the plunger 622 in a distal direction. In some examples, the plunger 622 can be movable within a channel such that a distal end of the channel serves as the distal stop feature 640.

The function of the adjustable biasing assembly 620b is similar to that of the adjustable biasing assembly 620a, where the recompression member 82 is configured to pull the plunger 222b toward the inner serrated teeth 654 upon rotation of the rotatable knob 122 in a direction configured to recompress the prosthetic valve 60, stopping when the plunger proximal tooth 628b engages the inner serrated teeth 654.

In some examples, the lateral edges of the plunger proximal teeth 628a, 628b are angled so as to properly abut against the serrated teeth 652, 654.

In some cases, the handle 100 can include a mechanism to prevent over-expansion of the prosthetic valve to minimize the risk of annulus rupture or damage to the surrounding anatomy.

FIGS. 25A-25C illustrate an exemplary valve expansion limiting mechanism 400 including a primary gear 420 having external gear teeth and a secondary gear 422 having external gear teeth that interconnects with the external gear teeth of the primary gear. The primary gear 420 is coupled to the rotatable knob 122 and rotates with the rotatable knob 122. The secondary gear 422 comprises a threaded bore. A rod 424 is threadedly engaged with the threaded bore such that when the primary gear 420 rotates in a direction to pull the third actuation member 40c, the secondary gear 422 rotates in an opposite direction, which is translated to an axial displacement of the rod 424 in the proximal direction. A proximal portion of the rod 424 is threaded along a length sufficient for the required range of its axial displacement. The rod 424 comprises a radially extending tab 426, which extends through a longitudinal slot 428 of the handle 100. Therefore, the tab 426 is guided along the slot 428 in a proximal direction during retraction of the actuation member 40c.

The valve expansion limiting mechanism 400 can further include a slidable knob 430 that is configured to slide along a lateral slot 432 such that at a first position the knob 430 does not overlap the longitudinal slot 428 and at a second position (shown in FIG. 25A), the knob 430 overlaps the longitudinal slot 428. When the knob 430 is positioned in the first position, the tab 426 is free to move axially in the proximal direction, towards a proximal end 104 of the handle 100, along the entire path defined by the slot 428. When the knob 430 is in the second position, the knob 430 obstructs the path defined by the slot 428 such that the tab 426 can move axially only until the tab 426 contacts the knob 430. At this point, any further movement of the tab 426 in the same direction is obstructed the knob 430. As the tab 426, and the attached rod 424, halt and cannot move further in the proximal direction beyond the position in which the tab 426 abuts the knob 430 in the second position, the rest of the components involved in the movement transmission, including the secondary gear 422 and the primary gear 420, halt as well, therefore preventing further retraction of the third actuation member 40c. When the third actuation member 40c halts, the prosthetic valve 60 is prevented from expanding any further. Thus, the position of the knob 430 defines the maximal allowed expansion of the valve 60. If the user desires further expansion of the valve, the user can slide the knob 430 manually to the first position.

The valve expansion mechanism 400 can further include a clicking sound mechanism that produces a clicking sound in response to movement of the knob 430 from the first position to the second position. As shown in FIGS. 25B and 25C, the clicking sound mechanism can include a stationary member 438 having an axial protrusion, for example in the form of a dimple, in front of a base member 434 of the knob 430. The base member 434 can be provided with two notches 436. The clicking sound is made when the knob 430 slides along with the base member 434 from one position to another and the protrusion of the stationary member 438 flexibly moves over the corresponding notches 436.

Figure 26A:
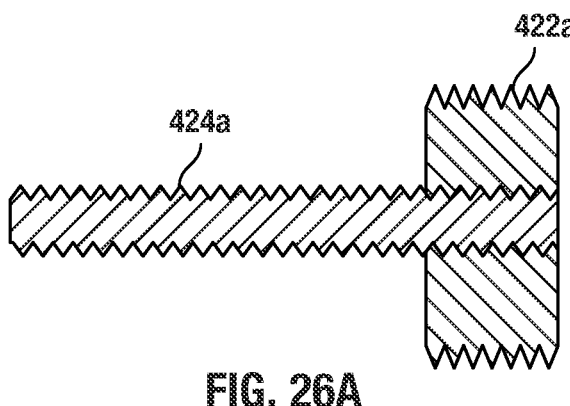
FIGS. 26A-26C illustrate another implementation of a valve expansion limiting mechanism for the handle.
Figure 26B:
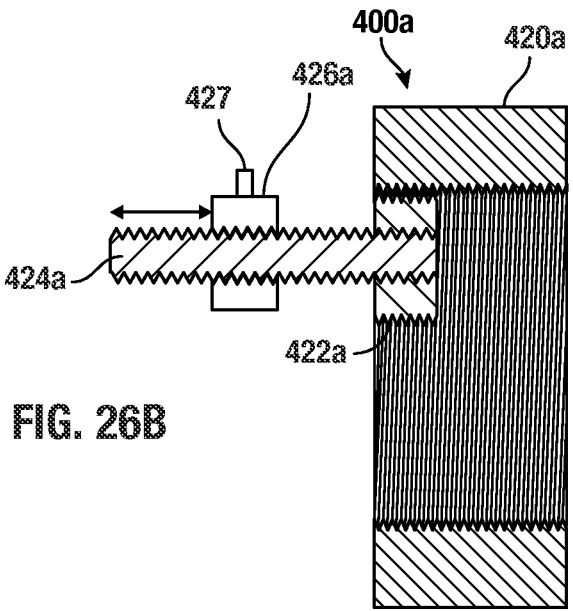
Figure 26C:
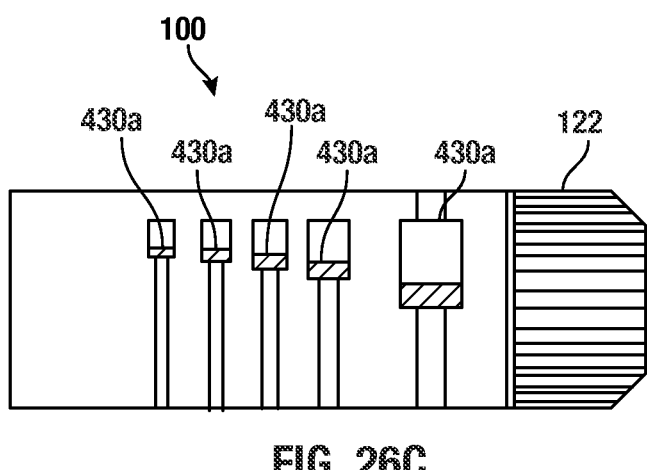

FIGS. 26A-26C illustrate an alternative valve expansion limiting mechanism 400a where the primary gear (420 in FIGS. 25A and 25B) with the external gear teeth is replaced by an internally threaded nut 420a that is configured to threadedly engage with a proximal threaded portion 422a of the rod 424a. Rotation of the nut 420a during retraction of the third actuation member 40c is translated, via the proximal threaded proximal portion 422a of the rod 424a, to an axial movement of the tab 426a to perform in an otherwise similar manner as described above with reference to FIGS. 25A and 25B.

In one example, the tab 426, 426a is detachably attachable to the rod 424, 424a such that it can be positioned at different positions along the length of the rod 424, 424a. As shown in FIG. 26B, the tab 426a can be attached to the rod 424a by a set screw 427. If it is desired to set the maximum expansion allowable by the mechanism to a higher value, the set screw 427 can be released so that the tab 426a can be displaced axially to a more distal position and then reattached to the rod 424a at the new position by screwing the set screw 427a. If it is desired to set the maximum expansion allowable to a lower value, the same procedure can be performed, positioning the tab 426a at a more proximal position along the rod 424a. The same procedure can be also performed for re-calibrating the mechanism to adapt to different valve sizes.

According to some examples, the handle 100 can include a plurality of knobs axially spaced from each other. FIG. 26C shows a series of knobs 430a slidable within respective lateral slots. The position of each knob 430a corresponds to a different expansion diameter. The knobs 430a can serve as switches that allow a single handle to be used with different valve sizes or according to the anatomy of different patients. For example, a clinician can slide the knob 430a having the desired maximum expansion limit to the second position while keeping the remaining knobs 430a at rest at the first position. Such a configuration can be also used to provide an expansion fine-tuning capability, where several knobs 430a can be positioned at the second position, enabling the clinician to slide each of the knobs 430a to the first position to allow further expansion of the valve.

The handle 100 can include a status indicator mechanism to provide indication regarding the valve expansion diameter.

An exemplary status indicator mechanism 450 is shown in FIGS. 27A-28C. The mechanism 450 is shown in a first state in FIGS. 27A-27C and in a second state in FIGS. 28A-28C. In some examples, the first state can be a state in which the prosthetic valve 60 is compressed, and the second state can be a state in which the prosthetic valve 60 is fully expanded, such that any transitional state between the first and second states is indicative of the current valve diameter.

Figures 27A, 27B:
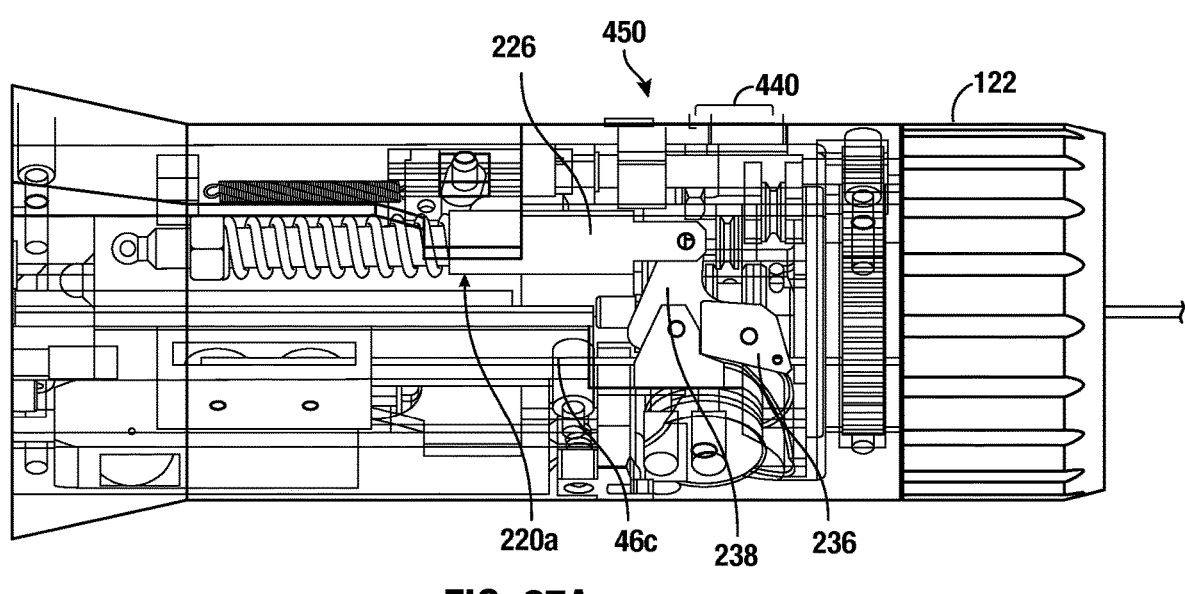
FIGS. 27A-28C are portions of a handle illustrating a status indicator mechanism.
Figure 27C:
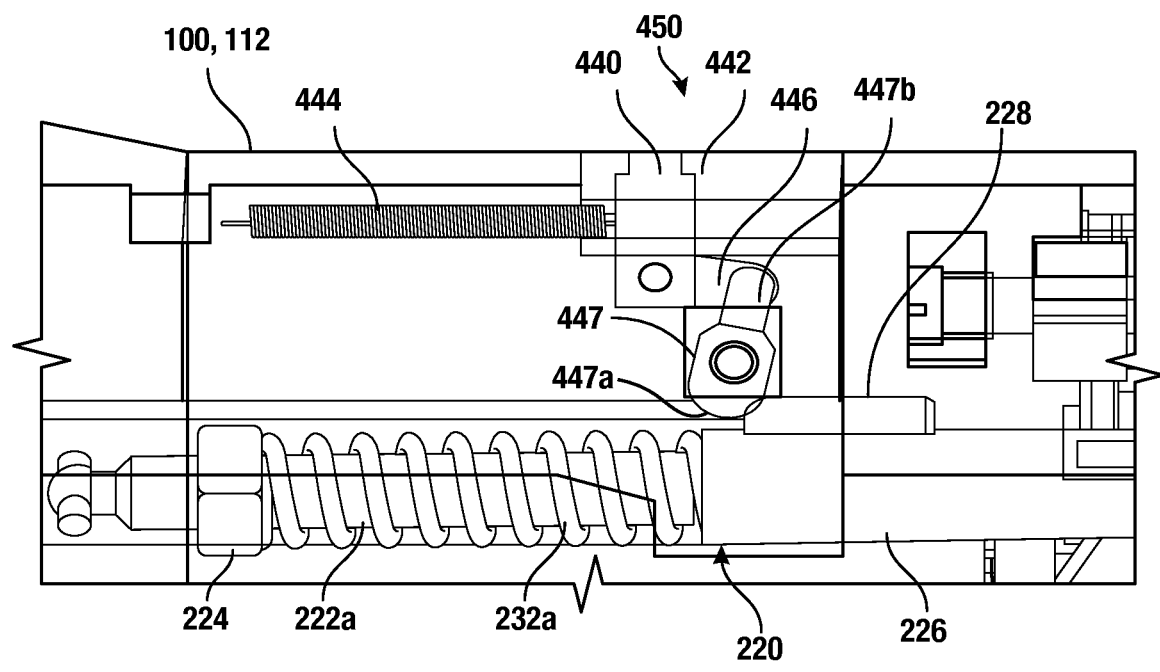

Referring to FIGS. 27A-27C, the status indicator mechanism 450 can include a radial extension 228 (shown in FIG. 27C) extending outwardly from the cylinder 226 (see FIGS. 22A-22C) of the adjustable biasing assembly 220 (see FIGS. 22A-22C). The status indicator mechanism 450 can further include a pivoting member 447 (shown in FIG. 27C) configured to pivot around a hinge fixedly attached to the handle 100 (e.g., to the proximal portion 112). The status indicator mechanism 450 can include an indication tab 440 and a transmission arm 446.

The pivoting member 447 comprises a first portion 447a (lower portion in FIG. 27C) configured to contact the radial extension 228 at least during a second state of the status indicator mechanism and a second portion 447b (upper portion in FIG. 27C) rotatably connected to the transmission arm 446. The transmission arm 446 is connected at its opposite end to the indication tab 440, which can be formed, for example, as a slidable knob. The indication tab 440 is configured to axially slide within a slot 442 of the handle 100, such that the position of the indication tab 440, between a slot distal and proximal ends, is visible through the slot 442 to an operator or user of the device.

The status indicator mechanism 450 can include a tab spring 444, which is connected to the indication tab 440 at its proximal end and to the handle 100 at its distal end. The tab spring 440 is an extension spring, shown in a free compressed state when the status indicator mechanism is in the first state as shown in FIGS. 27A-27C.

Figure 28A:
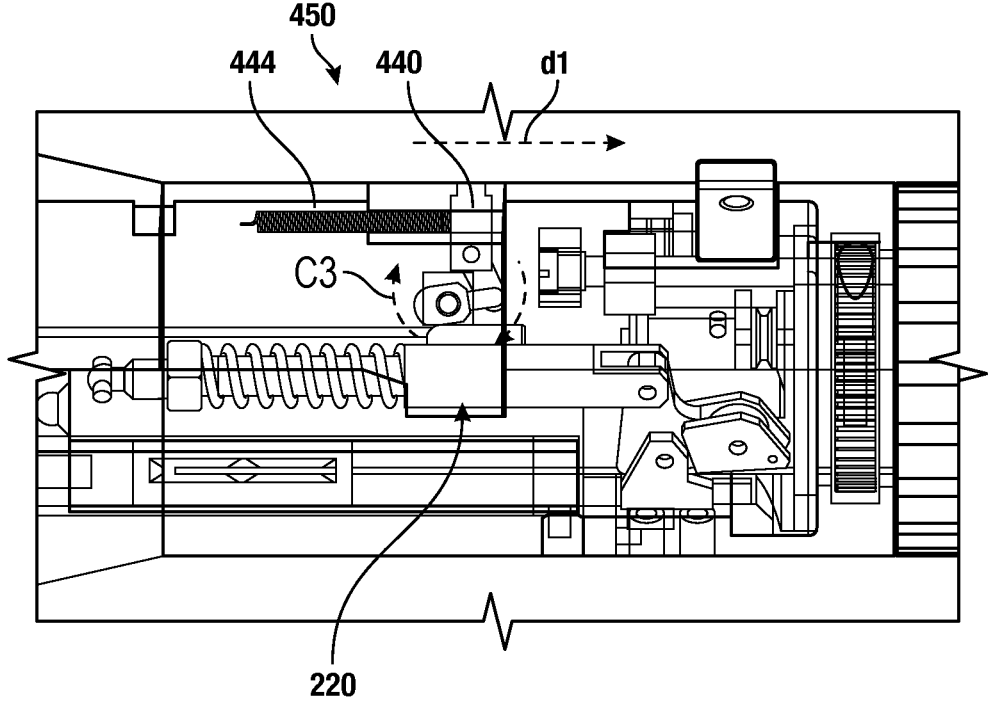
Figure 28B:
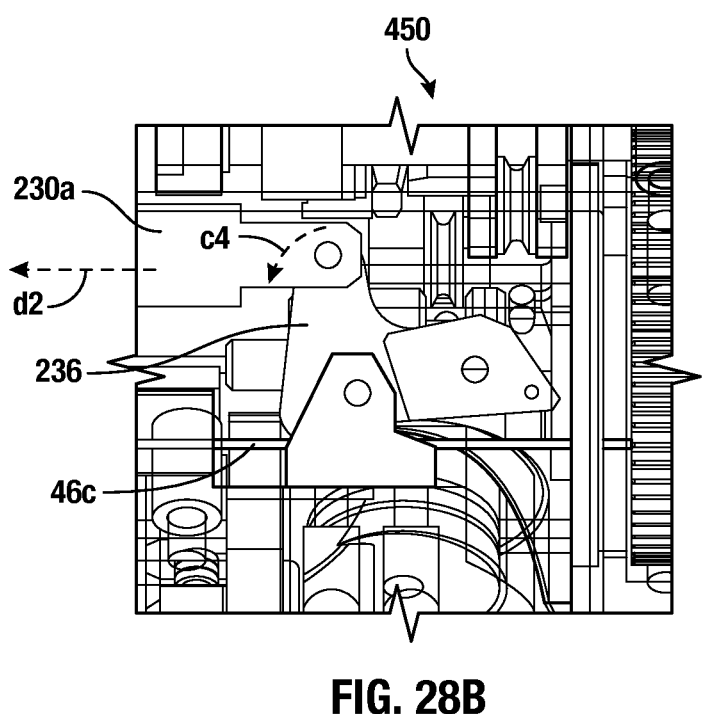
Figure 28C:
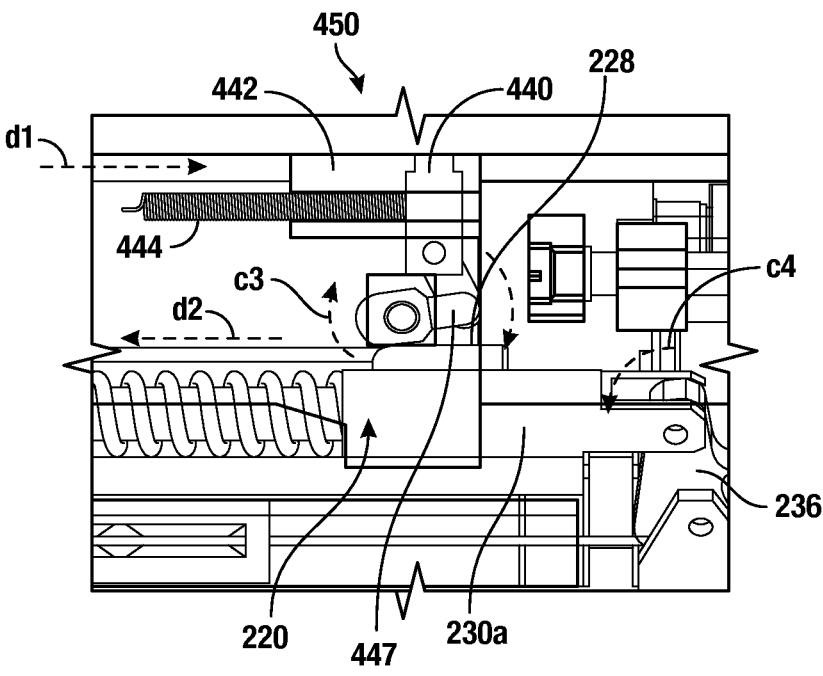

FIGS. 28A-28C show the status indicator mechanism 450 in a second state. When the third actuation member 40c is pulled in the proximal direction d1, the pivoting arm 236 rotates around its hinge 128 in the direction c4. The rotation of the arm first end portion 236 in direction c4 translates to axial movement of the cylinder 226 in the distal direction d2, acting to compress the spring 232.

The pivoting member 447 is positioned such that its lower portion 447a (shown in FIG. 27C) is configured to slide over the radial extension 228 (shown in FIG. 27C) when the cylinder 226 translates in a distal direction d2 during transition from the first state (FIGS. 27A-27C) to the second state (FIGS. 28A-28C). As a result, the pivoting member 447 rotates around its hinge such that its upper portion rotates in the direction c3, pulling the transmission arm 446 therealong. The transmission arm 446 translates the rotational movement of the pivoting member 447 to an axial movement of the indication tab 440, which is pulled axially in the proximal direction d1 toward the proximal end of the slot 442.

When the third actuation member 40c is released, the spring 444 returns to its extended state, such that the lower portion of the pivoting member 447 no longer abuts the outer edge of the radial extension 228, thereby releasing the indication tab 440. The tab spring 444 returns to its free compressed state, pulling the indication tab 440 there along toward the distal end of the slot 442, such that the status indicator mechanism returns to the first state of FIGS. 27A-27C.

In some examples, the handle 100 can include markings within or in the vicinity of the slot 442 to provide easy visual indication of the safe or unsafe ranges such that the clinician may compare the current position of the indication tab 440 with such markings.

Figures 29A, 29B:
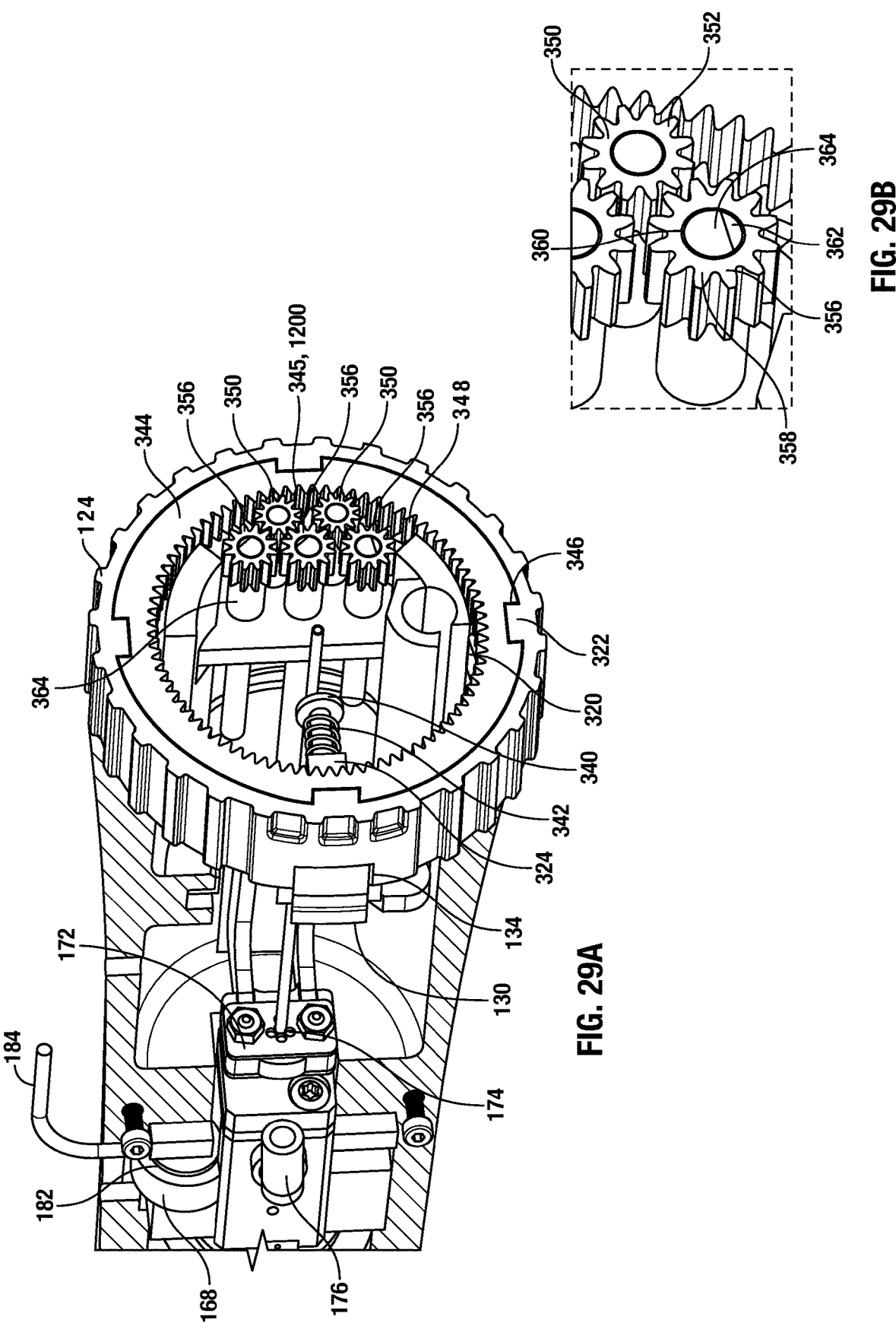
FIG. 29A is a detail of a handle illustrating coupling of a knob to a gear train.
FIG. 29B is a detail of the gear train shown in FIG. 29A.

FIGS. 29A and 29B illustrate a portion of a third mechanism 1200 (i.e., actuation release mechanism) that can be controlled by the rotatable knob 124 of the handle. As shown, the third mechanism 1200 can include a gear train 345 that is driven by the rotatable knob 124.

In one implementation, the gear train 345 includes an annular driver gear 344 and one or more driven pinion gears 356 (e.g., three pinion gears). The gear train 345 may further include one or more idler gears 350 (e.g., two idler gears). The rotatable knob 124 can be attached to the annular driver gear 344 such that rotation of the rotatable knob 124 in a first direction causes rotation of the annular driver gear 344 in the same direction. The rotatable knob 124 can include projections 322 extending radially inward. The annular driver gear 344 can include recesses 346 that receive and mate with the projections 322.

The annular driver gear 344 can include driver gear inner teeth 348 that mesh with idler gear teeth 352 of idler gears 350. The idler gear teeth 352 can in turn mesh with pinion gear teeth 358 of the pinion gears 356. The annular driver gear 344 can be meshed with, and configured to drive, two idler gears 350. One of the two idler gears 350 can be meshed with, and configured to drive, a single third pinion gear 356, while the other idler gear 350 is meshed with, and configured to drive, a single third pinion gear 356. While two idler gears 350 are shown for illustrative purposes, any number of idler gears may be used to translate rotational movement of the annular driver gear 344 to the pinion gears 356. In other examples, the idler gears 350 may be omitted and the pinion gears 356 can be designed to directly contact and mesh with the driver gear teeth 348.

Each pinion gear 356 can include a pinion gear bore 360 that is configured to receive an actuation tube 364 therein. In one example, the gear bore 360 can have a non-circular profile that is adapted to match with a non-circular profile of a portion of the actuation tube 364 extending therethrough. For example, the gear bore 360 may have a flat edge 362. The non-circular profile of the portion of the actuation 364 can allow the torque shaft to freely move axially in a proximal or distal direction relative to the pinion gear 356. At the same time, as the pinion gear 356 is driven by the driver gear 344, the actuation tube 364 rotates in the same direction as the pinion gear.

When the rotatable knob 124 is rotated in a first direction (which can be clockwise or counterclockwise), all three actuation tubes 364 are rotated via the gear train (i.e., via the drive gear 344, the idler gears 350 and the driven pinion gears 356). Since the actuation member torque transmitting portions 42 are attached to the actuation tubes 364, the actuation member torque transmitting portions 42 are rotated around their respective central axes, transmitting the rotational movement to their respective distal threaded heads 44, which may be unthreaded and disengaged from the rack member 68.

The safety knob 130 (see FIG. 11) can be configured to slide into a recess 134 within the rotatable knob 124. When the safety knob 130 is disposed within the recess 134, rotation of the rotatable knob 124 is prevented. This serves as a safety measure to prevent unintentional release of the delivery apparatus from the prosthetic valve. Once the prosthetic valve is sufficiently expanded, the safety knob 130 can be pushed along the slot 132 (shown in FIG. 11), away from the recess 134, to enable manual rotation of the third knob 134.

In some cases, rotation of the rotatable knob 124 in a first direction is translated to rotation of each of the actuation torque-transmitting portions 42 about their respective longitudinal axes, enabling the actuation torque-transmitting portions 42 to disengage from the prosthetic heart valve, while rotation of the rotatable knob 124 in a second direction that is opposite to the first direction is prevented. This can advantageously avoid damage that might otherwise result from over-tightening the distal threaded heads 44 due to accidental rotation of the rotatable knob 124 in the wrong direction.

Figure 30A:
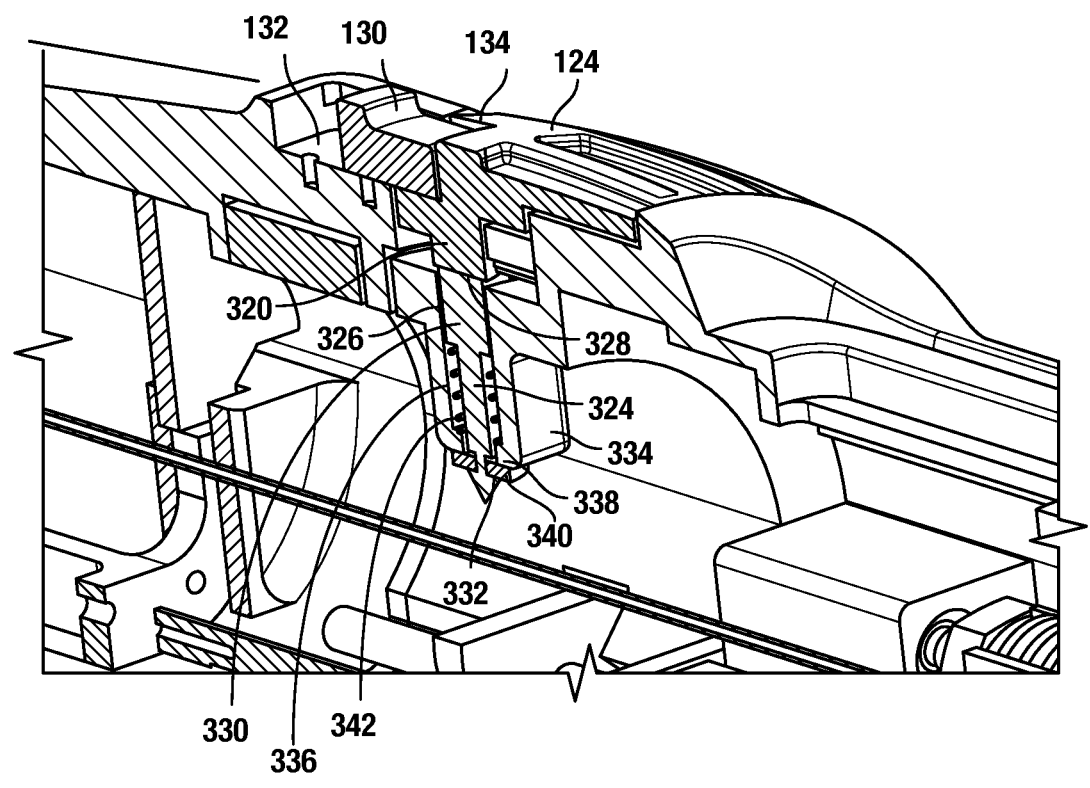
FIGS. 30A and 30B are details of a handle illustrating a ratcheting mechanism configured to limit the rotation of a knob to one direction.
Figure 30B:
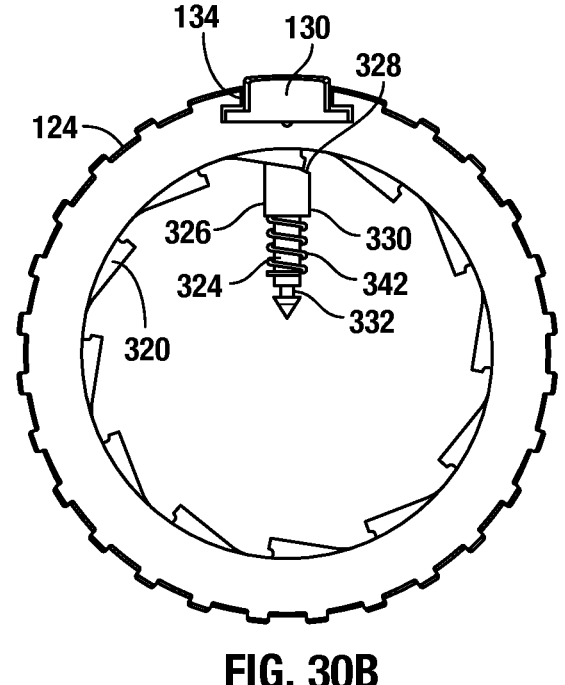

A ratcheting mechanism can be provided that allows the rotatable knob 124 to rotate in only one direction. Referring to FIGS. 30A and 30B, in one implementation, the ratcheting mechanism can include a pawl member 324 that is spring-biased against inner teeth 320 of the rotatable knob 124. The pawl member 324 can be retained within a channel 336 of a pawl member housing 334. The pawl member 324 may include an outward portion 326 configured to press against the inner teeth 320 of the rotatable knob 124. The outward portion 326 extends between an outward end 328, which is configured to contact the inner teeth 320, and a pawl member shoulder 330 formed at the opposite end thereof.

As shown in FIGS. 30A and 30B, the opposite end portion of the pawl member 324 extends radially out of the channel 336 and housing 334. The opposite end portion of the pawl member 324 can include a circumferential groove 332 configured to receive a fastener such as a disc 340. The pawl member housing 334 can include a ridge 338 at its radially innermost end extending toward the pawl member 324 such that the fastener 340 can abut or be pressed against the ridge 338. While the fastener 340 is shown in the illustrated example as a disc, it will be clear that a variety of other fasteners may be utilized, such as a cotter pin and the like. In one example, the ridge 338 can be formed by a bent end of the pawl member housing 334, as shown in FIG. 30A.

A pawl spring 342 can be positioned over the pawl member 324, between the housing ridge 338 and the pawl member should 330, to constantly bias the outward portion 326 against the third knob inner teeth 320. As shown in FIG. 30B, the inner teeth 320 of the rotatable knob 124 may be inclined in a specific direction, and the outward end 328 of the pawl member 324 may be similarly inclined, such that the rotatable knob 124 may freely rotate in a counterclockwise direction with the outward end 328 of the pawl member 324 pressed against and sliding over the inner teeth 320 during such rotation. However, rotation of the rotatable knob 124 in an opposite, clockwise direction, having the short edge of an inner tooth 320 pressed against a sidewall of the outward end 328 of the pawl member 324.

FIGS. 31A-33B illustrate a mechanism 300c that can be included in the handle 100. The mechanism 300c is configured to control axial displacement of the actuation members 40 and simultaneously disengage the actuation members 40 from the prosthetic valve 60. The mechanism 300c includes a central pull cable 48c that can be pulled in a proximal direction d1 by rotating the rotatable knob 122 (see FIG. 11) of the handle. The central pull cable 48c is coupled to a drag member 280c, which is coupled to the actuation members 40 such that axial movement of the central pull cable 48c is translated to axial displacement of the actuation members 40. The mechanism 300c includes a gear assembly 301c comprising an annular driver gear 344c that can be rotated by the rotatable knob 124 (see FIG. 11) of the handle and driven pinion gears 356c that are engaged with the annular driver gear 344c. The actuation members 40 are coupled to the driven pinion gears 356c such that rotation of the annular driver gear 344c results in simultaneous rotation of the actuation members 40.

Figure 31A:
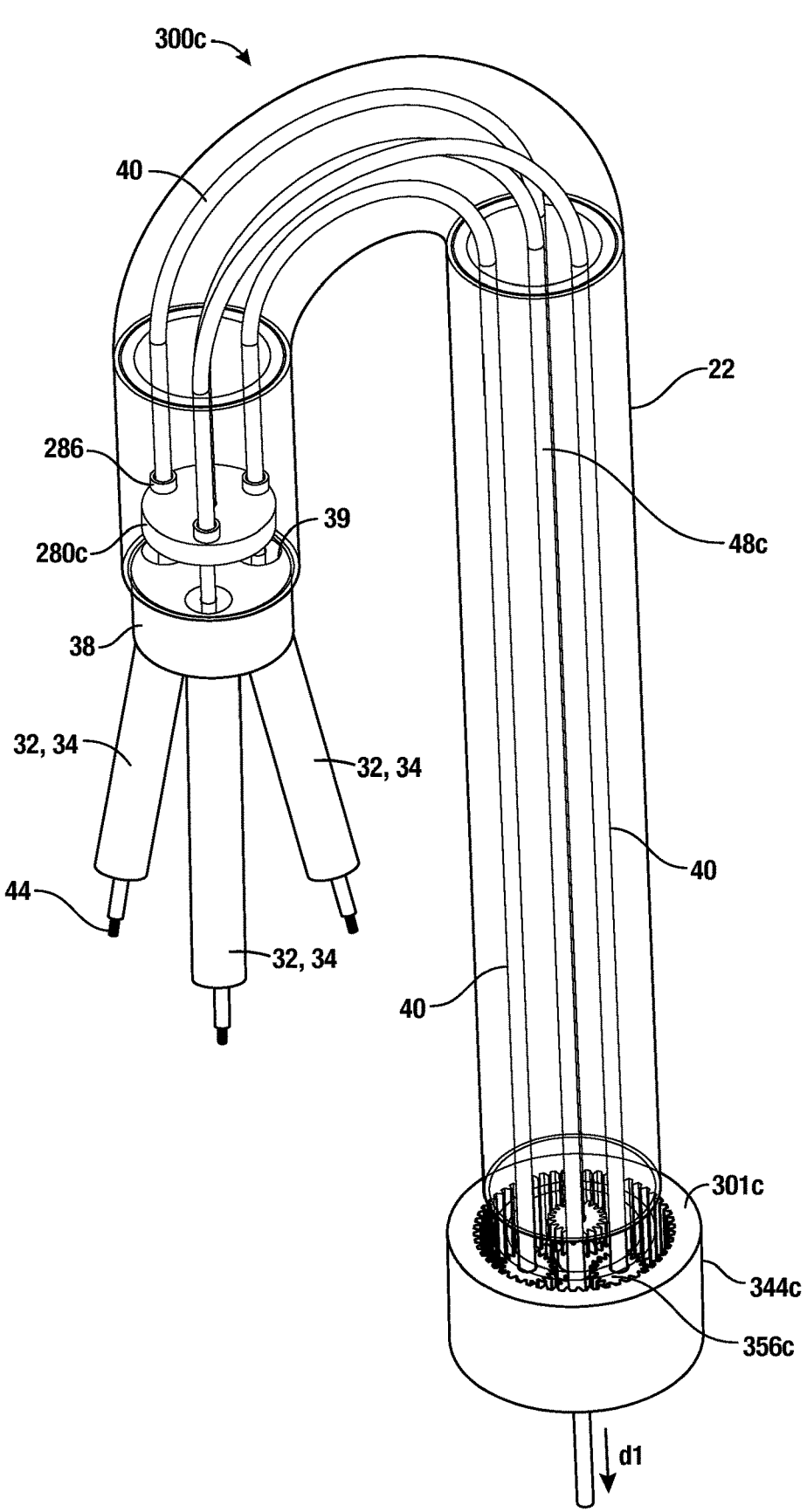
FIG. 31A illustrates a portion of a delivery apparatus with a mechanism for pulling actuation members, according to one example.
Figure 31B:
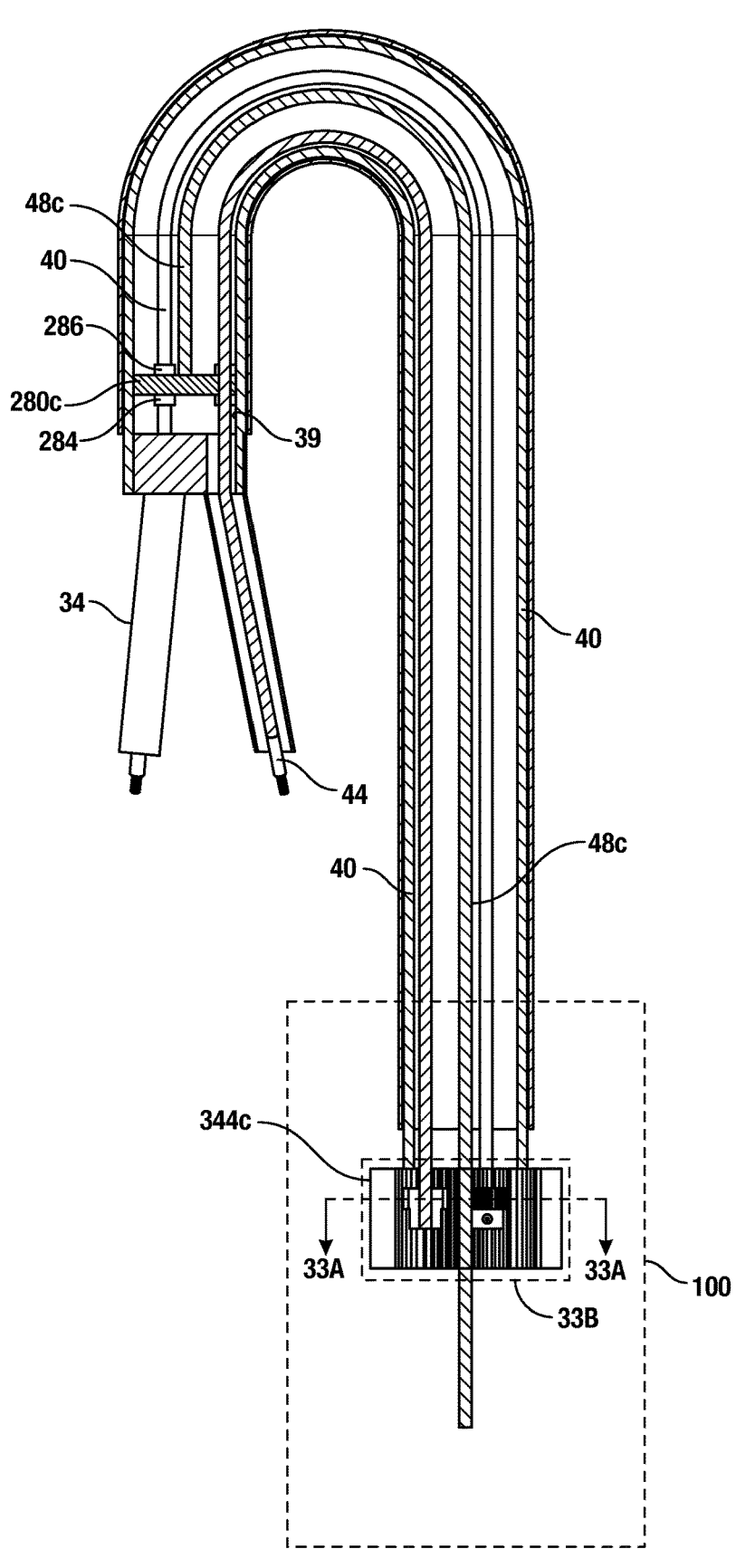
FIG. 31B is a cross-sectional view of the portion of the delivery apparatus shown in FIG. 31A.

The multi-lumen shaft 22 includes a sleeve coupler 38 at its distal end (it should be noted that the multi-lumen shaft 22 is shown as transparent in FIG. 31A for purposes of illustration). Proximal portions of the sleeve members 34 of the actuation assemblies 32 are coupled to the sleeve coupler 38. In the illustrated example, the sleeve coupler 38 has a cylindrical or disc shape. In other examples, the sleeve coupler 38 can have various other shapes (e.g., cube, prism, and the like). The sleeve coupler 38 includes a plurality of openings 39 extending axially through the coupler. The actuation members 40 extend through the respective sleeve members 34 and through respective openings 39 into the multi-lumen shaft 22. The openings 39 are configured such that the actuation members 40 can extend through and rotate freely relative to the sleeve coupler 38.

The drag member 280c is disposed within the multi-lumen shaft 22 (e.g., proximate to the distal end of the multi-lumen shaft 22) and is axially movable within the distal portion of the multi-lumen shaft 22. In some examples, the drag member 280c can be disc-shaped. In some examples, the sleeve coupler 38 can prevent displacement of the drag member 280c out of the distal end of the multi-lumen shaft 22.

The central pull cable 48c extends through a lumen of the multi-lumen shaft 22 (e.g., the central pull cable 48c can extend generally in parallel to the actuation members 40c) into a proximal portion of the cavity defined within the handle. The distal end portion of the central pull cable 48c is coupled to the drag member 280c such that axial movement of the central pull cable 48c can be translated to an axial movement of the drag member 280c. The central pull cable 48c is configured to be pulled via rotation of the rotatable knob 122 (shown in FIG. 11) of the handle. For example, the mechanism previously shown in FIG. 18 can be modified such that the central pull cable 48c is attached to the expansion reel 270 and configured to wrap around the expansion reel 270, replacing the third actuation flexible portion 46c.

The central pull cable 48c can be in the form of any flexible member known in the art, such as a cable, a string, a rope, and the like. When the central pull cable 48c is used in the displacement control mechanism, the actuation members 40 do not need to include an actuation member flexible portion as previously described. Instead, the entire length of each actuation member 40 can be in the form of a single torque-transferring portion.

The drag member 280c includes a plurality of drag member apertures 282c. Each actuation member 40 can extend through a respective aperture 282c. In some examples, each actuation member 40 is free to rotate around its axis of symmetry within the respective aperture 282c but cannot translate in the axial direction therethrough. In some examples, each actuation member 40c includes a distal radial extension 248 (or stopper) positioned distal to the drag member and a proximal radial extension 286c (or stopper) positioned proximal to the drag member 280. Each radial extension is attached to the actuation member 40 and extends radially therefrom beyond the outer circumferential edge of the respective aperture 282.

In some examples, both radial extensions 284c and 286c are situated near proximal and distal surfaces of the drag member 280c, thereby preventing axial movement of the actuation members 40 within the apertures 282c of the drag member 280c. In some examples, the inner diameter of each aperture 282c is larger than the outer diameter of the respective actuation member 40 to an extent that allows rotational movement of the actuation member 40 within the aperture 282c.

Figures 32, 33A, 33B:
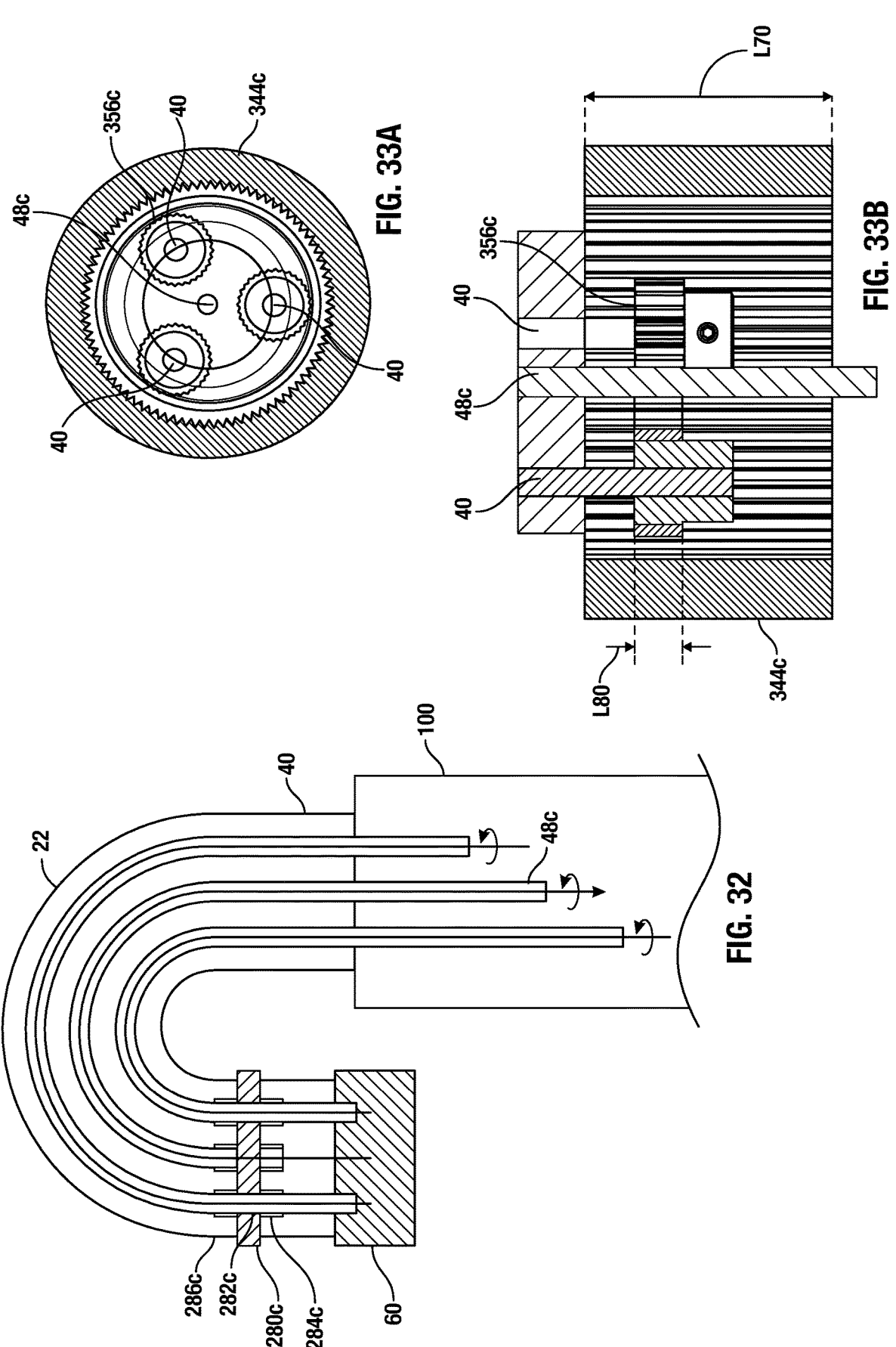
FIG. 32 is a simplified schematic view of the portion of the delivery apparatus shown in FIGS. 31A and 31B.
FIG. 33A is a cross-sectional view of the portion of the delivery apparatus shown in FIG. 31A, taken along line 33A-33A.
FIG. 33B is an enlarged view of the region 33B of FIG. 31B.

Each driven pinion gear 356c is attached to a proximal portion of a corresponding actuation member 40 and is engaged with the annular driver gear 344c. In this manner, rotation of the annular driver gear 344c is translated to rotation of the driven pinion gears 356c, which is translated to rotation of the actuation members 40. FIGS. 31A and 33A show the driven pinion gears 356c directly meshed with the internal teeth of the annular driver gear 344c. In alternative implementations, the gear train can include any number of idler gears to translate rotation from the annular driver gear 344c to the driven pinion gears 356c, as illustrated, for example, in FIGS. 29A and 29B.

In some examples, the axial length L70 (shown in FIG. 33B) of the annular driver gear 344c is greater than the axial length L80 (shown in FIG. 33B) of each driven pinion gear 356c. This allows each driven pinion gear 356c to remain engaged with the annular driver gear 344c as the driven pinion gear 356c and the annular driver gear 344c move axially relative to each other along the length L70.

If the actuation members 40 have identical lengths, the positions of the proximal ends of the actuation members 40 can differ when the actuation members 40 are positioned along a curved pathway (such as along a bend in the patient's vasculature). As illustrated by FIG. 32, while the distal portions of the actuation members 40 defined between the drag member 280c and the prosthetic valve 60 have identical lengths, the proximal ends of the actuation members 40 are located at different axial positions.

The slidable movement of the driven pinion gears 356c within the annular driver gear 344c permits free repositioning of the proximal portion of each actuation member 40 within the annular driver gear 344c, thereby compensating for the different travel paths of the actuation members 40. The axial length L70 can be defined by the range of allowable or expected positions of the driven pinion gear 356c, which may differ according to each patient's anatomy.

Once the prosthetic valve 60 is positioned at a desired implantation location, the central pull cable 48c is pulled in the proximal direction by rotating the rotatable knob 122. Since the central pull cable 48c is attached to the drag member 280c, the drag member 280c translates proximally, dragging all the actuation members 40 along via the distal radial extensions 284c. Pulling the actuation members 40 in the proximal direction results in expansion of the prosthetic valve 60.

To release the actuation members 40 after expanding the valve, the annular driver gear 344c is rotated by rotating the rotatable knob 122. Since all the driven pinion gears 356c are engaged (directly or indirectly via idler gears) with the annular driver gear 344c, the rotation of the annular driver gear 344c is translated to simultaneous rotation of the driven pinion gears 356c, which is translated to simultaneous rotation of the actuation members 40. Rotation of the actuation members 40 result in disengagement of the actuation members 40 from the respective rack members 68 of the lockers/actuators 62 of the valve.

Additional details regarding the displacement control and release mechanisms are elaborated in U.S. Provisional Application No. 62/945,039, which is incorporated herein by reference.

FIGS. 34A-34D illustrate a mechanism 300d that can be included in the handle 100. The mechanism 300d is configured to control an axial displacement of the actuation members 40 along the same length and simultaneously release the actuation members 40 from the prosthetic valve. The mechanism 300d includes a central pull cable 48d that can be pulled in a proximal direction d1 by rotating the rotatable knob 122. The central pull cable 48d pulls all the actuation members 40 along and thereby expands the valve. The mechanism 300d includes a gear assembly 301d comprising a distal driving spur gear 357d that is rotated by rotating the rotatable knob 124 and distal driven pinion gears

356 that are engaged with the distal driving spur gear 357*d*. The actuation members 40 are coupled to the distal driven pinion gears 356 such that rotation of the distal driven pinion gears 356 results in simultaneous rotation of the actuation members 40.

The driving spur gear 357*d* and the distal driven pinion gears 356*d* are disposed within the multi-lumen shaft 22 (it should be noted that the multi-lumen shaft 22 is shown as transparent for purposes of illustration). The multi-lumen shaft 22 can include a sleeve coupler 38 at its distal end, which can have the same characteristics described with reference to FIGS. 31A-33B. Proximal portions of the sleeve members 34 of the actuation members 40 are attached to the sleeve coupler 38. The mechanism 300*d* further includes a drag member 280*d*, which is disposed within the multi-lumen shaft 22 and between the gears 357*d*, 356*d* and the sleeve coupler 38. The drag member 280*d* is axially movable within the distal portion of the multi-lumen shaft 22.

The central pull cable 48*d* extends through the multi-lumen shaft 22. The distal end of the central pull cable 48 is coupled to the driving spur gear 357*d* (instead of being affixed to the drag member as described for the pull mechanism illustrated by FIGS. 31A and 31B). The distal driving spur gear 357*d* is in turn coupled to the drag member 280*d*. Axial movement of the central pull cable 48*d* is translated to axial movement of the drag member 280*d* within the distal portion of the multi-lumen shaft 22. Since the central pull cable 48*d* is not affixed to the drag member 280*d*, the central pull cable 48*d* can be rotated about its central axis, which would rotate the distal driving spur gear 357*d*.

The actuation members 40 are coupled to the drag member 280*d* such that the actuation members 40 can rotate about their respective axes but not move axially relative to the drag member 280*d*. For example, the actuation members 40 can extend through apertures of the drag member 280*d* and have proximal and distal radial projections. In addition, each actuation member 40 is attached at its distal portion to one of the distal driven pinion gears 356*d* (instead of to pinion gears within the handle as described for the pull mechanism illustrated in FIGS. 31A and 31B).

In some cases, the central pull cable 48*d* can include a pull cable rigid portion and a pull cable soft portion. The pull cable rigid portion can be coupled at a proximal portion thereof (i.e., a portion within the handle) to a proximal gear driven by the rotatable knob 124 (see FIGS. 29A-29B). In such cases, the pull cable rigid portion can be any flexible torque-transmitting material or structure known in the art to transmit torque applied to one end thereof to the opposite end thereof. The pull cable rigid torque transmitting portion can extend between the driving spur gear 357*d* and at least the proximal gear driven by the rotatable knob 124. The pull cable soft portion may be attached to the proximal end of the pull cable rigid portion, for example, via a coupler (not shown) and may include any flexible soft portions in the form of strings, cable, wires, and the like configured to wrap around pulleys and/or reels.

Figure 34A:
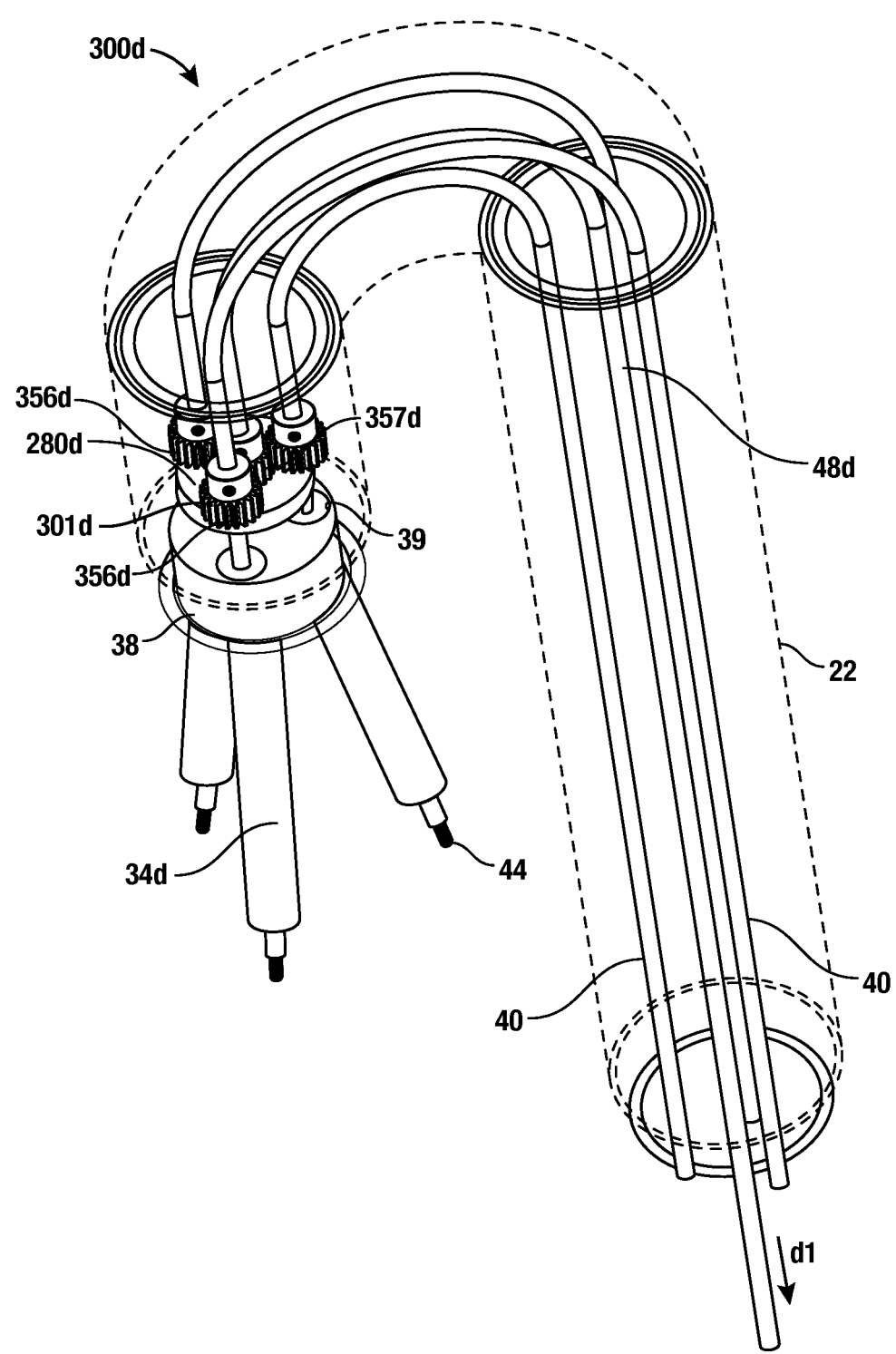
FIG. 34A is a perspective view of a portion of a delivery apparatus with a mechanism for pulling actuation members, according to another example.
Figure 34B:
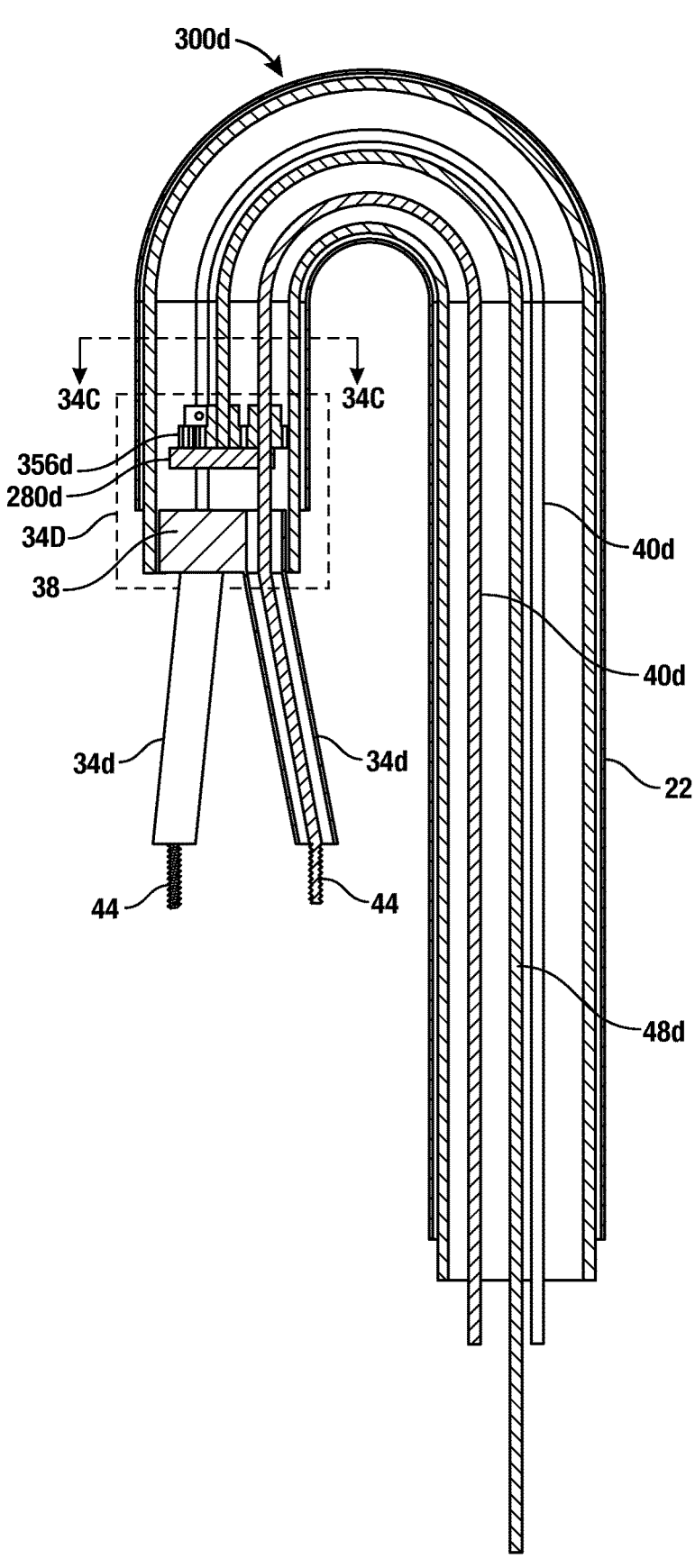
FIG. 34B is a cross-sectional view of the portion of the delivery apparatus illustrated in FIG. 34A.
Figure 34C:
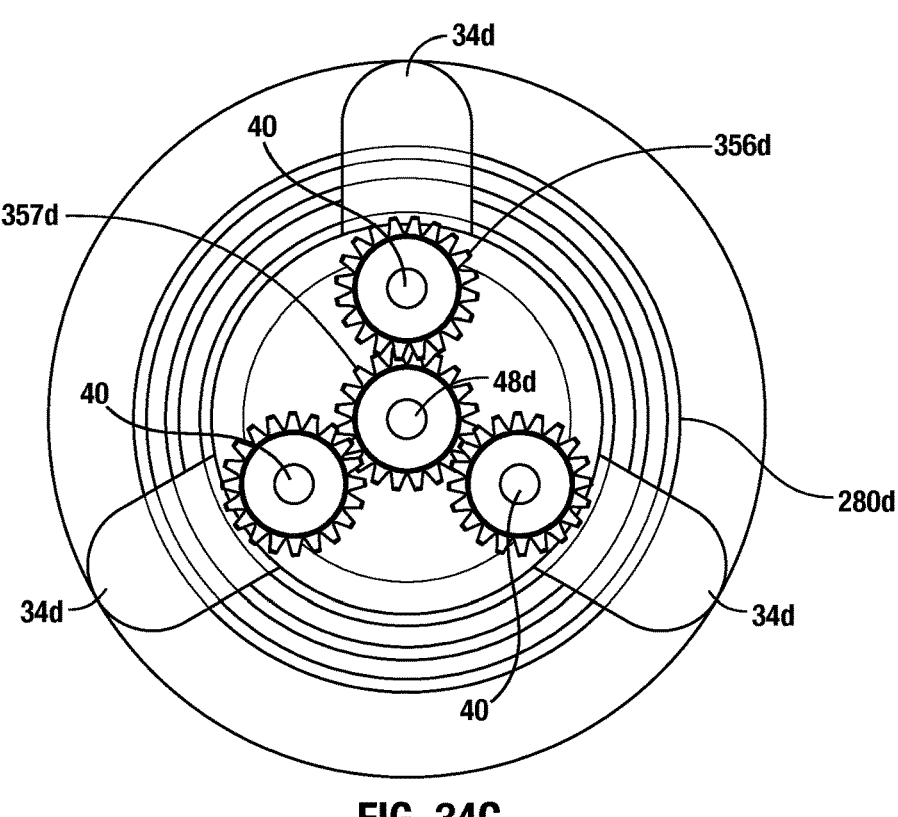
FIG. 34C is a cross-sectional view of the portion of the delivery apparatus illustrated in FIG. 34B taken along line 34C-34C.
Figure 34D:
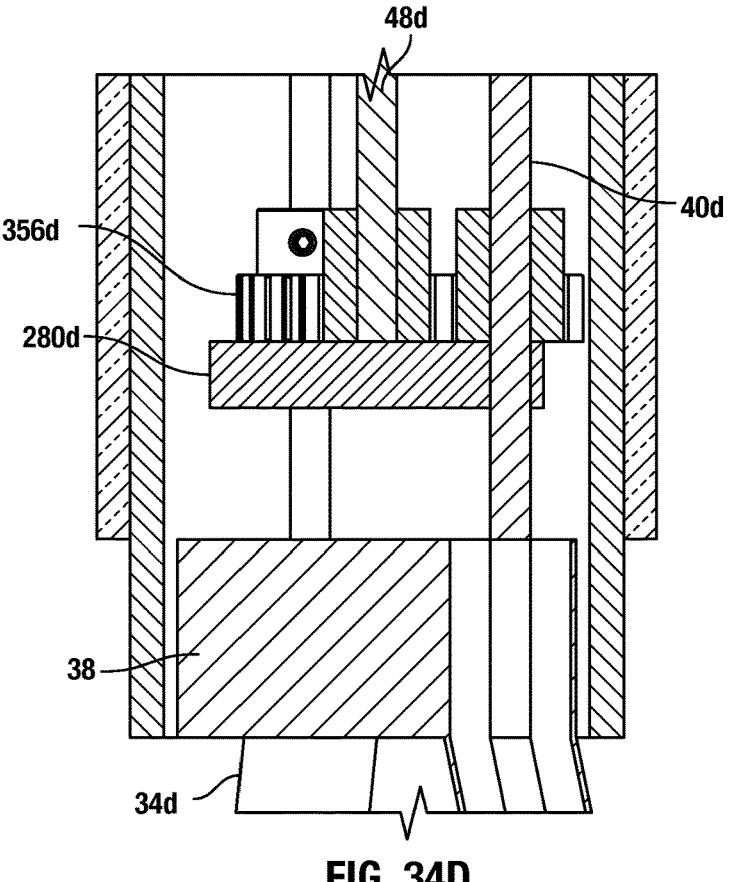
FIG. 34D is an enlarged view of the region 34D of FIG. 34B.

While the actuation members 40 are illustrated as extending along the entire length of the multi-lumen shaft 22 in FIGS. 34A and 34B, in other examples, the actuation members 40 may extend along a shorter length (e.g., between the distal driven pinion gear 356*d* and the distal threaded heads 44 of the actuation members 40) and configured to perform as torque-transmitting members at these portions.

Once the prosthetic valve 60 is positioned at the desired implantation site, the central pull cable 48*d* is pulled in the proximal direction by rotating the rotatable knob 122 (shown in FIG. 11), pulling the drag member 280 and all actuation members 40 along, thereby expanding the prosthetic valve 60. Once the prosthetic valve 60 is expanded, the distal driving spur gear 357*d* is rotated by rotating the rotatable knob 124 (shown in FIG. 11). Since all the distal driven pinion gears 356*d* are engaged (directly or indirectly via idler gears) with the driving spur gear 357*d*, the distal driven pinion gears 356*d* simultaneously rotate with the driving spur gear 357*d*, which results in disengagement of the actuation members 40 from the respective rack members 68 of the lockers/actuators 62 of the valve.

Additional details regarding the pull mechanism described in FIGS. 34A-34D can be found in U.S. Application No. 62/945,039.

Figure 35A:
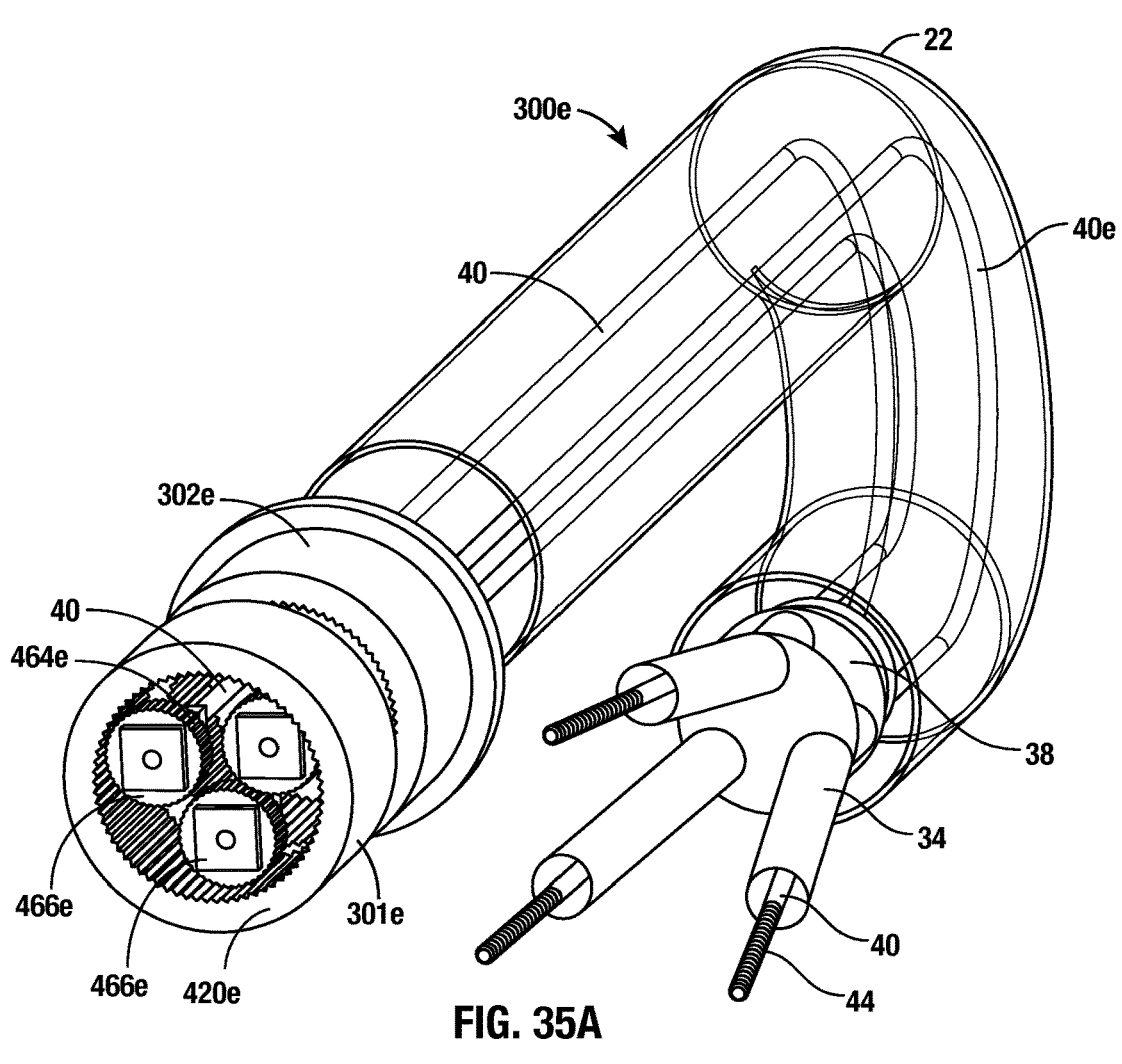
FIG. 35A illustrates a portion of a delivery apparatus with proximal actuation member pull mechanism and a proximal actuation member release mechanism.
Figure 35B:
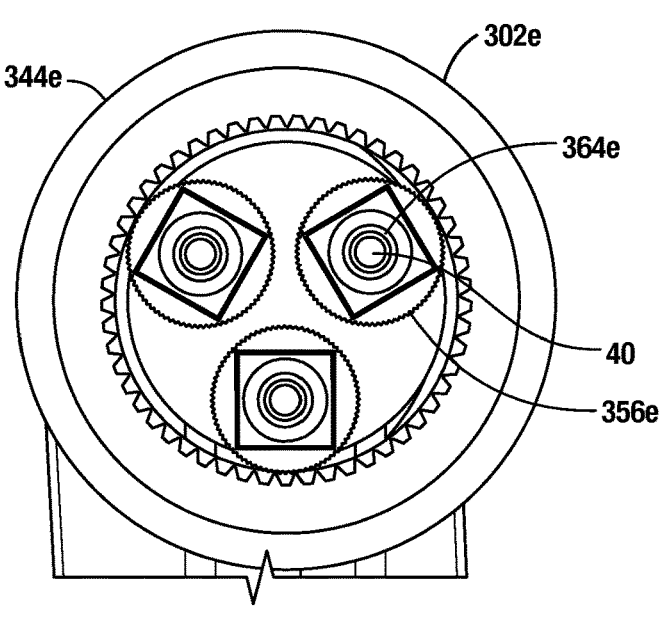
FIG. 35B is an end view of the release mechanism.
Figure 36A:
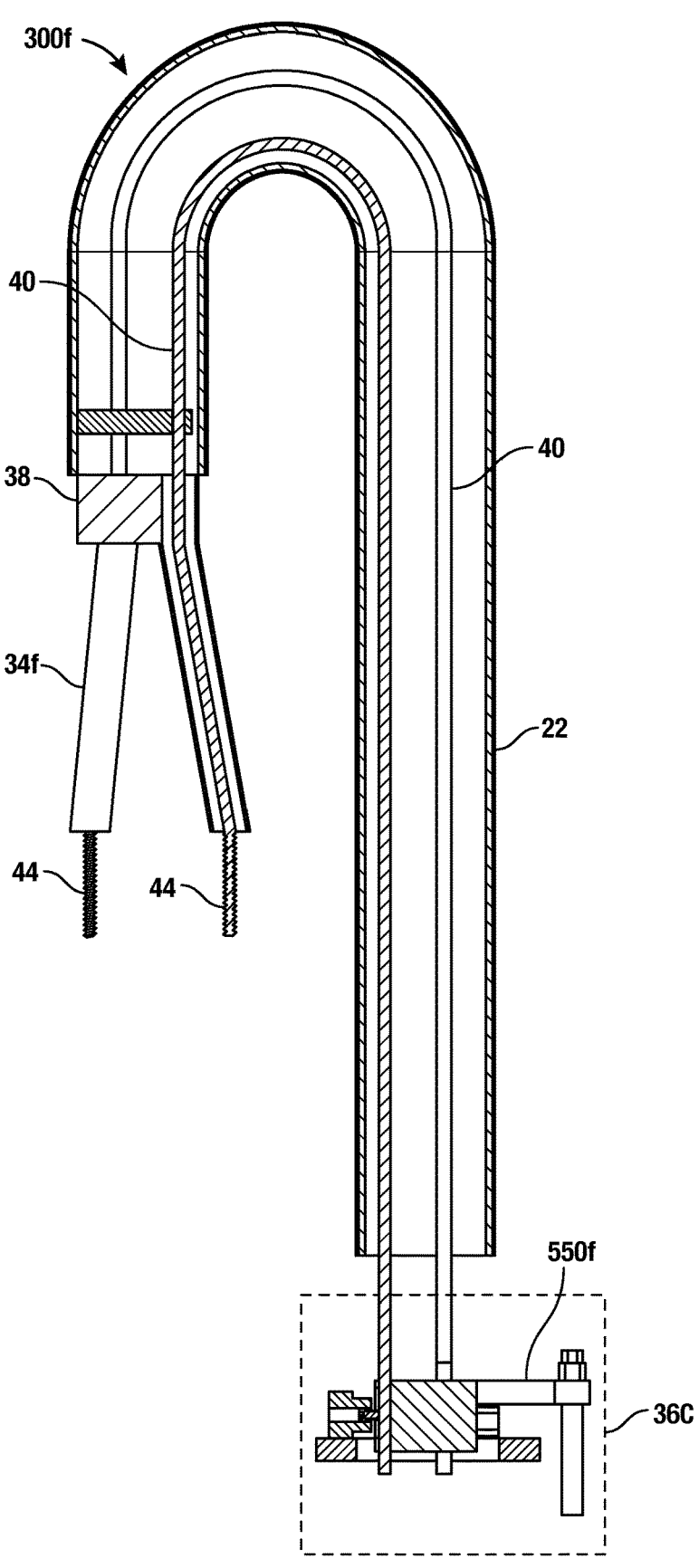
FIG. 36A is a cross-sectional view of a portion of a delivery apparatus including a displacement control mechanism.
Figure 36B:
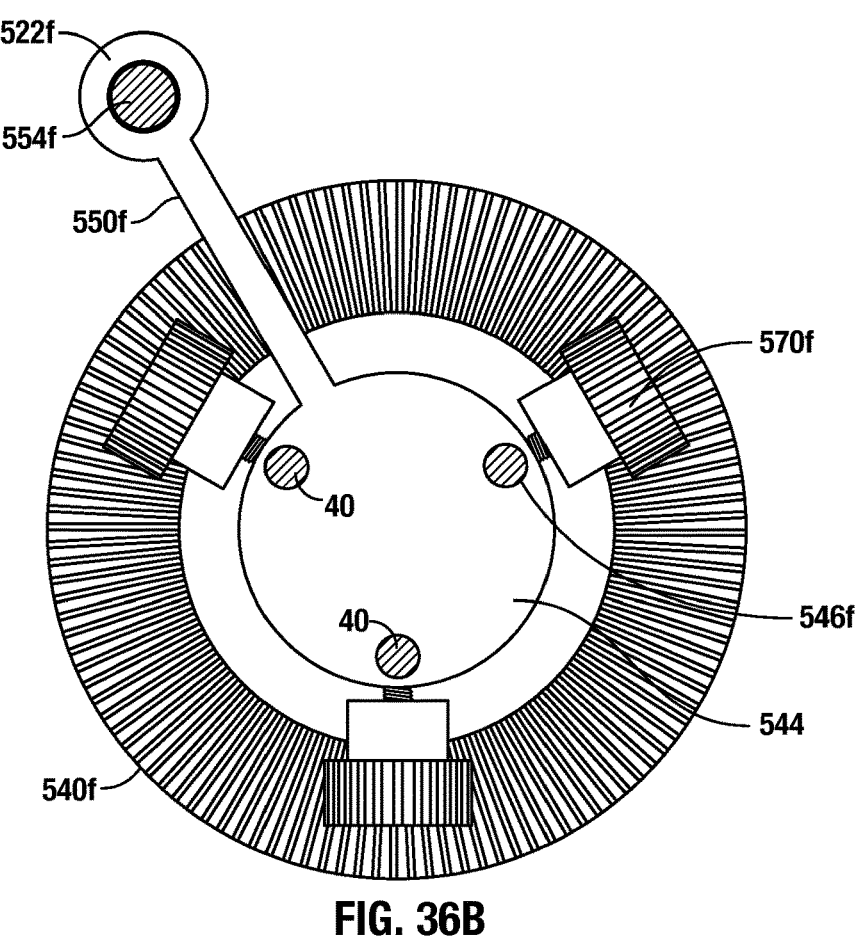
FIG. 36B is an end view of a gear assembly of the displacement control mechanism of FIG. 36A.
Figure 36C:
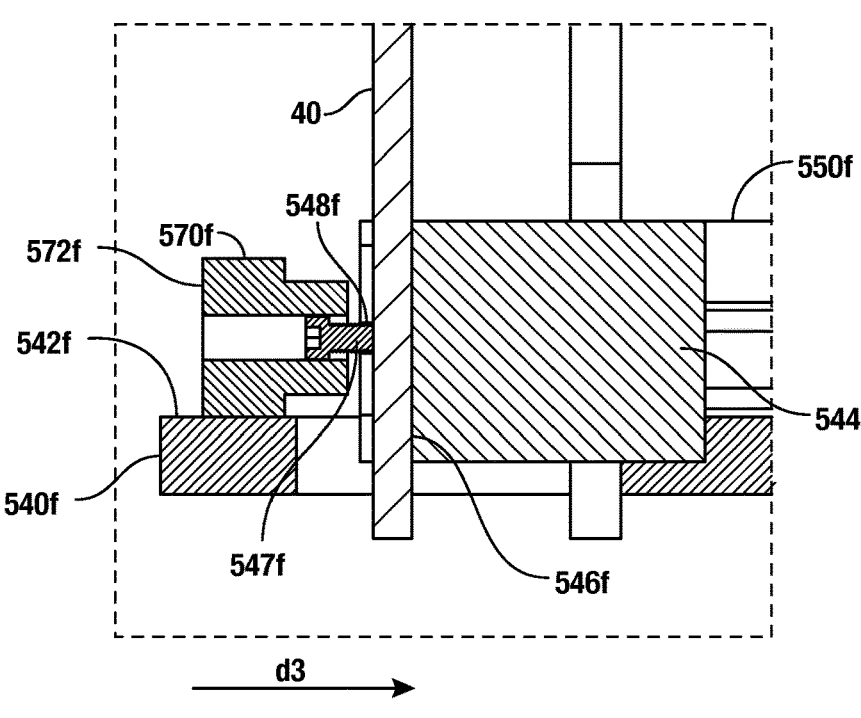
FIG. 36C is an enlarged view of the region 36C in FIG. 36A.
Figure 36D:
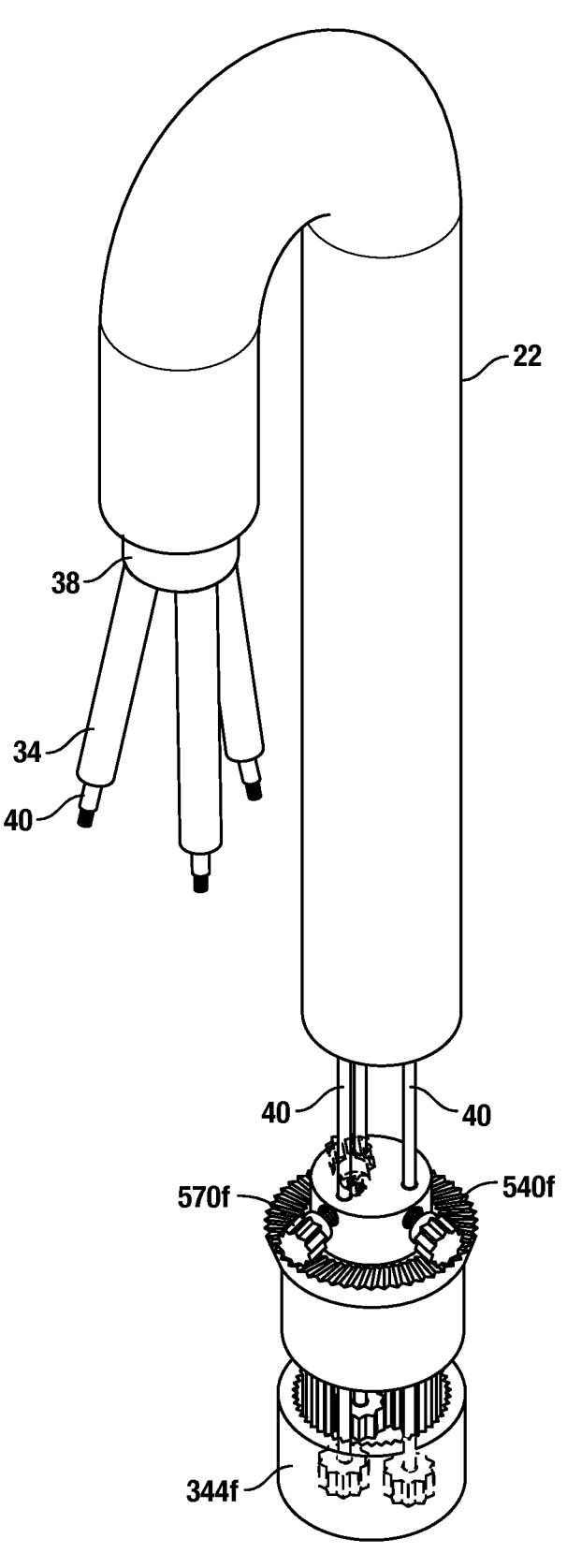
FIG. 36D illustrates the portion of the delivery apparatus of FIG. 36A with a release mechanism.
Figure 36E:
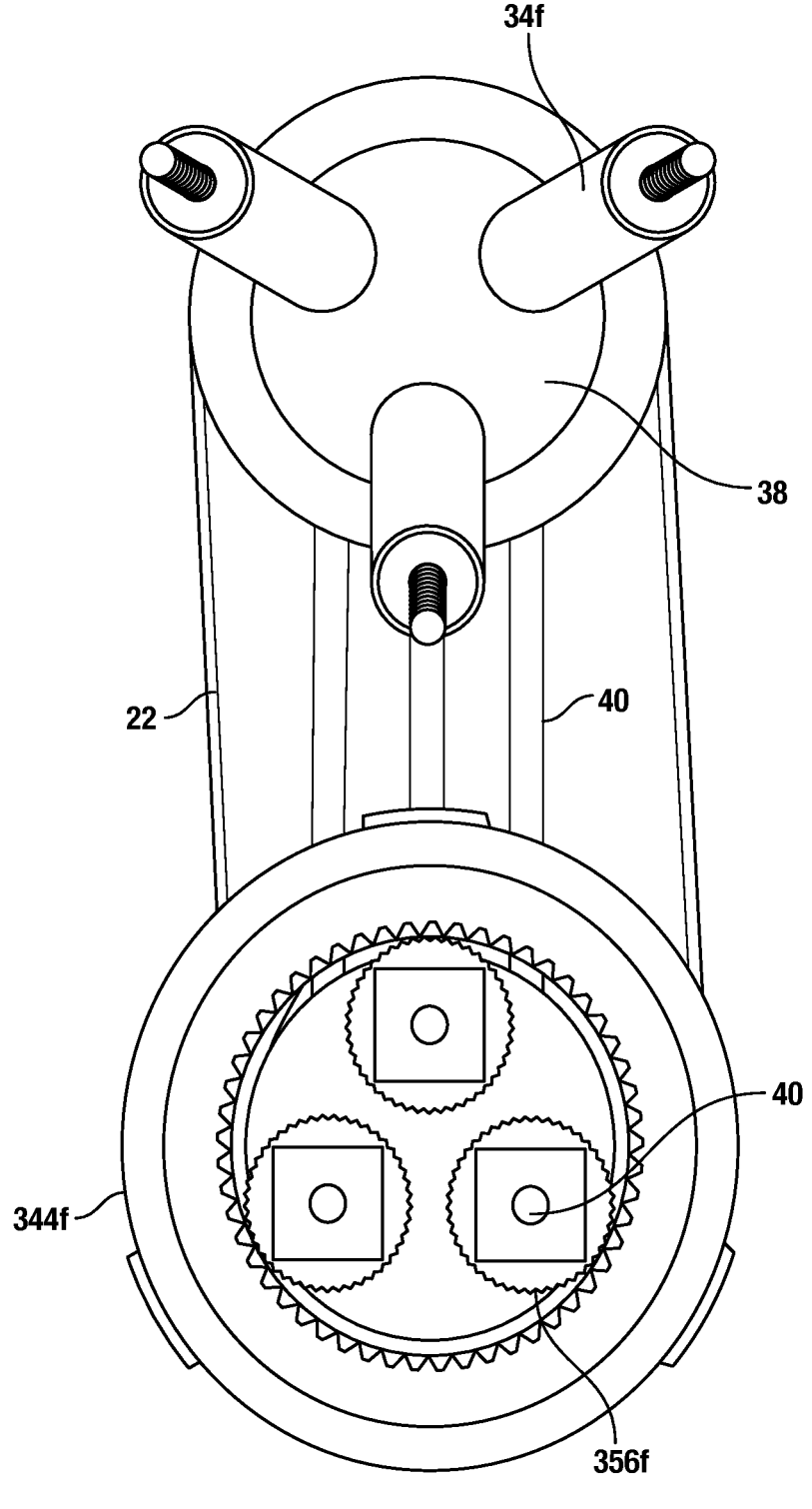
FIG. 36E is a bottom view of the portion of the delivery apparatus shown in FIG. 36D.

FIGS. 35A-35B illustrate a mechanism 300*e* that can be included in the handle 100. The mechanism 300*e* is configured to control axial displacement of the actuation members 40 and simultaneously disengage the actuation members 40 from the prosthetic valve 60. The mechanism 300*e* includes a first gear assembly 301*e* comprising a primary gear 420*e* and secondary gears 456*e*. The actuation members 40 are coupled to the secondary gears 456*e* such that rotation of the secondary gears 456*e* by the primary gear 420*e* results in rotation and axial translation of the actuation-members. The mechanism 300*e* includes a second gear assembly 302*e* that is coupled to the actuation members 40*e* and that can rotate the actuation members 40 to release the actuation members 40 from the valve.

The primary gear 420*e* is provided with internal teeth and is coupled to and rotatable with the rotatable knob 122 (shown in FIG. 11). The secondary gears 456*e* are provided with external gear teeth, which interconnect with the internal teeth of the primary gear 420*e*. Each secondary gear 456*e* is coupled, directly or indirectly, to a respective actuation member 40 to promote axial translation of the actuation member 40 in response to rotation of the primary gear 420*e*. In some examples, the axial length of the primary gear 420*e* is longer than the length of each secondary gear 456*e*, thereby allowing slidable movement of each secondary gear 456*e* along the length of the primary gear 420*e*. The secondary gears 456*e* are shown as directly meshed with the internal teeth of the primary gear 420*e*. In an alternative implementation, the gear train can include any number of idler gears to translate rotation of the primary gear 420*e* to the secondary gears 456*e* (such as illustrated with idler gears 350 in FIGS. 29A and 29B).

In some examples, a first adapter 464*e* is coupled to each secondary gear 456*e*. Each first adapter 464*e* has a threaded bore. In the example illustrated by FIGS. 35A-35B, the proximal portion of each actuation member 40 has a thread that matches the inner thread in the threaded bore of the respective first adapter 464*e*. The proximal portion of each actuation member 40 extends through the threaded bore of the respective first adapter 464*e* such that rotation of the first adapter 464*e*, via rotation of the respective secondary gear 456*e*, is translated to axial displacement of the actuation members 40.

In some examples, the first adapter 464*e* includes a polygonal outer shape that matches a polygonal-shaped central bore of a respective secondary gear 456*e* such that when the first adapter 464*e* is disposed in the polygonal-shaped central bore the first adapter 464*e* will not be able to rotate relative to the secondary gear 456*e*. Thus, when the secondary gear 456*e* rotates, the respective first adapter 464*e* rotates with the secondary gear 456*e*. In the implementation illustrated by FIG. 35A, the first adapters 464*e* are square-shaped. In other implementations, the central bore of the secondary gear 465*e* can include a bore flat edge (such as bore flat edge 362 shown in FIG. 29B) matching a similar flat edge of the first adapter 464e.

In some examples, the first adapter 464e can further include a proximal first adapter base 466e configured to abut the secondary gear 456e. In some examples, the first adapter 464e can be otherwise shaped to be affixed to the secondary gear 456e. In some examples, the first adapter 464e includes other features besides shape matching to prevent rotational movement thereof relative to the secondary gear 456e. In some examples, the first adapter 464e can be affixed to the secondary gear 456e, for example, by gluing, welding, and the like.

In some examples, the assembly 300e does not include first adapters 464e, and the threaded proximal portion of each actuation member 40e is configured to match an internal thread of a central bore of the secondary gear 456e. In this case, when the actuation member 40e extends through the central bore of the secondary gear 456e, rotation the secondary gear 456e is directly translated to axial displacement of the actuation member 40e.

The second gear assembly 302e includes an annular driver gear 344e and a plurality of driven pinion gears 356e engaged with the annular driver gear 344e. Each driven pinion gear 356e is coupled, directly or indirectly, to a respective actuation member 40 to promote rotation of the actuation member 40 around the central axis of the actuation member 40 in response to rotation of the driven pinion gear 356e. The pinion gears 356e are shown as directly meshed with the internal teeth of the annular driver gear 344e. In an alternative implementation, the gear train can include any number of idler gears to translate rotation of the annular driver gear 344e to the pinion gears 356e (such as illustrated with the idler gears 350 described with reference to FIGS. 29A-29B).

In some examples, the axial length of the annular driver gear 344e can be longer than the length of each driven pinion gear 356e, thereby allowing slidable movement of each pinion gear 356e along the length of the annular driver gear 344e.

In some examples, the actuation member 40e can be fixedly attached to a respective actuation tube and extend therethrough. The actuation tube can be affixed to a respective bore of a pinion gear 365e and extend therethrough. In other examples, the assembly may not include actuation tubes and each actuation member 40 can be directly affixed to the bore of a respective pinion gear 356e and extend therethrough.

When a prosthetic valve 60 is placed within a patient's body, the positions of the proximal ends of the actuation members 40 within the handle may differ even though the lengths of all actuation members 40 are identical. The positions of the proximal ends may differ due to the curved pathway along the patient's vasculature. The slidable movements of the secondary gears 456e within the primary gear 420e and of the pinion gear 356e within the driver gear 344e permit free repositioning of the proximal portion of each actuation member 40e. The lengths of the primary gear 420e and the driver gear 344e are defined by the range of allowable or expected positions of the secondary gears 456e and the pinion gears 356e, respectively, which may differ according to each patient's anatomy.

Once the prosthetic valve 60 is positioned at the desired implantation location, the rotatable knob 122 is rotated, causing the primary gear 420e to rotate. Since all the secondary gears 456e are engaged (directly or indirectly via idler gears) with the primary gear 420e, the secondary gears 456e simultaneously rotate along with the respective first adapters 464e. Rotation of the first adapters 464e results in axial translation of the actuation members 40. Rotation in a specific predefined direction will result in axial displacement of the actuation members 40 in the proximal direction. The pinion gears 356e are allowed to axially slide within the driver gear 344e during axial displacement of the actuation members 40. The simultaneous pull of all actuation members 40 along a constant distance results in uniform radial expansion of the valve 60. The mechanism 300e can operate without the expansion reel.

Once the prosthetic valve 60 is expanded, the driver gear 344e is rotated by manual rotation of the rotatable knob 124. Since all of the pinion gears 356e are engaged with the driver gear 344e, all the pinion gears 356e simultaneously rotate along with the respective actuation tubes 364e (or the actuation members 40 if the actuation members 40 are attached directly to the pinion gears), which in turn is translated to disengagement of the actuation members 40 from the rack members 68 of the lockers/actuators of the valve.

FIGS. 36A-36E illustrate an alternative mechanism 300f that can be included in the handle 100. The alternative mechanism 300f is configured to control axial displacement of the actuation members 40 and simultaneously disengage the actuation members 40 from the prosthetic valve. The mechanism 300f includes a main bevel gear 540f and a plurality of lock gears 570f that can be disposed within the handle. The main bevel gear 540f has a distal surface 542f that is provided with teeth that project in a distal direction. The lock gears 570f are engaged with the teeth. In some examples, the peripheral lock gears 570f are bevel gears designed to intersect with the main bevel gear 540f. Each lock gear 570f includes a threaded bore 572f. A lock screw 574f is threadedly engaged with the threaded bore 572f and configured to translate in the radial direction d3 when the respective lock gear 570f is rotated.

The mechanism 300f can include a core element 544f that is concentric with the main bevel gear 540f and disposed between the peripheral lock gears 570f. In some examples, the core element 544f is attached to the main bevel gear 540f. The core element 544f includes a plurality of axial channels 546f. Each axial channel 546f is configured to allow free axial movement of a respective actuation member 40 (corresponding to actuation member 40) extending therethrough. The core element 544f further includes an opening 548f extending radially from each axial channel 546f to the outer circumferential surface of the core element 544f. The opening 548f is aligned with the lock screw 574f situated in the threaded bore 572f. The opening 548f is configured to allow passage of the lock screw 574f therethrough.

When the lock screw 574f is translated radially inwards in the direction d3, the lock screw 574f passes through the opening 548f to press against the respective actuation member 40. The movement of the lock screw 574f in the direction d3 is stopped when the respective actuation member 40 is pressed against an inner wall of the respective axial channel 546f such that the actuation member 40 is locked in place and can no longer move axially relative to the core element 544f. In some examples, the lock screw 574f is provided with an atraumatic tip to avoid damaging the actuation member 40.

In some cases, a core element extension 550f extends in a radial direction from the core element 544f. The core element extension 550f is provided with a threaded extension bore 552f. A driving screw element 554f is threadedly engaged with the threaded extension bore 552f such that rotation of the driving screw element 544f translates to axial displacement of the core element 544*f*, along with translation of the actuation members 40 when the actuation members 40 are pinched within the axial channel 546*f*. Rotating the driving screw element 554*f* in a specific direction about its axis of symmetry translates to simultaneous displacement of all actuation members 40 in the proximal direction.

In some examples, the driving screw element 554*f* is operable by the rotatable knob 122 such that rotation of the rotatable knob 122 is translated to an axial movement of the driving screw element 554*f* along with the core element extension 550*f*.

In some examples, the handle can include a locking rotatable knob that is rotatable by a user of the handle and operable to rotate the main bevel gear 540*f*.

In some examples, the handle can include a release mechanism that is operable by the rotatable knob 124 (shown in FIG. 11).

The release mechanism includes an annular driver gear 344*f* and a plurality of driven pinion gears 356*f* engaged with the annular driver gear 344*f*. Each driven pinion gear 356*f* is coupled, directly or indirectly, to a respective actuation member 40 to promote rotation of the actuation member 40 around the central axis of the actuation member 40 in response to rotation of the driven pinion gear 356*f*. The pinion gears 356*f* can directly mesh with the internal teeth of the driver gear 344*f* as shown or can engage the driver gear 344*f* via any number of idler gears (such as illustrated with the idler gears 350 shown in FIGS. 29A-29B).

In some cases, the axial length of the annular driver gear 344*f* is longer than the length of each pinion gear 356*f*, thereby allowing slidable movement of each pinion gear 356*f* along the length of the annular driver gear 344*f*.

When the valve is releasably coupled to the actuation members 40 and placed within the patient's body, the positions of the proximal ends of the actuation members 40 within the handle may differ from each other due to the curved pathway along the patient's vasculature. The slidable axial movements of the actuation members 40 within the axial channels 546*f* and of the pinion gears 356*f* within the annular gear 344*f* permit free repositioning of the proximal portion of each actuation member 40. The length of the driver gear 344*f* is defined by the range of allowable or expected positions of the pinion gears 356*f*, which may differ according to each patient's anatomy.

Once the valve is positioned at the desired implantation site, the main bevel gear 540*f* can be rotated by manually rotating the locking knob on the handle. Since all the peripheral lock gears 570 are engaged with the main bevel gear 540*f*, the peripheral lock gears 570 simultaneously rotate as well. Rotation of each of the lock gears 570*f* results in displacement of the lock screws 574*f* radially inwards (i.e., in the direction d3) to pinch and lock the actuation members 40 relative to the core element 544*f*.

Once the actuation members 40 are locked in place, the driving screw element 554*f* can be rotated via the rotatable knob 122*f*, resulting in axial displacement in the proximal direction of the core element 544*f* along with the actuation members 40, the peripheral lock gears 570*f*, and the main bevel gear 540*f*. The simultaneous pull of all actuation members 40 along a constant distance results in uniform radial expansion of the valve. The mechanism formed by the assembly 300*f* does not require an expansion reel.

Once the prosthetic heart valve is expanded, the driver gear 344*f* can be rotated by manual rotation of the rotatable knob 124. Since all the pinion gears 356*f* are engaged with the driver gear 344*f*, the pinion gears 356*f* simultaneously rotate with the driver gear 344*f*. Rotation of the pinion gears 356*f* is in turn translated to disengagement of the actuation members 40 from the rack members 68 of the lockers/actuators of the valve.

Additional details regarding the mechanisms described in FIGS. 36A-36E are elaborated in U.S. Patent Application No. 62/945,039.

As mentioned above, while all the actuation members 40 are provided with equal lengths, their proximal portions may end up in different axial positions due to the curved path of the delivery system, as all actuation members 40 are disposed at different locations within the lumens of the multi-lumen shaft 22. While several different examples mentioned above are configured to overcome the differential pathways of the actuation members 40 by mechanisms that allow axial displacement of the proximal portions of the actuation members 40 within the handle, other examples can provide solutions that rely on the structure of the multi-lumen shaft itself.

FIGS. 37A-37C illustrate a twisted multi-lumen shaft 22*g* that is configured to overcome differential pathways of actuation members 40. The multi-lumen shaft 22*g* includes lumens 24*a*, 24*b*, 24*c*. Actuation members 40*a*, 40*b*, 40*c* extend respectively through lumens 24*a*, 24*b*, 24*c*. The number of lumens in the multi-lumen shaft 22*g* can differ from three and may generally match the number of actuation members.

The path of each lumen 24*a*, 24*b*, 24*c* is twisted along the length of the multi-lumen shaft 22*g* such that the actuation members 40*a*, 40*b*, 40*c* are at different positions relative to each other along the cross-sections of the multi-lumen shaft. The relative positions of the lumens 24*a*, 24*b*, 24*c* and the actuation members 40*a*, 40*b*, 40*c* extending through the lumens vary between the proximal end and the distal end of the multi-lumen shaft. Advantageously, the twisted paths of the lumens 24*a*, 24*b*, 24*c* result in uniform lengths of the lumens even when the multi-lumen shaft 22*g* is bent along the patient's vasculature.

Additional details regarding the twisted multi-lumen shaft are elaborated in are elaborated in U.S. Patent Application No. 62/945,039, which is incorporated herein by reference.

In some cases, when the prosthetic heart valve is delivered to the implantation location, the lockers/actuators 62 of the prosthetic valve 60 may be oriented such that they block or interfere with blood flow into the coronary ostia in the vicinity of the aortic annulus. In these cases, a mechanism that can enable rotation of the prosthetic valve 60 in order to reorient the lockers/actuators relative to the surrounding anatomy during the implantation procedure would be advantageous.

Figure 38A:
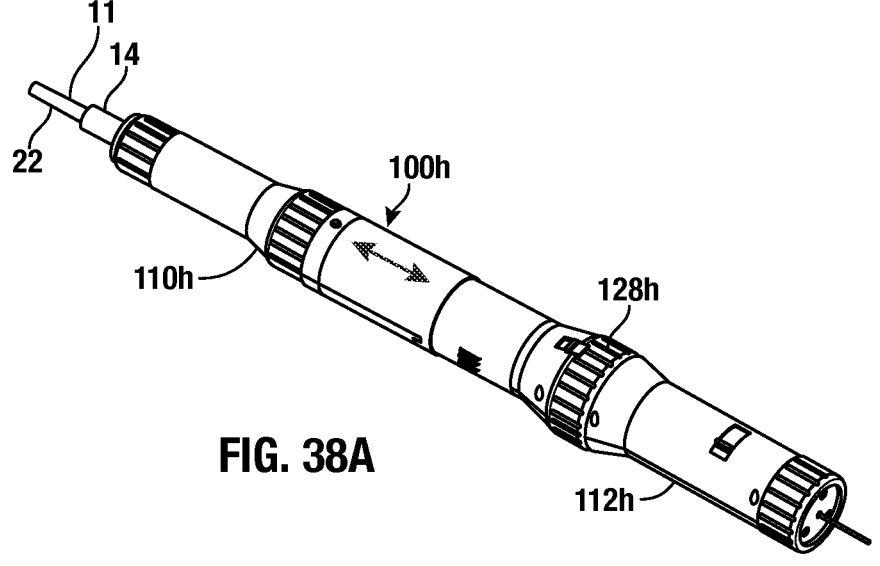
FIG. 38A is a perspective view of a handle, according to another implementation.

FIG. 38A illustrates a handle 100*h* including a distal portion 110*h* and a proximal portion 112*h*. The proximal portion 112*h* is axially movable and rotatable relative to the distal portion 110*h*. The proximal portion 112*h* has a receptacle 541 (shown in FIG. 38B). In one example, the receptacle 541 is fixedly attached within the proximal handle portion 112 such that there is no relative movement between the receptacle 541 and the proximal handle portion 112. In another example, the receptacle 541 can be embedded or attached within an adjustment knob, such as knob 128*h*, such that an operator of the handle can rotate the receptacle 541 instead of the whole proximal handle portion 112.

Figure 38B:
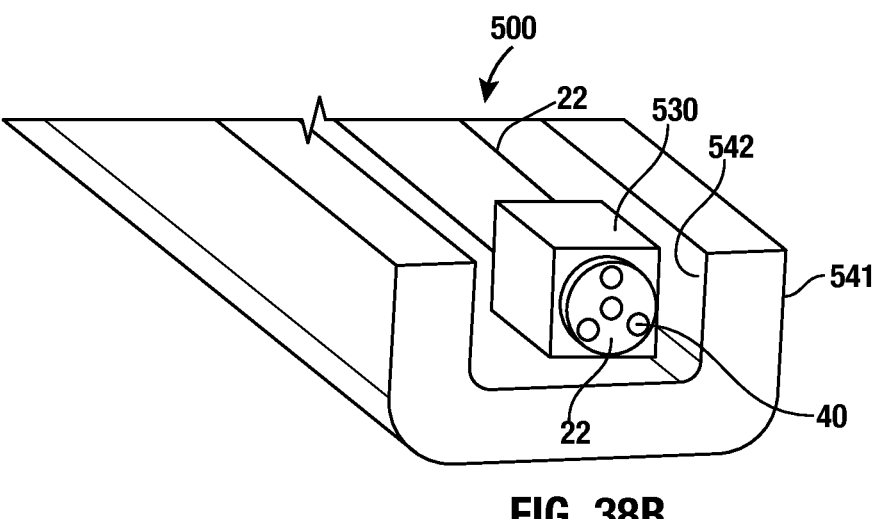
FIG. 38B is a detail of the handle of FIG. 38A illustrating a valve rotation mechanism.

As shown in FIG. 38B, the receptacle 541 is configured to accept a non-circular casing 530. For example, the receptacle 541 can include an inner bore or socket 542 that is sized and shaped to accommodate the non-circular casing 530 such that when the receptacle 541 rotates in one direction, the casing 530 rotates in the same direction. The shaft assembly 11 (see FIG. 38A) can extend into the handle such that the casing 530 is disposed around a proximal portion of the multi-lumen shaft 22. In some examples, the proximal portion of the multi-lumen shaft 22 can be fixedly attached to the casing 530 (e.g., by gluing, welding, and the like) such that there is no relative movement between the multi-lumen shaft 22 and the casing 530.

FIG. 38C shows the prosthetic valve 60 positioned at an implantation location. The actuation members 40 extending through the multi-lumen shaft 22 are connected to the lockers/actuators 62. In this position, if the lockers/actuators 62 need to be repositioned, the operator can rotate the receptacle 541 (e.g., by rotating the proximal handle portion 112h or by rotating the adjustment knob 128h), which would rotate the casing 530 and the multi-lumen shaft 22. Since the actuation members 40 are locked to the prosthetic valve 60, the valve will rotate as well (e.g., in direction c6). The valve 60 can be rotated while in the compressed state. If needed, the valve 60 can be recompressed prior to rotation. FIGS. 38D and 38E schematically show the position of three locker/actuators 62a, 62b, 62c of the valve 60 before and after rotation, respectively.

In some examples, a clicking sound mechanism 501 (shown in FIGS. 38F and 38G) can be provided to add a clicking sound to the rotational movement of the multi-lumen shaft 22. The clicking sound mechanism 501 can include a proximal protrusion 532 at the proximal end of the multi-lumen shaft 22. The proximal protrusion 532 can be in the form of a dimple. The clicking sound mechanism 501 can include a clicking member 520 positioned in opposing relation to the proximal end of the multi-lumen shaft 22. An end face 521 of the clicking member 520 can include a plurality of notches 522, which can be equally spaced in a circular pattern. Each notch 522 can selectively accommodate the protrusion 532, thereby making a clicking sound when the multi-lumen shaft 22 rotates and the protrusion 532 flexibly moves over a corresponding one of the series of notches 522.

While the prosthetic valve 60 is at a desired implantation location within the patient's body, the prosthetic valve 60 can be expanded by rotating the rotatable knob 122 to simultaneously pull the actuation members 40. Once the valve is expanded to a desirable diameter, the actuation members 40 can be rotated around their axes to release their respective distal threaded heads 44 from the rack members 68 of the lockers/actuators 62 of the valve, thereby allowing the delivery apparatus to be removed from the patient's body.

During valve expansion, the actuation members 40 are usually tensioned. In order to initiate a release process, an operator can release the rotatable knob 122 in order to reduce the tension, which may interfere with the opening torque required to release the actuation members 40 from the valve. One of the risks associated with such procedures is potential entanglement of flexible portions of the actuation members within the handle, which might result in application of an excessive pull force. A further risk is that releasing too much tension from the actuation members may result in actuation members that are too loose (i.e., not being tensioned at all), which might result in free spinning of the actuation members. Since the operator may not have an indication of whether the actuation members have been decoupled from the valve, pulling the delivery apparatus while the actuation members are still connected to the valve might displace the valve from its implantation position.

Figure 39A:
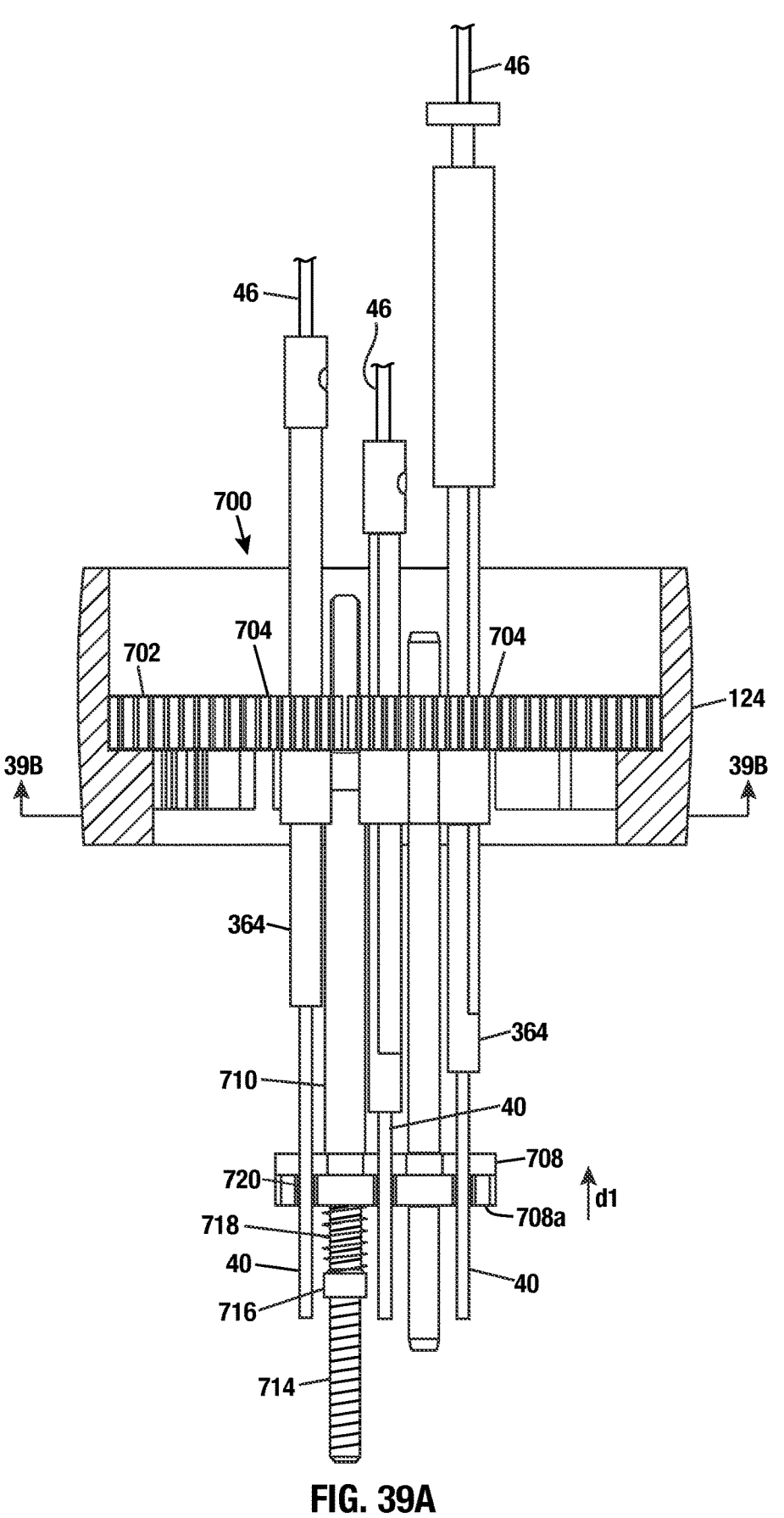
FIG. 39A is a cross-sectional view of an assembly including a mechanism configured to control release of actuation members from respective lockers/actuators.
Figure 39B:
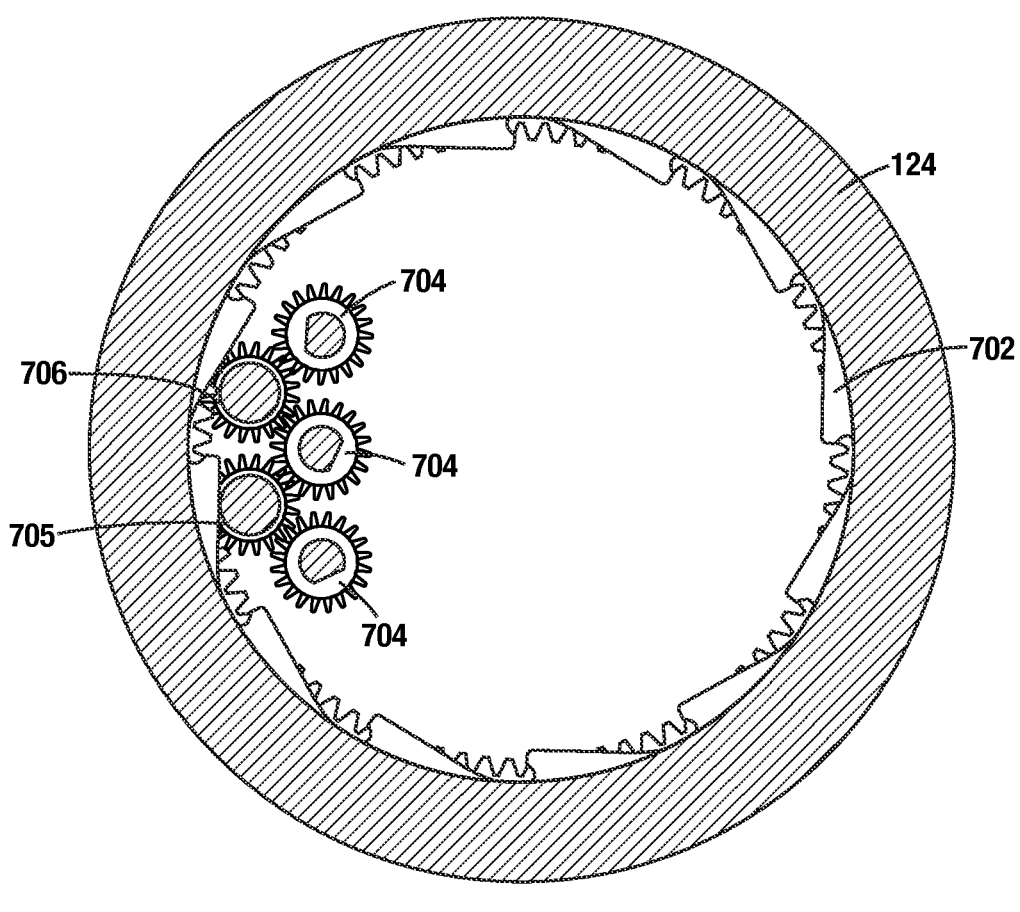
FIG. 39B is a cross-section of the assembly shown in FIG. 39A, taken along line 39B-39B as shown in FIG. 39A.
Figure 39C:
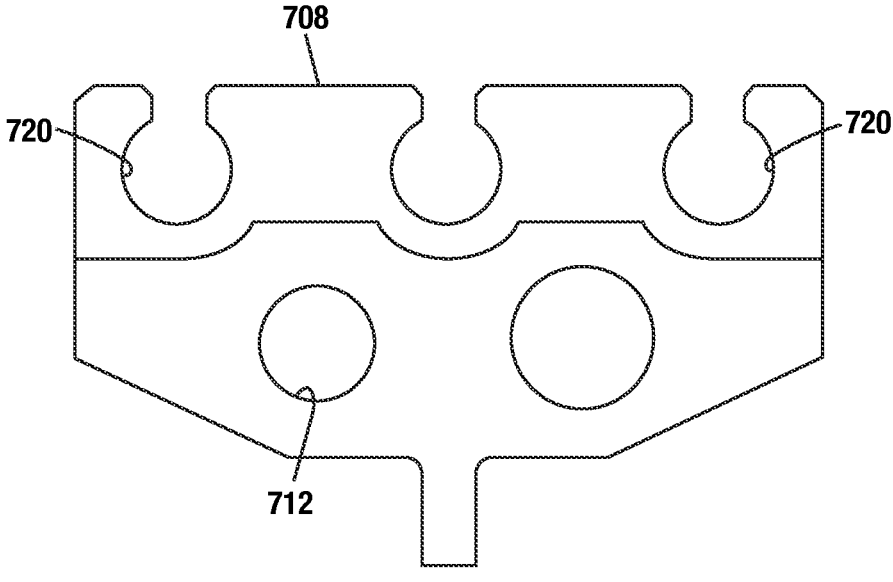
FIG. 39C is a plan view of a pull plate of the assembly shown in FIG. 39A.

FIGS. 39A-39C illustrate a mechanism 700 that can enable safe retraction of the actuation members only once the actuation members are fully disconnected from the valve. The mechanism 700 includes an annular driver gear 702 with internal teeth, first pinion gears 704 with external teeth, and a second pinion gear 706 with external teeth. Typically, there will be one pinion gear 704 for each actuation member 40 in the delivery apparatus. For illustrative purposes, three actuation members 40 and three first pinion gears 704 are shown. The annular driver gear 702 is configured to drive the first pinion gears 704 and the second pinion gear 706 directly or via idler gears (e.g., idler gear 705). In one example, the annular driver gear 702 can be rotated by the rotatable knob 124 (which can operate similarly to the mechanism shown in FIGS. 29A and 29B).

Each of the first pinion gears 704 is coupled to a respective actuation member 40. For example, each actuation member 40 can extend through and be coupled to a respective actuation tube 364 as previously described. Each first pinion gear 704 can be disposed around and coupled to a respective actuation tube 364, thereby coupling the first pinion gear 704 to the actuation member 40.

The second pinion gear 706 is coupled to a pull plate 708. In one example, the second pinion gear 706 is disposed around and coupled to a proximal portion of a plate rod 710. The plate rod 710 extends through a slot 712 in the pull plate 708 and includes a thread 714. A nut 716 is threadedly engaged with the plate rod 710 and positioned distal to the pull plate 708 such that rotation of the plate rod 710 is translated to axial movement of the nut 716 towards the distal end 708a of the pull plate 708. In one example, a spring 718 can be arranged between the nut 716 and the distal end 708a of the pull plate 708 to enable a gradual increase in the pull force applied to the pull plate 708 by the nut 716.

The pull plate 708 is positioned distal to the actuation tubes 364 and includes slots 720 for passage of the portion of the actuation members 40 extending distally from the actuation tubes 364. The pull plate 708 can slide over the actuation members 40 without interfering with movement of the actuation members 40. At the same time, the diameters of the slots 720 that receive the actuation members 40 are selected to be smaller than the diameters of the actuation tubes 364 such that once the pull plate 708 contacts the actuation tubes 364 further axial movement of the pull plate 708 in the proximal direction d1 will pull all the actuation tubes 364 and the attached actuation members 40.

The rotatable knob 124 can be rotated to move the pull plate 708 axially. The pull plate 708 is initially spaced away from the actuation tubes 364 to allow the pull plate 708 to freely slide along the actuation members 40 without pulling the actuation members 40 or interfering with their motion, thereby allowing the actuation members 40 to initially rotate around their axes to be fully released from the valve. After the pull plate 708 contacts the actuation tubes 364, additional rotation of the rotatable knob 124 will retract the actuation members 40.

Advantageously, the mechanism 700 allows the operator to pull the actuation members 40 from the prosthetic heart valve in a safe manner (i.e., only once the actuation members 40 are fully released from the prosthetic heart valve). Both the release of the actuation members 40 from the valve and retraction of the actuation members 40 can be performed in a continuous manner by operating a single rotatable knob (e.g., rotatable knob 124). Various parameters, such as thread pitch, design and number of idler gears, and the like, may be adjusted to provide adequate desirable performance of the mechanism.

The mechanism 700 can be combined with any mechanisms of the handle described in this disclosure. For example, the portions of the actuation members 40 extending proximally from the actuation tubes 364 can be coupled to the mechanism for second mechanism 1100 for expanding and compressing the valve described with reference to FIGS. 17-19. While the actuation members 40 are engaged with the lockers/actuators of the prosthetic valve 60, the second mechanism 1100 can be operable to expand and/or compress the valve.

After securing the prosthetic heart valve within the patient's anatomy, the actuation members are disconnected from the lockers/actuators of the valve so that the delivery apparatus can be retracted from the patient's body. It is important to ensure that the actuation members are completely disengaged from the valve prior to commencing retraction of the delivery apparatus. The implantation location is typically monitored under fluoroscopy or another X-ray imaging during an implantation procedure. A clinician can visually inspect the relatively opaque structures to determine whether the actuation members have been disconnected from the valve (e.g., by identifying a gap formed therebetween or by detecting spontaneous lateral movement of the distal ends of the actuation members). However, this method is rather subjective and can be inaccurate. It would be advantageous if the delivery apparatus could provide an objective indication when the actuation members are completely disengaged from the valve. Various mechanisms for detecting disengagement of actuation members from the locker/actuators of the prosthetic heart valve are described below.

Figure 40A:
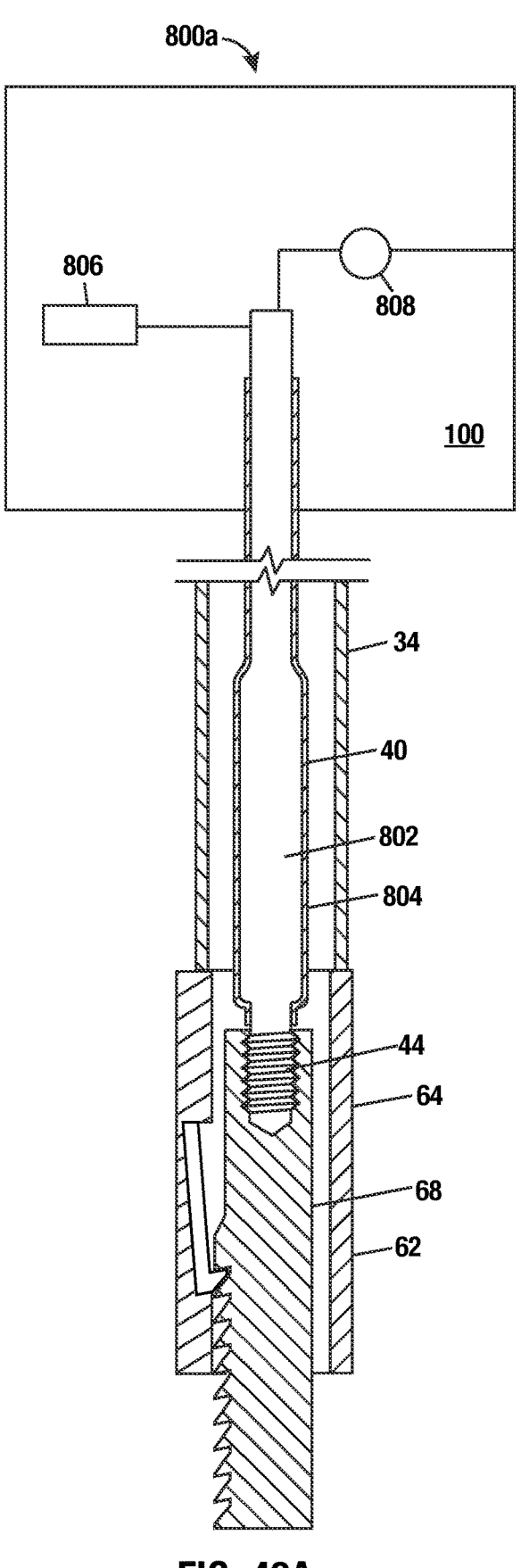
FIG. 40A illustrates an electrical mechanism configured to detect release of an actuation member from a respective locker/actuator.
Figure 40B:
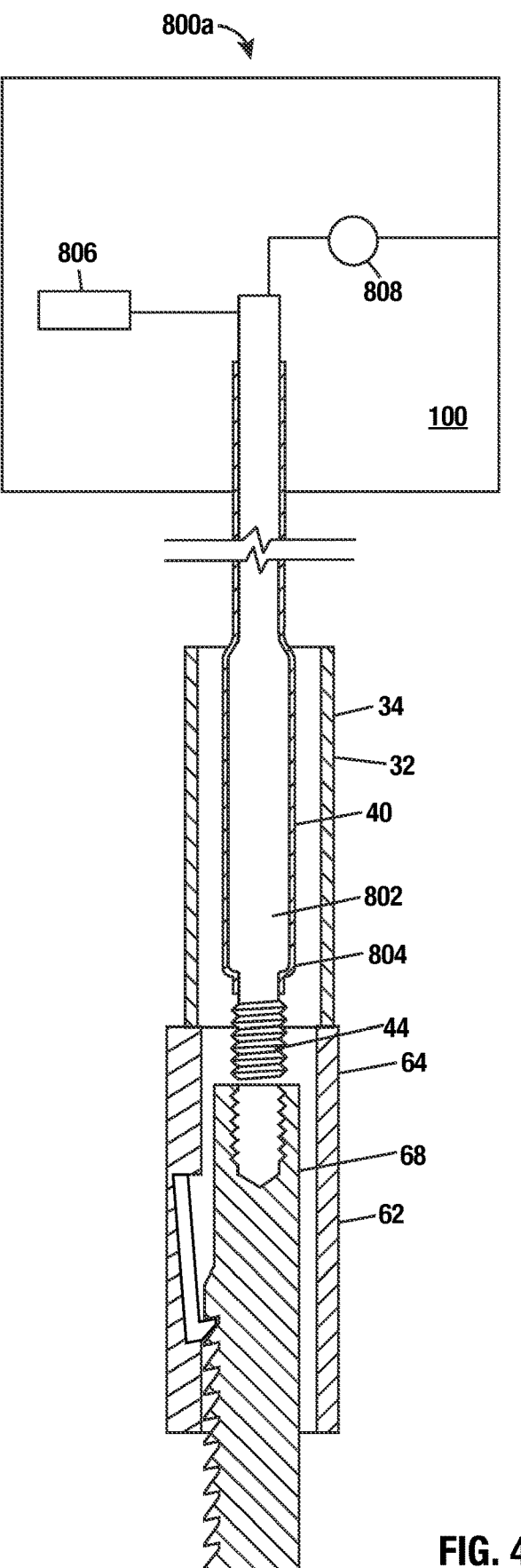
FIG. 40B shows the actuation member of FIG. 40A release from the locker/actuator.

FIGS. 40A and 40B illustrate an electrical mechanism 800a that can detect release of an actuation member 40 from a locker/actuator 62 of the prosthetic valve 60. The mechanism 800a is based on forming an electrical circuit that is closed when the actuation member 40 is engaged with the locker/actuator 62 and open when the actuation member 40 is released from the locker/actuator 62.

In the mechanism 800a, the actuation member 40 includes an electrically conductive medium 802 and an electrically insulating material (or insulator) 804 disposed around the electrically conductive medium 802. The electrically conductive medium 802 is connected to the distal threaded head 44 of the actuation member 40, which is also electrically conductive. The insulator 804 can extend substantially along the length of the actuation member 40, leaving the distal threaded head 44 electrically exposed.

In the state illustrated by FIG. 40A, a proximal portion of the actuation member 40 extends into the handle 100, and the distal threaded head 44 of the actuation member 40 is threadedly engaged with a threaded bore in the rack member 68 of the locker/actuator 62 of the valve. The electrically conductive medium 802 is electrically coupled to a power source 806 inside the handle. The sleeve member 34 that is disposed around the actuation member 40 preferably presses against the housing member 64 of the locker/actuator 62 when the distal threaded head 44 is engaged with the rack member 68, as previously described with reference to FIG. 6A. The sleeve member 34 can be made of an electrically non-conductive material.

The electrically conductive medium 802 is configured to complete an electrical circuit when the distal threaded head 44 is engaged with the rack member 68. Therefore, it is possible to determine whether the actuation member 40 is disengaged from the rack member by monitoring the current flowing through the electrical circuit. A current monitor (or current sensor) 808 (which can be within the handle 100)

monitors the current flowing through the electrical circuit. In some cases, the current monitor 808 is configured to provide an indication when the electrical circuit is open, which would correspond to release of the distal threaded head 44 from the rack member 68. The indication can be visual (e.g., via a digital screen, LED lights, and the like), auditory, and/or haptic.

After securing the valve at the implantation location, voltage can be fed to the electrically conductive medium 802 from the power source 806. The voltage can be very low to minimize any risks to the patient. The actuation member 40 can be disengaged from the rack member 68 by unscrewing the distal threaded bore 44 from the rack member 68. The current monitor 808 will detect electrical current if the distal threaded head 44 is threadedly engaged with the bore of the rack member 68. When the actuation member 40 is rotated up to the point that the distal threaded head 44 is completely disengaged from the rack member 68, as shown in FIG. 40B, no current will be detected by the current monitor 808.

The current monitor 808 can output an indication to the operator of the handle 100 when the actuation member 40 is completely disengaged from the rack member 68. Preferably, the sleeve member 34 remains pressed against the housing member 64 of the locker/actuator 62 until the actuation member 40 is completely disengaged from the rack member 68. When the current monitor 808 indicates that the actuation member 40 is completely disengaged from the rack member 68, the voltage fed to the actuation member 40 can be turned off, enabling the operator to safely retract both the actuation member 40 and the sleeve member 34.

For a valve with multiple lockers/actuators and a delivery apparatus with corresponding multiple actuation members, it may suffice to monitor disengagement of only one of the actuation members from the respective locker/actuators of the valve (e.g., in cases where the actuation members are simultaneously rotated to disengage the actuation members from the valve). In other cases, the disengagement of each actuation member from the respective locker/actuator can be monitored as described above. The current signals from each monitoring can be processed separately or can be combined into a single output.

Figures 41A, 41B:
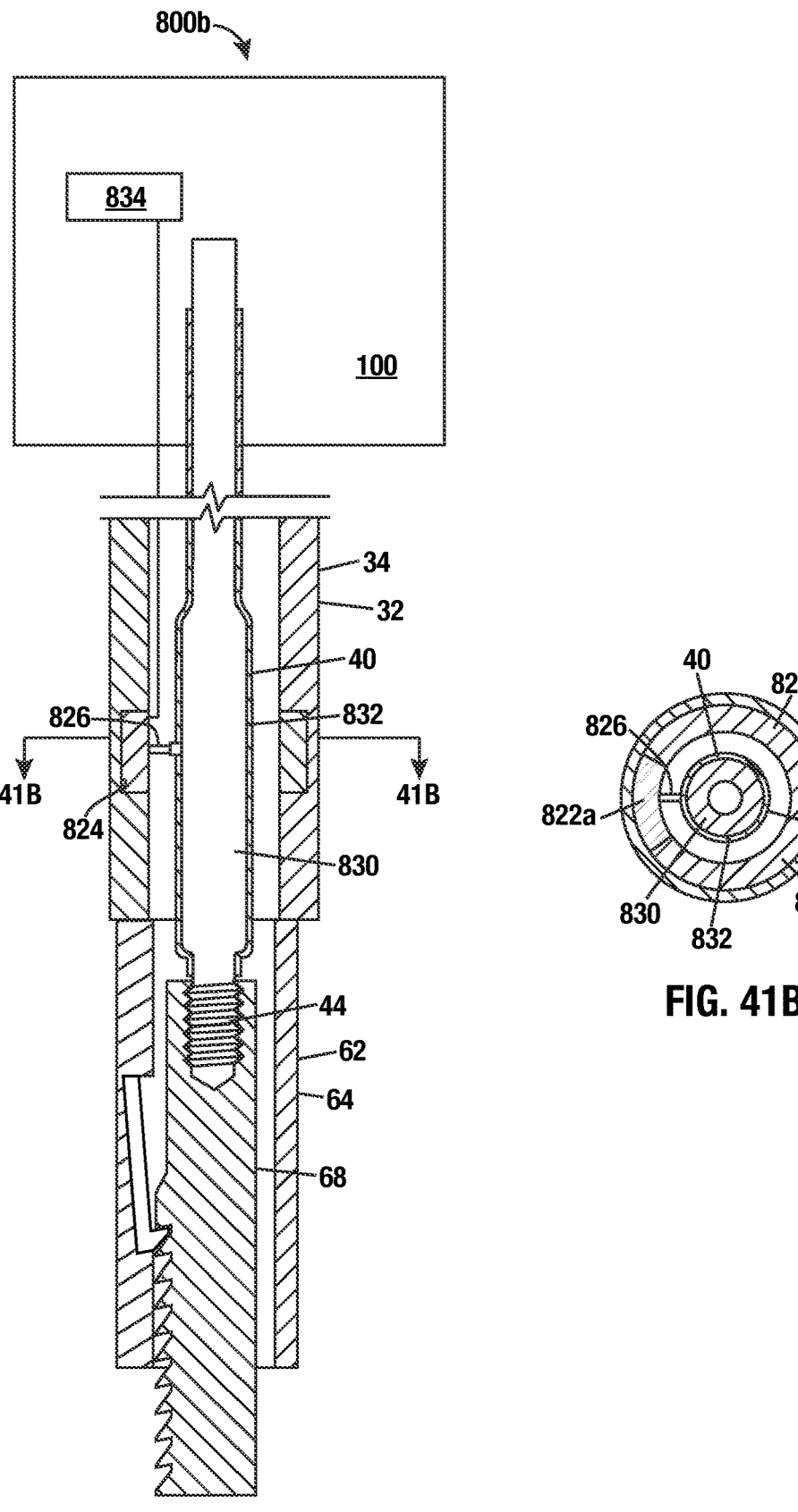
FIG. 41A illustrates an electric rotation-counting mechanism configured to detect release of an actuation member from a respective locker/actuator.
FIG. 41B is a cross-section of an actuation assembly, taken along line 41B-41B as shown in FIG. 41A.

FIGS. 41A and 41B illustrate an electrical rotation-counting mechanism 800b that can detect release of the actuation members 40 from the lockers/actuators 62 of the prosthetic valve 60. Although the electrical rotation-counting mechanism 820 is described below for a single actuation member 40, the electrical rotation-counting mechanism 820 is not limited to a single actuation member 40 and could be implemented for any number of the actuation members 40 in the delivery apparatus. The electrical rotation-counting mechanism 800b is based on counting the number of rotations of the actuation member 40 via electrical means as the actuation member 40 is rotated to unscrew the distal threaded head 44 from the rack member 68 of the respective locker/actuator 62 of the prosthetic valve 60.

The electrical rotation-counting mechanism 800b includes a ring member 822 having a conductive portion 822a that extends partly along a circumference of the ring and an insulated portion 822b that extends along the remainder of the circumference. The ring member 822 is disposed in a recess 824 formed in an inner surface of the sleeve member 34 disposed around the actuation member 40. In the electrical rotation-counting mechanism 800b, the sleeve member 34 is made of a non-conductive material, or an electrically insulating material.

The actuation member 40 comprises an electrically conductive medium 830 that is connected to the distal threaded head 44 at one end and to a power source 832 at another end. The power source 832 can be within the handle 100. A conductive arm 826 extends laterally from the electrically conductive member 830 at an axial position that is aligned with the position of the ring member 822 and that is proximal to the distal threaded head 44 of the actuation member 40. The conductive arm 826 is biased against an inner surface 828 of the ring member 822 (e.g., by a spring). The electrically conductive medium 830 is covered by a non-conductive layer 832 except for the area where the electrically conductive medium 830 is connected to the conductive arm 826. In addition, the conductive arm 826 is electrically exposed.

While the actuation member 40 is rotated around its central axis to unscrew the distal threaded head 44 from the rack member 68 of the locker/actuator 62 of the valve, the conductive arm 826 rotates with the actuation member 40. Since the conductive arm 826 is pressed against the inner surface of the ring member 822 at all times as the actuation member 40 rotates, electric current is transferred to the conductive portion 822a of the ring member 822 during a portion of the rotational cycle when the conductive arm 826 contacts the conductive portion 822a. This results in a "pulsed" electrical current generated during each rotational cycle of the actuation member 40.

A plurality of rotational cycles of the actuation member 40 will result in a similar number of electrical "pulses" conducted by the conductive portion 822a of the ring member 822, which can be transmitted to a counting mechanism in the handle. In one implementation the number of rotations required to release the actuation member 40 from the rack member 68 is known (e.g., the number of rotations may correspond to the number of threads on the distal threaded head 44). Exceeding this required number of rotations can indicate release of the actuation member 40 from the rack member 68.

In one example, a counter 834 within the handle can detect and count the number of electric pulses and provide an indication when the number of electric pulses exceed a predetermined threshold correlated to the required number of rotations to release the actuation member 40 from the rack member 68. The indication can be visual (e.g., via a digital screen, LED lights, and the like), auditory, and/or haptic.

Figure 42:
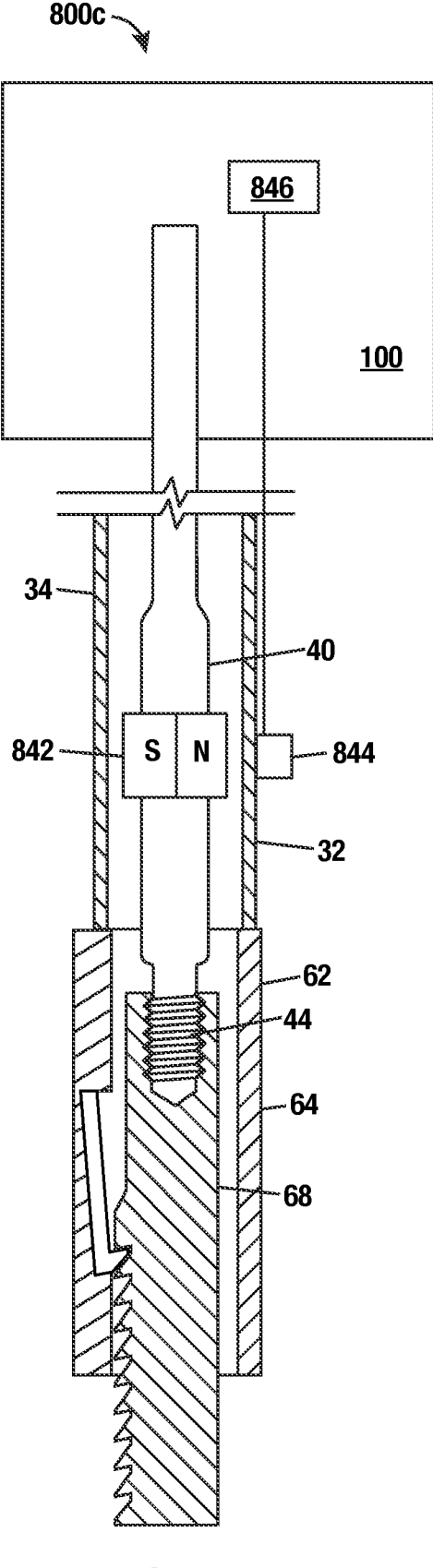
FIG. 42 illustrates a magnetic rotation-counting mechanism configured to detect release of an actuation member from a respective locker/actuator.

FIG. 42 illustrates a magnetic rotation-counting mechanism 800c that can detect release of the actuation members 40 from the lockers/actuators 62 of the prosthetic valve 60. Although the magnetic rotation-counting mechanism 800c is described below for a single actuation member 40, the magnetic rotation-counting mechanism 800c is not limited to a single actuation member 40 and can be implemented for any number of the actuation members 40 in the delivery apparatus. The magnetic rotation-counting mechanism 800c is based on counting the number of rotations of the actuation member 40 via magnetic means as the actuation member 40 is rotated to unscrew the distal threaded head 44 from the rack member 68 of the respective locker/actuator 62 of the prosthetic heart valve.

The magnetic rotation-counting mechanism 800c can include a magnetic ring 842 attached to the actuation member 40 at an axial position that is proximal to the distal threaded head 44 of the actuation member 40. The magnetic ring 842 comprises at least two regions provided with opposing polarities (S and N). Alternatively, at least two separate magnetic elements with opposing polarities can be substituted for the magnetic ring. The magnetic ring 842 (or magnetic elements) rotate with the actuation member 40.

The magnetic rotation-counting mechanism 800c includes a magnetic sensor 844 that is axially aligned with the magnetic ring 842 (or magnetic elements). The magnetic sensor 844 can be attached to the sleeve member 34 disposed around the actuation member 40 (for example, to the outer surface of the sleeve member 34) of the actuation assembly 32. The magnetic sensor 844 can communicate with a signal counter 846 within the handle 100. The magnetic sensor 844 senses rotation of the actuation member 40 (e.g., due to the change in polarity at different phases of the rotation cycle) and generates a corresponding signal, which is received by the signal counter 846.

In one implementation, the number of rotations required to release the actuation member 40 from the rack member 68 of the respective locker/actuator 62 is known, and the actuation member 40 considered as released when the number of rotations of the actuation member 40 exceeds the required number of rotations. In one example, the counter 846 counts the number of signals generated by the magnetic sensor 844 (which are indicative of the number of complete rotations of the actuation member).

In one example, the counter 846 is configured to provide an indication when the number of complete rotations of the actuation member 40 exceeds the required number of rotations to release the actuation member 40 from the rack member 68. The indication can be visual (e.g., via a digital screen, LED lights, and the like), auditory, and/or haptic.

Figure 43:
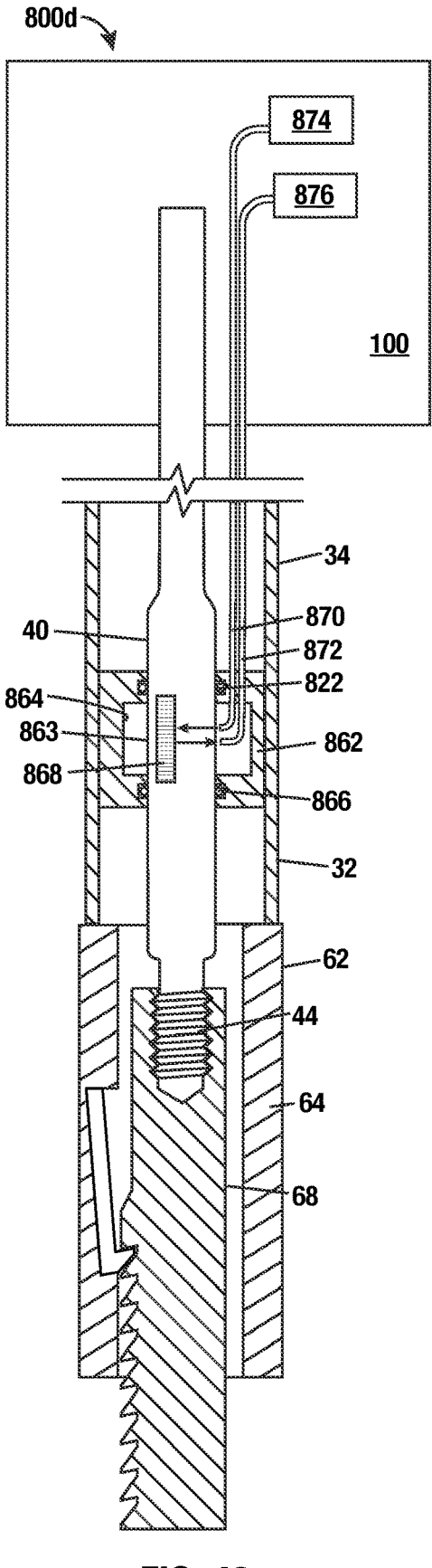
FIG. 43 illustrates an optic rotation-counting mechanism configured to detect release of an actuation member from a respective locker/actuator.

FIG. 43 illustrates an optic rotation-counting mechanism 800d configured to detect release of the actuation members 40 from the lockers/actuators 62 of the prosthetic valve 60. Although the optic rotation-counting mechanism 800d is described below for a single actuation member 40, the optic rotation-counting mechanism 800d is not limited to a single actuation member 40 and can be implemented for any number of actuation members 40 in the delivery apparatus. The optic rotation-counting mechanism 800d is based on counting the number of rotations of the actuation member 40 via optical means as the actuation member 40 is rotated to unscrew the distal threaded head 44 from the rack member 68 of the respective locker/actuator 62 of the prosthetic heart valve.

The optic rotation-counting mechanism 800d can include a housing 862 that is circumferentially disposed around the actuation member 40 at an axial position that is proximal to the distal threaded head 44 of the actuation member 40. The housing 862 can be fixed to the sleeve member 34 disposed around the actuation member 40 such that the housing 862 can be stationary while the actuation member 40 is rotated. An inner chamber 864 is defined between the housing 862 and the actuation member 40. Preferably, the inner chamber 864 is hermetically sealed (e.g., by providing seal members 866 in the interface between the housing 862 and the actuation member 40) to prevent blood flow into the inner chamber 864.

The optic rotation-counting mechanism 800d includes a light absorber 868 coupled to a surface 863 of the actuation member 40 exposed to the inner chamber 864. The light absorber 868 is coupled to a section of the surface 863 and does not extend around the circumference of the actuation member 40. The light absorber 868 can be in the form of dark markings or other light absorbing structure that can be coupled to the actuation member 40.

The optic rotation-counting mechanism 800d includes two optic cores 870, 872 extending into the inner chamber 864. The optic cores 870, 872 can extend into the inner chamber 864 from the handle 100. In one example, the optic cores 870, 872 can be provided as separate optical fibers. In another example, a single optical fiber with two cores can provide the optic cores 870, 872. The optic core 870 can be connected to a light source 874 (which may be within, or otherwise coupled to, the handle 100), and the optical fiber 870 can be connected to a light detector 876 (which may be within, or otherwise coupled to, the handle 100).

The optic core 870 is arranged to direct light towards the surface 863 of the actuation member 40 within the inner chamber 864. For example, the end of the optic core 870 inside the inner chamber 864 can be oriented transversely (or radially) to a longitudinal axis of the actuation member 40. The optic core 872 is arranged to detect light returned from the surface 863 of the actuation member exposed to the inner chamber 864. The optic core 872 can have the same orientation as described for the optic core 870.

As the actuation member 40 is rotated to unscrew the distal threaded head 44 from the rack member 68, the optic core 870 emits light in a direction towards the rotating surface 863 of the actuation member 40, and the optic core 872 receives light returned from the rotating surface 863 of the actuation member 40. During each rotational cycle of the actuation member 40, at a certain rotational angle of the actuation member 40, the light emitted from the optic core 870 will strike the light absorber 868, and the intensity of the light returned to the optic core 872 from the light absorber 868 will be correspondingly reduced. By monitoring the changes in intensity of the light returned to the optic core 872 and detected at the light detector 876, it is possible to determine the number of rotations of the actuation member 40.

In one implementation, the circuitry of the light detector 876 is configured to count the number of reduced light-intensity phases sensed by the optic core 872 (which are indicative of the number of complete rotations of the actuation member 40). In one example, the number of rotations required to release the actuation member 40 from the rack member 68 is known (e.g., based on the number of threads in the distal threaded head 44), and the circuitry of the light detector 876 is configured to generate an output when the count of reduced light-intensity phases sensed from the optic core 872 exceeds the required number of rotations.

In one example, the light detector 876 circuitry is configured to provide an indication when the number of complete rotations of the actuation member 40 exceeds the predetermined required number of rotations to release the actuation member 40 from the rack member 68. The indication can be visual (e.g., via a digital screen, LED lights, and the like), auditory, and/or haptic.

During a valve implantation procedure, a distal gap can form between the nosecone and the distal end of the prosthetic heart valve after retracting the outer shaft from the prosthetic heart valve at an implantation location. This can be the case especially for prosthetic heart valves with relatively large diameters, where the prosthetic heart valve assumes a pre-expanded or compressed diameter that is somewhat larger than the diameter of the distal capsule after the outer shaft is retracted. A distal gap creates a discontinuity in the delivery apparatus that can make it difficult to advance the prosthetic heart valve in the distal direction if repositioning of the prosthetic heart valve is required. In this case, it may be desirable to close or minimize the distal gap prior to attempting to reposition the valve.

After securing the prosthetic heart valve to the native anatomy, the delivery apparatus is released from the prosthetic heart valve so that the delivery apparatus can be withdrawn from the patient's body. If the nosecone is distal to the prosthetic heart valve after releasing the delivery apparatus from the prosthetic heart valve, the nosecone will have to be pulled through the valve in order to withdraw the delivery apparatus from the patient's body. While the nosecone is being pulled through the valve, the proximal edges of the nosecone may contact regions of the expanded prosthetic heart valve, including the distal lip of the prosthetic heart valve, posing a risk of valve migration as a result of the pull force exerted on the valve by the nosecone. In this case, it may be desirable to move the nosecone proximal to the prosthetic heart valve prior to releasing the delivery apparatus from the valve.

Figure 44:
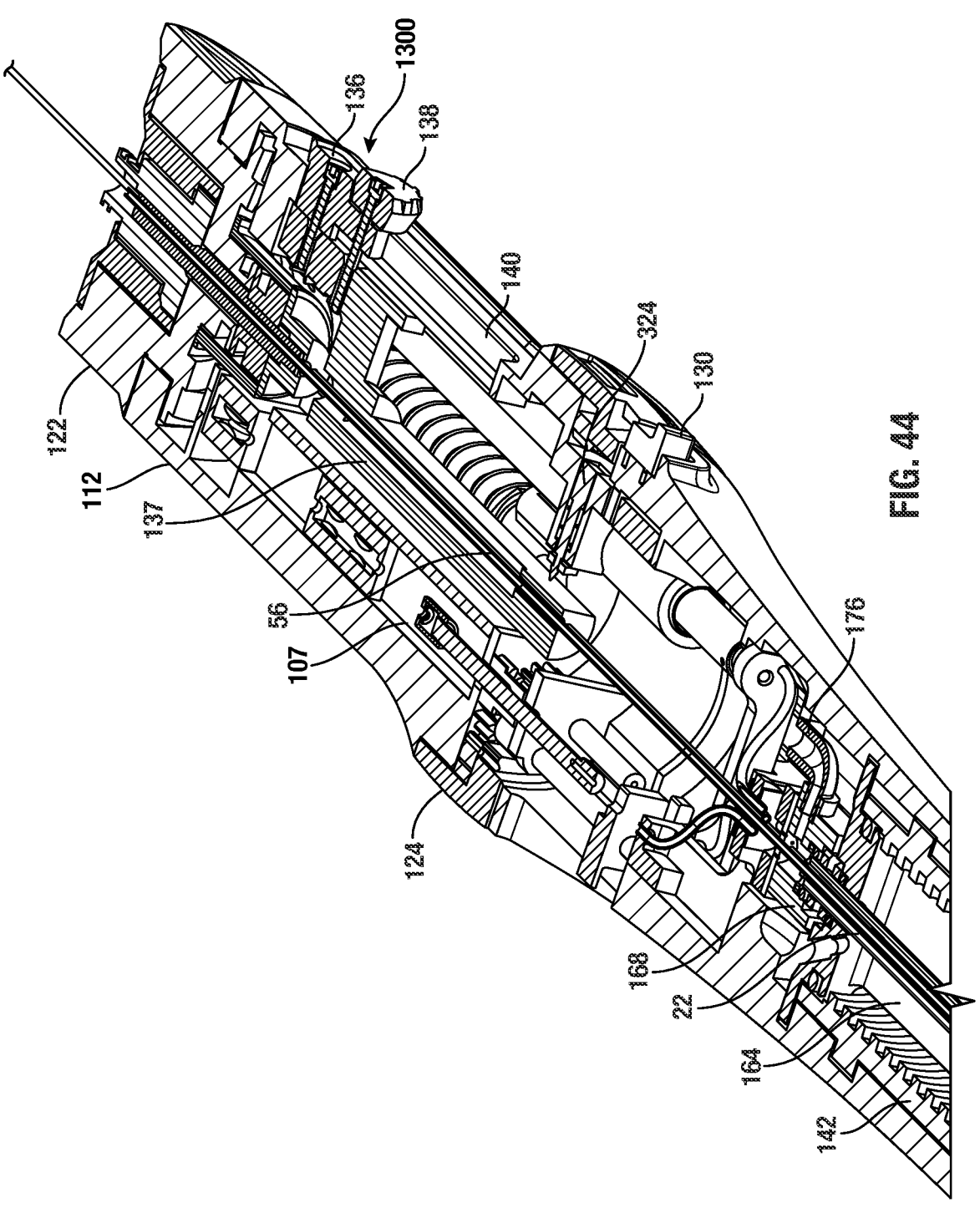
FIG. 44 is a detail view of the handle of FIG. 11 illustrating a mechanism for displacing a nosecone shaft of the delivery apparatus.

FIG. 44 illustrates a fourth mechanism 1300 (i.e., a shaft displacement mechanism) that can be controlled by the slidable knob 136. The fourth mechanism 1300 is configured to displace the nosecone shaft 56 relative to the handle 100. The mechanism 1300 includes a slider inner body 137 that is positioned within a proximal portion of the cavity 107 of the handle 100. The mechanism 1300 includes a slot 140 formed in the housing member 112. The slidable knob 136 is positioned to slide along the slot 140 and is coupled to the slider inner body 137. Movement of the slidable knob 136 along the slot 140 results in displacement of the slider inner body 137 in the axial direction of the handle.

The nosecone shaft 56 extends proximally from the multi-lumen shaft 22 and is coupled to the slider inner body 137 (e.g., by engaging with a recess in the slider inner body 137) such that axial movement of the slider inner body 137 produces axial movement of the nosecone shaft 56. In one example, movement of the slidable knob 136 within the slot 140 in a distal direction advances the nosecone shaft 56 in the distal direction, and movement of the knob 136 in a proximal direction retracts the nosecone shaft 56 in the proximal direction. The nosecone shaft 56 can be advanced or retracted to adjust the position of the nosecone at the distal end of the nosecone shaft 56 relative to other structures in the delivery assembly, such as the prosthetic valve 60 or the outer shaft 14.

A knob locker 138, which is an example of a safety knob, can be coupled to the slidable knob 136. The knob locker 138 can be adjustable to allow or prevent axial movement of the slidable knob 136 within the slot 140. The knob locker 138 can be, for example, a screw. The knob locker 138 can be rotatable in a first direction to engage the slidable knob 136, thereby applying frictional force to the slidable knob 136 that prevents axial movement of the slidable knob 136. The knob locker 138 can be rotatable in a second direction that is opposite to the first direction to space the knob locker 138 radially away from the slidable knob 136, thereby allowing the slidable knob 136 to freely slide axially along the slot 140.

FIGS. 45A-45C show different stages of maneuvering the nosecone 50 via axial displacement of the nosecone shaft 56. FIG. 45A illustrates two optional positions of the nosecone 50 relative to the prosthetic valve 60 and the multi-lumen shaft 22 of the delivery apparatus, wherein the nosecone 50 can be offset radially away from a centerline of prosthetic valve 60, from a first location of the nosecone 50 and the nosecone shaft 56, to a second location shown in dashed lines of the nosecone 50' and the nosecone shaft 56'. As shown in FIG. 45B, retraction of the nosecone 50' in a proximal direction, for example, during retrieval of the delivery apparatus after the prosthetic valve 60 has been mounted in place, may result in contact between the nosecone 50' and the distal edge of the valve. FIG. 45B shows a gap g1 that may be formed between the prosthetic valve 60 and the nosecone 50. FIG. 45C shows the nosecone 50 being pulled in the proximal direction d1 (e.g., by displacing the nosecone shaft 56 in a proximally oriented direction d1 using the slidable knob 136) in order to minimize the gap g1.

FIGS. 46A-46E show stages of a method of controlling the position of the nosecone 50 to assure safe retrieval of the nosecone 50 after the prosthetic valve 60 is secured at the implantation location. FIG. 46A shows a first stage of the method were the nosecone 50 is displaced in a distal direction relative to the expanded prosthetic valve 60 while the prosthetic heart valve is still attached to the delivery apparatus via the actuation assemblies of the delivery apparatus. FIG. 46B shows a second stage of the method where the nosecone 50 being pulled in a proximal direction d1 (e.g., by displacing the nosecone shaft 56 using the slidable knob 136). At this stage, the prosthetic valve 60, expanded against an aortic annulus, for example, is still attached to the delivery apparatus via the actuation assemblies. Using the slidable knob 136, the nosecone 50 may be pulled back in a proximal direction, as shown by arrow 135, through the expanded prosthetic valve 60, until the nosecone 50 is positioned proximal to the prosthetic valve 60 (e.g., until the nosecone is positioned between a proximal edge of the prosthetic valve 60 and a distal edge of multi-lumen shaft 22), as illustrated in FIG. 46C. FIG. 46C shows a third stage of the method where the prosthetic valve 60 is disengaged from the delivery apparatus. At this stage, since the nosecone 50 is proximal to the prosthetic valve 60, the nosecone 50 can be retrieved safely along with the entire delivery apparatus.

A fourth stage of the method can include using each of the slidable knob 136 and the rotatable knob 120 (see FIG. 11) to close the gap between the nosecone 50 and the distal end of the outer shaft 14. For example, as shown in FIG. 46D, the slidable knob 136 can be operated to displace the nosecone 50 in a distally oriented direction, as shown by the arrow 139, so that the nosecone 50 is distal to the actuation assemblies 32. As shown in FIG. 46E, the rotatable knob 120 can be operated to displace the outer shaft 14 in a distally oriented direction, as shown by arrow 141, to extend the outer shaft 14 over the actuation assemblies 32 and the nosecone shaft 56 and close the gap between the nosecone 50 and the distal end of the outer shaft 14. If needed, the slidable knob 136 can be operated to pull the nosecone 50 in a proximally oriented direction, as shown by arrow 143, to press against the distal end of the outer shaft 14. Closing or minimizing any gaps between the nosecone 50 and the distal end of the outer shaft 14 can enable safer and easier retrieval of the delivery apparatus from the patient's body.

Further details regarding methods in which nosecone displacement can be used can be found in U.S. Application No. 62/886,677.

FIG. 47A-47C illustrate another exemplary handle 100a including a distal portion 110a and a proximal portion 112a, which are telescopically movable relative to each other along a longitudinal axis 101a of the handle. The distal portion 110a and the proximal portion 112a define a cavity to contain the components of the handle. The handle 100a includes a rotatable knob 120a, a rotatable knob 122a, a rotatable knob 124a, a fourth knob 126a, which are illustrated as rotatable knobs. The handle 100a can further include a safety knob 130a and a knob 430a. The knobs 122a, 124a, 126a, 130a, 430a can have the corresponding functions described for the knobs 122, 124, 126, 130, 430.

A proximal portion of the shaft assembly 11 extends into the cavity of the handle. The shaft assembly 11 illustrated by FIGS. 47A-47C includes the outer shaft 14, the commander shaft 30, and the multi-lumen shaft 22 (as previously shown in FIG. 9A). The handle 110a includes a mechanism 1000a for retracting the outer shaft 14 and the commander shaft 30. The mechanism 1000a includes the rotatable knob 120a that is configured to retract the outer shaft 14. The mechanism 1000a further includes the proximal ends of the outer shaft 14 and the commander shaft 30 that are coupled to the distal portion 110a such that telescoping movement of the portions 110a, 112a can retract both the outer shaft 14 and the commander shaft 30.

In one example, the proximal portion 112a can be held relatively stationary while the distal portion 110a is moved towards the proximal portion 112a, which would retract both the outer shaft 14 and the commander shaft 30. For safety purposes, a removable cover 114a can be disposed between the distal portion 110a and the proximal portion 112a to prevent telescoping movement of the portions 110a, 112a until the telescoping movement is desired. This can prevent unintentional retraction of the commander shaft 30. When it is desired to retract the commander shaft 30 (e.g., after an initial retraction of the outer shaft 14), the removable cover 114a can be removed, as shown in FIG. 47C.

Thus, the rotatable knob 120 and the telescopically movable portions 110a, 112a of the handle form a two-staged shaft retraction mechanism 1000a configured to retract the outer shaft 14 and the commander shaft 30. In the first stage, the outer shaft 14 can be retracted by rotating the rotatable knob 120, while the commander shaft 30, covering the actuation assemblies 32, is retained in its position to prevent both axial displacement and undesired radial expansion of the valve at this stage (as shown in FIG. 9C). In the second stage, the outer shaft 14 is further retracted together with the commander shaft 30 by telescopically sliding the portions 110a, 112a of the handle 100a towards each other.

The handle 100a can be used generally as follows: the distal end of the delivery apparatus 12, with the prosthetic heart valve encapsulated therein, is inserted into the patient's body and advanced through the patient's vasculature. The fourth knob 126a can be operated if needed to steer the delivery apparatus 12 through the patient's vasculature. Once the prosthetic heart valve is positioned at the desired implantation location, the rotatable knob 120a is rotated to retract the outer shaft 14 and the distal capsule attached to the outer shaft 14, exposing the prosthetic heart valve. The commander shaft 30 retains its position at this state, pressed against the prosthetic heart valve to prevent proximal displacement of the prosthetic heart valve. Once the outer shaft 14 is sufficiently retracted, relative sliding movement between the distal portion 110a of the handle 100a is used to retract both the outer shaft 14 and the commander shaft 30, exposing the actuation assemblies 32 of the delivery apparatus 12.

Additional operations with the handle 100a can include operating the rotatable knob 122a to expand the prosthetic heart valve (e.g., the rotatable knob 122a can be operated to simultaneously pull the actuation members 40 as previously described) and operating the rotatable knob 124a to release the actuation members of the delivery apparatus 12 from the prosthetic heart valve (e.g., the rotatable knob 124a can be operated to simultaneously rotate the actuation members 40 and thereby unscrew the threaded heads 44 of the actuation members 40 from the respective rack members 68 of the lockers/actuators 62 of the prosthetic heart valve as previously described). The delivery apparatus 12 can be withdrawn from the patient's body after releasing the actuation members from the valve.

FIG. 48 illustrates another exemplary handle 100b including a distal end 102b, a proximal end 104b, and a longitudinal axis 101b extending from the distal end 102b to the proximal end 104*b* and defining an axial direction of the handle. The handle 100*b* includes housing members 110*b*, 112*b*, 113*b*, which are coupled together and extend along the longitudinal axis 101*b*. The housing members 110*b*, 112*b*, 113*b* define a cavity to contain the components of the handle. The handle 100*b* includes a rotatable knob 120*b*, a rotatable knob 122*b*, a rotatable knob 124*b*, and a fourth knob 126*b*, which are illustrated as rotatable knobs. The handle 100*b* can further include a knob 430. The knobs 122*b*, 124*b*, 126*b*, 430*b* can have the corresponding functions described for the knobs 122, 124, 126, 430.

A proximal portion of the shaft assembly 11 extends into the cavity of the handle. The shaft assembly 11 illustrated by FIG. 48 includes the outer shaft 14, the commander shaft 30, and the multi-lumen shaft 22 (as previously shown in FIG. 9A). FIGS. 49A-49D illustrate a two-staged shaft retraction mechanism 1000*b* that can be used to retract the outer shaft 14 and the commander shaft 30. In the example illustrated by FIGS. 49A-49D, a first axially movable component 148*b* is coupled to the proximal end of the outer shaft 14, and a second axially movable component 149*b* is coupled to the proximal end of the commander shaft 30. The first axially movable component 148*b* and the second axially movable component 149*b* are movable along an inner track 144*b* formed within the handle 100*b*.

In one example, the first axially movable component 148*b* can be an internal nut that is movable along the inner track 144*b* upon rotation of the rotatable knob 120*b* (shown in FIG. 48). The second axially movable component 149*b* is located proximal to the first axially movable component 148*b* and is slidable within the inner track 144*b*. In some cases, the mechanism can include a stopping feature 128*b* positioned to prevent distal displacement of the second axially movable component 149*b* beyond a predetermined position. In one example, the stopping feature 128*b* can be a rod that is disposed between the second axially movable component 149*b* and a distal end 102*b* of the handle.

Since the outer shaft 14 is attached to the first axially movable component 148*b*, proximal displacement of the first axially movable component 148*b* causes the outer shaft 14 to retract. The first axially movable component 148*b* and the second axially movable component 149*b* are configured to contact each other during proximal displacement of the first axially movable component 148*b*. For example, an inner surface of the first axially movable component 148*b* can be shaped to contact an adjacent outer surface of the second axially movable component 149*b* when the first and the second axially movable components 148*b*, 149*b* meet each other along the inner track 144*b*.

Figure 49A:
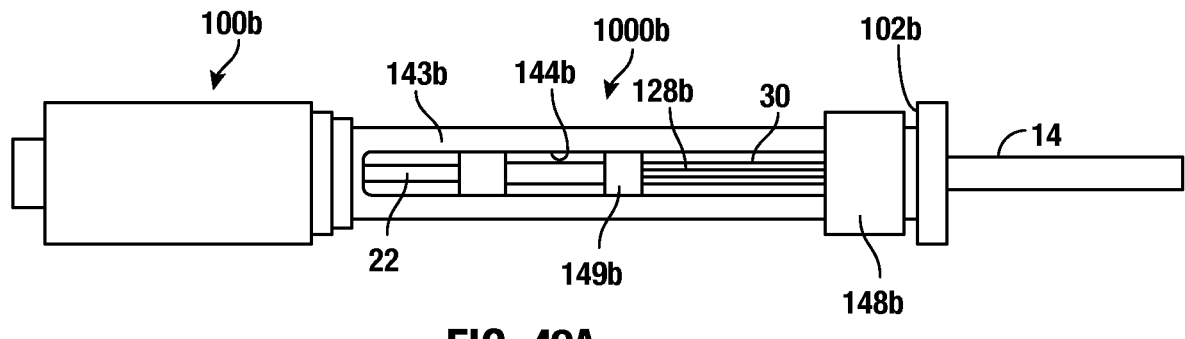
FIGS. 49A-49D illustrate a two-staged shaft retraction mechanism.
Figure 49B:
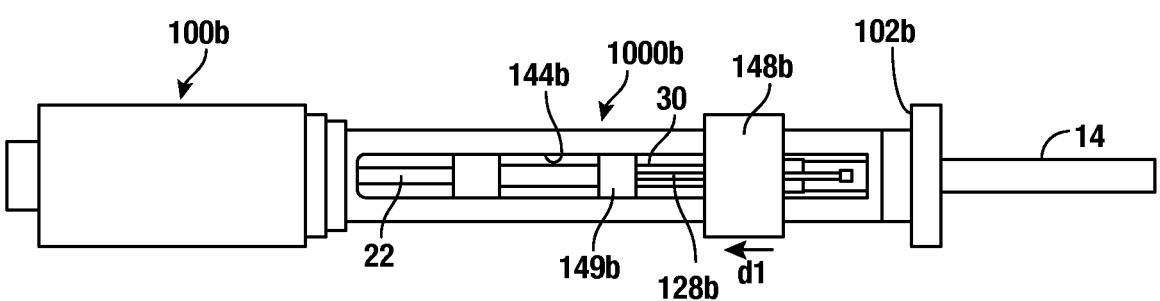
Figure 49C:
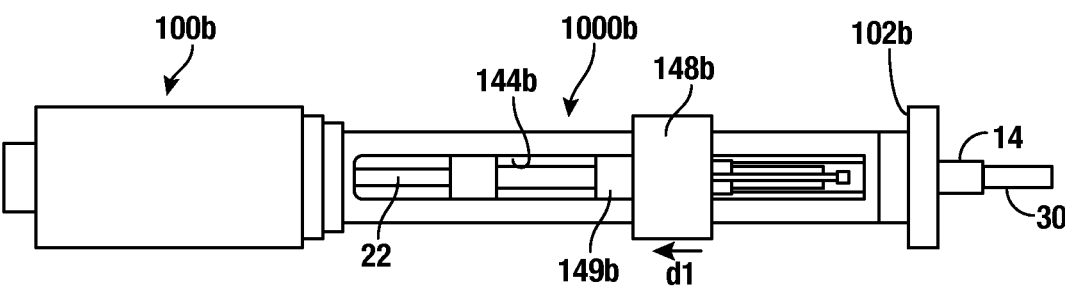
Figure 49D:
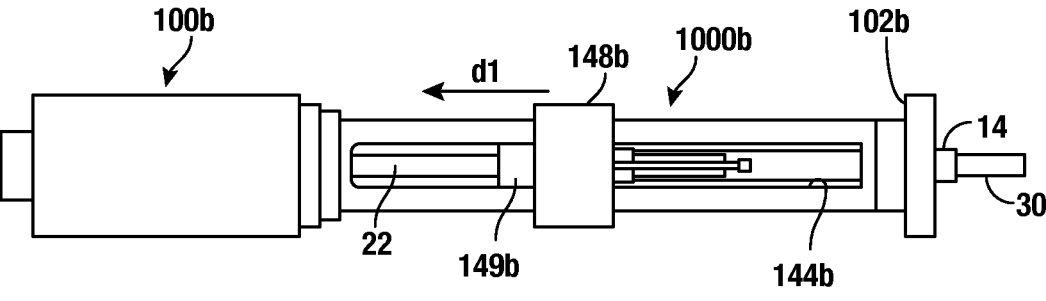

FIG. 49B shows the first axially movable component 148*b* moving away from a distal surface 102*b* of the handle but not yet reaching the second axially movable component 149*b*. FIG. 49C shows the first axially movable component 148*b* during a first contact with the second axially movable component 149*b*. Further movement of the first axially movable component 148*b* after this first contact will result in both first and second axially movable components 148*b*, 149*b* moving in the same proximally oriented direction d1, as shown in FIG. 49D. Since the commander shaft 30 is attached to the second axially movable component 149*b*, proximal displacement of the second axially movable component 149*b* retracts the commander shaft 30 (i.e., pulls the commander shaft 30 in the proximal direction).

Rotation of a single knob (e.g., the rotatable knob 120*b*) retracts the outer shaft 14 to expose the valve, while the commander shaft 30, covering the actuation assemblies 32, retains its position to prevent both axial displacement and undesired radial expansion of the valve. Further continuous rotation of the same knob retracts the commander shaft 30 to expose the actuation assemblies 32. The distance along which the first axially movable component 148*b* travels before reaching and contacting the second axially movable component 149*b* can be designed to match the amount by which the outer shaft 14 should be retracted to expose the valve. The distance can be defined, for example, by the stopping feature 128.

The two-staged shaft retraction mechanism described with reference to FIGS. 47A-47C requires an operator to first rotate a knob of the handle to retract the outer shaft 14 and then telescopically slide portions of the of the handle together to achieve the two-staged shaft retraction. The two-staged shaft retraction mechanism described with reference to FIGS. 49A-49D achieves the two-staged retraction in a continuous manner with a single knob.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

EXAMPLE 1: A delivery apparatus for implanting a prosthetic heart valve comprises one or more shafts and a handle coupled to the one or more shafts, wherein the handle comprises one or more knobs, one or more adjustment mechanisms, and/or one or more control mechanisms, wherein the knobs are configured for actuating the one or more adjustment mechanisms and/or the one or more control mechanisms, wherein the one or more adjustment mechanisms are configured for moving the shafts relative to each other and/or relative to the handle, and wherein the one or more control mechanisms are configured for limiting the direction of movement and/or force applied to the one or more shafts.

EXAMPLE 2: A delivery assembly comprises a delivery apparatus according to any example herein, particularly example 1, and a prosthetic heart valve coupled to the delivery apparatus.

EXAMPLE 3: The delivery assembly of any example herein, particularly example 2, wherein the prosthetic heart valve is a mechanically-expandable prosthetic heart valve.

EXAMPLE 4: The delivery assembly of any example herein, particularly example 3, wherein the mechanically-expandable prosthetic heart valve comprises a plurality of struts that are pivotably coupled together.

EXAMPLE 5: The delivery apparatus of any example herein, particularly any one of examples 1-4, wherein the one or more knobs of the handle includes 3-4 rotatable knobs.

EXAMPLE 6: The delivery apparatus of any example herein, particularly any one of examples 1-5, wherein the one or more knobs of the handle includes exactly three rotatable knobs.

EXAMPLE 7: The delivery apparatus of any example herein, particularly any one of examples 1-5, wherein the one or more knobs of the handle includes exactly four rotatable knobs.

EXAMPLE 8: A method of implanting a prosthetic heart valve comprises rotating a first knob of a handle of a delivery apparatus to retract a first shaft of the delivery apparatus relative to a prosthetic heart valve; rotating a second knob of the handle to adjust the radial expansion of the prosthetic heart valve; and rotating a third knob of the handle to release the prosthetic heart valve from the delivery apparatus.

EXAMPLE 9: The method of any example herein, particularly example 8, which further comprises rotating a slidable knob of the handle to adjust the curvature of the first shaft.

EXAMPLE 10: An assembly for implanting a prosthetic heart valve comprises a prosthetic heart valve configured to be moved from a compressed state to an expanded state and from the expanded state to the compressed state. The assembly further comprises a delivery apparatus comprising one or more shafts and a handle, wherein the prosthetic heart valve is releasably coupled to at least one of the one or more shafts of the delivery apparatus, and wherein the handle is configured for positioning the prosthetic heart valve and for adjusting the prosthetic heart valve from the compressed state to the expanded state and from the expanded state to the compressed state.

EXAMPLE 11: A delivery apparatus for implanting a prosthetic heart valve comprises a first shaft comprising a distal end portion and a proximal end portion, wherein the distal end portion of the first shaft comprises a capsule configured to receive the prosthetic heart valve in a radially compressed state; a second shaft comprising a distal end portion and a proximal end portion, wherein the second shaft extends through the first shaft, wherein the distal end portion of the second shaft is configured for contacting the prosthetic heart valve; a third shaft comprising a distal end portion and a proximal end portion, wherein the third shaft extends through the second shaft, wherein the distal end portion of the second shaft is configured to be releasably coupled to the prosthetic heart valve, and wherein the first shaft, the second shaft, and the third shaft are axially movable relative to each other; and a handle comprising a distal portion and a proximal portion, wherein the proximal end portion of the first shaft and the proximal end portion of the second shaft are coupled to the distal portion of the handle, wherein the proximal end portion of the third shaft is coupled to the proximal portion of the handle, wherein the handle is configured for a first mode of operation and a second mode of operation, wherein in the first mode of operation, the first shaft is axially movable relative to the second shaft and the third shaft, and wherein in the second mode of operation, the first shaft and the second shaft are axially movable relative to the third shaft.

EXAMPLE 12: The delivery apparatus of any example herein, particularly example 11, wherein the handle comprises a locking member configured to restrict the handle from being moved from the first mode of operation to the second mode of operation.

EXAMPLE 13: The delivery apparatus of any example herein, particularly example 12, wherein the locking member comprises a cover disposed between the distal portion of the handle and the proximal portion of the handle.

EXAMPLE 14: The delivery apparatus of any example herein, particularly any one of examples 11-13, wherein the handle further comprises a first knob rotatably coupled to the distal portion of the handle, wherein the handle is configured such that rotating the first knob relative to the distal portion of the handle results in the first shaft moving axially relative to the second shaft and the third shaft.

EXAMPLE 15: The delivery apparatus of any example herein, particularly any one of examples 11-14, wherein in the second mode of operation, the handle is configured such that the distal portion of the handle and the proximal portion of the handle can move axially relative to each other.

EXAMPLE 16: The delivery apparatus of any example herein, particularly any one of examples 11-15, wherein in the second mode of operation, the handle is configured such that the distal portion of the handle and the proximal portion of the handle can move telescopically relative to each other.

EXAMPLE 17: The delivery apparatus of any example herein, particularly any one of examples 11-16, wherein the handle further comprises a force balancing assembly.

EXAMPLE 18: The delivery apparatus of any example herein, particularly example 17, wherein the force balancing assembly comprises one or more pulleys.

EXAMPLE 19: The delivery apparatus of any example herein, particularly any one of examples 11-18, wherein the handle further comprises a displacement control mechanism.

EXAMPLE 20: The delivery apparatus of any example herein, particularly example 19, wherein the displacement control mechanism comprises a plurality of gears.

EXAMPLE 21: The delivery apparatus of any example herein, particularly any one of examples 11-18, further comprises a displacement control mechanism.

EXAMPLE 22: The delivery apparatus of any example herein, particularly example 21, wherein the displacement control mechanism comprises a plurality of gears.

EXAMPLE 23: The delivery apparatus of any example herein, particularly any one of examples 11-22, wherein the handle further comprises a second knob rotatably coupled to the proximal portion of the handle, wherein the handle is configured such that rotating the second knob in a first direction relative to the proximal portion of the handle results in radial expansion of the prosthetic heart valve, and wherein the handle is configured such that rotating the second knob in a second direction relative to the proximal portion of the handle results in radial compression of the prosthetic heart valve.

EXAMPLE 24: A delivery apparatus for implanting a prosthetic heart valve comprises a first shaft comprising a distal end portion and a proximal end portion, wherein the distal end portion of the first shaft comprises a capsule configured to receive the prosthetic heart valve in a radially compressed state; a second shaft comprising a distal end portion and a proximal end portion, wherein the second shaft extends through the first shaft, wherein the distal end portion of the second shaft is configured for contacting the prosthetic heart valve; a third shaft comprising a distal end portion and a proximal end portion, wherein the third shaft extends through the second shaft, wherein the distal end portion of the second shaft is configured to be releasably coupled to the prosthetic heart valve; and a handle comprising a main portion and a first knob, wherein the proximal end portions of the first shaft, the second shaft, and the third shaft are coupled to the main portion of the handle, wherein the first knob is rotatably coupled to the main portion, wherein the handle is configured such that rotating the first knob in a first direction from a first rotational position to a second rotational position relative to the main portion results in axial movement of the first shaft relative to the second shaft and the third shaft, and wherein the handle is configured such that rotating the first knob in the first direction from the second rotational position to a third rotational position relative to the main portion results in axial movement of the first shaft and the second shaft relative to the third shaft.

EXAMPLE 25: The delivery apparatus of any example herein, particularly example 24, wherein the handle further comprises a force balancing assembly disposed in the main portion and coupled to the second shaft.

EXAMPLE 26: The delivery apparatus of any example herein, particularly example 25, wherein the force balancing assembly comprises one or more pulleys.

EXAMPLE 27: The delivery apparatus of any example herein, particularly any one of examples 24-26, wherein the handle further comprises a displacement control mechanism disposed in the main portion and coupled to the second shaft.

EXAMPLE 28: The delivery apparatus of any example herein, particularly example 27, wherein the displacement control mechanism comprises a plurality of gears.

EXAMPLE 29: The delivery apparatus of any example herein, particularly any one of examples 24-26, which further comprises a displacement control mechanism disposed in the main portion and coupled to the second shaft.

EXAMPLE 30: The delivery apparatus of any example herein, particularly example 29, wherein the displacement control mechanism comprises a plurality of gears.

EXAMPLE 31: The delivery apparatus of any example herein, particularly any one of examples 24-30, wherein the handle further comprises a second knob rotatably coupled to the main portion, wherein the handle is configured such that rotating the second knob in a first direction relative to the main portion results in radial expansion of the prosthetic heart valve, and wherein the handle is configured such that rotating the second knob in a second direction relative to the main portion results in radial compression of the prosthetic heart valve.

EXAMPLE 32: The delivery apparatus of any example herein, particularly any one of examples 24-31, wherein the handle comprises a first axially movable component and a second axially movable component, wherein the handle is configured such that the first axially movable component is spaced apart from and moves axially relative to the second axially movable component as the first knob is rotated from the first rotational position to the second rotational position and such that the first axially movable component moves axially together with the second axially movable component as the first knob is rotated from the second rotational position to the third rotational position.

EXAMPLE 33: The delivery apparatus of any example herein, particularly example 32, wherein the first axially movable component is disposed distally relative to the second axially movable component.

EXAMPLE 34: The delivery apparatus of any example herein, particularly any one of examples 32-33, wherein the first axially movable component moves proximally relative to the second axially movable component as the first knob move from the first rotational position to the second rotational position.

EXAMPLE 35: The delivery apparatus of any example herein, particularly any one of examples 32-34, wherein the first axially movable component and the second axially movable component move proximally relative to the main portion as the first knob move from the second rotational position to the third rotational position.

EXAMPLE 36: The delivery apparatus of any example herein, particularly any one of examples 24-35, wherein the first knob is axially fixed relative to the main portion.

EXAMPLE 37: A delivery apparatus for implanting a prosthetic heart valve comprises a first shaft having a first end portion and a second end portion; a second shaft having a first end portion and a second end portion, wherein the second shaft extends through the first shaft; a nosecone coupled to the first end portion of the second shaft; and a handle comprising a main portion and an adjustment mechanism, wherein the second end portion of the first shaft is coupled to the main portion of the handle, wherein the second end portion of the second shaft is coupled to the adjustment mechanism, and wherein the adjustment mechanism is configured such that moving the adjustment mechanism axially relative to the main portion results in the second shaft moving axially relative to the first shaft.

EXAMPLE 38: The delivery apparatus of any example herein, particularly example 37, wherein the adjustment mechanism comprises a slidable knob extending from the main body.

EXAMPLE 39: The delivery apparatus of any example herein, particularly any one of examples 37-38, wherein the adjustment mechanism comprises a locking member configured to selectively restrict movement between the adjustment mechanism and the main portion.

EXAMPLE 40: The delivery apparatus of any example herein, particularly example 39, wherein the locking member comprises a rotatable knob.

EXAMPLE 41: The delivery apparatus of any example herein, particularly any one of examples 37-40, wherein the main body comprises a slot through which the adjustment mechanism extends.

EXAMPLE 42: The delivery apparatus of any example herein, particularly any one of examples 1-41, wherein the handle further comprises a force limiting assembly.

EXAMPLE 43: The delivery apparatus of any example herein, particularly any one of examples 1-42, wherein the handle further comprises an adjustable biasing assembly.

EXAMPLE 44: The delivery apparatus of any example herein, particularly any one of examples 1-43, wherein the handle further comprises a force distribution mechanism.

EXAMPLE 45: The delivery apparatus of any example herein, particularly any one of examples 1-44, wherein the handle further comprises a displacement control mechanism.

EXAMPLE 46: The delivery apparatus of any example herein, particularly any one of examples 1-45, wherein the handle further comprises an expansion limiting mechanism.

EXAMPLE 47: The delivery apparatus of any example herein, particularly any one of examples 1-46, wherein the handle further comprises an indicator configured to provide an indicium of expansion of a prosthetic heart valve.

EXAMPLE 48: A delivery apparatus for implanting a prosthetic heart valve comprises a first shaft having a first end portion and a second end portion, wherein the first end portion of the first shaft is configured to be releasably coupled to a prosthetic heart valve; and a handle comprising a main portion, a rotatable knob, and a locking mechanism, wherein the rotatable knob is rotatably coupled to the main portion and to the second end portion of the first shaft, wherein the locking mechanism is configured to restrict relative rotational movement of the rotatable knob and the main portion.

EXAMPLE 49: The delivery apparatus of any example herein, particularly example 48, wherein the locking mechanism comprise a first gear, a second gear, a threaded member, an extension member, and a switch, wherein the first gear is fixedly coupled to the rotatable knob, wherein the second gear is fixedly coupled to the threaded member and engaged with the first gear, wherein the extension member extends from the threaded member and is axially movable relative to the threaded member, wherein the switch is movable from a locked position to an unlocked position relative to the extension member, wherein in the locked position, the switch restricts axial movement of the extension member, and wherein in the unlocked position, the switch allows axial movement of the extension member.

EXAMPLE 50: The delivery apparatus of any example herein, particularly example 49, wherein the switch is a first switch of a plurality of switches, wherein each of the switches is spaced axially relative to an adjacent switch, and wherein each of the switches is movable between a locked position and an unlocked position.

EXAMPLE 51: The delivery apparatus of any example herein, particularly any one of examples 1-50, wherein the handle further comprises a ratcheting mechanism configured to selectively allow rotation of a knob relative to the handle in a first rotational direction to selectively restrict rotation of the knob relative to the handle in a second rotational direction.

EXAMPLE 52: The delivery apparatus of any example herein, particularly any one of examples 1-51, wherein the handle further comprises a valve rotation mechanism with a rotatable knob, wherein the valve rotation mechanism is configured to selectively allow rotation of a shaft of the delivery apparatus and a prosthetic heart valve releasably coupled to the shaft to rotate as the rotatable knob is rotated relative to the handle.

EXAMPLE 53: The delivery apparatus of any example herein, particularly any one of examples 1-52, wherein the handle further comprises an expansion mechanism comprising a rotatable knob and a pull plate configured to move axially relative to the rotated knob as the rotatable knob is rotated.

EXAMPLE 54: The delivery apparatus of any example herein, particularly any one of examples 1-53, which further comprises a current-monitoring mechanism configured for providing indicia of whether the delivery apparatus is coupled to a prosthetic heart valve.

EXAMPLE 55: The delivery apparatus of any example herein, particularly example 54, wherein a handle of the delivery apparatus comprises a current monitor coupled to an electric circuit, where the current monitor senses current when the delivery apparatus is coupled to the prosthetic heart valve and senses no current when the delivery apparatus is released from the prosthetic heart valve.

EXAMPLE 56: The delivery apparatus of any example herein, particularly any one of examples 1-55, which further comprises a magnetic rotation-counting mechanism.

EXAMPLE 57: The delivery apparatus of any example herein, particularly any one of examples 1-56, which further comprises an electric rotation-counting mechanism.

EXAMPLE 58: The delivery apparatus of any example herein, particularly any one of examples 1-57, which further comprises an optic rotation-counting mechanism.

EXAMPLE 59: The delivery apparatus of any example herein, particularly any one of examples 1-58, wherein the handle comprises one or more of a visual indicator, an auditory indicator, and a haptic indicator configured to indicate to a user whether the delivery apparatus is coupled to a prosthetic heart valve.

EXAMPLE 60: A delivery apparatus for a prosthetic heart valve comprises a handle having a proximal end, a distal end, and a cavity extending from the proximal end to the distal end; a plurality of actuation assemblies, each of the actuation assemblies comprising a movable portion, each movable portion having a proximal end portion disposed within the cavity and a distal end portion disposed outside of the cavity; a plate member disposed within the cavity and axially movable relative to the handle, the plate member having a first state in which the plate member moves freely relative to the movable portions and a second state in which the plate member engages the movable portions such that further axial movement of the plate member results in axial displacement of the movable portions; and a drive assembly operatively coupled to the plate member and operable to move the plate member axially relative to the handle.

EXAMPLE 61: The delivery apparatus according to any example herein, particularly example 60, wherein each of the movable portions comprises an actuation tube and an actuation member extending through and coupled to the actuation tube, and wherein the plate member is positioned distal to the actuation tubes such that axial movement of the plate member in a direction towards the proximal end of the handle results in contact between the plate member and the actuation tubes.

EXAMPLE 62: The delivery apparatus according to any example herein, particularly example 61, wherein the plate member comprises a plurality of slots for passage of the actuation members.

EXAMPLE 63: The delivery apparatus according to any example herein, particularly any one of examples 61 and 62, wherein the drive assembly comprises a driving gear operatively engaged with a first driven gear, and wherein the first driven gear is coupled to the plate member such that rotation of the driving gear results in axial movement of the plate member relative to the handle.

EXAMPLE 64: The delivery apparatus according to any example herein, particularly example 63, wherein the drive assembly further comprises a plurality of second driven gears operatively engaged with the driving gear, each of the second driven gears coupled to one of the actuation tubes such that rotation of the driving gear results in rotation of the actuation members.

EXAMPLE 65: The delivery apparatus according to any example herein, particularly example 64, which further comprises a first rotatable knob coupled to the driving gear, wherein rotation of the first rotatable knob results in rotation of the driving gear.

EXAMPLE 66: The delivery apparatus according to any example herein, particularly any one of examples 61 to 65, which further comprises a second rotatable knob coupled to the actuation members and the handle, wherein rotation of the second rotatable knob in a first direction applies a pull force to the actuation members and rotation of the second rotatable knob in a second direction that is opposite to the first direction releases the pull force from the actuation members.

EXAMPLE 67: The delivery apparatus according to any example herein, particularly example 66, further comprising a pull force mechanism, the pull force mechanism comprising a reel coupled to the second rotatable knob and to one of the actuation members, wherein the reel applies the pull force from the second rotatable knob to the one of the actuation members.

EXAMPLE 68: The delivery apparatus according to any example herein, particularly example 67, wherein the pull force mechanism further comprises one or more pulleys arranged to distribute the pull force applied to the one of the actuation members uniformly among the actuation members.

EXAMPLE 68A: The delivery apparatus according to any example herein, particularly example 67 or 68, wherein each actuation member comprises a threaded head, an actuation flexible portion, and an actuation torque-transferring portion extending between the threaded head and the actuation flexible portion, and wherein the actuation flexible portion of the one of the actuation members is coupled to the reel.

EXAMPLE 69: The delivery apparatus according to any example herein, particularly any one of examples 67, 68, and 68A, which further comprises a tensioning assembly coupled to the one of the actuation members, the tensioning assembly comprising a spring member arranged to apply tension to the one of the actuation members.

EXAMPLE 69A: The delivery apparatus according to any example herein, particularly any one of examples 61-69, further comprising: a first sensor member coupled to at least one of the actuation members and rotatable with the at least one of the actuation members; a second sensor member positioned to detect changes in a rotational position of the first sensor member; and circuitry to count a number of rotations of the at least one of the actuation members from an output of the second sensor member and generate an indication of response to the number of rotations of the at least one of the actuation members exceeding a predetermined threshold.

EXAMPLE 70: The delivery apparatus according to any example herein, particularly any one of examples 61-69A, further comprising a shaft assembly coupled to the handle, wherein the shaft assembly comprises: a first shaft axially movable relative to the handle, the first shaft having a first lumen; and a second shaft extending through the first lumen, the second shaft having one or more second lumens, wherein the actuation members extend through the one or more second lumens.

EXAMPLE 71: The delivery apparatus according to any example herein, particularly example 70, further comprising: a third shaft extending through one of the one or more second lumens, the third shaft having a proximal end portion extending into the cavity, a distal end portion disposed outside the cavity, and a third lumen; and a nosecone coupled to the distal end portion of the third shaft, the nosecone having a central opening aligned with the third lumen for passage of a guidewire.

EXAMPLE 72: A delivery assembly comprises a delivery apparatus according to any one of examples 60-71 and a mechanically-expandable prosthetic heart valve comprising a plurality of actuators operable to adjust a diameter of the prosthetic heart valve, wherein the movable portions of the actuation assemblies are releasably coupled to the plurality of actuators and axially movable to operate the plurality of actuators.

EXAMPLE 73: A method comprises inserting a distal end of the delivery assembly according to example 72 into a vasculature of a patient; advancing the distal end of the delivery assembly through the vasculature of the patient to position the prosthetic heart valve at a select implantation location; disengaging the movable portions of the actuation assemblies from the actuators of the prosthetic heart valve; axially moving the plate member relative to the handle until the plate member engages the movable portions of the actuation assemblies; and pulling the plate member and the movable portions of the actuation assemblies to retract the movable portions of the actuation assemblies from the prosthetic heart valve.

EXAMPLE 74: A delivery apparatus for a prosthetic heart valve comprises a handle having a proximal end, a distal end, and a cavity extending from the proximal end to the distal end; an actuation assembly comprising an actuation member and a sleeve member, the actuation member having a proximal end portion disposed within the cavity and a distal end portion disposed outside of the cavity, the sleeve member disposed around the distal end portion of the actuation member; a drive assembly coupled to the proximal end portion of the actuation member, the drive assembly operable to rotate the actuation member from within the cavity; a first sensor member coupled to the actuation member and rotatable with the actuation member; and a second sensor member positioned to detect changes in a rotational position of the first sensor member.

EXAMPLE 75: The delivery apparatus according to any example herein, particularly example 74, wherein the second sensor member comprises a conductive portion, wherein the first sensor member comprises a conductive arm extending radially from the at least one actuation member, and wherein the conductive arm contacts the conductive portion during a portion of each rotational cycle of the actuation member.

EXAMPLE 76: The delivery apparatus according to any example herein, particularly example 75, wherein the second sensor member further comprises a non-conductive portion, and wherein the first sensor member contacts the non-conductive portion during a remaining portion of each rotational cycle of the at least one actuation member.

EXAMPLE 77: The delivery apparatus according to any example herein, particularly any one of examples 75-76, wherein the second sensor member is mounted in a recess in the sleeve member.

EXAMPLE 78: The delivery apparatus according to any example herein, particularly example 74, wherein the first sensor member comprises at least two magnetic regions with opposing polarities, and wherein the second sensor member comprises a magnetic sensor positioned to detect changes in a magnetic field produced by the at least two magnetic regions.

EXAMPLE 79: The delivery apparatus according to any example herein, particularly example 74, wherein the first sensor member comprises a light absorbing material disposed on a portion of a surface of the actuation member, and wherein the second sensor member comprises a first optic core positioned to emit light towards the surface of the actuation member and a second optic core positioned to receive light returned from the surface of the actuation member.

EXAMPLE 80: The delivery apparatus according to any example herein, particularly any one of examples 74-79, which further comprises circuitry to count a number of rotations of the actuation member from an output of the second sensor member and generate an indication in response to the number of rotations of the actuation member exceeding a predetermined threshold.

EXAMPLE 81: The delivery apparatus of any example herein, particularly any one of examples 76 to 80, wherein the drive assembly comprises a gear train.

EXAMPLE 82: A delivery apparatus for a prosthetic heart valve comprises a handle having a proximal end, a distal end, and a cavity extending from the proximal end to the distal end; an actuation assembly comprising an electrically conductive actuation member and a sleeve member, the actuation member having a proximal end portion disposed within the cavity and a distal end portion disposed outside of the cavity, the sleeve member disposed around the distal end portion of the actuation member; a drive assembly coupled to the actuation members and the handle, the drive assembly operable to rotate the actuation members from within the cavity; an electrical circuit having an electrical transmission path comprising the handle and the electrically conductive actuation member, wherein the electrical circuit has an open state correspond to the electrically conductive actuation member being engaged with the prosthetic heart valve and a closed state corresponding to the electrically conductive actuation member being disengaged from the prosthetic heart valve; and a current sensor coupled to the electrical circuit to detect an electrical state of the electrical circuit.

EXAMPLE 83: A delivery apparatus for a prosthetic heart valve comprises a handle comprising a proximal portion, a distal portion, and a longitudinal axis, the proximal portion and the distal portion telescopically movable relative to each other along the longitudinal axis; a first shaft coupled to the distal portion and having a first lumen; a second shaft extending through the first lumen and coupled to the distal portion such that relative movement between the proximal portion and the distal portion results in axial movement of both the first shaft and the second shaft; and a knob coupled to the first shaft, wherein rotation of the knob moves the first shaft axially relative to the handle and independently of the second shaft.

EXAMPLE 84: A delivery apparatus for a prosthetic heart valve comprises a handle comprising an inner track; a first movable component positioned along the inner track and axially movable along the inner track; a first shaft having a proximal end and a distal end, the proximal end of the first shaft coupled to the first movable component; a second movable component positioned along the inner track and axially movable along the inner track; a second shaft having a proximal end and a distal end, the proximal end of the second shaft coupled to the second movable component; and a knob coupled to the first movable component and rotatable to move the first movable component along the inner track; wherein the first movable component is axially movable along the inner track between a first position in which the first movable component is axially separated from the second movable component and movement of the first movable component along the inner track results only in movement of the first shaft and a second position in which the first movable component engages the second movable component and movement of the first movable component results in movement of both the first shaft and the second shaft.

EXAMPLE 85: A delivery apparatus for a prosthetic heart valve comprises a handle; a first shaft having a first end portion, a second end portion, and a first lumen extending from the first end portion to the second end portion, wherein the first end portion is coupled to the handle; a second shaft having a first end portion, a second end portion, and one or more second lumens, the second shaft extending through the first shaft; a third shaft extending through one of the one or more second lumens; and a slider mechanism coupled to the handle and the third shaft and operable to displace the third shaft axially relative to the handle.

EXAMPLE 86: A delivery apparatus for a prosthetic heart valve comprises a handle having a first portion and a second portion, the second portion rotatable and slidable relative to the first portion; a receptacle formed within the second portion and rotatable with the second portion; a shaft having a first end portion, a second end portion, and one or more lumens, the first end portion of the shaft received within the receptacle; and a plurality of actuation members extending through the one or more lumens of the shaft, wherein the plurality of actuation members are rotatable by rotation of the receptacle.

EXAMPLE 87: The delivery apparatus according to any example herein, particularly example 86, which further comprises a knob coupled to the receptacle, wherein the receptacle is rotatable by rotation of the knob.

EXAMPLE 88: The delivery apparatus according to any example herein, particularly any one of examples 86-87, which further comprises a non-circular casing that mates with a socket within the receptacle, wherein the first end portion of the handle is coupled to the non-circular casing.

EXAMPLE 89: A delivery apparatus for a prosthetic heart valve comprising: a handle having a proximal portion, a distal portion, and a cavity extending from the proximal portion to the distal portion, the proximal portion having a slot formed therein; a slidable knob slidably engaged with the slot; a multi-lumen shaft having a proximal end portion, a distal end portion, and a plurality of first lumens, the proximal end portion of the multi-lumen shaft disposed within the cavity; and a first shaft extending through one of the first lumens, the first shaft having a proximal end portion and a distal end portion, the proximal end portion of the first shaft coupled to the slidable knob, wherein movement of the slidable knob along the slot results in axial displacement of the first shaft relative to the handle.

EXAMPLE 90: The delivery apparatus according to any example herein, particularly example 89, further comprising a slider inner body disposed within the cavity, wherein the slidable knob is coupled to the slider inner body.

EXAMPLE 91: The delivery apparatus according to any example herein, particularly example 90, wherein the slider inner body comprises a recess, and wherein the proximal end portion of the first shaft is received in the recess.

EXAMPLE 92: The delivery apparatus according to any example herein, particularly any one of examples 1 to 3, further comprising a nosecone coupled to the distal end portion of the first shaft.

EXAMPLE 93: The delivery apparatus according to any example herein, particularly any one of examples 1 to 4, further comprising an outer shaft having a proximal end portion, a distal end portion, and a second lumen, wherein the multi-lumen shaft extends through the second lumen.

EXAMPLE 94: The delivery apparatus according to any example herein, particularly example 5, further comprising a drive assembly coupled to the handle and the proximal end portion of the outer shaft, the drive assembly comprising a lead member rotatably supported within the cavity, wherein rotation of the lead member results in axial movement of the outer shaft relative to the handle.

EXAMPLE 95: The delivery apparatus according to any example herein, particularly example 94, further comprising a rotatable knob coupled to the lead member, wherein rotation of the rotatable knob results in rotation of the lead member.

EXAMPLE 96: The delivery apparatus according to any example herein, particularly example 94 or 95, wherein the drive assembly further comprises a nut threadedly engaged with the lead member and having a bore to receive the proximal end portion of the outer shaft, wherein rotation of the lead member results in axial movement of the nut and outer shaft.

EXAMPLE 97: The delivery apparatus according to any example herein, particularly example 96, wherein the drive assembly further comprises an axial guide positioned to guide movement of the nut in an axial direction.

EXAMPLE 98: The delivery apparatus according to any example herein, particularly example 96 or 97, further comprising a guide head disposed within the cavity, the guide head having a bore to receive the proximal end portion of the multi-lumen shaft.

EXAMPLE 99: The delivery apparatus according to any example herein, particularly example 98, further comprising a flushing port fluidly connected to the bore in the guide head, the flushing port extending outside of the handle.

EXAMPLE 100: The delivery apparatus according to any example herein, particularly example 98, further comprising a load cell positioned in contact with the guide head to measure a force transmitted through the multi-lumen shaft.

EXAMPLE 101: A delivery apparatus for a prosthetic heart valve, the delivery apparatus comprising: a handle having a proximal portion, a distal portion, and a cavity extending from the proximal portion to the distal portion; a multi-lumen shaft having a proximal end portion, a distal end portion, and a plurality of first lumens, the proximal end portion of the multi-lumen shaft disposed within the cavity; a plurality of actuation members extending through one or more of the first lumens, each of the actuation members having a distal threaded head, a proximal actuation flexible portion, and an actuation torque-transferring portion extending between the distal threaded head and the proximal actuation flexible portion; a recompression member extending through one of the first lumens; and a pull force mechanism disposed at least partially within the cavity, the pull force mechanism coupled to the proximal actuation flexible portions and the recompression member, the pull force operable to apply a pull force to the proximal actuation flexible portions in a first mode and apply the pull force to the recompression member in a second mode.

EXAMPLE 102: The delivery apparatus according to any example herein, particularly example 101, further comprising a first rotatable knob coupled to the pull force mechanism, wherein rotation of the first rotatable knob in a first direction applies the pull force to the proximal actuation flexible portions and rotation of the first rotatable knob in a second direction that is opposite to the first direction applies the pull force to the recompression member.

EXAMPLE 103: The delivery apparatus according to any example herein, particularly any one of examples 101 and 102, further comprising a gear mechanism coupled to the plurality of actuation members and operable to simultaneously rotate the plurality of actuation members.

EXAMPLE 104: The delivery apparatus according to any example herein, particularly example 103, further comprising a second rotatable knob engaged with the gear mechanism, wherein rotation of the second rotatable knob operates the gear mechanism.

The features described herein regarding any example can be combined with other features described in any one or more of the other examples, unless otherwise stated. For example, any example comprising a force control mechanism (and/or any component thereof) can be combined with any example comprising a displacement control mechanism (and/or any component thereof).

In view of the many possible ways in which the principles of the disclosure may be applied, it should be recognized that the illustrated configurations depict examples of the disclosed technology and should not be taken as limiting the scope of the disclosure nor the claims. Rather, the scope of the claimed subject matter is defined by the following claims and their equivalents.

The invention claimed is:

1. A delivery apparatus for a prosthetic heart valve, the delivery apparatus comprising:
   a handle having a proximal end, a distal end, and a cavity extending from the proximal end to the distal end;
   a plurality of actuation assemblies, each of the actuation assemblies comprising a movable portion, each movable portion having a proximal end portion disposed within the cavity and a distal end portion disposed outside of the cavity;
   a plate member disposed within the cavity and axially movable relative to the handle, the plate member having a first state in which the plate member moves freely relative to the movable portions and a second state in which the plate member engages the movable portions such that further axial movement of the plate member results in axial displacement of the movable portions; and a drive assembly operatively coupled to the plate member and operable to move the plate member axially relative to the handle.

2. The delivery apparatus of claim 1, wherein each of the movable portions comprises an actuation tube and an actuation member extending through and coupled to the actuation tube, and wherein the plate member is positioned distal to the actuation tubes such that axial movement of the plate member in a direction towards the proximal end of the handle results in contact between the plate member and the actuation tubes.

3. The delivery apparatus of claim 2, wherein the plate member comprises a plurality of slots for passage of the actuation members.

4. The delivery apparatus of claim 2, wherein the drive assembly comprises a driving gear operatively engaged with a first driven gear, and wherein the first driven gear is coupled to the plate member such that rotation of the driving gear results in axial movement of the plate member relative to the handle.

5. The delivery apparatus of claim 4, wherein the drive assembly further comprises a plurality of second driven gears operatively engaged with the driving gear, each of the second driven gears coupled to one of the actuation tubes such that rotation of the driving gear results in rotation of the actuation members.

6. The delivery apparatus of claim 5, further comprising a first rotatable knob coupled to the driving gear, wherein rotation of the first rotatable knob results in rotation of the driving gear.

7. The delivery apparatus of claim 2, further comprising a second rotatable knob coupled to the actuation members and the handle, wherein rotation of the second rotatable knob in a first direction applies a pull force to the actuation members and rotation of the second rotatable knob in a second direction that is opposite to the first direction releases the pull force from the actuation members.

8. The delivery apparatus of claim 7, further comprising a pull force mechanism, the pull force mechanism comprising a reel coupled to the second rotatable knob and to one of the actuation members, wherein the reel applies the pull force from the second rotatable knob to the one of the actuation members.

9. The delivery apparatus of claim 8, wherein the pull force mechanism further comprises one or more pulleys arranged to distribute the pull force applied to the one of the actuation members uniformly among the actuation members.

10. The delivery apparatus of claim 8, wherein each actuation member comprises a threaded head, an actuation flexible portion, and an actuation torque-transferring portion extending between the threaded head and the actuation flexible portion, and wherein the actuation flexible portion of the one of the actuation members is attached to the reel.

11. The delivery apparatus of claim 8, further comprising a tensioning assembly coupled to the one of the actuation members, the tensioning assembly comprising a spring member arranged to apply tension to the one of the actuation members.

12. The delivery apparatus of claim 2, further comprising:
   a first sensor member coupled to at least one of the actuation members and rotatable with the at least one of the actuation members;
   a second sensor member positioned to detect changes in a rotational position of the first sensor member; and
   circuitry to count a number of rotations of the at least one of the actuation members from an output of the second sensor member, wherein the circuitry outputs an indication in response to the number of rotations of the at least one of the actuation members exceeding a predetermined threshold.

13. The delivery apparatus of claim 2, further comprising a shaft assembly coupled to the handle, wherein the shaft assembly comprises:

a first shaft axially movable relative to the handle, the first shaft having a first lumen; and a second shaft extending through the first lumen, the second shaft having one or more second lumens, wherein the actuation members extend through the one or more second lumens.

14. The delivery apparatus of claim 13, further comprising:

a third shaft extending through one of the one or more second lumens, the third shaft having a proximal end portion extending into the cavity, a distal end portion disposed outside the cavity, and a third lumen; and a nosecone coupled to the distal end portion of the third shaft, the nosecone having a central opening aligned with the third lumen for passage of a guidewire.

15. A delivery assembly comprising:

a delivery apparatus comprising actuation assemblies, each of the actuation assemblies comprising a movable portion; and a mechanically-expandable prosthetic heart valve comprising a plurality of actuators operable to adjust a diameter of the prosthetic heart valve, wherein the movable portions of the actuation assemblies are releasably coupled to the plurality of actuators and axially movable to operate the plurality of actuators;

wherein the delivery apparatus comprises:

a handle having a proximal end, a distal end, and a cavity extending from the proximal end to the distal end;

a plate member disposed within the cavity and axially movable relative to the handle; and a drive assembly operatively coupled to the plate member and operable to move the plate member axially relative to the handle, and wherein each of the movable portions comprises a proximal end portion disposed within the cavity and a distal end portion disposed outside of the cavity.

16. The delivery assembly of claim 15, wherein the plate member has a first state in which the plate member moves freely relative to the movable portions and a second state in which the plate member engages the movable portions such that further axial movement of the plate member results in axial displacement of the movable portions.

17. A method comprising:

inserting a distal end of a delivery assembly into a vasculature of a patient, wherein the delivery assembly comprises a delivery apparatus comprising:

a handle having a proximal end, a distal end, and a cavity extending from the proximal end to the distal end;

a plurality of actuation assemblies, each of the actuation assemblies comprising a movable portion, each movable portion having a proximal end portion disposed within the cavity and a distal end portion disposed outside of the cavity;

a plate member disposed within the cavity and axially movable relative to the handle; and a drive assembly operatively coupled to the plate member and operable to move the plate member axially relative to the handle;

advancing the distal end of the delivery assembly through the vasculature of the patient to position the prosthetic heart valve at a select implantation location;

disengaging the movable portions of the actuation assemblies from the actuators of the prosthetic heart valve;

axially moving the plate member relative to the handle until the plate member engages the movable portions of the actuation assemblies; and pulling the plate member and the movable portions of the actuation assemblies to retract the movable portions of the actuation assemblies from the prosthetic heart valve.

18. The method of claim 17, wherein the plate member has a first state in which the plate member moves freely relative to the movable portions and a second state in which the plate member engages the movable portions such that further axial movement of the plate member results in axial displacement of the movable portions.

* * * * *